(12) United States Patent
Bellinger et al.

(10) Patent No.: US 11,576,866 B2
(45) Date of Patent: Feb. 14, 2023

(54) GASTRIC RESIDENCE SYSTEMS FOR SUSTAINED DELIVERY OF ADAMANTANE-CLASS DRUGS

(71) Applicant: Lyndra Therapeutics, Inc., Watertown, MA (US)

(72) Inventors: Andrew Bellinger, Wellesley, MA (US); Rosemary Kanasty, Cambridge, MA (US); Jung Hoon Yang, Watertown, MA (US); Bennett Carter, Stoughton, MA (US); Stephen Zale, Hopkinton, MA (US); Nupura Bhise, Cambridge, MA (US); Susan Low, Pepperell, MA (US); James Wright, Lexington, MA (US)

(73) Assignee: Lyndra Therapeutics, Inc., Watertown, MA (US)

( * ) Notice: Subject to any disclaimer, the term of this patent is extended or adjusted under 35 U.S.C. 154(b) by 158 days.

(21) Appl. No.: 16/333,582

(22) PCT Filed: Sep. 29, 2017

(86) PCT No.: PCT/US2017/054608
§ 371 (c)(1),
(2) Date: Mar. 14, 2019

(87) PCT Pub. No.: WO2018/064630
PCT Pub. Date: Apr. 5, 2018

(65) Prior Publication Data
US 2019/0231697 A1    Aug. 1, 2019

Related U.S. Application Data

(60) Provisional application No. 62/402,947, filed on Sep. 30, 2016, provisional application No. 62/490,466, filed on Apr. 26, 2017, provisional application No. 62/517,718, filed on Jun. 9, 2017.

(51) Int. Cl.
| | |
|---|---|
| *A61K 9/20* | (2006.01) |
| *A61K 31/13* | (2006.01) |
| *A61P 25/28* | (2006.01) |
| *A61P 31/16* | (2006.01) |
| *A61K 9/00* | (2006.01) |

(52) U.S. Cl.
CPC .......... *A61K 9/2072* (2013.01); *A61K 9/0065* (2013.01); *A61K 9/204* (2013.01); *A61K 9/2013* (2013.01); *A61K 9/2027* (2013.01); *A61K 9/2031* (2013.01); *A61K 31/13* (2013.01); *A61P 25/28* (2018.01); *A61P 31/16* (2018.01)

(58) Field of Classification Search
None
See application file for complete search history.

(56) References Cited

U.S. PATENT DOCUMENTS

| | | |
|---|---|---|
| 1,957,564 A | 5/1934 | West |
| 3,154,461 A | 10/1964 | Johnson |
| 3,531,368 A | 9/1970 | Okamoto |
| 3,716,614 A | 2/1973 | Watanabe |
| 3,844,285 A | 10/1974 | Laby |
| 3,976,764 A | 8/1976 | Watanabe |
| 4,304,767 A | 12/1981 | Heller |
| 4,451,260 A | 5/1984 | Mitra |
| 4,525,358 A | 6/1985 | Baltes |
| 4,676,507 A | 6/1987 | Patterson |
| 4,735,804 A | 4/1988 | Caldwell |
| 4,758,436 A | 7/1988 | Caldwell |
| 4,767,627 A | 8/1988 | Caldwell |
| 4,812,012 A | 3/1989 | Terada |
| 4,996,058 A | 2/1991 | Sinnreich |
| 5,002,772 A | 3/1991 | Curatolo |
| 5,007,790 A | 4/1991 | Shell |
| 5,047,464 A | 9/1991 | Pogany |

(Continued)

FOREIGN PATENT DOCUMENTS

| | | |
|---|---|---|
| AU | 643219 B2 | 1/1991 |
| AU | 6199090 A | 3/1991 |

(Continued)

OTHER PUBLICATIONS

Abraham, N. Dow Corning QP1-2 Liquid Silicone Rubber supports cost-effective medical device designs. Medical Design & Outsourcing. (Year: 2015).*

(Continued)

*Primary Examiner* — Jessica Worsham
(74) *Attorney, Agent, or Firm* — Morrison & Foerster LLP

(57) ABSTRACT

The invention provides gastric residence systems for administration of adamantane-class drugs or pharmaceutically acceptable salts thereof, such as memantine or pharmaceutically acceptable salts thereof, and methods for making and using such systems. The systems provide extended release of drug, reducing the frequency with which the drug must be administered to the patient. The gastric residence systems, or components of gastric residence system such as segments or elongate members of gastric residence systems, can have release rate-modulating films, which provide good control over release of adamantane-class drugs or pharmaceutically acceptable salts thereof present in the gastric residence system. Some embodiments of the films can provide resistance against burst release of adamantane-class drugs or pharmaceutically acceptable salts thereof upon exposure to alcohol.

22 Claims, 72 Drawing Sheets

(56) References Cited

U.S. PATENT DOCUMENTS

| | | |
|---|---|---|
| 5,121,329 A | 6/1992 | Crump |
| 5,340,433 A | 8/1994 | Crump |
| 5,369,142 A | 11/1994 | Culbertson |
| 5,443,843 A | 8/1995 | Curatolo |
| 5,491,586 A | 2/1996 | Phillips |
| 5,840,332 A | 11/1998 | Lerner |
| 5,939,467 A | 8/1999 | Wnuk et al. |
| 6,120,802 A | 9/2000 | Breitenbach et al. |
| 6,120,803 A | 9/2000 | Wong |
| RE37,314 E | 8/2001 | Hirai |
| 6,306,420 B1 | 10/2001 | Cheikh |
| 6,306,439 B1 | 10/2001 | Penners |
| 6,316,460 B1 | 11/2001 | Creekmore |
| 6,375,649 B1 | 4/2002 | Jellie |
| 6,436,069 B1 | 8/2002 | Jellie |
| 6,488,962 B1 | 12/2002 | Berner |
| 6,500,168 B1 | 12/2002 | Jellie |
| 6,548,083 B1 | 4/2003 | Wong |
| 6,685,962 B2 | 2/2004 | Friedman |
| 6,776,999 B1 | 8/2004 | Krumme |
| 6,780,168 B2 | 8/2004 | Jellie |
| 6,825,308 B1 | 11/2004 | Kulkarni |
| 6,962,579 B2 | 11/2005 | Jellie |
| 7,276,252 B2 | 10/2007 | Payumo |
| 7,691,151 B2 | 4/2010 | Kutsko |
| 7,964,196 B2 | 6/2011 | De |
| 8,021,384 B2 | 9/2011 | Weiss |
| 8,038,659 B2 | 10/2011 | Boyden |
| 8,158,143 B2 | 4/2012 | Lendlein |
| 8,267,888 B2 | 9/2012 | Marco et al. |
| 8,277,843 B2 | 10/2012 | Singh |
| 8,298,574 B2 | 10/2012 | Tsabari |
| 8,377,453 B2 | 2/2013 | Han |
| 8,414,559 B2 | 4/2013 | Gross |
| 8,586,083 B2 | 11/2013 | Mohammad |
| 8,609,136 B2 | 12/2013 | Tsabari |
| 8,753,678 B2 | 6/2014 | Tsabari |
| 8,771,730 B2 | 7/2014 | Navon |
| 9,072,663 B2 | 7/2015 | Navon |
| 9,107,816 B2 | 8/2015 | Lee |
| 9,220,688 B2 | 12/2015 | Alon |
| 9,259,387 B2 | 2/2016 | Navon |
| 10,182,985 B2 | 1/2019 | Bellinger |
| 10,195,143 B2 | 2/2019 | Zalit et al. |
| 10,485,758 B2 | 11/2019 | Menachem et al. |
| 10,517,820 B2 | 12/2019 | Bellinger |
| 10,532,027 B2 | 1/2020 | Bellinger |
| 10,610,482 B2 | 4/2020 | Bellinger |
| 10,716,751 B2 | 7/2020 | Bellinger et al. |
| 10,716,752 B2 | 7/2020 | Bellinger et al. |
| 2002/0022048 A1 | 2/2002 | Bromberg |
| 2002/0132008 A1 | 9/2002 | Mumper |
| 2003/0021822 A1 | 1/2003 | Lloyd |
| 2003/0232895 A1 | 12/2003 | Omidian |
| 2004/0180086 A1 | 9/2004 | Ramtoola |
| 2004/0219186 A1 | 11/2004 | Ayres |
| 2005/0033331 A1 | 2/2005 | Burnett |
| 2005/0165136 A1 | 7/2005 | Mays |
| 2005/0175702 A1 | 8/2005 | Muller-schulte |
| 2005/0249807 A1 | 11/2005 | Brown et al. |
| 2006/0069214 A1 | 3/2006 | Deiss |
| 2006/0142794 A1 | 6/2006 | Lendlein |
| 2006/0182788 A1 | 8/2006 | Singh |
| 2007/0048383 A1 | 3/2007 | Helmus |
| 2007/0104754 A1 | 5/2007 | Sterling |
| 2007/0123809 A1 | 5/2007 | Weiss |
| 2007/0129784 A1 | 6/2007 | Lendlein |
| 2007/0131144 A1 | 6/2007 | Winter et al. |
| 2007/0264307 A1 | 11/2007 | Chen |
| 2008/0075766 A1 | 3/2008 | Li |
| 2008/0153779 A1 | 6/2008 | Liao |
| 2008/0241238 A1 | 10/2008 | Dharmadhikari |
| 2008/0249156 A1 | 10/2008 | Palepu |
| 2008/0260824 A1 | 10/2008 | Nangia |
| 2008/0292691 A1 | 11/2008 | Lloyd |
| 2009/0092415 A1 | 4/2009 | Murakami |
| 2009/0105531 A1 | 4/2009 | Boyden |
| 2009/0182424 A1 | 7/2009 | Marco |
| 2009/0246142 A1 | 10/2009 | Bhatia |
| 2009/0324694 A1 | 12/2009 | Mohammad |
| 2010/0152410 A1 | 6/2010 | East |
| 2010/0168439 A1 | 7/2010 | Olson |
| 2010/0256342 A1 | 10/2010 | Salemme |
| 2010/0266655 A1 | 10/2010 | Dadey |
| 2010/0297009 A1 | 11/2010 | Olson |
| 2010/0316712 A1 | 12/2010 | Nangia |
| 2011/0038912 A1 | 2/2011 | Darby et al. |
| 2011/0040318 A1 | 2/2011 | Marco |
| 2011/0052700 A1 | 3/2011 | Han |
| 2011/0097395 A1 | 4/2011 | Babul et al. |
| 2011/0245909 A1 | 10/2011 | Schmid |
| 2011/0268666 A1 | 11/2011 | Friedman |
| 2011/0305685 A1 | 12/2011 | Tseng |
| 2012/0116285 A1 | 5/2012 | Duggirala |
| 2012/0165793 A1 | 6/2012 | Ortiz |
| 2012/0165794 A1 | 6/2012 | Ortiz |
| 2012/0301547 A1 | 11/2012 | Gan |
| 2012/0321706 A1 | 12/2012 | Masri |
| 2013/0045530 A1 | 2/2013 | Gracias |
| 2013/0131637 A1 | 5/2013 | Dicesare et al. |
| 2013/0226104 A1 | 8/2013 | Hyde |
| 2013/0273135 A1 | 10/2013 | Brooks |
| 2014/0050784 A1 | 2/2014 | Kagan |
| 2014/0052171 A1 | 2/2014 | Tegels |
| 2014/0249499 A1 | 9/2014 | Selaru |
| 2015/0265536 A1 | 9/2015 | Muley |
| 2015/0335592 A1 | 11/2015 | Barnscheid |
| 2015/0342877 A1 | 12/2015 | Menachem |
| 2016/0317796 A1 | 11/2016 | Zhang |
| 2017/0051099 A1 | 2/2017 | Diciccio |
| 2017/0106099 A1 | 4/2017 | Bellinger |
| 2017/0128576 A1 | 5/2017 | Zhang |
| 2017/0135954 A1 | 5/2017 | Bellinger |
| 2017/0266112 A1 | 9/2017 | Bellinger |
| 2018/0250226 A1 | 9/2018 | Betser et al. |
| 2018/0311154 A1 | 11/2018 | Kanasty |
| 2018/0369138 A1 | 12/2018 | Zalit et al. |
| 2019/0070107 A1 | 3/2019 | Bellinger |
| 2019/0070108 A1 | 3/2019 | Bellinger |
| 2019/0125667 A1 | 5/2019 | Bellinger |
| 2019/0133936 A1 | 5/2019 | Bellinger |
| 2019/0175500 A1 | 6/2019 | Bellinger |
| 2019/0254966 A1 | 8/2019 | Bellinger |
| 2019/0262265 A1 | 8/2019 | Bellinger |
| 2019/0365645 A1 | 12/2019 | Traverso et al. |
| 2019/0365646 A1 | 12/2019 | Menachem et al. |
| 2019/0366064 A1 | 12/2019 | Traverso et al. |
| 2020/0030589 A1 | 1/2020 | Menachem et al. |
| 2020/0085736 A1 | 3/2020 | Bellinger et al. |
| 2020/0085737 A1 | 3/2020 | Bellinger et al. |
| 2020/0146979 A1 | 5/2020 | Kanasty |
| 2020/0230244 A1 | 7/2020 | Traverso et al. |
| 2020/0376242 A1 | 12/2020 | Menachem et al. |
| 2020/0405635 A1 | 12/2020 | Menachem et al. |

FOREIGN PATENT DOCUMENTS

| | | |
|---|---|---|
| CA | 2951884 A1 | 12/2015 |
| CN | 1049787 A | 3/1991 |
| CN | 1754898 A | 4/2006 |
| CN | 102245127 A | 11/2011 |
| CN | 103654903 A | 3/2014 |
| EP | 0202159 A2 | 11/1986 |
| EP | 0253554 A2 | 1/1988 |
| EP | 0253554 A3 | 7/1988 |
| EP | 0344939 A2 | 12/1989 |
| EP | 0388234 A1 | 9/1990 |
| EP | 0415671 A2 | 3/1991 |
| EP | 0202159 B1 | 7/1991 |
| EP | 0344939 B1 | 1/1993 |
| EP | 0820258 B1 | 10/2002 |
| EP | 1124534 B1 | 1/2004 |
| EP | 1687379 A1 | 8/2006 |
| EP | 1911518 A1 | 4/2008 |

(56) References Cited

FOREIGN PATENT DOCUMENTS

| | | |
|---|---|---|
| EP | 2324822 A2 | 5/2011 |
| EP | 2329810 A1 | 6/2011 |
| EP | 1528916 B1 | 12/2012 |
| JP | S58174312 A | 10/1983 |
| JP | S6323815 A | 8/1987 |
| JP | H0229268 A | 11/1989 |
| JP | H03044318 A | 2/1991 |
| JP | H03128934 A | 5/1991 |
| JP | H03163011 A | 7/1991 |
| JP | 2006518392 A | 8/2006 |
| JP | 2013500293 A | 1/2013 |
| JP | 2013530193 A | 7/2013 |
| JP | 2004325508 A | 11/2018 |
| RU | 2070029 C1 | 12/1996 |
| RU | 2242219 C2 | 12/2004 |
| WO | WO199738969 A1 | 10/1997 |
| WO | WO200025742 A1 | 5/2000 |
| WO | WO200137812 A2 | 5/2001 |
| WO | WO200137812 A3 | 2/2002 |
| WO | WO2003015745 A1 | 2/2003 |
| WO | WO2004010978 A1 | 2/2004 |
| WO | WO2004073690 A1 | 9/2004 |
| WO | WO2004112755 A1 | 12/2004 |
| WO | WO2005065660 A2 | 7/2005 |
| WO | WO2006072948 A2 | 7/2006 |
| WO | WO2006084164 A2 | 8/2006 |
| WO | WO2006072948 A3 | 11/2006 |
| WO | WO2006084164 A3 | 11/2006 |
| WO | WO2007027812 A2 | 3/2007 |
| WO | WO2007048223 A2 | 5/2007 |
| WO | WO2005065660 A3 | 6/2007 |
| WO | WO2007048223 A3 | 6/2007 |
| WO | WO2007083309 A2 | 7/2007 |
| WO | WO2007093999 A1 | 8/2007 |
| WO | WO2007083309 A3 | 9/2007 |
| WO | WO2008015162 A1 | 2/2008 |
| WO | WO2008039698 A1 | 4/2008 |
| WO | WO2008140651 A2 | 11/2008 |
| WO | WO2008140651 A3 | 1/2009 |
| WO | WO2007027812 A3 | 4/2009 |
| WO | WO2009132461 A1 | 11/2009 |
| WO | WO2009144558 A1 | 12/2009 |
| WO | 2010042879 A2 | 4/2010 |
| WO | WO2010035273 A2 | 4/2010 |
| WO | 2010042879 A3 | 6/2010 |
| WO | WO2010064100 A1 | 6/2010 |
| WO | WO2010064139 A2 | 6/2010 |
| WO | WO2010035273 A3 | 7/2010 |
| WO | WO2010064139 A3 | 9/2010 |
| WO | WO2010099466 A2 | 9/2010 |
| WO | WO2010099466 A3 | 1/2011 |
| WO | WO2011012369 A2 | 2/2011 |
| WO | WO2011032087 A2 | 3/2011 |
| WO | WO2011032087 A3 | 6/2011 |
| WO | WO2011012369 A3 | 9/2011 |
| WO | WO2011139796 A2 | 11/2011 |
| WO | 2012003968 A1 | 1/2012 |
| WO | WO2011139796 A3 | 3/2012 |
| WO | WO2012087658 A1 | 6/2012 |
| WO | WO2013049188 A1 | 4/2013 |
| WO | WO2014014348 A1 | 1/2014 |
| WO | WO2015083171 A1 | 6/2015 |
| WO | 2015187746 A1 | 12/2015 |
| WO | WO-2015191920 A1 * | 12/2015 ........... A61K 9/0065 |
| WO | WO2015191920 A1 | 12/2015 |
| WO | WO2015191922 A1 | 12/2015 |
| WO | WO2015191925 A1 | 12/2015 |
| WO | WO2017070612 A1 | 4/2017 |
| WO | WO2017100367 A1 | 6/2017 |
| WO | WO2017205844 A2 | 11/2017 |
| WO | WO2017205844 A3 | 1/2018 |
| WO | WO2018227147 A1 | 12/2018 |
| WO | WO2019060458 A1 | 3/2019 |
| WO | 2019111132 A1 | 6/2019 |
| WO | 2020102650 A2 | 5/2020 |
| WO | 2020102650 A3 | 8/2020 |

OTHER PUBLICATIONS

Agrawal, A. et al. (Jul. 2006). "Clinical Relevance of the Nutcracker Esophagus: Suggested Revision of Criteria for Diagnosis," J Clin Gastroenterol. 40(6):504-509.

Ajili, S.H. et al. (Jun. 2009, e-pub. Jan. 3, 2009). "Polyurethane/ Polycaprolactane Blend With Shape Memory Effect as a Proposed Material for Cardiovascular Implants," Acta Biomaterialia 5(5):1519-1530.

Alhnan, M.A. et al. (Aug. 2016; e-published on May 18, 2016). "Emergence of 3D Printed Dosage Forms: Opportunities and Challenges," Pharm. Res. 33(8):1817-1832, 38 pages.

Barbucci, R. et al. (1989). "Vinyl Polymers Containing Amido and Carboxyl Groups as Side Substituents, 2 a). Thermodynamic and Fourier-Transform Infrared Spectroscopic Studies for the Protonation of poly(N-Acryloylglycine) and the poly(N-N-acryoyl-6-aminocaproic acid)," Makromol. Chem. 190:2627-2638.

Belknap, R. et al. (Jan. 7, 2013). "Feasibility of an Ingestible Sensor-Based System for Monitoring Adherence to Tuberculosis Therapy," Plos One 8(1):e53373, pp. 1-5.

Bellinger, A.M. et al. (Nov. 16, 2016). "Oral, Ultra-Long-Lasting Drug Delivery: Application Toward Malaria Elimination Goals," Sci. Transl. Med. 8(365ra157):1-12., (with Supplementary Material), 21 pages.

Byrne, C. et al. (Mar. 2007; e-pub. Dec. 18, 2006). "The Ingestible Telemetric Body Core Temperature Sensor: A Review of Validity and Exercise Applications," Brit J Sport Med. 41(3):126-133.

Cargill, R. et al. (Aug. 1988). "Controlled Gastric Emptying. 1. Effects of Physical Properties on Gastric Residence Times of Nondisintegrating Geometric Shapes in Beagle Dogs," Pharm Res. 5(8):533-536.

Cargill, R. et al. (Jun. 1989). "Controlled Gastric Emptying. II. In Vitro Erosion and Gastric Residence Times of an Erodible Device in Beagle Dogs," Pharm Res. 6(6):506-509.

Choudhry, N.K. et al. (Dec. 1, 2011; e-pub. Nov. 14, 2011). "Full Coverage for Preventive Medications After Myocardial Infarction," N Engl J Med. 365:2088-2097.

Cirillo, G. et al. (Jan. 21, 2014). "Carbon Nanotubes Hybrid Hydrogels in Drug Delivery: A Perspective Review," BioMed Res Intl. 2014(Article ID 825017), 17 pages.

Cong, H.-P. et al. (2013, e-pub. Jul. 23, 2013). "Stretchable and Self-Healing Graphene Oxide-Polymer Composite Hydrogels: A Dual-Network Design," Chem Mater. 25:3357-3362.

Dash, S. et al. (May-Jun. 2010). "Kinetic Modeling on Drug Release From Controlled Drug Delivery Systems," Acta Poloniae Pharmaceutica 67(3):217-223.

Davies, G.C. et al. (Mar. 1993). "Release Characteristics, Ovarian Activity and Menstrual Bleeding Pattern with a Single Contraceptive Implant Releasing 3-Ketodesogestrel," Contraception 47(3):251-261.

Dumortier, G. et al. (Dec. 2006, e-pub. Nov. 11, 2006). "A Review of Poloxamer 407 Pharmaceutical and Pharmacological Characteristics," Pharmaceutical Research 23(12):2709-2728.

Dunn, D.L. et al. (2005). Wound Closure Manual Ethicon, Inc. A Johnson and Johnson company, 127 pages.

Edwards, D.A.W. (Nov. 1961). "Physiological Concepts of the Pylorus," Proceedings of the Royal Society of Medicine 54:930-933.

Ereqat, S. et al. (Sep. 2011). "MDR Tuberculosis and Non-Compliance With Therapy," Lancet Infect Dis. 11(9):662.

European Extended Search Report dated Jul. 5, 2019, for Application No. EP 16873798.9, filed on Apr. 26, 2018, 9 pages.

European Search Report dated May 27, 2019 for Application No. EP 16858392.0, filed on Apr. 26, 2018, 10 pages.

Evonik Industries AG, (Dec. 2012). Eudragit Technical Information Sheet, Eudragit L 100 and Eudragit S 100, Specification and Test Methods, 7 pages.

(56) References Cited

OTHER PUBLICATIONS

Extended European Search Report dated Feb. 23, 2018 for Application No. EP 15806483.2, filed Jun. 11, 2015, 8 pages.
Extended European Search Report dated Dec. 20, 2017 for Application No. EP 15806017.8, filed on Apr. 26. 2018, 10 pages.
Extended European Search Report dated Nov. 20, 2019 for Application No. EP 17803732.1, 9 pages.
Fallon, S.C. et al. (Apr. 2013). "The Surgical Management of Rapunzel Syndrome: A Case Series and Literature Review," J Pediatr Surg. 48(4):830-834.
Farra, R. et al. (Feb. 22, 2012; e-pub Feb. 16, 2012.). "First-In-Human Testing of a Wirelessly Controlled Drug Delivery Microchip," Sci Transl Med. 4(122):122ra21, 12 pages.
Fix, J.A. et al. (1993). "Controlled Gastric Emptying. III. Gastric Residence Time of a Nondisintegrating Geometric Shape in Human Volunteers," Pharm. Res. 10(7):1087-1089.
Fuhrmann, G. et al. (Jul. 2013). "Sustained Gastrointestinal Activity of Dendronized Polymer-Enzyme Conjugates," Nat Chem. 5:582-589.
Genco, A. et al. (2005). "Bioenterics Intragastric Balloon: The Italian Experience With 2,515 Patients," Obes Surg. 15:1161-1164.
Gordi, T. et al. (May 2008). "Pharmacokinetics of Gabapentin After A Single Day and at Steady State Following The Administration of Gastric-Retentive-Extended-Release And Immediate-Release Tablets: A Randomized, Open-Label, Multiple-Dose, Three-Way Crossover, Exploratory Study in Healthy Subjects," Clin Ther. 30(5):909-916.
Harrison, S.K. et al. (2006). "Comparison of Shear Modulus Test Methods," Virginia Tech. 8 pages.
Haslauer, C.M. et al. (Jul. 2015; e-published on Sep. 17, 2014). "Translating Textiles To Tissue Engineering: Creation And Evaluation Of Microporous, Biocompatible, Degradable Scaffolds Using Industry Relevant Manufacturing Approaches And Human Adipose Derived Stem Cells," J. Biomed. Mater. Res. B Appl. Biomater. 103(5):1050-1058, 22 pages.
Hiemke, C. et al. (Sep. 2011; e-published on Sep. 27, 2011). "AGNP Consensus Guidelines for Therapeutic Drug Monitoring in Psychiatry: Update 2011," Pharmacopsychiatry 44(6):195-235.
Huang, W.M. et al. (Jul.-Aug. 2010). "Shape Memory Materials," Materials Today 13(7-8):54-61.
Hwang, S.-J. et al. (1998). "Gastric Retentive Drug-Delivery Systems," Crit Rev Ther Drug Carrier Syst. 15(3):243-284.
International Preliminary Report on Patentability for PCT/US2015/035425 dated Dec. 15, 2016, filed Jun. 11, 2015, 6 pages.
International Preliminary Report on Patentability for PCT/US2015/035429 dated Dec. 15, 2016, filed Jun. 11, 2015, 8 pages.
International Preliminary Report on Patentability dated Dec. 10, 2019 for PCT Application No. PCT/US2018/036743 filed on Jun. 8, 2018, 16 pages.
International Preliminary Report on Patentability dated Apr. 11, 2019 for PCT Application No. PCT/US2017/054608 filed on Sep. 29, 2017, 16 pages.
International Preliminary Report on Patentability dated Dec. 6, 2018 for PCT Application No. PCT/US2017/034856, filed on May 26, 2017, 11 pages.
International Preliminary Report on Patentability dated Dec. 22, 2016 for PCT Application No. PCT/US2015/035423 filed on Jun. 11, 2015, 11 pages.
International Preliminary Report on Patentability dated Jun. 21, 2018 for PCT Application No. PCT/US2016/065453 filed on Dec. 7, 2016, 11 pages.
International Preliminary Report on Patentability dated May 3, 2018 for PCT Application No. PCT/US2016/058309 filed on Oct. 21, 2016, 6 pages.
International Preliminary Report on Patentability dated Nov. 16, 2017 for PCT Application No. PCT/US2016/030020 filed on Apr. 29, 2016, 8 pages.
International Search Report and Written Opinion for PCT/US2015/035425 dated Sep. 15, 2015, filed Jun. 11, 2015, 8 pages.
International Search Report and Written Opinion for PCT/US2015/035429 dated Sep. 15, 2015, filed Jun. 11, 2015, 9 pages.
International Search Report and Written Opinion dated Dec. 14, 2017 for PCT Application No. PCT/US2017/054608 filed on Sep. 29, 2017, 18 pages.
International Search Report and Written Opinion dated Dec. 29, 2016 for PCT Application No. PCT/US2016/058309 filed on Oct. 21, 2016, 8 pages.
International Search Report and Written Opinion dated Feb. 28, 2017 for PCT Application No. PCT/US2016/065453 filed on Dec. 7, 2016, 14 pages.
International Search Report and Written Opinion dated Jul. 21, 2016 for PCT Application No. PCT/US2016/030020 filed on Apr. 29, 2016, 10 pages.
International Search Report and Written Opinion dated Nov. 13, 2017 for PCT Application No. PCT/US2017/034856, filed on May 26, 2017, 15 pages.
International Search Report and Written Opinion dated Sep. 10, 2018 for PCT Application No. PCT/US2018/036743 filed on Jun. 8, 2018, 26 pages.
International Search Report and Written Opinion dated Sep. 15, 2015 for PCT Application No. PCT/US2015/035423 filed on Jun. 11, 2015, 13 pages.
Invitation to Pay Additional Fees and, Where Applicable, Protest Fee, dated Sep. 5, 2017, for PCT Application No. PCT/US2017/034856, filed on May 26, 2017, 3 pages.
Jantratid, E. et al. (Jul. 2008; e-pub. Apr. 11, 2008). "Dissolution Media Simulating Conditions in the Proximal Human Gastrointestinal Tract: An Update," Pharm. Res. 25(7):1663-1676.
Javed, I. et al. (2014). "Drug Release Optimization From Microparticles of Poly(ε-caprolactone) and Hydroxypropyl Methylcellulose Polymeric Blends: Formulation and Characterization," J. Drug Del. Sci. Tech. 24(6);607-612.
Kanis, L.A. et al. (2014). "Cellulose Acetate Butyrate/Poly(caprolactonetriol) Blends: Miscibility, Mechanical Properties, and in vivo Inflammatory Response," J. of Biomaterials Applications 29(5):654-661.
Kao, E.C. et al. (Jan. 1996). "Preparation of Glass Ionomer Cement Using N-acryloyl Substituted Amino Acid Monomers-Evaluationof Physical Properties," Dent Mater. 12:44-51.
Karim, Q.A. et al. (Sep. 3, 2010, e-pub. Jul. 19, 2010). "Effectiveness And Safety Of Tenofovir Gel, An Antiretroviral Microbicide, For The Prevention Of HIV Infection In Women," Science 329(5996):1168-1174, 19 pages.
Kethu, S.R. et al. (2012). "Endoluminal Bariatric Techniques," Gastrointestinal Endoscopy 76(1):1-7.
Khaled, S.A. et al. (Jan. 30, 2014). "Desktop 3D Printing of Controlled Release Pharmaceutical Bilayer Tablets," International Journal of Pharmaceutics 461(1-2):105-111, 17 pages.
Khanna, S.C. et al. (Sep. 1969). "Epoxy Resin Beads as a Pharmaceutical Dosage Form. I.: Method of Preparation," Journal of Pharmaceutical Sciences 58(9):1114-1117.
Kim, B.K. et al. (1996). "Polyurethanes Having Shape Memory Effects," Polymer 37(26):5781-5793.
Kim, Y.J. et al. (Dec. 24, 2013). "Biologically Derived Melanin Electrodes In Aqueous Sodium-Ion Energy Storage Devices," P Natl Acad Sci USA. 110(52): 20912-20917.
Lam, P.L. et al. (2014). "Advanced Progress of Microencapsulation Technologies: In Vivo and In Vitro Models for Studying Oral and Transdermal Drug Deliveries," J. Control Release 178:25-45.
Laulicht, B. et al. (Feb. 8, 2011). "Localization of Magnetic Pills," Proc Natl Acad Sci. 108(6):2252-2257.
Li, L.C. et al. (Oct. 16, 2002). "Polyanhydride Implant for Antibiotic Delivery—From the Bench to the Clinic," Adv Drug Deliv Rev. 54(7):963-986.
Lipton, S.A. (Jan. 2004). "Failures and Successes of NMDA Receptor Antagonists: Molecular Basis For the Use of Open-Channel Blockers Like Memantine in the Treatment of Acute and Chronic Neurologic Insults," NeuroRx: The Journal of the American Society for experimental Neuro Therapeutics 1(1):101-110.
Liu, Y. et al. (2009; e-pub. Aug. 29, 2008). "Review of Electro-Active Shape-Memory Polymer Composite," Compos Sci and Technol. 69(13):2064-2068.

(56) References Cited

OTHER PUBLICATIONS

López-Pousa, S. et al. (Sep. 2012). "Consumption of Pharmaceuticals in Primary Non-Alzheimer's Degenerative Dementias: A Cross-Sectional Study By the Registry of Dementias of Girona (ReDeGi)," Drugs Aging 29(9):733-740, 22 pages.

Marrazzo, J.M. et al. (Feb. 5, 2015). "Tenofovir-Based Preexposure Prophylaxis for HIV Infection Among African Women," N Engl J Med. 372(6):509-518.

Meng, Q. et al. (2009). "A Review of Shape Memory Polymer Composites and Blends," Composites Part A: Applied Science and Manufacturing 40(11):1661-1672.

Miao, L. et al. (2015). "Exploring the Tumor Microenvironment With Nanoparticles," Cancer Treat Res. 166:193-226, 36 pages.

Mintchev, M.P. et al. (Feb. 2010; e-pub Dec. 11, 2009). "Pilot Study of Temporary Controllable Gastric Pseudobezoars for Dynamic Non-Invasive Gastric Volume Reduction," Physiol Meas. 31(2):131-144.

Moes, A.J. (Jan. 1993). "Gastroretentive Dosage Forms," Crit Rev Ther Drug Carrier Syst. 10(2):143-195.

Mohr, R. et al. (Mar. 7, 2006; e-pub Feb. 28, 2006.). "Initiation of Shape-Memory Effect by Inductive Heating of Magnetic Nanoparticles in Thermoplastic Polymers," Proc Natl Acad Sci USA. 103(10):3540-3545.

Muthu, M.S. et al. (2008). "Studies on Biodegradable Polymeric Nanoparticles of Risperidone: in vitro and in vivo Evaluation," Nanomedicine 3(3):305-319.

Neto-Ferreira, R. et al. (2013). "Pleiotropic Effects of Rosuvastatin on the Glucose Metabolism and the Subcutaneous and Visceral Adipose Tissue Behavior in C57Bl/6 Mice," Diabetology Metabol Synd. 5:32, 10 pages.

Olson, A.J. et al. (Dec. 26, 2007; e-pub Dec. 18, 2007). "Chemical Mimicry of Viral Capsid Self-Assembly," Proc Natl Acad Sci USA 104(52):20731-20736.

Osterberg, L. et al. (Aug. 4, 2005). "Adherence to Medication," N Engl J Med. 353(5):487-497.

Phadke, A. et al. (Mar. 20, 2012; e-pub Mar. 5, 2012). "Rapid Self-Healing Hydrogels," Proc Natl Acad Sci USA 109(12):4383-4388.

Phillips, M.R. et al. (Jul. 1998). "Gastric Trichobezoar: Case Report and Literature Review," Mayo Clin Proc. 73(7):653-656.

Pittenger, C. (Jun. 2015, e-published on Jun. 11, 2015). "Glutamate Modulators in the Treatment of Obsessive-Compulsive Disorder," Psychiatr. Ann. 45(6):308-315, 13 pages.

Puso, M. A. et al. (Jan. 1, 2006). "A Stabilized Nodally Integrated Tetrahedral," International Journal for Numerical Methods in Engineering 67(6):841-867.

Rammes, G. et al. (Mar. 2008). "Pharmacodynamics of Memantine: An Update," Curr. Neuropharmacol. 6(1):55-78.

Ren, S. et al. (2009). "Noncovalently Connected Micelles Based on a β-cyclodextrin-Contaiing Polymer and Adamantane End-Capped Poly(e-ecaprolactone) via Host-Guest Interactions," J Polym Sci. 47:4267-4278.

Richter, J.E. et al. (Jun. 1987). "Esophageal Manometry in 95 Healthy Adult Volunteers. Variability of Pressures With Age and Frequency of "Abnormal" Contractions," Dig Dis Sci. 32(6):583-592.

Salessiotis, N. (Sep. 1972). "Measurement of the Diameter of the Pylorus in Man: Part I. Experimental Project for Clinical Application," The Amer J of Surgery. 124:331-333.

Salunke, D.M. et al. (Sep. 12, 1986). "Self-Assembly of Purified Polyomavirus Capsid Protein VP1," Cell 46(6):895-904, 10 pages.

Singer, S.J. et al. (Feb. 18, 1972). "The Fluid Mosaic Model of the Structure of Cell Membranes," Science 175(4023):720-731.

Singh, B.N. et al. (Feb. 3, 2000). "Floating Drug Delivery Systems: An Approach to Oral Controlled Drug Delivery Via Gastric Retention," J Control Release 63(3):235-259.

Singh, P. et al. (2015, e-pub, Dec. 18, 2014). "Synthesis and Characterization of Nano Micelles of poly(N-acrylamidohexanoic acid)-b-poly(N-vinylcaprolactam) Via RAFT Process: Solubilizing and Releasing of Hydrophobic Molecules," Polymer. 57:51-61.

Six-Pentagons (Dec. 23, 2017). "Six-Pentagons Polylink," retreived from http://makingmathvisible.com/polylinks/polylinks-3.html, lasted visited Dec. 23, 2017, 4 pages.

Szakács, R. et al. (2012). "The "Blue" Side of Glutamatergic Neurotransmission: NMDA Receptor Antagonists as Possible Novel Therapeutics for Major Depression," Neuropsychopharmacol. Hung. 14(1):29-40.

Tao, H. et al. (Feb. 21, 2012). "Silk-Based Conformal, Adhesive, Edible Food Sensors," Adv Mater. 24(8):1067-1072.

Timmer, C.J. et al. (Sep. 2000). "Pharmacokinetics of Etonogestrel and Ethinylestradiol Released From a Combined Contraceptive Vaginal Ring," Clin Pharmacokinet. 39(3):233-242.

Traverso, G. et al. (Mar. 26, 2015). "Special Delivery for the Gut," Nature. 519:S19.

Uhrich, K.E. et al. (1999, e-pub. Oct. 26, 1999). "Polyermic Systems for Controlled Drug Relase," Chem. Rev. 99:3181-3198.

Ursan, I.D. et al. (Mar.-Apr. 2013). "Three-Dimensional Drug Printing: A Structured Review," J. Am. Pharm. Assoc. 53(2):136-144.

US Dept Health "Q3C—Tables and List Guidance for Industy," (2017). Retrieved from www.fda.gov/downloads/drugs/guidances/ucm073395.pdf, last visited Jun. 2017, 10 pages.

US Dept. Health "Guidance for Industry: Size, Shape, and Other Physical Attributes of Generic Tables and Capsules," (2013). Retrieved from www:v.regulations.gov/#!documentDetail;D=FDA-2013-N-1434-0002, last visited Dec. 2013, 11 pages.

Whitesides, G.M. et al. (Mar. 29, 2002). "Self-Assembly at all Scales," Science 295(5564):2418-2421.

Wilber, A.W. et al. (Nov. 7, 2009). "Self-Assembly of Monodisperse Clusters: Dependence on Target Geometry," J Chem Phys. 131(17):175101, 14 pages.

Wilber, A.W. et al. (Nov. 7, 2009; e-pub. Nov. 2, 2009). "Monodisperse Self-Assembly in a Model With Protein-Like Interactions," J Chem Phys. 131(17):175102, 11 pages.

Won, Y.W. et al. (Dec. 2014). "Oligopeptide Complex for Targeted Non-Viral Gene Delivery to Adipocytes," Nat Mater.13:1157-1164.

Yerragunta, B. et al. (Jan.-Mar. 2015). "Development of a Novel 3-Month Drug Releasing Risperidone Microspheres," J. Pharm Bioall Sci. 7(1):37-44.

Yu, D.G. et al. (Sep. 2008). "Three-Dimensional Printing in Pharmaceutics: Promises and Problems," J. Pharm. Sci. 97(9):3666-3690.

Zhang, S. et al. (Oct. 2015; e-pub. Jul. 27, 2015). "A Ph-Responsive Supramolecular Polymer Gel as an Enteric Elastomer for Use in Gastric Devices," Nature Materials 14(10):1065-1071, 19 pages.

Zhang, X. et al. (2013; e-pub Oct. 15, 2012). "Biodegradable Shape Memory Nanocomposites With Thermal and Magnetic Field Responsiveness," J Biomater Sci Polym Ed. 24(9):1057-1070.

Zu, Y. et al. (2008, e-pub. Sep. 26, 2008). "Effect of Neutralization of poly(methacrylic acid-co-ethyl acrylate) on Drug Release from Enteric-Coated Pellets Upon Accelerated Storage," Drug Dev. Ind. Pharm. 33(4):457-473.

Extended European Search Report dated Jun. 4, 2021 for Application No. EP 18813515.6, 8 pages.

Murphy, C.S. et al. (Oct. 2009). "Gastro-Retentive Drug Delivery Systems: Current Developments in Novel System Design and Evaluation," Curr. Drug Deliv. 6(5):451-460.

Welding Techniques for Thermoplastics (2021). retrieved from the Internet: URL:https://www.twi-global.com/technical-knowledge/job-knowledge/welding-techniques-forthermoplastics-055 (http://web.archive.org/web/20150416235739/http://www.twiglobal.com/technical-knowledge/job-knowledge/welding-techniques-for-thermoplastics-055/, last visited Mar. 17, 2021, 8 pages.

Yang X, et al. (May 14, 2014), e-pub. May 5, 2014) "Triple Shape Memory Effect of Star-Shaped Polyurethane," ACS Appl Mater Interfaces 6(9):6545-6554.

Chourasia, M.K. et al. (2003). "Pharmaceutical Approaches To Colon Targeted Drug Delivery Systems," J. Pharm. Pharmaceut Sci. 6(1):33-66.

Nakamichi, K. (2004). "The Preparation of Enteric Solid Dispersions With Hydroxypropylmethylcellulose Acetate Succinate Using a Twin-Screw Extruder," J. Drug Del. Sci. Tech. 3(14):193-198.

(56) References Cited

OTHER PUBLICATIONS

Woodruff, M.A. et al. (Apr. 2010, e-pub. Apr. 7, 2010). "The Return of a Forgotten Polymer—Polycaprolactone in the 21st Century," Progress in Polymer Science 35:1217-1256.

* cited by examiner

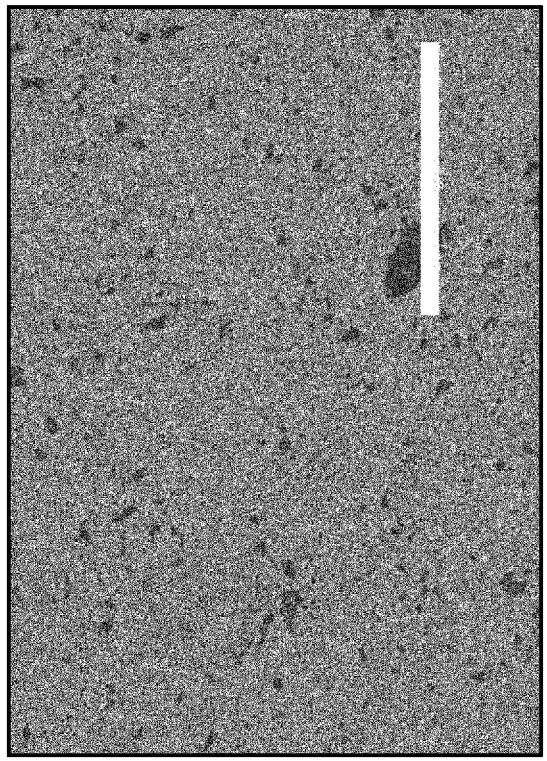
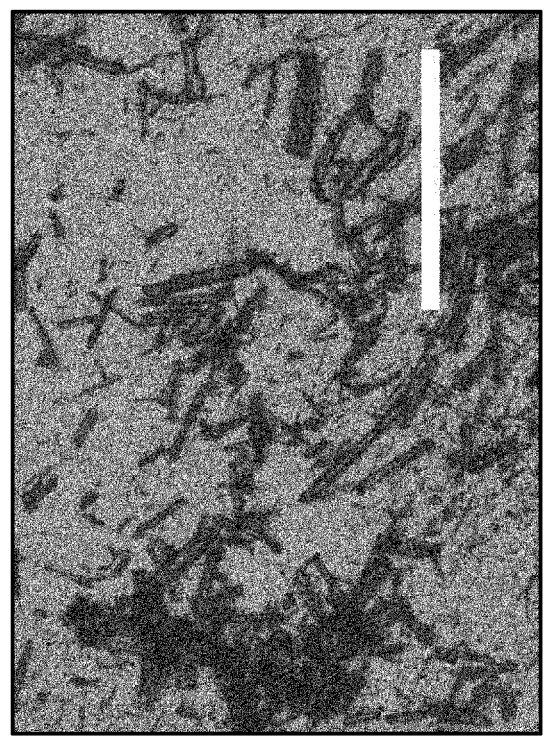
FIG. 34

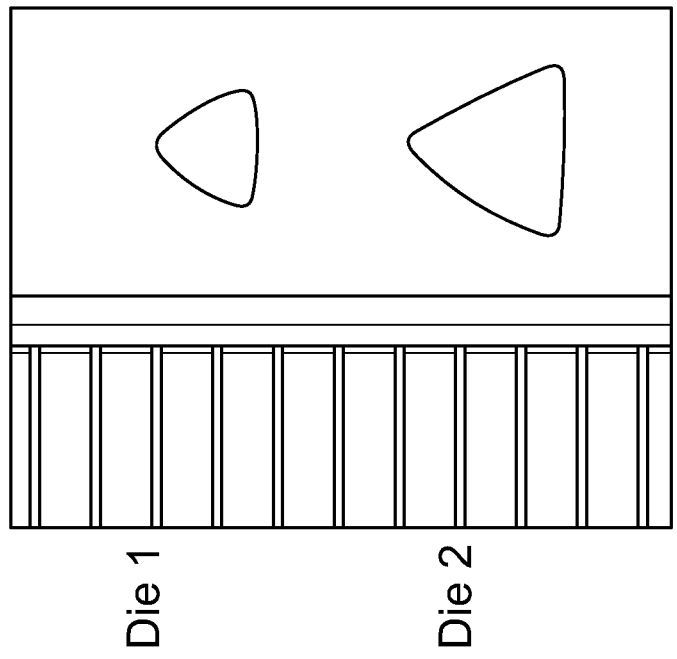
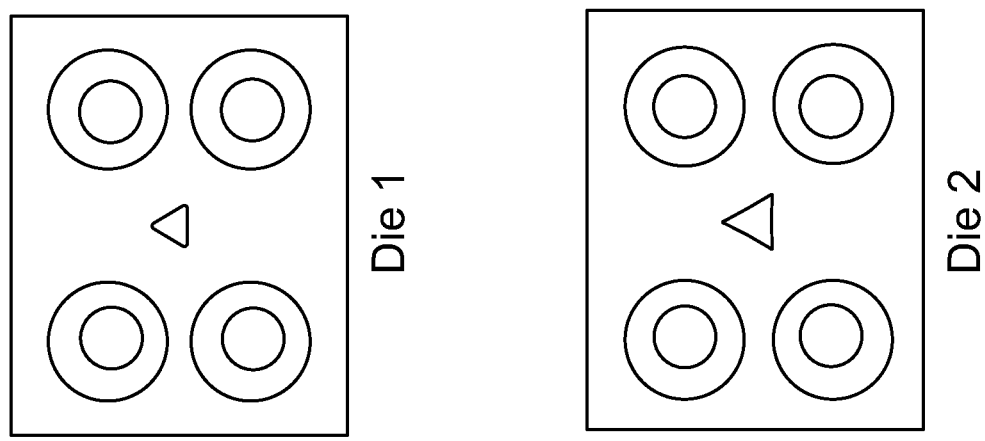
FIG. 36

| Hound # | Weight (kg) | Deployed correctly | ~24 hr post-admin | ~48 hr post-admin | ~72 hr post-admin | ~96 hr post-admin | |
|---|---|---|---|---|---|---|---|
| 1 (938) | 25.2 | Yes Intact | Intact in stomach | Intact in stomach | Intact in stomach | Intact in stomach | (table continues in FIG. 38B) |
| 2 (357) | 21.5 | Yes Intact | Intact in stomach | Intact in stomach | Intact in stomach | Intact in intestine | |
| 3 (420) | 20.7 | Yes 1 Arm Lost | In stomach 2 Arms Lost | In stomach 3 Arms Lost | In stomach 4 Arms Lost | In stomach 4 Arms Lost | |
| 4 (438) | 19.2 | Yes 1 Arm Lost | In stomach 1 Arm Lost | In stomach 1 Arm Lost | In stomach 1 Arm Lost | In stomach 1 Arm Lost | |

FIG. 38A (table continued from FIG. 38A)

| Hound # | 5 d post-admin | 6 d post-admin | 7 d post-admin | 9 d post-admin | 11 d post-admin | 14 d post-admin |
|---|---|---|---|---|---|---|
| 1 (938) | Intact in stomach | Intact in stomach | Intact in stomach | In stomach 2 Arms Lost | In stomach 3 Arms Lost | Passed |
| 2 (357) | Passed | | | | | |
| 3 (420) | In intestine 6 Arms Lost | Passed | | | | |
| 4 (438) | In stomach 6 Arms Lost | In stomach 6 Arms Lost | 1 in stomach 3 Arms lost, 1 in intestine 3 Arms Lost | 1 in stomach; 3 Arms Lost | Passed | |

FIG. 38B

| Coating Identifier | Coating solution composition |
|---|---|
| C5 | 1g Eudragit RS, 3 mL Dichloromethane |
| C8 | 1g PCL 55K, 6 mL Dichloromethane |
| C31 | 1.5 g Cellulose Acetate, 15mL Acetone |
| C25 | 1g Ethyl Cellulose, 15mL Acetone |

| Solvent | Maximum PCL concentration observed | Dissolution conditions | Coating appearance | Coating performance |
|---|---|---|---|---|
| Dichloromethane | Up to 25% wt/vol | Dissolution of PCL in minutes at room temperature. | Acceptable at low PCL concentrations, Uneven at >10% wt/vol | Able to modulate release profile |
| Ethyl acetate | Up to 15% wt/vol | Requires heating to 40°C for several hours for dissolution. Precipitates slowly after cooling to room temperature | Acceptable | Able to modulate release profile |
| Acetone | Up to 10% wt/vol | Requires heating to 40°C for several hours for dissolution. Precipitates slowly after cooling to room temperature | Appears uneven, possibly poorly adhered to underlying matrix | No reliable control over release profile |

FIG. 47

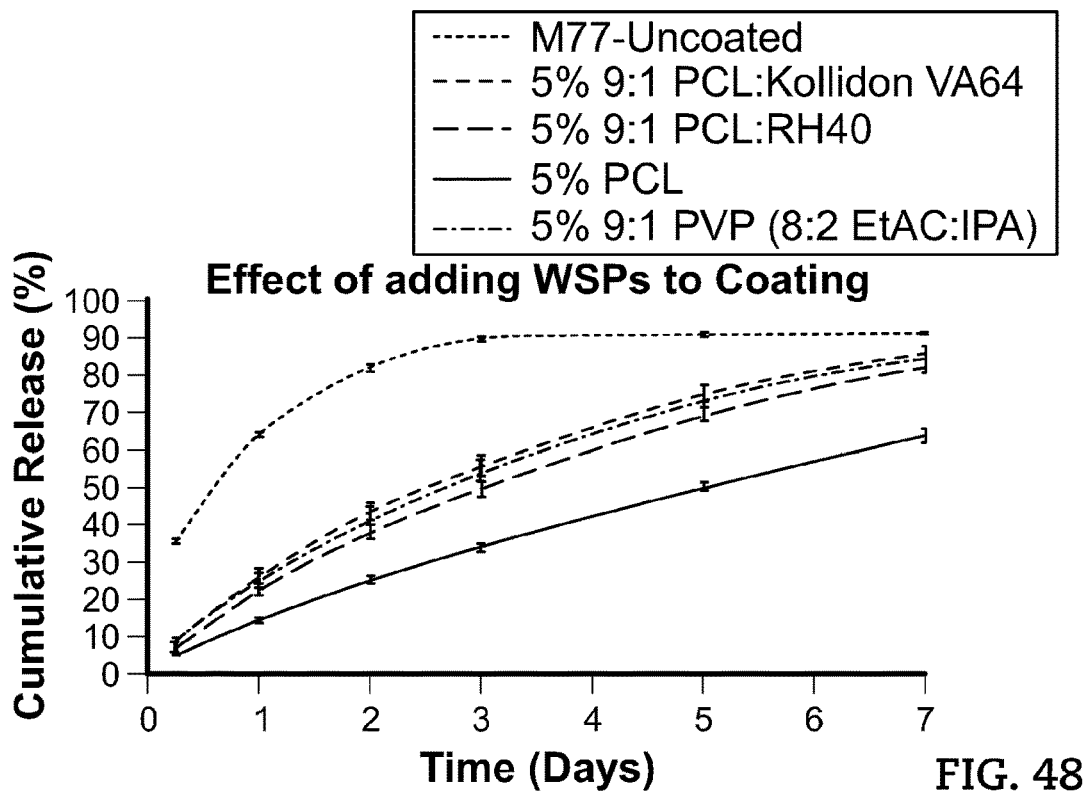

FIG. 48

Effect of WSP Level on Coating (Dip Coating)

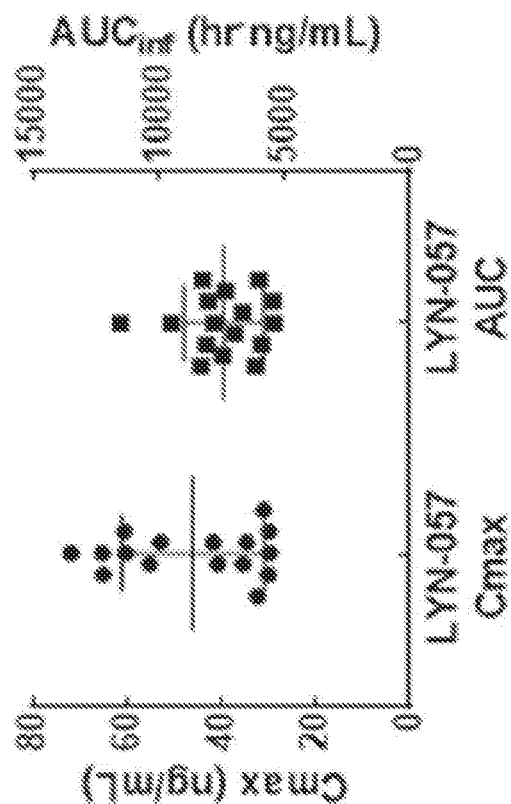
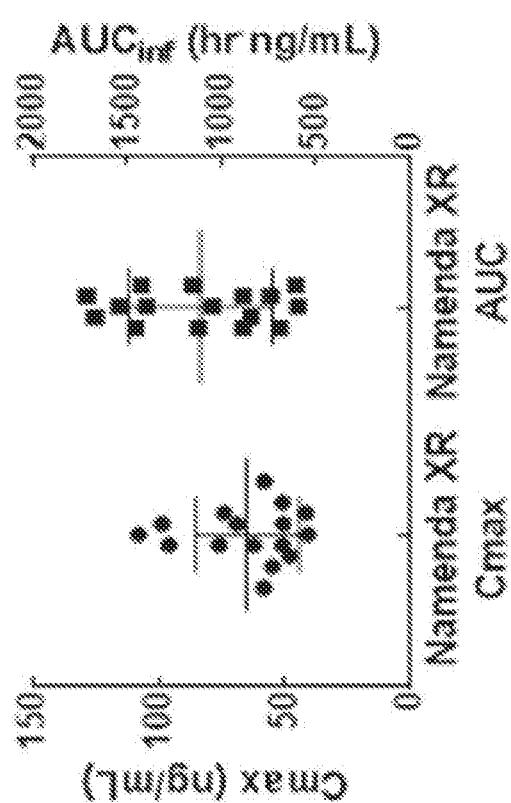
FIG. 59

GASTRIC RESIDENCE SYSTEMS FOR SUSTAINED DELIVERY OF ADAMANTANE-CLASS DRUGS

CROSS REFERENCE TO RELATED APPLICATIONS

This application is a national stage application under 35 U.S.C. § 371 of International Application No. PCT/US2017/054608 having an International Filing Date of Sep. 29, 2017, and claims priority benefit of U.S. Provisional Patent Application No. 62/402,947 filed Sep. 30, 2016, U.S. Provisional Patent Application No. 62/490,466 filed Apr. 26, 2017, and U.S. Provisional Patent Application No. 62/517,718 filed Jun. 9, 2017. The entire contents of those applications are hereby incorporated by reference herein.

FIELD OF THE INVENTION

The invention relates to systems which remain in the stomach for extended periods for sustained release of adamantane-class pharmaceuticals, and methods of use thereof.

BACKGROUND OF THE INVENTION

The drug memantine is used to treat Alzheimer's Disease, and is typically administered once or twice daily. In view of the cognitive decline associated with Alzheimer's Disease, and the heavy burden on caregivers for patients with Alzheimer's Disease, there is a need for a dosage form which can be administered less frequently, such as once every three days, once weekly, etc., in order to reduce the risk of a missed dose.

Gastric residence systems are delivery systems for therapeutic agents which remain in the stomach for periods of time, such as days, or one or two weeks, during which time drugs or other agents can elute from the systems for absorption in the gastrointestinal tract. Examples of such systems are described in International Patent Application Nos. WO 2015/191920 and WO 2015/191925, and in United States Patent Application Nos. 62/245,789, 62/264,795, 62/245,797, 62/264,799, 62/264,806, 62/264,811, 62/342,798, and 62/342,815. Gastric residence systems can obviate the need to take medication several times daily, and can be of great utility for patients with cognitive disabilities and the caretakers of those patients.

Gastric residence systems are designed to be administered to the stomach of a patient, typically in a capsule which is swallowed or introduced into the stomach by an alternate method of administration (for example, feeding tube or gastric tube). Upon dissolution of the capsule in the stomach, the systems expand or unfold to a size which remains in the stomach and resists passage through the pyloric sphincter over the desired residence period (such as three days, seven days, or two weeks). This requires mechanical stability over the desired residence period. Portions of the gastric residence system can comprise a carrier material blended with one or more agents or drugs. Upon exposure of the carrier material/agent(s) to the gastric environment, the system releases the agent or agents over the period of residence in the stomach. The agents are preferably released with minimal burst release. The carrier material for the agent or agents must be carefully selected in order to provide the desired release profile. While resident in the stomach, the system should not interfere with the normal passage of food or other gastric contents. The system should pass out of the stomach at the end of the desired residence time, and be readily eliminated from the patient. If the system prematurely passes from the stomach into the small intestine, it should not cause intestinal obstruction, and again should be readily eliminated from the patient. These characteristics require careful selection of the various materials from which the system is constructed, and the dimensions and arrangement of the system.

The current invention describes advancements in design and manufacture of gastric residence systems for administration of the drug memantine, and similar drugs. The gastric residence systems also provide for a more constant release of drug over time than the release provided by immediate-release formulations, which reduces fluctuations in serum plasma level of the drug.

SUMMARY OF THE INVENTION

The invention provides gastric residence systems for sustained release of adamantane-class drugs, including memantine, or sustained release of a pharmaceutically acceptable salt of adamantane-class drugs, such as a pharmaceutically acceptable salt of memantine.

In any embodiment disclosed herein, a reference to an agent or a salt thereof can refer to an adamantane-class drug or pharmaceutically acceptable salt thereof, such as memantine; amantadine; adapromine; nitromemantine; rimantadine; bromantane; tromantadine; or neramexane; or a pharmaceutically acceptable salt of memantine, amantadine, adapromine, nitromemantine, rimantadine, bromantane, tromantadine, or neramexane.

In any of the embodiments of the gastric residence systems described herein, the gastric residence system can comprise at least one segment which has or is covered by a release rate-controlling polymer film.

In any of the embodiments described herein, the invention provides a gastric residence system which provides an extended release drug dosage form. The gastric residence system can comprise a therapeutically effective amount of an adamantane-class drug or a pharmaceutically acceptable salt thereof, such as memantine or a pharmaceutically acceptable salt of memantine, and a component adapted to provide extended release of the drug or salt thereof in an aqueous environment. The gastric residence system can have a dissolution profile characterized by about 10% to 20% dissolution of the initial amount of drug present in the system during an initial 24 hour period in the aqueous environment. The gastric residence system can have a dissolution profile characterized by about 20% to 40% dissolution of the initial amount of drug present in the system during an initial 48 hour period in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per day in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per day during the first two days in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per day during the first three days in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per day during the first four days in the aqueous environment.

In any of the embodiments described herein, the gastric residence system can elute about 20 mg to about 36 mg of the adamantane-class drug, pharmaceutically acceptable salt of an adamantane-class drug, memantine, or pharmaceutically acceptable salt of memantine per 24-hour period during the period between 24 hours and 72 hours in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per 24-hour period during the period between 24 hours and 96 hours in the aqueous environment. The gastric residence system can elute about 20 mg to about 36 mg of the adamantane-class drug, pharmaceutically acceptable salt of an adamantane-class drug, memantine, or pharmaceutically acceptable salt of memantine per 24-hour period during the period between 48 hours and 96 hours in the aqueous environment. The aqueous environment can be the stomach of a human patient. The aqueous environment can be the stomach of a mammal. The aqueous environment can be the stomach of a pig, dog, or cat. The aqueous environment can be simulated gastric fluid. The aqueous environment can be fasted-state simulated gastric fluid. The aqueous environment can be fed-state simulated gastric fluid. The aqueous environment can be 0.1N HCl.

In any of the embodiments described herein, the gastric residence systems as disclosed herein can have a gastric residence period of about four days, or of at least about four days, when administered to a human patient. In some embodiments, the gastric residence systems as disclosed herein can have a gastric residence period of about four days to about eight days when administered to a human patient. In some embodiments, the gastric residence systems as disclosed herein can have a gastric residence period of about four days to about ten days when administered to a human patient. In some embodiments, the gastric residence systems as disclosed herein can have a gastric residence period of about seven days, or at least about seven days, when administered to a human patient. In some embodiments, the gastric residence systems as disclosed herein can have a gastric residence period of about seven days to about ten days when administered to a human patient.

In any of the embodiments of the gastric residence systems described herein, the release of the adamantane-class drug or pharmaceutically-acceptable salt thereof increases by no more than about 40% in 40% ethanol/60% 0.1N HCl in water versus the release over the same period of time in 0.1N HCl, or by no more than about 40% in 40% ethanol/60% simulated gastric fluid versus the release over the same period of time in simulated gastric fluid, or by no more than about 40% in 40% ethanol/60% fasted-state simulated gastric fluid versus the release over the same period of time in fasted-state simulated gastric fluid, or by no more than about 40% in 40% ethanol/60% fed-state simulated gastric fluid versus the release over the same period of time in fed-state simulated gastric fluid. The period of time can be about 15 minutes, about 30 minutes, about 45 minutes, about 60 minutes, about 90 minutes, or about 120 minutes.

Any of the gastric residence systems as disclosed herein can comprise an adamantane-class drug or a pharmaceutically acceptable salt thereof, blended with a component adapted to provide extended release of the drug or salt thereof. The component adapted to provide extended release of the drug or salt thereof can comprise a carrier polymer and at least one additional excipient.

In some embodiments, the invention provides gastric residence systems which comprise a therapeutically effective amount of an adamantane-class drug or a pharmaceutically acceptable salt thereof, where the gastric residence system is characterized by one or more of the following characteristics: a) the gastric residence system provides a human in vivo plasma profile which is characterized by a drug $t_{max}$ of about 25 hours±15 hours after administration of a single gastric residence system to a human patient; b) the gastric residence system provides a human in vivo plasma profile which is characterized by a $C_{max}/D$ of about 1 ng/mL/mg±0.5 ng/mL/mg after administration of a single gastric residence system to a human patient, where D is the total mass in milligrams of the drug in the gastric residence system; c) the gastric residence system provides a human in vivo plasma profile which is characterized by a $C_{max}/D'$ of about 1 ng/mL/mg±0.5 ng/mL/mg after administration of a single gastric residence system to a human patient, where D' is the total mass in milligrams of the drug released from the gastric residence system during its residence period in the stomach; d) the gastric residence system provides a human in vivo plasma profile which is characterized by a drug AUC/D for 0 to 72 hours of about 55 hours-ng/mL/mg±25 hours-ng/mL/mg after administration of a single gastric residence system to a human patient; or e) the gastric residence system provides a human in vivo plasma profile which is characterized by a drug AUC/D' for 0 to 72 hours of about 55 hours-ng/mL/mg±25 hours-ng/mL/mg after administration of a single gastric residence system to a human patient.

In some embodiments, the invention provides gastric residence systems comprising a therapeutically effective amount of an adamantane-class drug or a pharmaceutically acceptable salt thereof, wherein the gastric residence system provides a human in vivo plasma profile at steady state which is characterized by a fluctuation F of about 40%±35%.

In any of the embodiments disclosed herein, the adamantane-class drug or a pharmaceutically acceptable salt thereof can comprise memantine or can comprise a pharmaceutically acceptable salt of memantine, such as about 25 mg to about 40 mg of memantine or a pharmaceutically acceptable salt thereof, such as about 28 mg of memantine or a pharmaceutically acceptable salt thereof.

In some embodiments, the invention provides gastric residence systems which comprise memantine or a pharmaceutically acceptable salt thereof, wherein the gastric residence system is characterized by one or more of the following characteristics: a) the gastric residence system provides a human in vivo plasma profile which is characterized by a drug $t_{max}$ of about 25 hours±15 hours after administration of a single gastric residence system to a human patient; b) the gastric residence system provides a human in vivo plasma profile which is characterized by a $C_{max}/D$ of about 1 ng/mL/mg±0.5 ng/mL/mg after administration of a single gastric residence system to a human patient, where D is the total mass in milligrams of the drug in the gastric residence system; c) the gastric residence system provides a human in vivo plasma profile which is characterized by a $C_{max}/D'$ of about 1 ng/mL/mg±0.5 ng/mL/mg after administration of a single gastric residence system to a human patient, where D' is the total mass in milligrams of the drug released from the gastric residence system during its residence period in the stomach; d) the gastric residence system provides a human in vivo plasma profile which is characterized by a drug AUC/D for 0 to 72 hours of about 55 hours-ng/mL/mg±25 hours-ng/mL/mg after administration of a single gastric residence system to a human patient; e) the gastric residence system provides a human in vivo plasma profile which is characterized by a drug AUC/D' for 0 to 72 hours of about 55 hours-ng/mL/mg±25 hours-ng/mL/mg after administration of a single gastric residence system to a human patient; f) the gastric residence system provides a human in vivo plasma profile which is characterized by a $C_{max}$ of about 30 ng/mL±15 ng/mL after administration of a single gastric residence system to a human patient; and g) the gastric residence system provides a human in vivo plasma profile which is characterized by a drug AUC for 0 to 72 hours of about 1500 hours-ng/mL±750 hours-ng/mL after administration of a single gastric residence system to a human patient. In some embodiments, the invention provides gastric residence systems which comprise memantine or a pharmaceutically acceptable salt thereof, wherein the gastric residence system is characterized by one or more of the following characteristics: a) the gastric residence system provides a human in vivo plasma profile at steady state having a $C_{max,ss}$ of about 140 ng/mL±50 ng/mL; b) the gastric residence system provides a human in vivo plasma profile at steady state having a $C_{min,ss}$ of about 90 ng/mL±40 ng/mL, with the caveat that $C_{min,ss}$ is less than $C_{max,ss}$; c) the gastric residence system provides a human in vivo plasma profile at steady state having a $C_{ave,ss}$ of about 115 ng/mL±15 ng/mL, with the caveat that $C_{ave,ss}$ is greater than $C_{min,ss}$ and $C_{ave,ss}$ is less than $C_{max,ss}$; and d) the gastric residence system provides a human in vivo plasma profile at steady state having an $AUC_\tau$ of about 2750 hour-ng/mL·±750 hour-ng/mL, where τ (tau) is the dosing interval; the dosing interval can be about four days, about five days, about six days, about seven days, about eight days, about nine days, or about ten days, preferably seven days or about seven days. The gastric residence systems can comprise about 140 mg to about 420 mg of memantine or a pharmaceutically acceptable salt thereof, about 140 mg to about 280 mg of memantine or a pharmaceutically acceptable salt thereof, or about 196 mg or about 200 mg of memantine or a pharmaceutically acceptable salt thereof. The gastric residence systems can comprise about 20 mg to about 60 mg of memantine or a pharmaceutically acceptable salt thereof, about 20 mg to about 40 mg of memantine or a pharmaceutically acceptable salt thereof, or about 28 mg of memantine or a pharmaceutically acceptable salt thereof.

In any of the embodiments described herein, the invention can provide gastric residence systems which comprise a therapeutically effective amount of an adamantane-class drug or a pharmaceutically acceptable salt thereof, where the gastric residence system has a compacted configuration and an uncompacted configuration, the gastric residence system comprises a plurality of elongate members affixed to a central elastomer, each elongate member comprises at least two segments joined by linkers, where the linkers are configured to weaken or degrade to allow passage of the gastric residence system through the pylorus after the specified gastric residence period (for example, the linkers may soften and become flexible, or the linkers may no longer join the at least two segments of each elongate member after the specified gastric residence period); and where the segments of the elongate members comprise a carrier polymer and the adamantane-class drug or the pharmaceutically acceptable salt thereof, or the segments of the elongate members comprise a) a carrier polymer, b) at least one excipient, and c) the adamantane-class drug or the pharmaceutically acceptable salt thereof; where the gastric residence system is configured to release the adamantane-class drug or the pharmaceutically acceptable salt thereof over the specified gastric residence period. The adamantane-class drug or a pharmaceutically acceptable salt thereof can be memantine or a pharmaceutically acceptable salt thereof. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the embodiments described herein, the invention can provide gastric residence systems which comprise a therapeutically effective amount of an adamantane-class drug or a pharmaceutically acceptable salt thereof, where the gastric residence system has a compacted configuration and an uncompacted configuration, the gastric residence system comprises a plurality of elongate members affixed to a central elastomer by linkers, where the linkers are configured to weaken or degrade to allow passage of the gastric residence system through the pylorus after the specified gastric residence period (for example, the linkers may soften and become flexible, or the linkers may no longer join the elongate members to the central elastomer after the specified gastric residence period). The elongate members comprise a carrier polymer and the adamantane-class drug or the pharmaceutically acceptable salt thereof. In another embodiment, the elongate members further comprise at least one excipient. The gastric residence system is configured to release the adamantane-class drug or the pharmaceutically acceptable salt thereof over the specified gastric residence period. The adamantane-class drug or a pharmaceutically acceptable salt thereof can be memantine or a pharmaceutically acceptable salt thereof. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the gastric residence systems disclosed herein, the carrier polymer can be polycaprolactone. One or more additional excipients can be mixed in with the carrier polymer. The one or more additional excipients can be selected from the group consisting of soluble excipients, insoluble wicking excipients, degradable excipients, insoluble swellable excipients, and surfactants. The one or more additional excipients can be selected from the group consisting of P407, Eudragit E, PEG, Polyvinylpyrrolidone (PVP), Polyvinyl acetate (PVAc), Polyvinyl alcohol (PVA), Eudragit RS, Eudragit RL, PLA, PLGA, PLA-PCL, polydioxanone, Crospovidone, Croscarmellose, HPMCAS, Lecithin, Taurocholate, SDS, Soluplus, Fatty acids, Kolliphor RH40; and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate, such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%); linear copolymers of caprolactone (95%) and glycolide (5%); polyaxial block copolymers of glycolide (68%), caprolactone (29%), and trimethylene carbonate (3%); polyaxial block copolymers of glycolide (86%), trimethylene carbonate (9%), and lactide (5%); polyaxial block copolymers of glycolide (70%), trimethylene carbonate (27%) and polypropylene succinate (2%); polyaxial block copolymers of caprolactone (35%), lactide (34%), glycolide (17%), and trimethylene carbonate (14%); polyaxial block copolymers of glycolide (55%), trimethylene carbonate (25%), and caprolactone (20%); and linear block copolymers of lactide (39%), caprolactone (33%), and trimethylene carbonate (28%).

In any of the gastric residence systems disclosed herein, when at least one of the linkers is an enteric polymer, the enteric polymer can be selected from the group consisting of poly(methacrylic acid-co-ethyl acrylate), cellulose acetate phthalate, cellulose acetate succinate, hydroxypropyl methylcellulose phthalate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methacrylic acid methylmethacrylate copolymer, methyl acrylate-methacrylic acid copolymer, methacrylate-methacrylic acid-octyl acrylate copolymer; and copolymers, mixtures, blends and combinations thereof.

In any of the gastric residence systems disclosed herein having a central elastomer, the central elastomer can comprise silicone rubber.

In any of the gastric residence systems disclosed herein, the system can further comprise a dispersant selected from the group comprising silicon dioxide, hydrophilic fumed silicon dioxide, a stearate salt, calcium stearate, magnesium stearate, microcrystalline cellulose, carboxymethylcellulose, hydrophobic colloidal silica, hypromellose, magnesium aluminum silicate, a phospholipid, a polyoxyethylene stearate, zinc acetate, alginic acid, lecithin, a fatty acid, sodium lauryl sulfate, a non-toxic metal oxide, aluminum oxide, a porous inorganic material, and a polar inorganic material.

In any of the gastric residence systems disclosed herein, the adamantane-class drug or pharmaceutically acceptable salt thereof can comprise particles of memantine or a pharmaceutically acceptable salt thereof in the form of particles disposed in the carrier polymer, where at least about 80% of the mass of particles have sizes between about 1 micron and about 50 microns in diameter.

In any of the gastric residence systems disclosed herein, the adamantane-class drug or pharmaceutically acceptable salt thereof is memantine or a pharmaceutically acceptable salt thereof, and the gastric residence system can comprise about 150 mg to about 350 mg of memantine or a pharmaceutically acceptable salt thereof.

In any of the embodiments described herein, the invention provides a formulation for extended release of an adamantane-class drug or a pharmaceutically acceptable salt thereof, comprising about 10% to about 30% of an adamantane-class drug or a pharmaceutically acceptable salt thereof; about 0.1% to about 4% of silica; about 5% to about 30% of an acrylate polymer or co-polymer; and about 0.2% to about 10% of a polyalkylene glycol; where the remainder of the composition comprises a polylactone. The formulation can further comprise about 0.1% to about 2% of an anti-oxidant material. The anti-oxidant material can comprise one or more compounds selected from the group consisting of Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate. (Vitamin E can refer to alpha-tocopherol, beta-tocopherol, gamma-tocopherol, delta-tocopherol, alpha-tocotrienol, beta-tocotrienol, gamma-tocotrienol, or delta-tocotrienol, or to any combinations of any two or more of the foregoing.) The silica can comprise hydrophilic fumed silica particles. The acrylate polymer or co-polymer can comprise a co-polymer of ethyl acrylate, methyl methacrylate and trimethylammonioethyl methacrylate, such as a co-polymer comprising ethyl acrylate, methyl methacrylate and trimethylammonioethyl methacrylate in a molar ratio of about 1:2:0.1. The polyalkylene glycol can be selected from the group consisting of polyethylene glycol (PEG), polypropylene glycol (PPG), and a block copolymer of PEG and PPG. When the polyalkylene glycol comprises a block copolymer of PEG and PPG, it can comprise a copolymer of the formula H—(OCH$_2$CH$_2$)$_x$—(O—CH(CH$_3$)CH$_2$)$_y$—(OCH$_2$CH$_2$)$_z$—OH, where x and z are about 101 and y is about 56. The polylactone can comprise polycaprolactone, such as a polycaprolactone having an average $M_n$ of about 60,000 to about 100,000, an average $M_n$ of about 75,000 to about 85,000, or an average $M_n$ of about 80,000. In any embodiment disclosed herein, including the foregoing embodiments, the adamantane-class drug or pharmaceutically acceptable salt thereof can be selected from the group consisting of memantine; amantadine; adapromine; nitromemantine; rimantadine; bromantane; tromantadine; and neramexane; and a pharmaceutically acceptable salt of memantine, amantadine, adapromine, nitromemantine, rimantadine, bromantane, tromantadine, and neramexane. In any embodiment disclosed herein, including the foregoing embodiments, the adamantane-class drug or pharmaceutically acceptable salt thereof can be memantine or a pharmaceutically acceptable salt thereof. In any embodiment disclosed herein, including the foregoing embodiments, the adamantane-class drug or pharmaceutically acceptable salt thereof can be memantine. In any embodiment disclosed herein, including the foregoing embodiments, the adamantane-class drug or pharmaceutically acceptable salt thereof can be a pharmaceutically acceptable salt of memantine. In any embodiment disclosed herein, including the foregoing embodiments, the adamantane-class drug or pharmaceutically acceptable salt thereof can be memantine hydrochloride.

In any of the embodiments described herein, the invention can provide one or more elongate members formed from a material comprising a formulation for extended release of an adamantane-class drug or a pharmaceutically acceptable salt thereof as described herein. In some embodiments, the invention provides gastric residence systems comprising one or more elongate members formed from a material comprising a formulation for extended release of an adamantane-class drug or a pharmaceutically acceptable salt thereof as described herein.

In further embodiments, the invention provides a method of making a gastric residence system, comprising preparing at least three elongate members formed from a material comprising any of the formulations for extended release of an adamantane-class drug or a pharmaceutically acceptable salt thereof as described herein; and attaching the elongate members to a central elastomer, to form a gastric residence system having elongate members projecting radially from the central elastomer.

In further embodiments, the invention provides methods of treating a neurological or psychiatric disorder in a subject in need of treatment for the disorder, comprising administering any of the gastric residence systems as disclosed herein to the subject. The neurological or psychiatric disorder can be a central nervous system disorder. The neurological or psychiatric disorder can be Alzheimer's Disease. The neurological or psychiatric disorder can be dementia. The neurological or psychiatric disorder can be Lewy Body dementia. The neurological or psychiatric disorder can be HIV-associated dementia. The neurological or psychiatric disorder can be vascular dementia. The neurological or psychiatric disorder can be organic brain syndrome. The neurological or psychiatric disorder can be spasticity. The neurological or psychiatric disorder can be stroke or the resulting effects of stroke. The neurological or psychiatric disorder can be an autism spectrum disorder. The neurological or psychiatric disorder can be Parkinson's Disease. The neurological or psychiatric disorder can be neuropathic pain. The neurological or psychiatric disorder can be attention deficit/hyperactivity disorder (ADHD). The neurological or psychiatric disorder can be obsessive-compulsive disorder (OCD). The neurological or psychiatric disorder can be major depression.

In further embodiments, the invention provides methods of treating glaucoma in a subject in need of treatment for glaucoma, comprising administering any of the gastric residence systems as disclosed herein to the subject.

In further embodiments, the invention provides methods of treating a viral infection in a subject in need of treatment for the viral infection, comprising administering any of the gastric residence systems as disclosed herein to the subject. The viral infection can be influenza.

In any embodiment of the methods of treatment disclosed herein, the gastric residence system can administered to the patient on an approximately weekly basis over a period of at least about one month, at least about two months, at least about three months, or indefinitely, or for a period up to about one month, about two months or about three months.

The invention additionally provides gastric residence systems for administration of adamantane-class drugs or salts thereof which have segments or elongate members covered with release rate-modulating polymer films, elongate members of such gastric residence systems which have segments covered with release rate-modulating polymer film, segments covered with release rate-modulating polymer films suitable for use in such gastric residence systems, and elongate members covered with release rate-modulating polymer films suitable for use in such gastric residence systems. Methods of making the segments, elongate members, and gastric residence systems containing adamantane-class drugs and salts thereof are also provided. Methods of using the gastric residence systems containing adamantane-class drugs and salts thereof are also provided.

In further embodiments, the invention provides a segment of a gastric residence system, the segment comprising a carrier polymer; an adamantane-class drug or a salt thereof; and a release rate-modulating polymer film configured to control the release rate of the adamantane-class drug, wherein over a seven-day incubation of the segment in simulated gastric fluid, the amount of the adamantane-class drug or salt thereof released during day 5 is at least about 40% of the amount of adamantane-class drug or salt thereof released during day 2; and wherein at least about 7% of the total amount of adamantane-class drug in the segment is released on day 2 and at least about 7% of the total amount of adamantane-class drug is released on day 5.

In further embodiments, the invention provides a segment of a gastric residence system, the segment comprising a carrier polymer; an adamantane-class drug or a salt thereof; and a release rate-modulating polymer film configured to control the release rate of the adamantane-class drug, wherein over a seven-day incubation of the segment in simulated gastric fluid, the amount of the adamantane-class drug or salt thereof released from the segment during day 7 is at least about 20% of the amount of adamantane-class drug or salt thereof released during day 1; and wherein at least about 4% of the total amount of adamantane-class drug in the segment is released on day 1 and at least about 4% of the total amount of adamantane-class drug is released on day 7.

In further embodiments, the invention provides a segment of a gastric residence system, the segment comprising a carrier polymer, an adamantane-class drug or a salt thereof; and a release rate-modulating polymer film configured to control the release rate of the adamantane-class drug, wherein the release rate-modulating polymer film is configured such that the release of adamantane-class drug from the segment in 40% ethanol/60% simulated gastric fluid over one hour is no more than about 40% higher compared to release of adamantane-class drug from an equivalent segment in 100% simulated gastric fluid over one hour.

In further embodiments, the invention provides a segment of a gastric residence system, the segment comprising a carrier polymer, an adamantane-class drug or a salt thereof; and a release rate-modulating polymer film configured to control the release rate of the adamantane-class drug, wherein the release rate-modulating polymer film is configured such that the release of adamantane-class drug from the segment in 40% ethanol/60% simulated gastric fluid over one hour is at least about 40% lower than the release of adamantane-class drug from a second segment in 40% ethanol/60% simulated gastric fluid over one hour, the second segment comprising the same combination of carrier polymer and adamantane-class drug or salt thereof but lacking the release rate-modulating polymer film.

In further embodiments, the invention provides a segment of a gastric residence system, the segment comprising a carrier polymer, an adamantane-class drug or a salt thereof; and a release rate-modulating polymer film configured to control the release rate of the adamantane-class drug, wherein the release rate-modulating polymer film is configured such that the release of adamantane-class drug from the segment in simulated gastric fluid over an initial 6 hour period is at least about 40% lower than the release of adamantane-class drug from a second segment in simulated gastric fluid over an initial 6 hour period, the second segment comprising the same combination of carrier polymer and adamantane-class drug or salt thereof but lacking the release rate-modulating polymer film; and wherein the release of adamantane-class drug from the segment in simulated gastric fluid over a seven-day period is at least about 60%, at least 70%, or at least 80% of the total amount of adamantane-class drug originally present in the segment.

In further embodiments, the invention provides a segment of a gastric residence system, the segment comprising a carrier polymer; an adamantane-class drug or a salt thereof; and a release rate-modulating polymer film, wherein the polymer film is configured to control the release rate of the adamantane-class drug such that a best-fit linear regression model of the release rate of adamantane-class drug from the segment in simulated gastric fluid has a coefficient of determination $R^2$ of at least about 0.8, at least 0.85, or at least 0.9 over an initial period of seven days; and wherein the segment releases about 40% to about 60% of the adamantane-class drug or salt thereof within a time of about 40% to about 60% of the seven-day period.

In further embodiments, the invention provides a segment of a gastric residence system, the segment comprising a carrier polymer; an adamantane-class drug or a salt thereof; and a release rate-modulating polymer film, wherein the polymer film is configured to control the release rate of the adamantane-class drug from the segment over a seven-day period in simulated gastric fluid such that the release rate from the segment over any one of the seven days varies by no more than about 25% from the average daily total release from the segment over the seven days.

In any of the embodiments of the invention described herein, the release rate-modulating polymer film can comprise one or more polyester materials. The polymer film can comprise polyester with a repeating unit of the form: —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms. The polymer film can comprise polycaprolactone or polydioxanone, such as polycaprolactone of about 10,000 to about 150,000 Mn, polycaprolactone of about 80,000 Mn to about 110,000 Mn, polycaprolactone of about 90,000 Mn, or polycaprolactone having intrinsic viscosity of about 1.0 dL/g to about 2.5 dL/g or about 1.5 dL/g to about 2.1 dL/g.

In any of the embodiments of the invention described herein, the release rate-modulating polymer film can comprise one or more porogens. The porogen can comprise a water-soluble polymer, a water-soluble small molecule, an inorganic salt, or an organic salt. The porogen can comprise about 1% to about 30% by weight of the film. The porogen can be selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum. The porogen can be selected from the group consisting of povidone, copovidone, and polyoxyl castor oil.

In further embodiments, the invention provides a segment of a gastric residence system, the segment comprising a carrier polymer; an adamantane-class drug or a salt thereof; and a release rate-modulating polymer film, wherein the polymer film comprises a material selected from the group consisting of polycaprolactone, cellulose acetate, and ethyl cellulose.

In any of the embodiments disclosed herein, the release rate-modulating polymer film can comprise about 0.1% to about 10% of the total weight of the segment, about 0.1% to about 5% of the total weight of the segment, about 0.5% to about 5% of the total weight of the segment, about 0.5% to about 2% of the total weight of the segment, or about 1% to about 2% of the total weight of the segment.

In any of the embodiments disclosed herein, the release rate-modulating polymer film can comprise a thickness between about 1 micron and about 20 microns, such as between about 5 microns and about 15 microns.

In any of the embodiments disclosed herein, the release rate-modulating polymer film can further comprise a plasticizer. The plasticizer can comprise about 1% to about 40% by weight of the film, such as about 1% to about 30%, or about 1% to about 20%, or about 1% to about 15%, or preferably about 5% to about 20%, or more preferably about 10% to about 20%. The plasticizer can be selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, and poloxamer. The plasticizer can be selected from the group consisting of triethyl citrate and triacetin.

In any of the embodiments disclosed herein, the release rate-modulating polymer film can further comprise a permeable component which is permeable to the adamantane-class drug or salt thereof and permeable to water. The permeable component can be a polymer or a swellable material. The permeable component can comprise about 1% to about 30% by weight of the film. The permeable component can be selected from the group consisting of SSG, crospovidone, croscarmellose, and Carbopol (PAA).

The invention further provides gastric residence systems for administration to a patient, comprising at least one segment of any of the segment embodiments disclosed herein.

The invention further provides gastric residence systems for administration to a patient, comprising an elastomer component, and at least three elongate members attached to the elastomer component, wherein each elongate member comprises a proximal end, a distal end, and an outer surface therebetween, the proximal end of each elongate member is attached to the elastomer component and projects radially from the elastomer component, each elongate member has its distal end not attached to the elastomer component and located at a larger radial distance from the elastomer component than the proximal end; wherein at least one elongate member comprises a segment of any of the segment embodiments disclosed herein, such as a segment coated with a release rate-modulating polymer film or wherein at least one elongate member is coated with a release rate-modulating polymer film. The central elastomer of the gastric residence system can be formed from liquid silicone rubber. The elongate members of the gastric residence system can be attached to the central elastomer via a disintegrating matrix, such as a disintegrating matrix comprising HPMC-AS and polycaprolactone.

The invention further provides methods of making a segment of a gastric residence system comprising coating a segment comprising a carrier polymer and an adamantane-class drug or a salt thereof with a solution of a polymer film formulation to produce a film-coated segment; and drying the film-coated segment. The coating can be performed by dip coating, pan coating, spray coating, or fluidized bed coating. The solvent used in the solution of polymer film formulation can comprise an organic solvent, such as ethyl acetate, dichloromethane, acetone, isopropyl alcohol, or any combination thereof. The invention further provides a method of making a segment of a gastric residence system comprising co-extruding a polymer film and a mixture of a carrier polymer and an adamantane-class drug or a salt thereof.

The invention further provides methods of making an elongate member of a gastric residence system comprising coating an elongate member comprising a carrier polymer and an adamantane-class drug or a salt thereof with a solution of a polymer film formulation to produce a film-coated elongate member; and drying the film-coated elongate member. The coating can be performed by dip coating, pan coating, spray coating, or fluidized bed coating. The solvent used in the solution of polymer film formulation can comprise an organic solvent, such as ethyl acetate, dichloromethane, acetone, isopropyl alcohol, or any combination thereof. The invention further provides a method of making an elongate member of a gastric residence system comprising co-extruding a polymer film and a mixture of a carrier polymer and an adamantane-class drug or a salt thereof.

The invention further comprises methods of administering a gastric residence system to a patient, comprising administering a container containing any embodiment of the gastric residence systems disclosed herein in a compacted state to a patient, wherein the container enters the stomach of the patient and dissolves after entry into the stomach, releasing the gastric residence system which then adopts its uncompacted state. Preferably, the patient is a human. The container containing the gastric residence system can be administered by swallowing, by feeding tube, or by gastrostomy tube.

Any features from any embodiment disclosed herein, such as the embodiments disclosed above, can be combined with any features from any other embodiment where possible.

BRIEF DESCRIPTION OF THE DRAWINGS

FIG. 34 shows unprocessed memantine (left panel) and memantine after milling (right panel).

FIG. 36 shows die designs for hot melt extrusion of star arms for gastric residence systems.

FIG. 38A and FIG. 38B show the residence periods of gastric residence systems in hounds in an in vivo study. Two six-arm stellate systems were administered to each dog, for a total of 12 arms in each dog.

FIG. 47 depicts solvents used for dip coating PCL films. Dichloromethane and ethyl acetate were both able to dissolve PCL at high concentrations and to form uniform coatings with good performance.

FIG. 48 depicts release rate profiles of M77 uncoated formulation and M77 formulations with coatings of PCL only and PCL with the addition of porogens (Water Soluble Polymers, WSPs) Kollidon VA64 and Kolliphor RH40.

FIG. 59 depicts a comparison of pharmacokinetic parameters for dosage forms consisting of 60 A durometer LSR elastomers IR welded to 50/50 PCL/HPMAS disintegrating matrices and M77 drug arms that were coated with a solution of 4.5% PCL/0.5% Kollidon VA64 w/v in ethyl acetate, versus a single dose of Namenda XR, a commercially available extended release formulation of memantine. The left chart shows the Namenda XR reference product single dose variability, with $C_{max}$ (ng/mL) on the left axis and the left grouping of points, and AUC (hr-ng/mL) on the right axis and the right grouping of points. The right chart shows the dosage form variability, with $C_{max}$ (ng/mL) on the left axis and the left grouping of points, and AUC (hr·ng/mL) on the right axis and the right grouping of points. Compared to the reference product, the dosage form achieves nearly 7-fold higher AUC with a lower $C_{max}$ and potentially lower inter-subject variability.

DETAILED DESCRIPTION OF THE INVENTION

Definitions

Figure 1A:
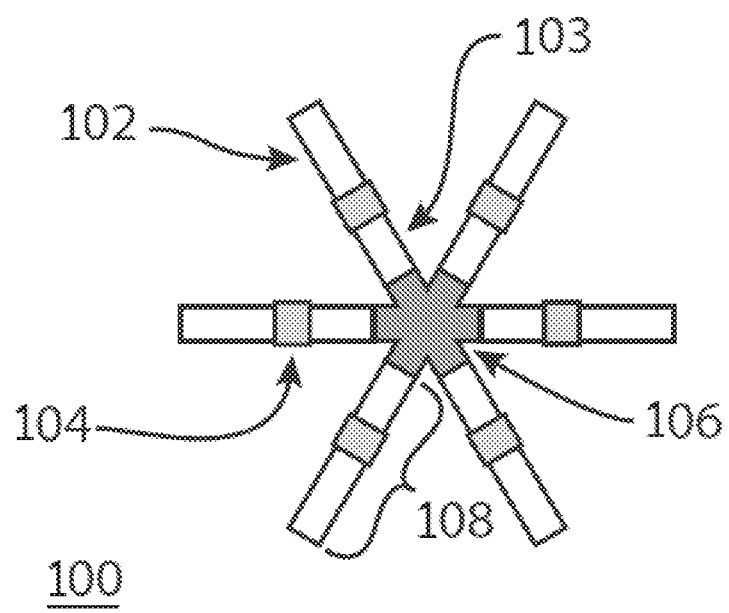
FIG. 1A shows a stellate design of a gastric residence system in its uncompacted state.

A "carrier polymer" is a polymer suitable for blending with an agent, such as a drug, for use in the invention.

An "agent" is any substance intended for therapeutic, diagnostic, or nutritional use in a patient, individual, or subject. Agents include, but are not limited to, drugs, nutrients, vitamins, and minerals.

A "dispersant" is defined as a substance which aids in the minimization of particle size of agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of an agent that is not the agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-drug component to a second carrier polymer-drug component. Coupling polymers typically form the linker regions between other components.

A "time-dependent polymer" or "time-dependent coupling polymer" is a polymer that degrades in a time-dependent manner when a gastric residence system is deployed in the stomach. A time-dependent polymer is typically not affected by the normal pH variations in the stomach.

"Approximately constant plasma level" refers to a plasma level that remains within a factor of two of the average plasma level (that is, between 50% and 200% of the average plasma level) measured over the period that the gastric residence system is resident in the stomach.

"Substantially constant plasma level" refers to a plasma level that remains within plus-or-minus 25% of the average plasma level measured over the period that the gastric residence system is resident in the stomach.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

A "patient," "individual," or "subject" refers to a mammal, preferably a human or a domestic animal such as a dog or cat. In a preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional agents or drugs, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional agents or drugs, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of a therapeutic agent, such as a drug, is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Partitioning behavior of an adamantane-class drug can be measured between a polycaprolactone phase (PCL phase) and a simulated gastric fluid phase (SGF phase), to give the partition coefficient $P_{PCL-SGF}$ between the two phases. Log $P_{PCL-SGF}$ can also be calculated. A 5:1 mixture of polycaprolactone diol (MW 530):ethyl acetate can be used as the PCL phase, and fasted-state simulated gastric fluid (FaSSGF) can be used as the SGF phase, such that $P_{PCL-SGF}$=(concentration in polycaprolactone diol)/(concentration in FaSSGF)).

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

Figure 2:
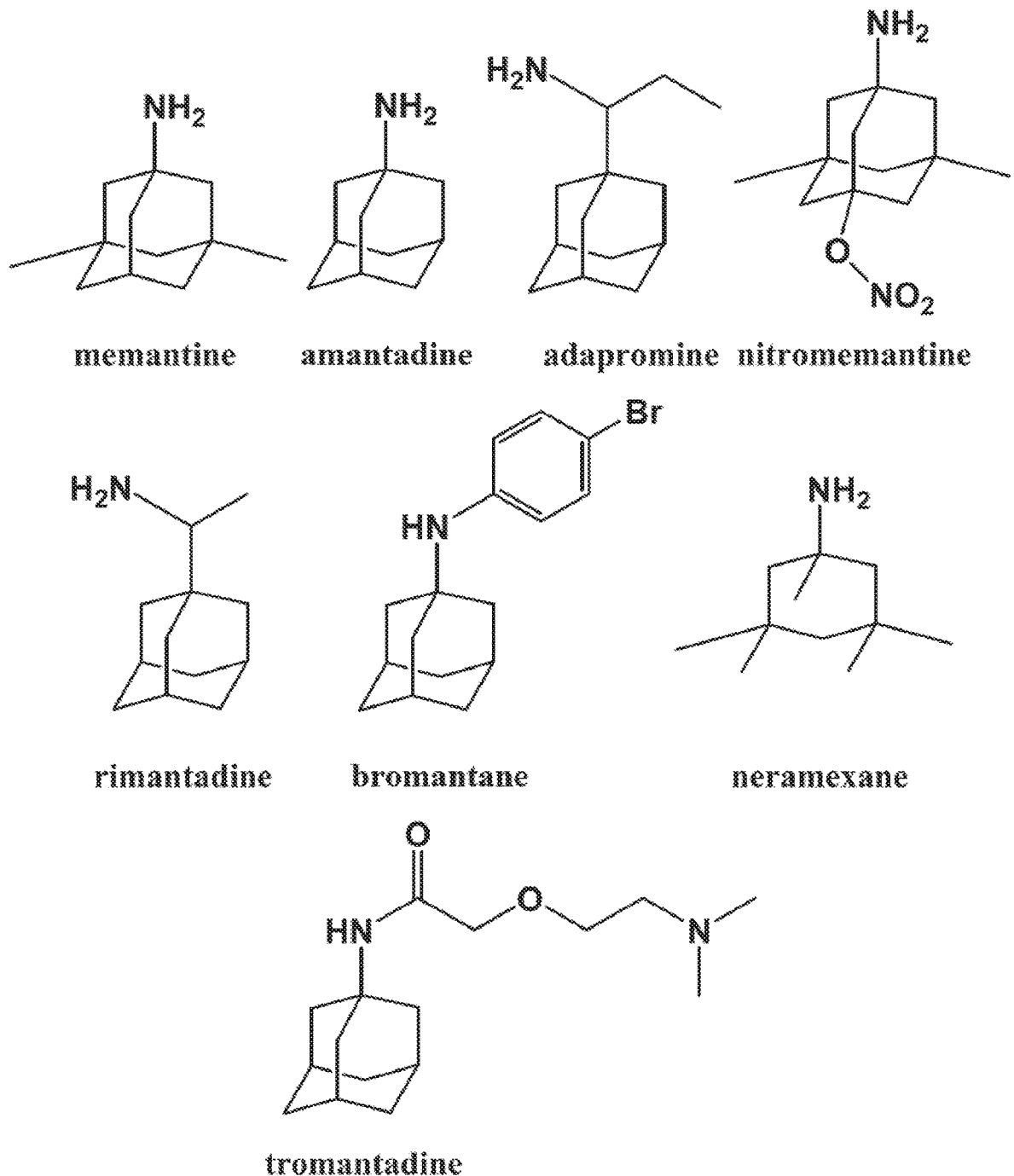
FIG. 2 shows several drugs of the adamantane class: memantine, amantadine, adapromine, nitromemantine, rimantadine, bromantane, neramexane, and tromantadine.

Adamantane-Class Drugs as Therapeutic Agents for Use in Gastric Residence Systems The gastric residence systems described herein are particularly well adapted for administration of drugs in the adamantane class, which can be administered to or via the gastrointestinal tract. Memantine is the preferred drug of the adamantane class. Other drugs which can be used in the gastric residence systems include amantadine, adapromine, nitromemantine, rimantadine, bromantane, and tromantadine. Neramexane (1,3,3,5,5-pentamethylcyclohexanamine), which is a cyclohexanamine, is also included in the adamantane class of drugs due to its similarities to memantine. The structures of these drugs are depicted in FIG. 2.

Drug-Polymer Formulations for Gastric Residence Systems

Careful selection of the carrier material for memantine or other adamantane-class drug is required in order to provide the desired release profile of drug during the period of gastric residence. Release of drug can be modulated by a wide variety of excipients. Soluble excipients include P407, Eudragit E, PEG, Polyvinylpyrrolidone (PVP), and Polyvinyl alcohol (PVA). Insoluble, wicking excipients include Eudragit RS and Eudragit RL. Degradable excipients include PLA, PLGA, PLA-PCL, polydioxanone, and linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate; such as linear copolymers of caprolactone (95%) and glycolide (5%); polyaxial block copolymers of glycolide (68%), caprolactone (29%), and trimethylene carbonate (3%); polyaxial block copolymers of glycolide (86%), trimethylene carbonate (9%), and lactide (5%); polyaxial block copolymers of glycolide (70%), trimethylene carbonate (27%) and polypropylene succinate (2%); polyaxial block copolymers of caprolactone (35%), lactide (34%), glycolide (17%), and trimethylene carbonate (14%); polyaxial block copolymers of glycolide (55%), trimethylene carbonate (25%), and caprolactone (20%); and linear block copolymers of lactide (39%), caprolactone (33%), and trimethylene carbonate (28%). Insoluble, swellable excipients include Polyvinyl acetate (PVAc), Crospovidone, Croscarmellose, HPMCAS, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%). Surfactants include Lecithin, Taurocholate, SDS, Soluplus, Fatty acids, and Kolliphor RH40.

Various formulations of carrier polymers and excipients blended with memantine were tested, and were designated as M1, M2, etc. Release rates of memantine from the formulations are described in Example 3 and FIG. 3 through FIG. 22.

Release Rate-Modulating Polymer Films

The current invention provides, inter alia, gastric residence systems, elongate members of gastric residence systems, and segments for use in gastric residence systems and elongate members of gastric residence systems, which are coated with a release rate-modulating film. Use of a release rate-modulating polymer film with the gastric residence systems, such as on the carrier polymer-agent segments of the gastric residence systems or on the elongate members of the gastric residence systems, provides several significant advantages over systems with carrier polymer-agent segments lacking a release rate-modulating film. Release rate-modulating polymer films reduce the burst release of agent upon initial contact with gastric fluid. Linearity of agent release over the residence period is improved by using release rate-modulating polymer films. Both of these advantages provide better regulation of dosing from the gastric residence systems. Some compositions of the release rate-modulating polymer films can also significantly reduce burst release upon exposure to alcohol, as compared to systems lacking such films.

The release rate-modulating polymer films are coatings which can coat all or part of a carrier polymer-agent segment. The films can be continuous, discontinuous, flat, or textured. They can be a smooth coating over a segment, or can follow contours of pores that may be present on the surface of a segment.

In a preferred embodiment, the release rate modulating film of any of the gastric residence systems disclosed herein does not cover the coupling polymers, enteric polymers, enteric linkers, time-dependent linkers, disintegrating polymers, disintegrating matrices, or other linkers of the gastric residence system. If a release rate-modulating polymer film is coated on the surface of an elongate member which comprises one or more linkers, such as a coupling polymer, enteric polymer, enteric linker, time-dependent linker, disintegrating polymer, disintegrating matrix, or other linker, the film is discontinuous and does not cover or coat the linkers. This is readily accomplished by applying a release rate-modulating film to segments which will comprise an elongate member, and then linking the coated segments together with linkers to form an elongate member; the segments comprising carrier polymer-agent (or agent salt) will thus be coated with the release rate-modulating film, but the linkers will not be coated with the release rate-modulating film.

The films are typically applied to segments of the gastric residence systems. The films can also be applied to multi-segment elongate members prior to attachment of the multi-segment elongate members to a central elastomer. The films can also be applied to non-segmented elongate members (that is, elongate members which comprise only one segment) prior to attachment of the non-segmented elongate members to a central elastomer. An example of segments of a gastric residence system is shown in FIG. 1A, where segment 102 and segment 103 are linked by linker 104, and attached to a central elastomer 106. The segments 102 and 104 comprise carrier polymer and agent (such as a drug). Using a release rate-modulating polymer film on the segments of the gastric residence system provides the advantageous characteristics described herein.

Several parameters of the films can be adjusted in order to generate desired agent release characteristics, and are discussed below.

Chemical Composition of Release Rate-Modulating Polymer Films

Polyesters are a useful class of compounds for preparation of release rate-modulating polymer films. Polyesters that can be used in the invention include polyesters with aliphatic groups as their main chains, including polylactones such as polycaprolactone (PCL); polyglycolic acid (PGA); polylactic acid (PLA); poly(lactic-co-glycolic acid) (PLGA); polyhydroxyalkanoates (PHA) such as polyhydroxybutyrate (PHB), polyhydroxyvalerate (PHV), and poly(3-hydroxybutyrate-co-3-hydroxyvalerate) (PHBV); polyethylene adipate (PEA); polybutylene succinate (PBS); and polyesters with aromatic groups in their main chains, such as polyethylene terephthalate (PET), polybutylene terephthalate (PBT), polytrimethylene terephthalate (PTT), and polyethylene naphthalate (PEN). Mixtures of two or more polyesters can also be used.

In addition to polyesters, cellulose acetate (CA), ethyl cellulose (EC), and copolymers of acrylate and methacrylate esters (e.g., Eudragit RS) can also be used as release rate-modulating polymer films.

Release rate-modulating polymer films can comprise polyesters with a repeating unit of the form:

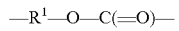

wherein $R^1$ is selected from the group consisting of $C_1$-$C_{12}$ alkylene groups, such as $C_1$-$C_8$ alkylene groups or $C_1$-$C_4$ alkylene groups, ethers containing between two and twelve carbon atoms, two and eight carbon atoms or two and four carbon atoms, and polyethers containing between three and twelve carbon atoms or between three and eight carbon atoms. The polyesters can terminate with hydroxy groups, hydrogens, —$C_1$-$C_{12}$ alkyl groups, —$C_1$-$C_8$ alkyl groups, or —$C_1$-$C_4$ alkyl groups, or —$C_1$-$C_{12}$—OH, —$C_1$-$C_8$—OH, or —$C_1$-$C_4$—OH (alcohol) groups as appropriate.

Preferred polyesters for use as release rate-modulating polymer films are polycaprolactone and polydioxanone, particularly polycaprolactone (PCL). PCL having number-average molecular weight of about 10,000 Mn to about 150,000 Mn; about 20,000 Mn to about 120,000 Mn; about 30,000 Mn to about 120,000 Mn; about 40,000 Mn to about 120,000 Mn; about 50,000 Mn to about 110,000 Mn; about 80,000 to about 120,000 Mn; about 80,000 Mn to about 110,000 Mn, about 60,000 Mn to about 100,000 Mn; about 70,000 Mn to about 90,000 Mn; about 80,000 Mn; about 90,000 Mn; about 100,000 Mn; about 10,000 Mn to about 100,000 Mn; about 10,000 Mn to about 80,000 Mn; about 40,000 Mn to about 70,000 Mn; about 50,000 Mn to about 60,000 Mn; or about 55,000 Mn can be used for release rate-modulating polymer films. PCL of about 80,000 Mn to about 110,000 Mn is preferred, such as about 85,000 Mn to 95,000 Mn, or about 90,000 Mn.

Polycaprolactone can also be characterized by its intrinsic viscosity. PCL of about 1.0 dL/g to about 2.5 dL/g or about 1.5 dL/g to about 2.1 dL/g can be used. The intrinsic viscosity can be measured in CHCl3 at 25° C.

Porogens, Plasticizers, and Other Additives to Release Rate-Modulating Polymer Films Porogens, plasticizers, or both porogens and plasticizers can be added to the release rate-modulating polymer films to further tune the release rate of the agent in the carrier polymer-agent segment.

Porogens are soluble additives that dissolve out of the release rate-modulating polymer films, creating pores in the films. In some embodiments, the porogens dissolve out of the films when the gastric residence systems are deployed in the gastric environment. That is, after preparation of the segments, the porogens are left in the segments which are assembled into the gastric residence system, and in the gastric residence system as administered to a patient; the porogens then dissolve out of the release rate-modulating polymer film when the gastric residence system is administered to the patient and contacts the gastric environment. In another embodiment, the porogens are removed from the film-covered carrier polymer-agent segments before the segments are assembled into the gastric residence system, or the porogens are removed from the gastric residence system before deployment of the gastric residence system in the gastric environment.

Porogens can be organic or inorganic materials. Examples of porogens include alkali metal salts such as sodium chloride, sodium bromide, potassium chloride, potassium sulfate, potassium phosphate, sodium benzoate, sodium acetate, sodium citrate, potassium nitrate and the like; alkaline earth metal salts such as calcium chloride, calcium nitrate, and the like; and transition metal salts such as ferric chloride, ferrous sulfate, zinc sulfate, cupric chloride, and the like. Additional examples of porogens include saccharides and sugars, such as sucrose, glucose, fructose, mannose, galactose, aldohexose, altrose, talose, lactose, cellulose, monosaccharides, disaccharides, and water soluble polysaccharides. Additional examples of porogens include sorbitol, mannitol, organic aliphatic and aromatic oils, including diols and polyols, as exemplified by polyhydric alcohols, poly(alkylene glycols), polyglycols, alkylene glycols, poly(a,m)alkylenediol esters or alkylene glycols, poly vinylalcohol, poly vinyl pyrrolidone, and water soluble polymeric materials. Further examples of porogens that can be used include Poloxamer; hypromellose (HPMC); Kolliphor RH40; polyvinyl caprolactam; polyvinyl acetate (PVAc); polyethylene glycol (PEG); Soluplus (available from BASF; a copolymer of polyvinyl caprolactam, polyvinyl acetate, and polyethylene glycol); copovidone; Eudragits (E, RS, RL); poly(methyl vinyl ether-alt-maleic anhydride); polyoxyethylene alkyl ethers; polysorbates; polyoxyethylene stearates; polydextrose; polyacrylic acid; alginates; sodium starch glycolate; crosslinked polyacrylic acid (carbopol); crosslinked PVP (crospovidone); crosslinked cellulose (croscarmellose); calcium silicate; xanthan gum; and gellan gum. Some particularly useful porogens include povidone, copovidone, and polyoxyl castor oil.

Porogens can be added to make up between about 1% to about 30% by weight of the release rate-modulating polymer film. Porogens can be added to make up about 1% to about 25%, about 1% to about 20%, about 1% to about 15%, about 1% to about 10%, about 1% to about 8%, about 1% to about 5%, about 1% to about 3%, about 5% to about 30%, about 10% to about 30%, about 15% to about 30%, about 20% to about 30%, or about 25% to about 30% by weight of the release rate-modulating polymer film. A preferred range of porogen is about 5% to about 20%, more preferably about 10% to about 20%, by weight of the release rate-modulating polymer film.

Plasticizers can also be added to further tune the properties of the release rate-modulating polymer films. Plasticizers that can be used include the classes of phthalates, phosphates, citrates, tartrates, adipates, sebacates, sulfonamides, succinates, glycolates, glycerolates, benzoates, myristates, and halogenated phenyls. Specific plasticizers that can be used include triacetin, triethyl citrate, PEG, poloxamer, tributyl citrate, and dibutyl sebacate. Triacetin and triethyl citrate (TEC) are particularly useful.

Plasticizers can be added to make up about 1% to about 35%, about 1% to about 30%, about 1% to about 25%, about 1% to about 20%, about 1% to about 15%, about 1% to about 10%, about 1% to about 8%, about 1% to about 5%, about 1% to about 3%, about 5% to about 40%, about 10% to about 40%, about 15% to about 40%, about 20% to about 40%, about 25% to about 40%, about 30% to about 40%, about 10% to about 30%, about 15% to about 30%, about 20% to about 30%, about 25% to about 30%, or about 10%, about 15%, about 20%, about 25%, about 30%, about 35%, or about 40% by weight of the release rate-modulating polymer film. A preferred range of plasticizer is about 5% to about 20%, more preferably about 10% to about 20%, by weight of the release rate-modulating polymer film.

Processing aids can also be added to release rate-modulating polymer films. Anti-tack agents, such as magnesium stearate, talc, or glycerol monostearate can be added to aid in processing of the films. Such anti-tack agents can be added in amounts of about 0.5% to about 5%, about 1% to about 3%, or about 2%.

Film Combinations

Various options that can be used for the release rate-modulating polymer film for segments and elongate members are as follows (percentages are weight percentages):

Polymer used in film, about 40% to about 80%; porogen, about 3% to about 20%; plasticizer, about 3% to about 20%; anti-tack agent, about 0.5% to about 5%;

Polymer used in film, about 50% to about 72%; porogen, about 5% to about 20%; plasticizer, about 5% to about 20%; anti-tack agent, about 0.5% to about 5%; or Polymer used in film, about 53% to about 65%; porogen, about 10% to about 20%; plasticizer, about 10% to about 20%; anti-tack agent, about 1% to about 3%.

Examples of polymers that can be used in any of these options are polycaprolactone and polydioxanone; preferably, polycaprolactone is used as the polymer. Examples of porogens that can be used in any of these options are povidone, copovidone, and polyoxyl castor oil. Examples of plasticizers that can be used in any of these options include triethyl citrate, triacetin, PEG, poloxamer, tributyl citrate, and dibutyl sebacate. Examples of anti-tack agents that can be used in any of these options include magnesium stearate, talc, and glycerol monostearate. A preferred combination for the release-rate modulating polymer film is polycaprolactone, copovidone, triethyl citrate, and Mg stearate.

Specific polymer-porogen-plasticizer-anti-tack agent combinations that can be used include polycaprolactone-povidone-triethyl citrate-Mg stearate; polycaprolactone-copovidone-triethyl citrate-Mg stearate; polycaprolactone-polyoxyl castor oil-triethyl citrate-Mg stearate; polycaprolactone-povidone-triacetin-Mg stearate; polycaprolactone-copovidone-triacetin-Mg stearate; polycaprolactone-polyoxyl castor oil-triacetin-Mg stearate; polycaprolactone-povidone-PEG-Mg stearate; polycaprolactone-copovidone-PEG-Mg stearate; polycaprolactone-polyoxyl castor oil-PEG-Mg stearate; polycaprolactone-povidone-poloxamer-Mg stearate; polycaprolactone-copovidone-poloxamer-Mg stearate; polycaprolactone-polyoxyl castor oil-poloxamer-Mg stearate; polycaprolactone-povidone-tributyl citrate-Mg stearate; polycaprolactone-copovidone-tributyl citrate-Mg stearate; polycaprolactone-polyoxyl castor oil-tributyl citrate-Mg stearate; polycaprolactone-povidone-dibutyl sebacate-Mg stearate; polycaprolactone-copovidone-dibutyl sebacate-Mg stearate; polycaprolactone-polyoxyl castor oil-dibutyl sebacate-Mg stearate; polycaprolactone-povidone-triethyl citrate-talc; polycaprolactone-copovidone-triethyl citrate-talc; polycaprolactone-polyoxyl castor oil-triethyl citrate-talc; polycaprolactone-povidone-triacetin-talc; polycaprolactone-copovidone-triacetin-talc; polycaprolactone-polyoxyl castor oil-triacetin-talc; polycaprolactone-povidone-PEG-talc; polycaprolactone-copovidone-PEG-talc; polycaprolactone-polyoxyl castor oil-PEG-talc; polycaprolactone-povidone-poloxamer-talc; polycaprolactone-copovidone-poloxamer-talc; polycaprolactone-polyoxyl castor oil-poloxamer-talc; polycaprolactone-povidone-tributyl citrate-talc; polycaprolactone-copovidone-tributyl citrate-talc; polycaprolactone-polyoxyl castor oil-tributyl citrate-talc; polycaprolactone-povidone-dibutyl sebacate-talc; polycaprolactone-copovidone-dibutyl sebacate-talc; polycaprolactone-polyoxyl castor oil-dibutyl sebacate-talc; polycaprolactone-povidone-triethyl citrate-glycerol monostearate; polycaprolactone-copovidone-triethyl citrate-glycerol monostearate; polycaprolactone-polyoxyl castor oil-triethyl citrate-glycerol monostearate; polycaprolactone-povidone-triacetin-glycerol monostearate; polycaprolactone-copovidone-triacetin-glycerol monostearate; polycaprolactone-polyoxyl castor oil-triacetin-glycerol monostearate; polycaprolactone-povidone-PEG-glycerol monostearate; polycaprolactone-copovidone-PEG-glycerol monostearate; polycaprolactone-polyoxyl castor oil-PEG-glycerol monostearate; polycaprolactone-povidone-poloxamer-glycerol monostearate; polycaprolactone-copovidone-poloxamer-glycerol monostearate; polycaprolactone-polyoxyl castor oil-poloxamer-glycerol monostearate; polycaprolactone-povidone-tributyl citrate-glycerol monostearate; polycaprolactone-copovidone-tributyl citrate-glycerol monostearate; polycaprolactone-polyoxyl castor oil-tributyl citrate-glycerol monostearate; polycaprolactone-povidone-dibutyl sebacate-glycerol monostearate; polycaprolactone-copovidone-dibutyl sebacate-glycerol monostearate; and polycaprolactone-polyoxyl castor oil-dibutyl sebacate-glycerol monostearate.

In addition to the coatings listed above, any coating from Table COAT-1 and Table COAT-2 may be used as a release rate-modulating polymer film, for example in amounts of 1%, 1.5%, 2%, 2.5%, 3%, 3.5%, 4%, 4.5%, or 5% by weight of the elongate member or segment to which they are applied.

TABLE COAT-1

| Coating Formulation |
| --- |
| Eudragit RS |
| PCL 55k |
| Ethyl Cellulose |
| 75:25 PLGA |
| 50:50 PLGA |
| 25:75 PLGA |
| 50:50 PLGA |
| Ethyl Cellulose |
| Cellulose Acetate |
| PCL 55k |
| PCL 15k |
| PLGA 50:50 Ester Terminated 35-45k |
| PLGA 50:50 Acid Terminated 35-45k |
| PCL 80k |
| Ethyl Cellulose Cp 10 |
| Ethyl Cellulose Cp 10 |
| Polycaprolactone, copovidone, triethyl citrate, Mg stearate |
| Ethyl Cellulose: PVP 1.3M |
| PCL 80k:TEC |
| Ethyl Cellulose Cp10:TEC |
| 80k PCL:PVP |
| 80k PCL:Kolliphor RH40 |
| 80k PCL:Kollidon VA64 |
| PCL 80k:TEC |
| Ethyl Cellulose Cp10:TEC |
| PCL 55k:P407 |
| PCL 55k:P188 |
| PCL 55k:PEG 10k |
| PCL 55k:PEG 100k |
| PCL 55k:P407 |
| PCL 55k:P188 |
| PCL 55k:PVP 1M |
| Ethyl Cellulose:PEG 1M |
| Ethyl Cellulose:PEG 100k |
| PCL 80k:TEC |
| Ethyl Cellulose Cp10:TEC |
| PVP |
| 80k PCL:Kolliphor RH40 |
| 80k PCL:Kollidon VA64 |

Table COAT-2 lists specific amounts of ingredients that can be used in the film formulations. The amounts listed in Table COAT-2 can be varied by plus-or-minus 20% of each ingredient (for example, a composition with 10% P407 can vary between 8% P407 to 12% P407).

TABLE COAT-2

| Coating Formulation |
|---|
| 9:1, PCL 55k:P407 |
| 9:1, PCL 55k:P188 |
| Eudragit RS |
| 9:1 PCL 55k:PEG 10k |
| 9:1 PCL 55k:PEG 100k |
| PCL 55k |
| 9:1, PCL 55k:P407 |
| 9:1, PCL 55k:P188 |
| 9:1 PCL 55k:PVP 1M |
| Ethyl Cellulose |
| 9:1 Ethyl Cellulose:PVP 1.3M |
| 9:1 Ethyl Cellulose:PEG 1M |
| 9:1 Ethyl Cellulose:PEG 100k |
| 75:25 PLGA |
| 25:75 PLGA |
| 50:50 PLGA |
| Ethyl Cellulose |
| Cellulose Acetate |
| 9:1 Ethyl Cellulose:PEG 1M |
| 9:1 Cellulose Acetate:PEG 1M |
| Cellulose Acetate |
| PCL 55k |
| PCL 15k |
| PLGA 50:50 Ester Terminated 35-45k |
| PLGA 50:50 Acid Terminated 35-45k |
| PCL 80k |
| 9:1 PCL 80k:TEC |
| 8:2 PCL 80k:TEC |
| 7:3 PCL 80k:TEC |
| Ethyl Cellulose |
| Ethyl Cellulose Cp 10 |
| 9:1 Ethyl Cellulose Cp10:TEC |
| 8:2 Ethyl Cellulose Cp10:TEC |
| 7:3 Ethyl Cellulose Cp10:TEC |
| 7:3 80k PCL:PVP |
| 9:1 PVP |
| 7:3 80k PCL:Kolliphor RH40 |
| 9:1 80k PCL:Kolliphor RH40 |
| 7:3 80k PCL:Kollidon VA64 |
| 9:1 80k PCL:Kollidon VA64 |
| polycaprolactone 83.8%, copovidone 4.4%, Triethyl citrate 9.%8, Magnesium stearate % 2.0 |
| polycaprolactone 66.7% copovidone 16.6%, Triethyl citrate 14.7%, Magnesium stearate 2.0% |
| polycaprolactone 48.0%, copovidone 20.6%, Triethyl citrate, 29.4%, Magnesium stearate 2.0%, |
| polycaprolactone 54.9%, copovidone 13.7%, Triethyl citrate 29.4%, Magnesium stearate 2.0% |
| polycaprolactone 54.9%, copovidone 23.5%, Triethyl citrate 19.6%, Magnesium stearate 2.0% |
| polycaprolactone 62.7%, copovidone 15.7%, Triethyl citrate 19.6%, Magnesium stearate 2.0% |
| polycaprolactone 62.5%, copovidone 20.8%, Triethyl citrate 14.7%, Magnesium stearate 2.0% |
| polycaprolactone 70.6%, copovidone 17.6%, Triethyl citrate 9.8%, Magnesium stearate 2.0% |

Film Thickness

The release rate-modulating polymer films should be very thin in comparison to the carrier polymer-agent segment of the gastric residence system that they cover. This allows for diffusion of water into the carrier polymer-agent segment, and diffusion of agent out of the segment.

Figure 1B:
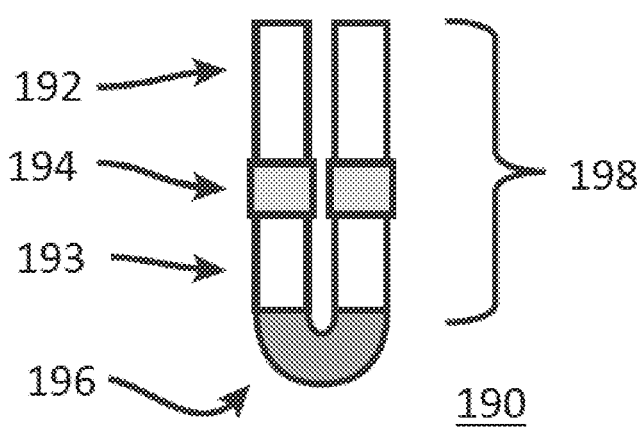
FIG. 1B shows a stellate design of a gastric residence system in a compacted or folded state.

The films are typically between about 1 micrometer to about 20 micrometers, such as between about 1 micrometer to about 20 micrometers, about 1 micrometer to about 15 micrometers, about 1 micrometer to about 10 micrometers, about 1 micrometer to about 5 micrometers, about 1 micrometer to about 4 micrometers, about 1 micrometer to about 3 micrometers, about 1 micrometer to about 2 micrometers, about 2 micrometers to about 10 micrometers, about 5 micrometers to about 20 micrometers, about 5 micrometer to about 10 micrometers, about 10 micrometer to about 15 micrometers, or about 15 micrometers to about 20 micrometers.

In further embodiments, the release rate-modulating polymer film does not add substantially to the strength of the carrier polymer-agent segment that it covers. In further embodiments, the release rate-modulating polymer film adds less than about 20%, less than about 10%, less than about 5%, or less than about 1% to the strength of the segment. The strength of the segment can be measured by the four-point bending flexural test (ASTM D790) described in Example 18 of WO 2017/070612 and Example 13 of PCT/US2016/065453.

Film Weight

The release rate-modulating polymer films can make up about 0.1% to 10% of the weight of the film-covered carrier polymer-agent segment of the gastric residence system. The weight of the film can make up about 0.1% to about 8%, about 0.1% to about 5%, about 0.1% to about 4%, about 0.1% to about 3%, about 0.1% to about 2%, about 0.1% to about 1%, about 0.5% to about 10%, about 0.5% to about 8%, about 0.5% to about 5%, about 0.5% to about 4%, about 0.5% to about 3%, about 0.5% to about 2%, about 0.5% to about 1%, about 1% to about 10%, about 1% to about 8%, about 1% to about 5%, about 1% to about 4%, about 1% to about 3%, or about 1% to about 2% of the film-covered carrier polymer-agent segment of the gastric residence system.

Application of Release Rate-Modulating Polymer Films onto Segments for Use in Gastric Residence Systems The release rate-modulating polymer films can be applied to segments for use in gastric residence systems using various techniques. Several of the techniques involve coating a segment, comprising a carrier polymer and agent, with a solution of a formulation of a release rate-modulating polymer film, producing a film-coated segment. The film-coated segment is then dried.

Various methods of coating films onto objects are known in the art, and include dip coating, pan coating, spray coating, and fluidized bed coating. Fluidized bed coating is also known as Wurster coating or air suspension coating. For these coating methods, a formulation of a release rate-modulating polymer film, including the polymer, and any porogens and plasticizers if present, is prepared as a solution. The solvent used for the solution of the polymer film formulation is typically an organic solvent, such as ethyl acetate, dichloromethane, acetone, methanol, ethanol, isopropanol, or any combination thereof. Preferably, Class 3 solvents as listed in the guidance from the United States Food and Drug Administration at URL www.fda.gov/downloads/drugs/guidances/ucm073395.pdf (which include ethanol, acetone, and ethyl acetate) are used; however, Class 2 solvents (which include dichloromethane and methanol) can be used if necessary for the formulation. Class 1 and Class 4 solvents should be used only when the formulation cannot be prepared with a suitable Class 3 or Class 2 solvent.

Release rate-modulating polymer films can also be integrated onto segments by co-extrusion, where the segment formulation is co-extruded with a surrounding thin layer of the release rate-modulating polymer film.

The Examples below illustrate the use of some of these coating techniques for preparation of segments with a release rate-modulating polymer film.

Overall System Configuration

Various configurations of gastric residence systems are suitable for use as gastric residence systems, which are designed to provide sustained drug release of memantine and other adamantane-class drugs while resident in the stomach. One configuration is a "stellate" configuration of a gastric residence system, also known as a "star" (or "asterisk") configuration. An example of a stellate system 100 is shown schematically in FIG. 1A. Multiple elongate members, or "arms" (only one such arm, 108, is labeled for clarity), are affixed to disk-shaped central elastomer 106. The elongate members or arms depicted in FIG. 1A are comprised of segments 102 and 103, joined by a coupling polymer or linker region 104 (again, the components are only labeled in one arm for clarity) which serves as a linker region. This configuration permits the system to be folded or compacted at the central elastomer. FIG. 1B shows a folded configuration 190 of the gastric residence system of FIG. 1A (for clarity, only two arms are illustrated in FIG. 1B). Segments 192 and 193, linker region 194, elastomer 196, and arm 198 of FIG. 1B correspond to segments 102 and 103, linker region 104, elastomer 106, and arm 108 of FIG. 1A, respectively. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

While the linker regions 104 are shown as slightly larger in diameter than the segments 102 and 103 in FIG. 1A, they can be the same diameter as the segments, so that the entire elongate member 102-104-103 has a smooth outer surface.

In some embodiments, the stellate system may have an elongate member or arm composed of only one segment, which is attached to the central elastomer by a linker region. This corresponds to FIG. 1A with the segments 103 omitted. The single-segment elongate members comprising segments 102 are then directly attached to central elastomer 106 via the linkers 104. The linkers can comprise a coupling polymer or a disintegrating matrix.

A stellate system can be described as a gastric residence system for administration to the stomach of a patient, comprising an elastomer component, and a plurality of at least three carrier polymer-agent components comprising a carrier polymer and an agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member independently comprises one or more segments, each segment comprising a proximal end, a distal end, and an outer surface therebetween; and wherein, when two or more segments are present in an elongate member, each segment is attached to an adjacent segment via a linker region. The linker region can be a coupling polymer or a disintegrating matrix. The elongate members can be attached to the central elastomer via a coupling polymer or a disintegrating matrix, and can have intervening portions of interfacing polymers. For the plurality of at least three elongate members, or for a plurality of elongate members, a preferred number of elongate members is six, but three, four, five, seven, eight, nine, or ten elongate members can be used. The elongate members should be equally spaced around the central elastomer; if there are N elongate members, there will be an angle of about 360/N degrees between neighboring elongate members.

Figure 1C:
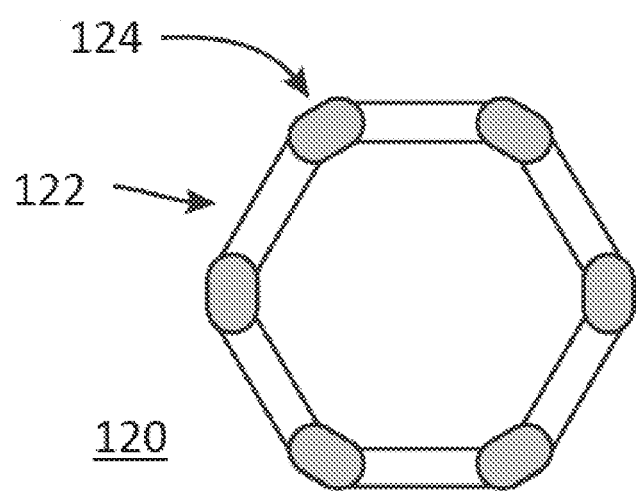
FIG. 1C shows a ring design of a gastric residence system in an uncompacted state.

FIG. 1C shows another possible overall configuration for a gastric residence system, which is a ring configuration. Segments 122 are joined by coupling polymer or linker region 124 (only one segment and one coupling linkage are labeled for clarity). The coupling polymer/linker region in this design must also function as an elastomer, to enable the ring to be twisted into a compacted state for placement in a container, such as a capsule.

In one embodiment of the stellate configuration, the segments 102 and 103 comprise a carrier polymer blended with a drug of the adamantane class, such as memantine. In one embodiment of the ring configuration, the segments 122 comprise a carrier polymer blended with a drug of the adamantane class, such as memantine.

Segments and elongate members of the gastric residence systems can have cross-sections in the shape of a circle (in which case the segments are cylindrical), a polygon (such as segments with a triangular cross-section, rectangular cross-section, or square cross-section), or a pie-shaped cross-section (in which case the segments are cylindrical sections). Segments with polygon-shaped or pie-shaped cross-sections, and ends of cylindrically-shaped sections which will come into contact with gastric tissue, can have their sharp edges rounded off to provide rounded corners and edges, for enhanced safety in vivo. That is, instead of having a sharp transition between intersecting edges or planes, an arc is used to transition from one edge or plane to another edge or plane. Thus, a "triangular cross-section" includes cross-sections with an approximately triangular shape, such as a triangle with rounded corners. An arm with a triangular cross-section includes an arm where the edges are rounded, and the corners at the end of the arm are rounded. Rounded corners and edges are also referred to as fillet corners, filleted corners, fillet edges, or filleted edges.

As discussed herein, the segments of the gastric residence system, comprising carrier polymer and agent, can be covered with a release rate-modulating polymer film. In some embodiments, one or more of any coupling polymer, disintegrating matrix, or interfacing polymer affixed to the segments are also covered by the release rate-modulating polymer film. In some embodiments, one or more of any coupling polymer, disintegrating matrix, or interfacing polymer affixed to the segments are not covered by the release rate-modulating polymer film. If the coupling polymer (which may be an enteric polymer) or the disintegrating matrix is covered by the release rate-modulating polymer film, the kinetics of de-coupling or disintegration should be determined on the film-covered coupling polymer or the film-covered disintegrating matrix.

The coupling polymers of the gastric residence system, which serve as linker regions, are designed to break down gradually in a controlled manner during the residence period of the system in the stomach. If the gastric residence system passes prematurely into the small intestine in an intact form, the system is designed to break down much more rapidly to avoid intestinal obstruction. This is readily accomplished by using enteric polymers as coupling polymers. Enteric polymers are relatively resistant to the acidic pH levels encountered in the stomach, but dissolve rapidly at the higher pH levels found in the duodenum. In the event of undesired passage of the intact gastric residence system into the small intestine, the use of enteric coupling polymers as safety elements results in rapid breakdown of the system in order to avoid potential intestinal obstruction. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient. In the system shown in FIG. 1A, at least the coupling polymer used for the couplings 104 are made from such enteric polymers.

In additional embodiments, a time-dependent coupling polymer or linker can be used. Such a time-dependent coupling polymer or linker degrades in a predictable, time-dependent manner. In some embodiments, the degradation of the time-dependent coupling polymer or linker may not be affected by the varying pH of the gastrointestinal system.

In additional embodiments, different types of linkers can be used in the gastric residence systems. That is, both enteric linkers (or enteric coupling polymers) and time-dependent linkers (or time-dependent coupling polymers) can be used. In some embodiments, a single multi-segment elongate member (arm) of a stellate system can use both an enteric linker at some linker regions between segments, and a time-dependent linker at other linker regions between segments.

Linker regions are typically about 100 microns to about 1 millimeter in width, such as about 200 um to about 1000 um, about 300 um to about 1000 um, about 400 um to about 1000 um, about 500 um to about 1000 um, about 600 um to about 1000 um, about 700 um to about 1000 um, about 800 um to about 1000 um, or about 900 um to about 1000 um; or about 100 um to about 900 um about 100 um to about 800 um, about 100 um to about 700 um, about 100 um to about 600 um, about 100 um to about 500 um, about 100 um to about 400 um, about 100 um to about 300 um, or about 100 um to about 200 um. Linker regions can be about 100 um, about 200 um, about 300 um, about 400 um, about 500 um, about 600 um, about 700 um, about 800 urn, about 900 um, or about 1000 um in width, where each value can be plus or minus 50 um (±50 um).

The central elastomeric polymer of a stellate system, such as polymer 106 of FIG. 1A, is typically not an enteric polymer; however, the central elastomeric polymer can also be made from such an enteric polymer where desirable and practical. In a ring system, such as that shown in FIG. 1C, at least one, and preferably all, of the couplings 124 are made from such enteric polymers.

The central elastomer should have a specific durometer and compression set. The durometer is important because it determines the folding force of the dosage form and whether it will remain in the stomach; a preferred range is from about 60 to about 90 A. The compression set should be as low as possible to avoid having permanent deformation of the gastric residence system when stored in the capsule in its compacted configuration. A preferred range is about 10% to about 20% range. Materials that fit these requirements are the QP1 range of liquid silicone rubbers from Dow Corning. In any embodiments with a central elastomer, the QP1-270 (70 A durometer) liquid silicone rubber can be used.

Evaluation of Release Characteristics

The release characteristics of agent from segments, elongate members, and gastric residence systems can be evaluated by various assays. Assays for agent release are described in detail in the examples. Release of agent in vitro from segments, elongate members, and gastric residence systems can be measured by immersing a segment, elongate member, or gastric residence system in a liquid, such as water, 0.1N HCl, fasted state simulated gastric fluid (FaSSGF), or fed state simulated gastric fluid (FeSSGF). Fasted state simulated gastric fluid (FaSSGF) is preferred for release assays. Simulated gastric fluid indicates either fasted state simulated gastric fluid (FaSSGF) or fed state simulated gastric fluid (FeSSGF); when a limitation is specified as being measured in simulated gastric fluid (SGF), the limitation is met if the limitation holds in either fasted state simulated gastric fluid (FaSSGF) or fed state simulated gastric fluid (FeSSGF). For example, if a segment is indicated as releasing at least 10% of an agent over the first 24 hours in simulated gastric fluid, the limitation is met if the segment releases at least 10% of the agent over the first 24 hours in fasted state simulated gastric fluid, or if the segment releases at least 10% of the agent over the first 24 hours in fed state simulated gastric fluid.

Ethanol burst release is typically measured by immersing a segment, elongate member, or gastric residence system in a solution of 40% ethanol and 60% fasted state simulated gastric fluid for one hour, followed by immersing the same segment, elongate member, or gastric residence system in 100% fasted state simulated gastric fluid for the remainder of the test period, and measuring release of agent at appropriate time points. This test is designed to simulate the effects of consumption of alcoholic beverages by a patient having a gastric residence system of the invention deployed in the patient's stomach.

While in vitro tests can be performed using segments, elongate members, or gastric residence systems, use of segments for in vitro tests is most convenient for rapid evaluation of the release characteristics. When in vitro tests are done to compare release rates under different conditions (such as release in 100% FaSSGF versus release in 40% ethanol/60% FaSSGF), the comparison solutions are kept at the same temperature, such as room temperature, 25° C., or 37° C. Room temperature (ambient temperature) is a preferred temperature for comparisons; in one embodiment, the ambient temperature does not drop below 20° C. or exceed 25° C. (although it may fluctuate between 20° C. and 25° C.).

In vivo tests can be performed in animals such as dogs (for example, beagle dogs or hound dogs) and swine. For in vivo tests, a gastric residence system is used, since an individual segment or elongate member would not be retained in the stomach of the animal. Blood samples can be obtained at appropriate time points, and, if desired, gastric contents can be sampled by cannula or other technique.

Clinical trials in humans, conducted in accordance with appropriate laws, regulations, and institutional guidelines, also provide in vivo data.

Release Profiles

The increased linearity profiles of the segments with release rate-modulating polymer films provides advantageous release characteristics over a segment with the same carrier polymer-agent composition, but lacking the release rate-modulating polymer films. For example, a segment of a gastric residence system comprising a carrier polymer, an agent or a salt thereof, and a release rate-modulating polymer film configured to control the release rate of the agent, can have a release profile where the release rate-modulating polymer film is configured such that, over a seven-day incubation in simulated gastric fluid, the amount of the agent or salt thereof released during day 5 is at least about 40% of the amount of agent or salt thereof released during day 2. That is, over the seven day incubation period, the amount of the agent or salt thereof released from hours 96-120 (day 5) is at least about 40% of the amount of agent or salt released during hours 24-48 (day 2) of the incubation. In some embodiments, release over day 5 is at least about 50%, at least about 60%, at least about 70%, at least about 80%, or at least about 90% of the amount of agent or salt released over day 2. In some embodiments, release over day 5 is at least about 40% to about 90%, at least about 50% to about 90%, at least about 60% to about 90%, at least about 70% to about 90%, at least about 80% to about 90%, or at least about 40% to about 100%, of the amount of agent or salt released over day 2. In any of these embodiments, at least about 5% of the total amount of agent is released on day 2 and at least about 5% of the total amount of agent is released on day 5, at least about 5% of the total amount of agent is released on day 2 and at least about 7% of the total amount of agent is released on day 5, or at least about 7% of the total amount of agent is released on day 2 and at least about 7% of the total amount of agent is released on day 5. "Total amount of agent" refers to the amount of agent originally present in the segment.

In another embodiment, a segment of a gastric residence system comprising a carrier polymer, an agent or a salt thereof, and a release rate-modulating polymer film configured to control the release rate of the agent, can have a release profile where the release rate-modulating polymer film is configured such that, over a seven-day incubation in simulated gastric fluid, the amount of the agent or salt thereof released during day 7 is at least about 20% of the amount of agent or salt thereof released during day 1. That is, over the seven day incubation period, the amount of the agent or salt thereof released from hours 144-168 (day 7) is at least about 20% of the amount of agent or salt released during hours 0-24 (day 1) of the incubation. In some embodiments, release over day 7 is at least about 30%, at least about 40%, at least about 50%, at least about 60%, or at least about 70% of the amount of agent or salt released over day 1. In some embodiments, release over day 7 is at least about 20% to about 70%, at least about 30% to about 70%, at least about 40% to about 70%, at least about 50% to about 70%, at least about 60% to about 70%, or at least about 20% to about 100%, of the amount of agent or salt released over day 1. In any of these embodiments, at least about 7% of the total amount of agent is released on day 1 and at least about 4% of the total amount of agent is released on day 7, at least about 4% of the total amount of agent is released on day 1 and at least about 4% of the total amount of agent is released on day 7, or at least about 7% of the total amount of agent is released on day 1 and at least about 7% of the total amount of agent is released on day 7. "Total amount of agent" refers to the amount of agent originally present in the segment.

Segments with release rate-modulating polymer films of the invention also have lower burst release when initially immersed in simulated gastric fluid. In one embodiment, a segment of a gastric residence system comprising a carrier polymer and an agent or a salt thereof, where the segment has a release rate-modulating polymer film configured to control the release rate of the agent, can have a release profile where the release rate-modulating polymer film is configured such that the release of agent from the segment in simulated gastric fluid over an initial 24 hour period is at least about 40% lower than the release of agent from a second segment in simulated gastric fluid over an initial 6 hour period, where the second segment comprises the same combination of carrier polymer and agent or salt thereof, but lacks the release rate-modulating polymer film; and wherein the release of agent from the segment with the polymer film in simulated gastric fluid over a seven-day period is either i) at least about 60% of the release of agent from the second segment lacking the polymer film over a seven-day period, or ii) at least 60% of the total amount of agent originally present in the segment. In further embodiments, the release of agent from the segment with the film in simulated gastric fluid over an initial 24 hour period is at least about 40% lower, about 40% to about 50% lower, about 40% to about 60% lower, or about 40% to about 70% lower than the release of agent from a second segment without the film in simulated gastric fluid over an initial 6 hour period, while the release of agent from the segment with the film in simulated gastric fluid over a seven day period is either i) at least about 60%, at least about 70%, at least about 80%, or about 60% to about 80% of the release of agent from the second segment in simulated gastric fluid lacking the polymer film over a seven-day period, or ii) at least about 60%, at least about 70%, at least about 80%, or about 60% to about 80% of the total amount of agent originally present in the segment. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) at least about 60%, at least about 70%, at least about 75%, or at least about 80% (such as about 60% to about 70%, about 60% to about 80%, about 60% to about 90%, or about 60% to about 99%) of the total amount of agent originally present in the segment.

Segments with release rate-modulating polymer films of the invention also have lower burst release in an ethanol challenge as compared to segments lacking the films. In one embodiment, a segment of a gastric residence system comprising a carrier polymer and an agent or a salt thereof, where the segment has a release rate-modulating polymer film configured to control the release rate of the agent, can have a release profile where the release rate-modulating polymer film is configured such that the release of agent from the segment in 40% ethanol/60% simulated gastric fluid over one hour is at least about 40% lower than the release of agent from a second segment in 40% ethanol/60% simulated gastric fluid over one hour, the second segment comprising the same combination of carrier polymer and agent or salt thereof but lacking the release rate-modulating polymer film. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) i) at least about 60%, at least about 70%, at least about 75%, or at least about 80% (such as about 60% to about 70%, about 60% to about 80%, about 60% to about 90%, or about 60% to about 99%) of the total amount of agent originally present in the segment. In one embodiment, a segment of a gastric residence system comprising a carrier polymer and an agent or a salt thereof, where the segment has a release rate-modulating polymer film configured to control the release rate of the agent, can have a release profile where the release rate-modulating polymer film is configured such that the release of agent from the segment in 40% ethanol/60% simulated gastric fluid over one hour is no more than about 40% higher compared to release of agent from an equivalent segment in 100% simulated gastric fluid over one hour. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) at least about 60%, at least about 70%, at least about 75%, or at least about 80% (such as about 60% to about 70%, about 60% to about 80%, about 60% to about 90%, or about 60% to about 99%) of the total amount of agent originally present in the segment.

Linearity of release of agent from segments having a release rate-modulating polymer film coating is also improved. In one embodiment, a segment of a gastric residence system comprising a carrier polymer and an agent or a salt thereof, where the segment has a release rate-modulating polymer film configured to control the release rate of the agent, can have a release profile where the release rate-modulating polymer film is configured such that a best-fit linear regression model of the release rate of agent has a coefficient of determination R2 of at least about 0.8, at least about 0.85, or at least about 0.9 over an initial period of seven days in simulated gastric fluid (where the initial period of seven days is measured from the start time when the segment is initially immersed in simulated gastric fluid; that is, the period of seven days includes the time at t=0 or origin point of the release profile); and wherein the segment releases about 30% to about 70% of the agent or salt thereof within a time of about 40% to about 60% of the seven-day period.

In one embodiment, a segment of a gastric residence system comprising a carrier polymer and an agent or a salt thereof, where the segment has a release rate-modulating polymer film configured to control the release rate of the agent, can have a release profile where the release rate-modulating polymer film is configured such that the release rate over any one of the seven days varies by no more than about 50%, no more than about 40%, no more than about 30%, no more than about 25%, no more than about 20%, or no more than about 10% from the average daily total release over the seven days.

System Dimensions

The system must be able to adopt a compacted state with dimensions that enable the patient to swallow the system (or for the system to be introduced into the stomach by alternate methods, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in Table 1 (see "Draft Guidance for Industry on Size, Shape, and Other Physical Attributes of Generic Tablets and Capsules" at URL www.regulations.gov/#!documentDetail;D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in Table 1.

TABLE 1

| Capsule Size | Outer Diameter (mm) | Length (mm) |
| --- | --- | --- |
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule. Once the capsule dissolves in the stomach, the system will adopt a configuration suitable for gastric retention. Preferred capsule sizes are 00 and 00el (a 00el-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In one embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter.

For star-shaped polymers with N arms (where N is greater than or equal to three), the arms can have dimensions such that the system has at least two perpendicular dimensions, each of length as noted above. These two perpendicular dimensions are chosen as noted above in order to promote retention of the gastric residence system.

The system is designed to eventually break apart in the stomach at the end of the desired residence time. Once the coupling polymers break, the remaining components of the system are of dimensions that permit passage of the system through the pyloric sphincter, small intestine, and large intestine. Finally, the system is eliminated from the body by defecation, or by eventual complete dissolution of the system in the small and large intestines.

System Polymeric Composition

The choice of the individual polymers for the carrier polymer, coupling polymer, and elastomer influence many properties of the system, such as drug elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of drug from the carrier polymer-drug component is affected by numerous factors, including the composition and properties of the carrier polymer, which may itself be a mixture of several polymeric and non-polymeric components; the properties of the drug such as hydrophilicity/hydrophobicity, charge state, pKa, and hydrogen bonding capacity; and the properties of the gastric environment. In the aqueous environment of the stomach, avoiding burst release of a drug (where burst release refers to a high initial delivery of active pharmaceutical ingredient upon initial deployment of the system in the stomach), particularly a hydrophilic drug, and maintaining sustained release of the drug over a period of time of days to one or two weeks is challenging.

The residence time of the systems in the stomach is adjusted by the choice of coupling polymers used in the linker regions. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

Carrier Polymers for Carrier Polymer-Drug Component

The carrier polymer-drug component contains the drug or salt thereof to be eluted from the gastric residence system in the gastric environment. Drug (or salt thereof) is blended into the carrier polymer to form a carrier polymer-drug mixture. This mixture can be formed into the desired shape or shapes for use as carrier polymer-drug components in the systems. After the drug or drug salt is blended into the carrier polymer to form the carrier polymer-drug mixture, the drug or drug salt is distributed or dispersed throughout the blended mixture. If excipients, anti-oxidants, or other ingredients are included in the carrier polymer-drug blend, they will also be distributed or dispersed throughout the blended mixture.

Preferably, carrier polymers have the following characteristics. They should be thermoplastic, to allow extrusion using hot melt extrusion or 3D printing techniques. They should also have a high enough melt strength and viscosity to enable extrusion into the required geometry. They should have low melting temperatures (for example, less than about 120° C.), to avoid exposing agents or drugs to high temperatures during manufacture. They should have sufficient mechanical strength (Young's modulus, compression strength, tensile strength) to avoid breaking in the stomach during the desired residence period. They should be capable of forming stable blends with agents, drugs, drugs, excipients, dispersants, and other additives.

Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylo-maltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer. In another embodiment, polydioxanone is used as the carrier polymer. In any of the embodiments of the gastric residence system, the carrier polymer used in the gastric residence system can comprise polycaprolactone, such as linear polycaprolactone with a number-average molecular weight (Mn) range between about 60 kiloDalton (kDa) to about 100 kDa; 75 kDa to 85 kDa; or about 80 kDa; or between about 45 kDa to about 55 kDa.

Other excipients can be added to the carrier polymers to modulate the release of drug. Such excipients can be added in amounts from about 1% to about 30% or 1% to about 15%, preferably from about 5% to about 10%, more preferably about 5% or about 10%. Examples of such excipients include Poloxamer 407 (available as Kolliphor P407, Sigma Cat #62035), poly(ethylene glycol)-block-poly(propylene glycol)-block-poly(ethylene glycol), CAS No. 9003-11-6; H—$(OCH_2CH_2)_x$—(O—$CH(CH_3)CH_2)_y$—$(OCH_2CH_2)_z$—OH where x and z are about 101 and y is about 56); Pluronic P407; Eudragit E, Eudragit EPO (available from Evonik); hypromellose (available from Sigma, Cat # H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), and Soluplus (available from BASF; a copolymer of polyvinyl caprolactam, polyvinyl acetate, and polyethylene glycol). Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. EUDRAGIT RS and EUDRAGIT RL are registered trademarks of Evonik (Darmstadt, Germany) for copolymers of ethyl acrylate, methyl methacrylate and methacrylic acid ester with quaternary ammonium groups (trimethylammonioethyl methacrylate chloride), having a molar ratio of ethyl acrylate, methyl methacrylate and trimethylammonioethyl methacrylate of about 1:2:0.2 in Eudragit® RL and about 1:2:0.1 in Eudragit® RS. Preferred insoluble, swellable excipients include crospovidone, croscarmellose, hypromellose acetate succinate (HPMCAS), carbopol, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%).

Methods of Manufacture of Carrier Polymer-Drug Components

Blending temperatures for incorporation of the drug into polymeric matrices typically range from about 80° C. to about 120° C., although higher or lower temperatures can be used for polymers which are best blended at temperatures outside that range. When drug particles of a particular size are used, and it is desired that the size of the particles be maintained during and after blending, blending can be done at temperatures below the melting point of the drug, so as to maintain the desired size of the drug. Otherwise, temperatures can be used which melt both the polymer and the drug. Blending temperatures should be below the degradation temperature of the drug. In one embodiment, less than about 2% of the drug is degraded during manufacture. In one embodiment, less than about 1.5% of the drug is degraded during manufacture. In one embodiment, less than about 1% of the drug is degraded during manufacture. In one embodiment, less than about 0.75% of the drug is degraded during manufacture. In one embodiment, less than about 0.5% of the drug is degraded during manufacture. In one embodiment, less than about 0.4% of the drug is degraded during manufacture. In one embodiment, less than about 0.3% of the drug is degraded during manufacture. In one embodiment, less than about 0.2% of the drug is degraded during manufacture. In one embodiment, less than about 0.15% of the drug is degraded during manufacture. In one embodiment, less than about 0.1% of the drug is degraded during manufacture. In one embodiment, less than about 0.05% of the drug is degraded during manufacture. In one embodiment, less than about 0.04% of the drug is degraded during manufacture. In one embodiment, less than about 0.03% of the drug is degraded during manufacture. In one embodiment, less than about 0.02% of the drug is degraded during manufacture. In one embodiment, less than about 0.01% of the drug is degraded during manufacture.

Hot melt extrusion can be used to prepare the carrier polymer-drug components. Single-screw or, preferably, twin-screw systems can be used. As noted, if it is desired that the size of the particles be maintained during and after blending, carrier polymers should be used which can be melted at temperatures which do not degrade the drug. Otherwise, temperatures can be used which melt both the polymer and the drug.

Melting and casting can also be used to prepare the carrier polymer-drug components. The carrier polymer and drug, and any other desired components, are mixed together. The carrier polymer is melted and the melt is mixed so that the drug particles are evenly distributed in the melt, poured into a mold, and allowed to cool.

Solvent casting can also be used to prepare the carrier polymer-drug components. The polymer is dissolved in a solvent, and particles of drug are added. If the size of the drug particles are to be maintained, a solvent should be used which does not dissolve the drug particles, so as to avoid altering the size characteristics of the particles; otherwise, a solvent which dissolves both the polymer and drug particles can be used. The solvent-carrier polymer-drug particle mixture (or solvent-carrier particle-drug solution), is then mixed to evenly distribute the particles (or thoroughly mix the solution), poured into a mold, and the solvent is evaporated.

Manufacture of Feed Polymers for Three-Dimensional Printing

Three-dimensional printing is often accomplished by feeding a rod or fiber of a solid material to a print head, where it is melted and deposited with subsequent solidification, in a technique known as fused deposition modeling (sometimes also called extrusion deposition); see U.S. Pat. Nos. 5,121,329 and 5,340,433. The methods described herein for the manufacture of carrier polymer-drug components can also be used to manufacture feed material, which can be used in the manufacture via three-dimensional printing of components of the gastric residence systems.

Drug Particle Size and Milling

Control of the particle size of the adamantane-class drugs, such as memantine, used in the gastric residence systems is important for both optimal drug release and mechanical stability of the systems. The particle size of the drug affects the surface area of the drug available for dissolution when gastric fluid permeates the carrier polymer-drug components of the system. Also, as the "arms" (elongate members) of the systems are relatively thin in diameter (for example, 1 millimeter to 5 millimeters), the presence of an drug particle of a size in excess of a few percent of the diameter of the arms will result in a weaker arm, both before the drug elutes from the device, and after elution when a void is left in the space formerly occupied by the drug particle. Such weakening of the arms is disadvantageous, as it may lead to premature breakage and passage of the system before the end of the desired residence period. FIG. 34 shows unprocessed memantine (left panel) and memantine after milling (right panel), showing the reduction in particle size and increase uniformity of the milled drug.

In one embodiment, the drug particles used for blending into the carrier polymer-drug components are smaller than about 100 microns in diameter. In some embodiments, the therapeutic drug particles are smaller than about 75 microns in diameter. In some embodiments, the drug particles are smaller than about 50 microns in diameter. In some embodiments, the drug particles are smaller than about 40 microns in diameter. In some embodiments, the drug particles are smaller than about 30 microns in diameter. In some embodiments, the drug particles are smaller than about 25 microns in diameter. In some embodiments, the drug particles are smaller than about 20 microns in diameter. In some embodiments, the drug particles are smaller than about 10 microns in diameter. In some embodiments, the drug particles are smaller than about 5 microns in diameter.

In one embodiment, at least about 80% of the total number of drug particles used for blending into the carrier polymer-drug components are smaller than about 100 microns in diameter. In some embodiments, at least about 80% of the total number of drug particles are smaller than about 75 microns in diameter. In some embodiments, at least about 80% of the total number of drug particles are smaller than about 50 microns in diameter. In some embodiments, at least about 80% of the total number of drug particles are smaller than about 40 microns in diameter. In some embodiments, at least about 80% of the total number of drug particles are smaller than about 30 microns in diameter. In some embodiments, at least about 80% of the total number of drug particles are smaller than about 25 microns in diameter. In some embodiments, at least about 80% of the total number of drug particles are smaller than about 20 microns in diameter. In some embodiments, at least about 80% of the total number of drug particles are smaller than about 10 microns in diameter. In some embodiments, at least about 80% of the total number of drug particles are smaller than about 5 microns in diameter.

In one embodiment, at least about 80% of the mass of drug particles used for blending into the carrier polymer-drug components have sizes between about 1 micron and about 100 microns in diameter. In some embodiments, at least about 80% of the mass of drug particles have sizes between about 1 micron and about 75 microns in diameter. In some embodiments, at least about 80% of the mass of drug particles have sizes between about 1 micron and about 50 microns in diameter. In some embodiments, at least about 80% of the mass of drug particles have sizes between about 1 micron and about 40 microns in diameter. In some embodiments, at least about 80% of the mass of drug particles have sizes between about 1 micron and about 30 microns in diameter. In some embodiments, at least about 80% of the mass of drug particles have sizes between about 1 micron and about 25 microns in diameter. In some embodiments, at least about 80% of the mass of drug particles have sizes between about 1 micron and about 20 microns in diameter. In some embodiments, at least about 80% of the mass of drug particles have sizes between about 1 micron and about 10 microns in diameter. In some embodiments, at least about 80% of the mass of drug particles have sizes between about 1 micron and about 5 microns in diameter.

In one embodiment, at least about 80% of the mass of drug particles used for blending into the carrier polymer-drug components have sizes between about 2 microns and about 100 microns in diameter. In some embodiments, at least about 80% of the mass of drug particles have sizes between about 2 microns and about 75 microns in diameter. In some embodiments, at least about 80% of the mass of drug particles have sizes between about 2 microns and about 50 microns in diameter. In some embodiments, at least about 80% of the mass of drug particles have sizes between about 2 microns and about 40 microns in diameter. In some embodiments, at least about 80% of the mass of drug particles have sizes between about 2 microns and about 30 microns in diameter. In some embodiments, at least about 80% of the mass of drug particles have sizes between about 2 microns and about 25 microns in diameter. In some embodiments, at least about 80% of the mass of drug particles have sizes between about 2 microns and about 20 microns in diameter. In some embodiments, at least about 80% of the mass of drug particles have sizes between about 2 microns and about 10 microns in diameter. In some embodiments, at least about 80% of the mass of drug particles have sizes between about 2 microns and about 5 microns in diameter.

In one embodiment, at least about 80% of the mass of drug particles used for blending into the carrier polymer-drug components have sizes between about 5 microns and about 100 microns in diameter. In some embodiments, at least about 80% of the mass of drug particles have sizes between about 5 microns and about 75 microns in diameter. In some embodiments, at least about 80% of the mass of drug particles have sizes between about 5 microns and about 50 microns in diameter. In some embodiments, at least about 80% of the mass of drug particles have sizes between about 5 microns and about 40 microns in diameter. In some embodiments, at least about 80% of the mass of drug particles have sizes between about 5 microns and about 30 microns in diameter. In some embodiments, at least about 80% of the mass of drug particles have sizes between about 5 microns and about 25 microns in diameter. In some embodiments, at least about 80% of the mass of drug particles have sizes between about 5 microns and about 20 microns in diameter. In some embodiments, at least about 80% of the mass of drug particles have sizes between about 5 microns and about 10 microns in diameter.

The particle size of the drugs can be readily adjusted by milling Several milling techniques are available to reduce larger particles to smaller particles of desired size. Fluid energy milling is a dry milling technique which uses inter-particle collisions to reduce the size of particles. A type of fluid energy mill called an air jet mill shoots air into a cylindrical chamber in a manner so as to maximize collision between drug particles. Ball milling utilizes a rolling cylindrical chamber which rotates around its principal axis. The drug and grinding material (such as steel balls, made from chrome steel or CR—NI steel; ceramic balls, such as zirconia; or plastic polyamides) collide, causing reduction in particle size of the drug. Ball milling can be performed in either the dry state, or with liquid added to the cylinder where the drug and the grinding material are insoluble in the liquid. Further information regarding milling is described in the chapter by R. W. Lee et al. entitled "Particle Size Reduction" in *Water-Insoluble Drug Formulation, Second Edition* (Ron Liu, editor), Boca Raton, Fla.: CRC Press, 2008; and in the chapter by A. W. Brzeczko et al. entitled "Granulation of Poorly Water-Soluble Drugs" in *Handbook of Pharmaceutical Granulation Technology, Third Edition* (Dilip M. Parikh, editor), Boca Raton, Fla.: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Milling Additives

Substances can be added to the drug material during milling to assist in obtaining particles of the desired size, and minimize aggregation during handling. Silica (silicon dioxide, $SiO_2$) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 20% of milling additive, such as silica, can be used for fluid milling or ball milling, or about 0.1% to about 15%, or about 0.1% to about 10%, or about 0.1% to about 5%, or about 0.1% to about 4%, about 0.1% to about 3%, about 0.1% to about 2%, about 0.1% to about 1%, about 1% to about 20%, about 1% to about 15%, about 1% to about 10%, about 1% to about 5%, about 1% to about 4%, about 1% to about 3%, about 1% to about 2%, or about 0.1%, about 0.5%, about 1%, about 2%, about 3%, about 4% or about 5%.

Particle Sizing

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

Dispersants for Modulation of Drug Release and Stability of Polymer Blend

The use of a dispersant in the carrier polymer-drug component provides numerous advantages. The rate of elution of drug from the carrier polymer-drug component is affected by numerous factors as previously noted, including the composition and properties of the carrier polymer (which may itself comprise multiple polymeric and non-polymeric components); the physical and chemical properties of the drug; and the gastric environment. Avoiding burst release of drug and maintaining sustained release of the drug over the residence period is an important characteristic of the systems. The use of a dispersant according to the invention enables better control of release rate and suppression of burst release. Burst release and release rate can be tuned by using varied concentrations of dispersant.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant. One particularly useful silicon dioxide is sold by Cabot Corporation (Boston, Mass., USA) under the registered trademark CAB-O-SIL® M-5P (CAS#112945-52-5), which is hydrophilic-fumed silicon dioxide having a BET surface area of about 200 $m^2/g \pm 15\ m^2/g$ The mesh residue for this product on a 45 micron sieve is less than about 0.02%. The typical primary aggregate size is about 150 to about 300 nm, while individual particle sizes may range from about 5 nm to about 50 nm.

In addition to anti-aggregation/anti-flocculation activity, the dispersant can help prevent phase separation during fabrication and/or storage of the systems. This is particularly useful for manufacture of the systems by hot melt extrusion.

The weight/weight ratio of dispersant to drug substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Dispersants can also be used to modulate the amount of burst release during the initial period when the gastric residence system is administered. In embodiments of a gastric residence system that is to be administered once weekly, the burst release over the approximately first six hours after initial administration is less than about 8%, preferably less than about 6%, of the total amount of drug in the system. In embodiments of a gastric residence system that is to be administered once every three days, the burst release over the approximately first six hours after initial administration is less than about 12%, preferably less than about 10%, of the total amount of drug in the system. In embodiments of a gastric residence system that is to be administered once daily, the burst release over the approximately first six hours after initial administration is less than about 40%, preferably less than about 30%, of the total amount of drug in the system. In general, if a new gastric residence system is administered every D days, and the total mass of drug is M, then the gastric residence system releases less than about [(M divided by D) times 0.5], preferably less than about [(M divided by D) multiplied by 0.4], or less than about [(M divided by D) multiplied by ⅜], more preferably less than about [(M divided by D) multiplied by 0.3], over the approximately first six hours after initial administration. In further embodiments, the gastric residence system releases at least about [(M divided by D) multiplied by 0.25] over the approximately first six hours after initial administration, that is, the system releases at least about one-quarter of the daily dosage over the first one-quarter of the first day of administration.

Coupling Polymers

The coupling polymer is used to link one or more carrier polymer-drug components to one or more carrier polymer-drug components, to link one or more carrier polymer-drug components to one or more elastomer components, or to link one or more elastomer components to one or more elastomer components. Thus, the coupling polymers form linker regions between other components of the system. Enteric polymers and time-dependent polymers are preferred for use as coupling polymers. In some embodiments, enteric polymers are used as coupling polymers. In some embodiments, time-dependent polymers which are pH-resistant, that is, less sensitive to changes in pH than enteric polymers, are used as coupling polymers. In some embodiments, both enteric polymers and time-dependent polymers which are less sensitive to changes in pH than enteric polymers are used as coupling polymers.

Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. Thus, the gastric residence systems are designed to uncouple rapidly in the intestinal environment by dissolution of the coupling polymer, within 48 hours, preferably within 24 hours, more preferably within 12 hours, yet more preferably within 1-2 hours, so as to avoid potential intestinal blockage. If, during treatment, the gastric residence system must be removed quickly for any reason, the patient can drink a mildly basic aqueous solution (such as a bicarbonate solution) in order to induce immediate de-coupling of the gastric residence system.

By "time-dependent polymer which are pH-resistant" (or equivalently, "pH-resistant time-dependent polymers") is meant that, under conditions where an enteric polymer would degrade to the point that it would no longer link the components together, the time-dependent polymer will still have sufficient mechanical strength to link the components together. In some embodiments, the time-dependent polymer retains about the same linking capacity, that is, about 100% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 90% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 75% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 60% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 50% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 25% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer resists breaking under a flexural force of about 0.2 Newtons (N), about 0.3 N, about 0.4 N, about 0.5 N, about 0.75 N, about 1 N, about 1.5 N, about 2 N, about 2.5 N, about 3 N, about 4 N, or about 5 N, after exposure to a solution between about pH 7 to about pH 8, where the exposure is for about an hour, about a day, about three days, or about a week. Linkage strength can be measured by any relevant test that serves to test coupling ability, such as a four-point bending flexural test (ASTM D790).

Exemplary coupling polymers include, but are not limited to, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in Table 2, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Röhm GmbH, Darmstadt, Germany) is a preferred enteric polymer. Another preferred enteric polymer is hydroxypropylmethylcellulose acetate succinate (hypromellose acetate succinate or HPMCAS; Ashland, Inc., Covington, Ky., USA), which has a tunable pH cutoff from about 5.5 to about 7.0. Cellulose acetate phthalate, cellulose acetate succinate, and hydroxypropyl methylcellulose phthalate are also suitable enteric polymers.

In one embodiment, the enteric polymers used in the gastric residence system dissolve at a pH above about 4. In some embodiments, the enteric polymers used in the gastric residence system dissolve at a pH above about 5. In some embodiments, the enteric polymers used in the gastric residence system dissolve at a pH above about 6. In some embodiments, the enteric polymers used in the gastric residence system dissolve at a pH above about 7. In some embodiments, the enteric polymers used in the gastric residence system dissolve at a pH above about 7.5. In some embodiments, the enteric polymers used in the gastric residence system dissolve at a pH between about 4 and about 5. In some embodiments, the enteric polymers used in the gastric residence system dissolve at a pH between about 4 and about 6. In some embodiments, the enteric polymers used in the gastric residence system dissolve at a pH between about 4 and about 7. In some embodiments, the enteric polymers used in the gastric residence system dissolve at a pH between about 4 and about 7.5. In some embodiments, the enteric polymers used in the gastric residence system dissolve at a pH between about 5 and about 6. In some embodiments, the enteric polymers used in the gastric residence system dissolve at a pH between about 5 and about 7. In some embodiments, the enteric polymers used in the gastric residence system dissolve at a pH between about 5 and about 7.5. In some embodiments, the enteric polymers used in the gastric residence system dissolve at a pH between about 6 and about 7. In some embodiments, the enteric polymers used in the gastric residence system dissolve at a pH between about 6 and about 7.5.

TABLE 2

| Polymer | Dissolution pH |
| --- | --- |
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are polymers that degrade in a time-dependent manner in the gastric environment. The liquid plasticizer triacetin releases from a polymer formulation in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture (that is, using less triacetin in the mixture), while the degradation time can be decreased by decreasing the amount of Plastoid B used in the mixture (that is using more triacetin in the mixture).

A variety of time-dependent mechanisms are available. Water-soluble time-dependent polymers break down as water penetrates through the polymer. Examples of such polymers are hydroxypropyl methylcellulose and poly vinyl acetate. Acid soluble time-dependent polymers break down over time in an acidic environment. Examples include Eudragit EPO. Time-dependent polymers can use water soluble plasticizers; as plasticizer is released, the remaining polymer becomes brittle and breaks under gastric forces. Examples of such polymers include triacetin and triethyl citrate.

In some embodiments, the carrier polymer-drug components are elongate members comprised of segments attached by enteric polymers. In some embodiments, the carrier polymer-drug components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

In some embodiments, the carrier polymer-drug components are non-segmented elongate members attached to the elastomer component of the system by enteric polymers, time-dependent linkers, or disintegrating matrices, or by any combination of enteric polymers, time-dependent linkers, and/or disintegrating matrices.

In any of the embodiments of the gastric residence systems described herein, the coupling polymers or linkers can comprise hydroxypropyl methyl cellulose acetate succinate (HPMCAS) and polycaprolactone (PCL). These blends can be used to form disintegrating linkers or disintegrating matrices. The ratio of HPMCAS to polycaprolactone in the disintegrating linker or disintegrating matrix can be between about 80% HPMCAS:20% PCL to about 20% HPMCAS:80% PCL. the ratio of HPMCAS to polycaprolactone can be between about 80% HPMCAS:20% PCL to about 20% HPMCAS:80% PCL; between about 70% HPMCAS:30% PCL to about 30% HPMCAS:70% PCL; between about 60% HPMCAS:40% PCL to about 40% HPMCAS:60% PCL; between about 80% HPMCAS:20% PCL to about 50% HPMCAS:50% PCL; between about 80% HPMCAS:20% PCL to about 60% HPMCAS:40% PCL; between about 70% HPMCAS:30% PCL to about 50% HPMCAS:50% PCL; between about 70% HPMCAS:30% PCL to about 60% HPMCAS:40% PCL; between about 20% HPMCAS:80% PCL to about 40% HPMCAS:60% PCL; between about 20% HPMCAS:80% PCL to about 50% HPMCAS:50% PCL; between about 30% HPMCAS:70% PCL to about 40% HPMCAS:60% PCL; between about 30% HPMCAS:70% PCL to about 50% HPMCAS:50% PCL; or about 80% HPMCAS:20% PCL, about 70% HPMCAS:30% PCL, about 60% HPMCAS:40% PCL, about 50% HPMCAS:50% PCL, about 40% HPMCAS:60% PCL, about 30% HPMCAS:70% PCL, or about 20% HPMCAS:80% PCL. The linker can further comprise a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

The linkers are chosen to weaken sufficiently after a specified period of time in order to allow the gastric residence systems to reach a point where they de-couple and pass through the pylorus and out of the stomach after the desired residence period or weaken sufficiently such that the gastric residence system is no longer retained in the stomach; that is, the linkers weaken to the point of uncoupling (the uncoupling point) or to the point where the gastric residence system can pass through the pylorus (the pyloric passage point, or passage point). Thus, in one embodiment, linkers are used that uncouple after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In one embodiment, linkers are used that uncouple after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In one embodiment, linkers are used that uncouple after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In one embodiment, linkers are used that uncouple after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In one embodiment, linkers are used that uncouple after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In one embodiment, linkers are used that uncouple after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In one embodiment, linkers are used that uncouple after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

The de-coupling or pyloric passage point in human, dog, or pig occurs when the system passes out of the stomach, that is, when it passes through the pylorus. For the in vitro measurements in simulated gastric fluid or acidic water, the de-coupling or pyloric passage point occurs when the linker weakens to the point where it will break under the normal compressive forces of the stomach, typically about 0.1 Newton to 0.2 Newton. Linkage strength (breaking point) can be measured by any relevant test that serves to test coupling ability, that is, the force required to break the linker, such as the four-point bending flexural test (ASTM D790) described in Example 18 of WO 2017/070612, or Examples 12, 13, 15, 17, or 18 of PCT/US2016/065453. In one embodiment, the de-coupling or pyloric passage point is reached when the linkers uncouple at about 0.2 N of force. In another embodiment, the de-coupling or pyloric passage point is reached when the linkers uncouple at about 0.1 N of force.

The gastric residence systems can reach the pyloric passage point without any or all of the linkers actually breaking. If the linkers weaken or degrade to the point where they can no longer hold the gastric residence system in the stomach, even if one, some, or all of the linkers do not break, the gastric residence system will pass through the pylorus and into the small intestine (the pyloric passage point or passage point). In some embodiments, linkers are used that weaken to the passage point after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In some embodiments, linkers are used that weaken to the passage point after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In some embodiments, linkers are used that weaken to the passage point after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In some embodiments, linkers are used that weaken to the passage point after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In some embodiments, linkers are used that weaken to the passage point after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In some embodiments, linkers are used that weaken to the passage point after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In some embodiments, linkers are used that weaken to the passage point after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

Elastomers

Elastomers (also referred to as elastic polymers or tensile polymers) can be used as coupling polymers, and enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In one embodiment, the elastomer is a silicone elastomer. In one embodiment, the elastomer is formed from a liquid silicone rubber, such as sold in the Dow Corning QP-1 liquid silicone rubber kit. In one embodiment, the elastomer is crosslinked polycaprolactone. In one embodiment, the elastomer is an enteric polymer, such as those listed in Table 2. In some embodiments, the coupling polymer(s) used in the system are also elastomers. Elastomers are preferred for use as the central polymer in the star-shaped or stellate design of the gastric residence systems.

In one embodiment, both the coupling polymer and elastomer are enteric polymers, which provides for more complete breakage of the system into the carrier polymer-drug pieces if the system enters the intestine, or if the patient drinks a mildly basic solution in order to induce passage of the system.

Examples of elastomers which can be used include silicones, such as those formed using Dow Corning QP-1 kits; urethane-cross-linked polycaprolactones; poly(acryloyl 6-aminocaproic acid) (PA6ACA); poly(methacrylic acid-co-ethyl acrylate) (EUDRAGIT L 100-55); and mixtures of poly(acryloyl 6-aminocaproic acid) (PA6ACA) and poly(methacrylic acid-co-ethyl acrylate) (EUDRAGIT L 100-55).

Flexible coupling polymers, i.e., elastomeric coupling polymers or elastomers, are used as the central polymer in the star-shaped or stellate design of the gastric residence systems. A particularly preferred elastomer for use as the central elastomer of the stellate or star configuration is silicone rubber. Liquid silicone rubber (LSR) can be molded easily and cured into a desired shape. The Dow Corning QP-1 series, comprising cross-linked dimethyl and methyl-vinyl siloxane copolymers and reinforcing silica, are examples of such silicone rubber polymers (see, for example, the Web site www.dowcorning.com/DataFiles/090276fe8018ed07.pdf). Non-segmented elongate members or elongate members comprising segments of carrier polymer-agent components can then be attached to the central silicone rubber elastomer. Another elastomer which can be used as the central elastomer in the stellate design is cross-linked polycaprolactone.

Other System Characteristics

Stabilization of Drugs

Many drugs are prone to oxidative degradation when exposed to reactive oxygen species, which can be present in the stomach. A drug contained in the system may thus oxidize due to the prolonged residence in the stomach of the system, and the extended release period of drug from the system. Accordingly, it is desirable to stabilize the drug to prevent oxidative and other degradation.

Anti-oxidant stabilizers that can be included in the systems to reduce or prevent oxidation of the drug include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm). Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate can be used as anti-oxidant stabilizers.

Certain drugs can be pH-sensitive, especially at the low pH present in the gastric environment. Should the adamantane-class drug, such as memantine, in the gastric residence system require stabilization, stabilizer compounds can be included in the systems to reduce or prevent degradation of drug at low pH. Such stabilizers include calcium carbonate, calcium lactate, calcium phosphate, sodium phosphate, and sodium bicarbonate. They are typically used in an amount of up to about 2% w/w.

The anti-oxidant stabilizers, pH stabilizers, and other stabilizer compounds are blended into the polymers containing the drug by blending the stabilizer(s) into the molten carrier polymer-drug mixture. The stabilizer(s) can be blended into molten carrier polymer prior to blending the drug into the polymer-stabilizer mixture; or the stabilizer(s) can be blended with drug prior to formulation of the blended drug-stabilizer mixture in the carrier polymer; or stabilizer(s), drug, and molten carrier polymer can be blended simultaneously. Drug can also be blended with molten carrier polymer prior to blending the stabilizer(s) into the polymer-drug mixture.

In one embodiment, less than about 10% of the drug remaining in the system is degraded or oxidized after a gastric residence period of about 24 hours. In one embodiment, less than about 10% of the drug remaining in the system is degraded or oxidized after a gastric residence period of about 48 hours. In one embodiment, less than about 10% of the drug remaining in the system is degraded or oxidized after a gastric residence period of about 72 hours. In one embodiment, less than about 10% of the drug remaining in the system is degraded or oxidized after a gastric residence period of about 96 hours. In one embodiment, less than about 10% of the drug remaining in the system is degraded or oxidized after a gastric residence period of about five days. In some embodiments, less than about 10% of the drug remaining in the system is degraded or oxidized after a gastric residence period of about a week. In some embodiments, less than about 10% of the drug remaining in the system is degraded or oxidized after a gastric residence period of about two weeks.

In one embodiment, less than about 5% of the drug remaining in the system is degraded or oxidized after a gastric residence period of about 24 hours. In one embodiment, less than about 5% of the drug remaining in the system is degraded or oxidized after a gastric residence period of about 48 hours. In one embodiment, less than about 5% of the drug remaining in the system is degraded or oxidized after a gastric residence period of about 72 hours. In one embodiment, less than about 5% of the drug remaining in the system is degraded or oxidized after a gastric residence period of about 96 hours. In one embodiment, less than about 5% of the drug remaining in the system is degraded or oxidized after a gastric residence period of about five days. In some embodiments, less than about 5% of the drug remaining in the system is degraded or oxidized after a gastric residence period of about a week. In some embodiments, less than about 5% of the drug remaining in the system is degraded or oxidized after a gastric residence period of about two weeks.

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days (about one week), or up to about 7 days (about one week). In one embodiment, the gastric residence system has a residence time of about 10 days, or up to about 10 days. In one embodiment, the gastric residence system has a residence time of about 14 days (about two weeks), or up to about 14 days (about two weeks).

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

The gastric residence system releases a therapeutically effective amount of drug during at least a portion of the residence time or residence period during which the system resides in the stomach. In one embodiment, the system releases a therapeutically effective amount of drug during at least about 25% of the residence time. In one embodiment, the system releases a therapeutically effective amount of drug during at least about 50% of the residence time. In one embodiment, the system releases a therapeutically effective amount of drug during at least about 60% of the residence time. In one embodiment, the system releases a therapeutically effective amount of drug during at least about 70% of the residence time. In one embodiment, the system releases a therapeutically effective amount of drug during at least about 75% of the residence time. In one embodiment, the system releases a therapeutically effective amount of drug during at least about 80% of the residence time. In one embodiment, the system releases a therapeutically effective amount of drug during at least about 85% of the residence time. In one embodiment, the system releases a therapeutically effective amount of drug during at least about 90% of the residence time. In one embodiment, the system releases a therapeutically effective amount of drug during at least about 95% of the residence time. In one embodiment, the system releases a therapeutically effective amount of drug during at least about 98% of the residence time. In one embodiment, the system releases a therapeutically effective amount of drug during at least about 99% of the residence time.

Radiopacity

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or are added to a small portion of the system. Examples of suitable radiopaque substances are barium sulfate, bismuth subcarbonate, bismuth oxychloride, and bismuth trioxide. It is preferable that these materials should not be blended into the polymers used to construct the gastric residence system, so as not to alter drug release from the carrier polymer, or desired properties of other system polymers. Metal striping or tips on a small portion of the system components can also be used, such as tungsten.

Carrier Polymer-Drug/Drug Salt Combinations with Excipients and Other Additives

The blend of carrier polymer-adamantane-class drug or carrier polymer-adamantane-class drug salt can comprise various excipients and other additives. The following Table CPE-1 lists combinations of excipients and other additives that can be used in combination with adamantane-class drug or salt thereof and carrier polymer in the compositions making up the elongate members or segments of elongate members of the gastric residence systems. These excipients and other additives can be combined with adamantane-class drug or salt thereof (where the drug or drug salt comprises between about 10% to about 60% by weight of the composition) with the carrier polymer, such as polycaprolactone, making up the remainder of the composition. Excipients include the following, which can be used individually or in any combination, in amounts ranging from about 1% to about 30%, such as about 5% to about 20%, by weight of the composition: Kolliphor P407 (poloxamer 407, poly(ethylene glycol)-block-poly(propylene glycol)-block-poly(ethylene glycol)), Eudragit RS (Poly[Ethyl acrylate, methyl methacrylate, trimethylammonioethyl methacrylate chloride] 1:2:0.1), Eudragit RL (Poly[Ethyl acrylate, methyl methacrylate, trimethylammonioethyl methacrylate chloride] 1:2:0.2), PDO (polydioxanone), PEG-PCL, SIF (FaSSIF/FaSSGF powder from BioRelevant), EPO (dimethylaminoethyl methacrylate-butyl methacrylate-methyl methacrylate copolymer), Kollidon VA64 (vinylpyrrolidone-vinyl acetate copolymer in a ratio of 6:4 by mass), polyvinyl acetate, polyvinyl pyrrolidine.

Other additives include silicon dioxide (comprising, for example, about 0.1% to about 5% by weight of the composition, such as about 0.1% to 1% or about 0.5%) and an anti-oxidant, such as alpha-tocopherol (comprising, for example, about 0.1% to about 5% by weight of the composition, such as about 0.1% to 1% or about 0.5%).

TABLE CPE-1

Excipients and additives, in combination with adamantane-class drug or salt thereof and carrier polymer EPO, P407, Silica, α-tocopherol
EPO, Silica, α-tocopherol
Eudragit RL, Eudragit RS, Kolliphor P407, Silica, α-tocopherol
Eudragit RL, Kolliphor P407, Silica, α-tocopherol
Eudragit RL, Eudragit RS, Kolliphor P407, Silica, α-tocopherol
Eudragit RL, Kolliphor P407, Silica, α-tocopherol
Eudragit RL, Kolliphor P407, Silica, α-tocopherol
Eudragit RS, P407, Silica, α-tocopherol
Eudragit RS, Silica, α-tocopherol
Kollidon VA64, Silica, α-tocopherol
Kolliphor P407, Silica, α-tocopherol
Kolliphor RH40, Silica, α-tocopherol
PDO, Silica, α-tocopherol
PEG-PCL, Silica, α-tocopherol
Poly Vinyl Acetate, Silica, α-tocopherol
PVP, Silica, α-tocopherol
SIF, Silica, α-tocopherol
Silica, P188, P407, α-tocopherol
Silica, α-tocopherol Table CPE-2 lists specific amounts of excipients and other additives that can be used in combination with adamantane-class drug or salt thereof and carrier polymer in the compositions making up the elongate members or segments of elongate members of the gastric residence systems.

The amounts listed in Table CPE-2 can be varied by plus-or-minus 20% of each ingredient (for example, 0.5% silica can vary between 0.4% and 0.6% silica, as 20% of 0.5% is 0.1%).

TABLE CPE-2

Excipients and additives, in combination with adamantane-class drug or salt thereof and carrier polymer 0.5% Silica, 0.5% α-tocopherol
0.5% Silica, 2% P407, 0.5% α-tocopherol
0.5% Silica, 2% P188, 2% P407, 0.5% α-tocopherol
0.5% Silica, 3% Eudragit RS, 2% P407, 0.5% α-tocopherol
1% Kolliphor P407, 0.5% Silica, 0.5% α-tocopherol TABLE CPE-2-continued Excipients and additives, in combination with adamantane-class drug or salt thereof and carrier polymer 10% Eudragit RS, 2.5% P407, 2% Silica, 0.5% α-tocopherol
10% Eudragit RS, 5% P407, 0.5% Silica, 0.5% α-tocopherol
10% Eudragit RS, 5% P407, 2% Silica, 0.5% α-tocopherol
12% Eudragit RL, 3% Kolliphor P407, 0.5% Silica, 0.5% α-tocopherol
12% Eudragit RL, 5% Kolliphor P407, 0.5% Silica, 0.5% α-tocopherol
14.78% Eudragit RS, 0.226% P407, 0.5% Silica, 0.5% α-tocopherol
17.5% Eudragit RS, 5% P407, 0.5% Silica, 0.5% α-tocopherol
19.8% Eudragit RS, 0.5% Silica, 0.5% α-tocopherol
2% Kolliphor P407, 0.5% Silica, 0.5% α-tocopherol
2% P407, 0.5% Silica, 0.5% α-tocopherol
20% Eudragit RS, 2% P407, 0.5% Silica, 0.5% α-tocopherol
21.25% Eudragit RS, 2.5% P407, 0.5% Silica, 0.5% α-tocopherol
25% Eudragit RL, 5% P407, 0.5% Silica, 0.5% α-tocopherol
25% Eudragit RS, 0.5% Silica, 0.5% α-tocopherol
25% Eudragit RS, 5% P407, 0.5% Silica, 0.5% α-tocopherol
3% Eudragit RL, 9% Eudragit RS, 5% Kolliphor P407, 0.5% Silica, 0.5% α-tocopherol
3.5% Eudragit RS, 2.5% P407, 2% Silica, 0.5% α-tocopherol
3.5% Eudragit RS, 5% P407, 2% Silica, 0.5% α-tocopherol
30% PDO, 0.5% Silica, 0.5% α-tocopherol
39.5% PEG-PCL, 0.36% Silica, 0.36% α-tocopherol
4.5% EPO, 4.5% P407, 0.5% Silica, 0.5% α-tocopherol
5% Kolliphor P407, 0.5% Silica, 0.5% α-tocopherol
5% Kolliphor RH40, 0.5% Silica, 0.5% α-tocopherol
5% SIF, 0.5% Silica, 0.5% α-tocopherol
6% Eudragit RL, 5% Kolliphor P407, 0.5% Silica, 0.5% α-tocopherol
6% Eudragit RL, 6% Eudragit RS, 5% Kolliphor P407, 0.5% Silica, 0.5% α-tocopherol
6.75% Eudragit RS, 3.75% P407, 2% Silica, 0.5% α-tocopherol
7% EPO, 2% P407, 0.5% Silica, 0.5% α-tocopherol
9% EPO, 0.5% Silica, 0.5% α-tocopherol
9% Eudragit RL, 3% Eudragit RS, 5% Kolliphor P407, 0.5% Silica, 0.5% α-tocopherol
9% Kollidon VA64, 0.5% Silica, 0.5% α-tocopherol
9% Poly Vinyl Acetate, 0.5% Silica, 0.5% α-tocopherol
9% PVP, 0.5% Silica, 0.5% α-tocopherol
9% SIF, 0.5% Silica, 0.5% α-tocopherol Manufacture/Assembly of System: Three-Dimensional Printing Three-dimensional printing of components of the gastric residence system, such as arm or arm segments, is performed using commercially-available equipment. Three-dimensional printing has been used for pharmaceutical preparation; see Khaled et al., "Desktop 3D printing of controlled release pharmaceutical bilayer tablets," International Journal of Pharmaceutics 461:105-111 (2014); U.S. Pat. No. 7,276,252; Alhnan et al., "Emergence of 3D Printed Dosage Forms: Opportunities and Challenges," Pharm. Res., May 18, 2016, PubMed PMID: 27194002); Yu et al., "Three-dimensional printing in pharmaceutics: promises and problems," J. Pharm. Sci. 97(9):3666-3690 (2008); and Ursan et al., "Three-dimensional drug printing: A structured review," J. Am. Pharm. Assoc. 53(2):136-44 (2013).

The initial feedstocks for three-dimensional printing are polymers or polymer blends (e.g. enteric polymers, time-dependent polymers, or blends of one or more of an agent, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer or blended polymer material is extruded through a circular die, creating a cylindrical fiber which is wound around a spool.

Multiple spools are fed into the 3D printer (such as a Hyrel Printer, available from Hyrel 3D, Norcross, Ga., United States), to be fed into their representative print heads. The print heads heat up and melt the material at the nozzle, and lay down a thin layer of material (polymer or polymer blend) in a specific position on the piece being manufactured. The material cools and hardens within seconds, and the next layer is added until the complete structure is formed. The quality of the dosage form is dependent on the feed rate, nozzle temperature, and printer resolution; feed rate and nozzle temperature can be adjusted to obtain the desired quality.

Three-dimensional printing can be used to manufacture individual elongate members, or segments of elongate members. Three-dimensional printing can also be used to prepare a bulk configuration, such as a consolidated "slab," similar to that prepared by co-extrusion methods described herein. The bulk configuration can be cut into individual pieces (that is, individual elongate members or individual segments) as needed.

In some embodiments of the invention, producing an entire elongate member, or "arm," of the gastric residence system by three-dimensional printing of the elongate member is contemplated. In some embodiments of the invention, producing a segment of an elongate member, or "arm," of the gastric residence system by three-dimensional printing of the segment of an elongate member is contemplated. In some embodiments, an elongate member or a segment thereof is produced by three-dimensional printing of adjacent portions of carrier polymer-drug blend and linker material in a bulk configuration, such as a slab configuration. The three-dimensional printing can be followed by cutting the bulk configuration into pieces which have the desired shape of the elongate member or segment thereof. The three-dimensional printing can be followed by compression molding of portions of the bulk configuration into pieces which have the desired shape of the elongate member or segment thereof.

Manufacture/Assembly of System: Co-Extrusion

Components of the gastric residence systems can be manufactured by co-extrusion. Most of the various configurations for the segments discussed herein, such as the "islands-in-the-sea" configurations, can be made by either three-dimensional printing or co-extrusion. However, co-extrusion is less expensive, and can be run as a continuous process, as opposed to three-dimensional printing, which is generally run as a batch process.

Co-extrusion of the "islands-in-the-sea" configuration is used in the textile industry and for production of fiber optics, but has rarely been applied in biomedical systems. See U.S. Pat. Nos. 3,531,368; 3,716,614; 4,812,012; and Haslauer et al., J. Biomed. Mater. Res. B Appl. Biomater. 103(5):1050-8 (2015)).

Co-extrusion of components of the gastric residence system, such as an elongate member (arm), or a segment of an elongate member (arm), can be performed using commercially-available equipment, combined with customized co-extruder plumbing and customized dies for the desired configuration. The initial feedstocks for co-extrusion are polymers or polymer blends (e.g. enteric polymers, time-dependent polymers, or blends of one or more of an agent, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer pellets thus formed are placed into hoppers above single screw extruders and dried to remove surface moisture. Pellets are gravimetrically fed into individual single-screw extruders, where they are melted and pressurized for co-extrusion. The appropriate molten polymers are then pumped through custom designed dies with multiple channels where they form the required geometry. The composite polymer block is cooled (water-cooled, air-cooled, or both) and cut or stamped into the desired shape, including, but not limited to, such shapes as triangular prisms, rectangular prisms, or cylinder sections (pie-shaped wedges).

In some embodiments of the invention, producing an entire elongate member, or "arm," of the gastric residence system by co-extruding the elongate member is contemplated. In some embodiments of the invention, producing a segment of an elongate member, or "arm," of the gastric residence system by co-extruding the segment of an elongate member is contemplated. In some embodiments, an elongate member or a segment thereof is produced by co-extruding adjacent portions of carrier polymer-drug blend and linker material in a bulk configuration, such as a slab configuration. The co-extruding can be followed by cutting the bulk configuration into pieces which have the desired shape of the elongate member or segment thereof. The co-extruding can be followed by compression molding of portions of the bulk configuration into pieces which have the desired shape of the elongate member or segment thereof.

In some embodiments, an elongate member or a segment thereof is produced by co-extruding adjacent portions of carrier polymer-drug blend and linker material in a bulk configuration, such as a slab configuration, while also co-extruding an additional polymer or polymers within the carrier polymer-drug blend, the linker material, or both the carrier polymer-drug blend and the linker material. The co-extruding the additional polymer or polymers within the carrier polymer-drug blend, the linker material, or both the carrier polymer-drug blend and the linker material can be performed in an islands-in-the-sea configuration. The co-extruding can be followed by cutting the bulk configuration into pieces which have the desired shape of the elongate member or segment thereof. The co-extruding can be followed by compression molding of portions of the bulk configuration into pieces which have the desired shape of the elongate member or segment thereof.

Manufacture/Assembly of System: Affixing Elongate Members to Central Elastomer

For a stellate gastric residence system, the elongate members, or "arms" of the gastric residence system can be affixed to the central elastomer in a number of ways. The central polymer can be cast or molded with short "asterisk" arms, and a linker polymer can be used to affix the elongate members to the asterisk arms of the central elastomer. Alternatively, the central elastomer can be formed in a mold into which the proximal ends of the elongate members protrude. The elastomer sets, cures, or otherwise hardens into its desired form with a portion of the elongate members extending into the body of the central elastomer. Alternatively, the central elastomer can be prepared with cavities into which the elongate members can be firmly inserted.

The invention thus includes a method of making a gastric residence system, comprising preparing at least three elongate members formed from a material comprising any drug-carrier polymer-excipient formulation as disclosed herein; and attaching the elongate members to a central elastomer to form a gastric residence system. The elongate members of the gastric residence system project radially from the central elastomer, such as in a "hub and spoke" arrangement.

In some embodiments, arms comprising any drug-carrier polymer-excipient formulation as disclosed herein can be heat-welded to polycaprolactone segments, such as short polycaprolactone "asterisk" arms affixed to a central elastomer. Linker segments can be welded to the short "asterisk"

arms prior to affixing the drug-carrier polymer-excipient formulation arms. As shown in Example 13, heat welding of drug-carrier polymer-excipient formulation arms to MW 80,000 PCL segments at temperatures between 140° C. to 170° C., followed by cooling for 24 hours at 8° C., resulted in stronger welds. Thus, in one embodiment, attaching the elongate members comprising any drug-carrier polymer-excipient formulation as disclosed herein to a central elastomer to form a gastric residence system, can comprise heat-welding the elongate members to other system components, such as asterisk arms or other segments comprising at least about 90%, at least about 95%, or at least about 99% polycaprolactone (such as MW 80,000 PCL), at a temperature between about 140° C. to about 170° C., followed by cooling of the welded members attached to other system components for about 12 to about 48 hours at a temperature of about 2° C. to about 14° C., such as about 5° C. to about 10° C., or about 8° C. The other system components can alternatively be linker elements.

The invention thus includes a method of making a gastric residence system, comprising preparing at least three elongate members formed from a material comprising any drug-carrier polymer-excipient formulation as disclosed herein; and attaching the elongate members to a central elastomer to form a gastric residence system. The elongate members can comprise at least one segment with a release rate-controlling polymer film. The elongate members of the gastric residence system project radially from the central elastomer, such as in a "hub and spoke" arrangement. A preferred number of elongate members or "arms" is six. However, stellate systems with three, four, five, seven, or eight elongate members can also be used.

In some embodiments, elongate members or "arms" comprising any carrier polymer-agent formulation, including arms comprising segments having release rate-modulating polymer films, can be heat-welded, solvent-welded, or otherwise affixed to other elements, including disintegrating matrices, coupling polymers, or interfacing polymers, which are then affixed to a central elastomer. In some embodiments, the arms are directly affixed to a central elastomer. Disintegrating matrices, coupling polymers, or interfacing polymer segments can be welded or otherwise affixed to the central elastomer prior to affixing the elongate members.

Manufacture/Assembly of System: Packaging of Gastric Residence Systems into Capsules Once the elongate members of the gastric residence system have been affixed to the central elastomer, the system is ready to be folded into its compacted configuration and placed into a capsule for storage, transport, and eventual administration. The system can be folded in an automated mechanical process, or by hand, and placed into a capsule of the appropriate size and material. More detail regarding manufacture and assembly of gastric residence systems, and of packaging the gastric residence system into capsules, can be found in International Patent Application Nos. WO 2015/191920, WO 2015/191925, WO 2017/070612, PCT/US2016/065453, and PCT/US2017/034856.

Carrier Polymer-Agent/Release Rate-Modulating Film Combinations

A variety of carrier polymer-agent segment formulations can be used with any given release rate-modulating film to provide desired release characteristics from the film-coated segment. Likewise, a variety of release rate-modulating films can be used with any given carrier polymer-agent segment formulation. One useful combination of carrier polymer-agent/film comprises a segment with about 15% to about 40% agent, about 3% to about 15% of excipients selected from one or more of P407, silica, and vitamin E succinate, with the balance of the segment made up of polycaprolactone (PCL); and a release rate-modulating film that is about 75% to about 95% polycaprolactone with the balance of the film comprising copovidone porogen, where the weight of the film is about 0.5% to about 2% of the weight of the underlying segment, and/or where the thickness of the film ranges from about 3 microns to about 10 microns. An exemplary combination is 27.5% agents, 6% excipients (P407, silica, vitamin E succinate), and 66.5% PCL, with a film that is 90% PCL 10% copovidone porogen, where the weight of the film is about 1% of the weight of the underlying segment.

Another useful combination of carrier polymer-agent/film comprises a segment with about 30% to about 50% agent, about 10% to about 30% plasticizer, about 0% to about 10% of excipients selected from one or more of P407, silica, and vitamin E succinate, with the balance of the segment made up of polycaprolactone (PCL); and a release rate-modulating film that is about 75% to about 95% polycaprolactone with the balance of the film comprising copovidone porogen, where the weight of the film is about 0.5% to about 3% of the weight of the underlying segment, and/or where the thickness of the film ranges from about 3 microns to about 12 microns.

Dissolution Profile, Bioavailability and Pharmacokinetics for Gastric Residence Systems Dissolution:

The gastric residence systems described herein provide a steady release of drug over an extended period of time. The systems are designed to release a therapeutically effective amount of an adamantane-class drug, such as memantine, over the period of residence in the stomach. The release of drug can be measured in vitro or in vivo to establish the dissolution profile (elution profile, release rate) of the drug from a given residence system in a specific environment. The dissolution profile can be specified as a percentage of the original amount of drug present in the system which elutes from the system over a given time period.

Thus, in some embodiments, the drug contained in a gastric residence system can have a dissolution profile of 10-20% release between zero hours and 24 hours in a given environment. That is, over the 24-hour period after initial introduction of the gastric residence system into the environment of interest, 10-20% of the initial drug contained in the system elutes from the system.

The environment of interest can be 1) the stomach of a patient (that is, an in vivo environment), or 2) simulated gastric fluid (that is, an in vitro environment).

The gastric residence systems of the invention provide for high bioavailability of the drug as measured by $AUC_{inf}$ after administration of the systems, relative to the bioavailability of a conventional oral formulation of the drug. The systems also provide for maintenance of a substantially constant plasma level of the drug.

Parameters of interest for release include the linearity of release over the residence period of the gastric residence systems, the standard deviation of release over the residence period (which is related to linearity of release; a standard deviation of zero indicates that release is linear over the entire residence period), the release over the initial six hours of residence (that is, burst release upon initial administration), and total release of drug over the residence period. A preferable residence period is seven days, although other periods, such as two, three, four, five, six, eight, nine, ten, 11, 12, 13, or 14 days can be useful.

Linearity of drug release over the residence period refers to the amount released during each 24-hour period of residence. For a seven-day period of residence, it is desirable that about the amount of drug is released each day, i.e., that linearity of drug release is maximized. This will minimize the standard deviation of daily drug release over the residence period. In some embodiments, the gastric release systems have a variation (or a standard deviation) for daily drug release of less than about 100%, less than about 90%, less than about 80%, less than about 70%, less than about 60%, less than about 50%, less than about 40%, less than about 30%, less than about 25%, less than about 20%, less than about 15%, less than about 10%, or less than about 5%, over the period of residence. In some embodiments, the period of residence can be about three days, about seven days, about ten days, or about two weeks.

Minimization of burst release, that is, release over the initial period of residence (such as six hours, twelve hours, or 24 hours after administration of a gastric residence system) is desirable in order to maintain a predictable and steady release profile. If T is the total drug release over the residence period (in units of mass), and D is the number of days of the residence period, then completely linear release would mean that about T/D mass of drug is released per day. If the period over which burst release is measured is the first six hours, then a linear release profile will result in 0.25×T/D mass of drug released during the first six hours. In percentage terms of the total amount of drug released over the residence period of D days, linear release would be about 100/D % of drug per day, and a linear release over the first six hours would be 25/D %. (Note that 100% in this context indicates the total amount of drug released, regardless of how much drug is contained in the initial formulation.) Thus, for a seven day residence period, linear release over the first six hours would be about 3.6% of the total amount of drug released over the seven-day period.

In some embodiments, during the initial six hours of residence after administration the gastric residence systems release about 0.2 to about 2 times T/D of the total mass of drug T released over the residence period of D days, or about 0.2 to about 1.75 times T/D of the total mass of drug T released over the residence period of D days, or about 0.2 to about 1.5 times T/D of the total mass of drug T released over the residence period of D days, or about 0.2 to about 1.25 times T/D of the total mass of drug T released over the residence period of D days, or about 0.2 to about 1 times T/D of the total mass of drug T released over the residence period of D days, or about 0.2 to about 0.8 times T/D of the total mass of drug T released over the residence period of D days, or about 0.2 to about 0.75 times T/D, or about 0.2 to about 0.7 times T/D, or about 0.2 to about 0.6 times T/D, or about 0.2 to about 0.5 times T/D, or about 0.2 to about 0.4 times T/D, or about 0.2 to about 0.3 times T/D, or about 0.25 to about 2 times T/D, or about 0.3 to about 2 times T/D, or about 0.4 to about 2 times T/D, or about 0.5 to about 2 times T/D, or about 0.6 to about 2 times T/D, or about 0.7 to about 2 times T/D, or about 0.25 to about 1.5 times T/D, or about 0.3 to about 1.5 times T/D, or about 0.4 to about 1.5 times T/D, or about 0.5 to about 1.5 times T/D, or about 0.6 to about 1.5 times T/D, or about 0.7 to about 1.5 times T/D, or about 0.25 to about 1.25 times T/D, or about 0.3 to about 1.25 times T/D, or about 0.4 to about 1.25 times T/D, or about 0.5 to about 1.25 times T/D, or about 0.6 to about 1.25 times T/D, or about 0.7 to about 1.25 times T/D, or about 0.25 to about 1 times T/D, or about 0.3 to about 1 times T/D, or about 0.4 to about 1 times T/D, or about 0.5 to about 1 times T/D, or about 0.6 to about 1 times T/D, or about 0.7 to about 1 times T/D, or about 0.25 times T/D, or about 0.25 to about 0.8 times T/D, or about 0.3 to about 0.8 times T/D, or about 0.4 to about 0.8 times T/D, or about 0.5 to about 0.8 times T/D, or about 0.6 to about 0.8 times T/D, or about 0.7 to about 0.8 times T/D, or about 0.8 times T/D., about 1 times T/D, about 1.25 times T/D, about 1.5 times T/D, or about 2 times T/D.

In some embodiment of the gastric residence systems, during the initial six hours of residence after administration the gastric residence systems release about 2% to about 10% of the total mass of drug released over the residence period, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments of the gastric residence systems, where the gastric residence systems have a residence period of about seven days, during the initial six hours of residence after administration the gastric residence systems release about 2% to about 10% of the total mass of drug released over the residence period of seven days, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments, during the initial 24 hours of residence after administration, the gastric residence systems release about 10% to about 35% of the total mass of drug released over the residence period, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

In some embodiments, where the gastric residence systems have a residence period of about seven days, during the initial 24 hours of residence after administration the gastric residence systems release about 10% to about 35% of the total mass of drug released over the residence period of seven days, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

Bioavailability and Pharmacokinetics:

Relative bioavailability, $F_{REL}$, of two different formulations, formulation A and formulation B, is defined as:

$$F_{REL} = 100 \times (AUC_A \times Dose_B)/(AUC_B \times Dose_A)$$

where $AUC_A$ is the area under the curve for formulation A, $AUC_B$ is the area under the curve for formulation B, $Dose_A$ is the dosage of formulation A used, and $Dose_B$ is the dosage of formulation B used. AUC, the area under the curve for the plot of drug plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the drug has dropped to a negligible amount.

The gastric residence systems of the invention can provide bioavailability of drug released from the system of at least about 50%, at least about 60%, at least about 70%, or at least about 80% of that provided by an immediate release form comprising the same amount of drug. As indicated above, the bioavailability is measured by the area under the plasma concentration-time curve (AUCinf).

In one embodiment, the substantially constant plasma level of drug provided by the gastric residence systems of the invention can range from at or above the trough level of the plasma level of drug when administered daily in a conventional oral formulation (that is, $C_{min}$ of drug administered daily in immediate-release formulation) to at or below the peak plasma level of drug when administered daily in a conventional oral formulation (that is, $C_{max}$ of drug administered daily in immediate-release formulation). In some embodiments, the substantially constant plasma level of drug provided by the gastric residence systems of the invention can be about 50% to about 90% of the peak plasma level of drug when administered daily in a conventional oral formulation (that is, $C_{max}$ of drug administered daily in immediate-release formulation). The substantially constant plasma level of drug provided by the gastric residence systems of the invention can be about 75% to about 125% of the average plasma level of drug when administered daily in a conventional oral formulation (that is, $C_{ave}$ of drug administered daily in immediate-release formulation). The substantially constant plasma level of drug provided by the gastric residence systems of the invention can be at or above the trough level of plasma level of drug when administered daily in a conventional oral formulation (that is, $C_{min}$ of drug administered daily in immediate-release formulation), such as about 100% to about 150% of $C_{min}$.

Table 3 lists conversion between concentrations of memantine measured in units of ng/mL and in units of micromolar. The molecular weight of memantine is 179.30. (The molecular weight of memantine hydrochloride is 215.77)

TABLE 3

| Plasma concentration (ng/mL units) | Plasma concentration (micromolar units) |
| --- | --- |
| 179.3 ng/mL | 1.00 micromolar |
| 89.7 ng/mL | 0.500 micromolar |
| 84.3 ng/mL | 0.470 micromolar |
| 60 ng/mL | 0.334 micromolar |
| 53.8 ng/mL | 0.300 micromolar |
| 17.9 ng/mL | 0.100 micromolar |

The maximum therapeutically relevant concentration of memantine is approximately 1 micromolar (Rammes et al., Curr. Neuropharmacol. 6(1): 55-78 (2008)), corresponding to a plasma level of about 180 ng/mL. A recommended therapeutic range is about 90 ng/mL to 150 ng/mL, while the laboratory alert value is 300 ng/mL (Hiemke et al., Pharmacopsychiatry 44:195 (2011)). Thus, in one embodiment, the gastric residence systems of the invention provide a minimum plasma concentration $C_{min}$ of no less than about 50 ng/mL of memantine and a maximum plasma concentration $C_{max}$ of no greater than about 200 ng/mL. In one embodiment, the gastric residence systems of the invention provide a $C_{min}$ of no less than about 60 ng/mL of memantine and a $C_{max}$ of no greater than about 190 ng/mL. In one embodiment, the gastric residence systems of the invention provide a $C_{min}$ of no less than about 70 ng/mL of memantine and a $C_{max}$ of no greater than about 180 ng/mL. In one embodiment, the gastric residence systems of the invention provide a $C_{min}$ of no less than about 75 ng/mL of memantine and a $C_{max}$ of no greater than about 175 ng/mL. In one embodiment, the gastric residence systems of the invention provide a $C_{min}$ of no less than about 80 ng/mL of memantine and a $C_{max}$ of no greater than about 170 ng/mL. In one embodiment, the gastric residence systems of the invention provide a $C_{min}$ of no less than about 90 ng/mL of memantine and a $C_{max}$ of no greater than about 150 ng/mL.

In one embodiment, the gastric residence systems of the invention provide an average memantine plasma concentration $C_{ave}$, of about 50 ng/mL±10%, about 60 ng/mL±10%, about 70 ng/mL±10%, about 75 ng/mL±10%, about 80 ng/mL±10%, about 90 ng/mL±10%, about 100 ng/mL±10%, about 110 ng/mL±10%, about 120 ng/mL±10%, about 130 ng/mL±10%, about 140 ng/mL±10%, about 150 ng/mL±10%, about 160 ng/mL±10%, about 170 ng/mL±10%, about 180 ng/mL±10%, about 190 ng/mL±10%, about or 200 ng/mL±10 ng/mL. In one embodiment, the average memantine plasma concentration provided by the gastric residence systems of the invention is about 90 ng/mL±10%, about 100 ng/mL±10%, about 110 ng/mL±10%, about 120 ng/mL±10%, about 130 ng/mL±10%, about 140 ng/mL±10%, or about 150 ng/mL±10%.

In one embodiment, the gastric residence systems of the invention provide an average memantine plasma concentration $C_{ave}$, of about 50 ng/mL±5%, about 60 ng/mL±5%, about 70 ng/mL±5%, about 75 ng/mL±5%, about 80 ng/mL±5%, about 90 ng/mL±5%, about 100 ng/mL±5%, about 110 ng/mL±5%, about 120 ng/mL±5%, about 130 ng/mL±5%, about 140 ng/mL±5%, about 150 ng/mL±5%, about 160 ng/mL±5%, about 170 ng/mL±5%, about 180 ng/mL±5%, about 190 ng/mL±5%, or about 200 ng/mL±5 ng/mL. In one embodiment, the average memantine plasma concentration provided by the gastric residence systems of the invention is about 90 ng/mL±5%, about 100 ng/mL±5%, about 110 ng/mL±5%, about 120 ng/mL±5%, about 130 ng/mL±5%, about 140 ng/mL±5%, or about 150 ng/mL±5%.

In one embodiment, the gastric residence systems of the invention provide an average memantine plasma concentration $C_{ave}$, of about 50 ng/mL±10 ng/mL, about 60 ng/mL±10 ng/mL, about 70 ng/mL±10 ng/mL, about 75 ng/mL±10 ng/mL, about 80 ng/mL±10 ng/mL, about 90 ng/mL±10 ng/mL, about 100 ng/mL±10 ng/mL, about 110 ng/mL±10 ng/mL, about 120 ng/mL±10 ng/mL, about 130 ng/mL±10 ng/mL, about 140 ng/mL±10 ng/mL, about 150 ng/mL±10 ng/mL, about 160 ng/mL±10 ng/mL, about 170 ng/mL±10 ng/mL, about 180 ng/mL±10 ng/mL, about 190 ng/mL±10 ng/mL, about or 200 ng/mL±10 ng/mL. In one embodiment, the average memantine plasma concentration provided by the gastric residence systems of the invention is about 90 ng/mL±10 ng/mL, about 100 ng/mL±10 ng/mL, about 110 ng/mL±10 ng/mL, about 120 ng/mL±10 ng/mL, about 130 ng/mL±10 ng/mL, about 140 ng/mL±10 ng/mL, or about 150 ng/mL±10 ng/mL.

In one embodiment, the gastric residence systems of the invention provide an average memantine plasma concentration $C_{ave}$, of about 50 ng/mL±5 ng/mL, about 60 ng/mL±5 ng/mL, about 70 ng/mL±5 ng/mL, about 75 ng/mL±5 ng/mL, about 80 ng/mL±5 ng/mL, about 90 ng/mL±5 ng/mL, about 100 ng/mL±5 ng/mL, about 110 ng/mL±5 ng/mL, about 120 ng/mL±5 ng/mL, about 130 ng/mL±5 ng/mL, about 140 ng/mL±5 ng/mL, about 150 ng/mL±5 ng/mL, about 160 ng/mL±5 ng/mL, about 170 ng/mL±5 ng/mL, about 180 ng/mL±5 ng/mL, about 190 ng/mL±5 ng/mL, or about 200 ng/mL±5 ng/mL. In one embodiment, the average memantine plasma concentration provided by the gastric residence systems of the invention is about 90 ng/mL±5 ng/mL, about 100 ng/mL±5 ng/mL, about 110 ng/mL±5 ng/mL, about 120 ng/mL±5 ng/mL, about 130 ng/mL±5 ng/mL, about 140 ng/mL±5 ng/mL, or about 150 ng/mL±5 ng/mL.

In one embodiment, the gastric residence systems of the invention provide an average memantine plasma concentration $C_{ave}$, of about 50 ng/mL, about 60 ng/mL, about 70 ng/mL, about 75 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about or 200 ng/mL. In one embodiment, the average memantine plasma concentration provided by the gastric residence systems of the invention is about 90 ng/mL, about 100 ng/mL, about 110 ng/mL, about 120 ng/mL, about 130 ng/mL, about 140 ng/mL, or about 150 ng/mL.

A preferred range for $C_{ave}$ is about 100 ng/mL to about 130 ng/mL, more preferably about 110 ng/mL to about 120 ng/mL.

Methods of Treatment Using the Gastric Residence Systems

The gastric residence systems can be used to treat conditions requiring administration of a drug over an extended period of time. For long-term administration of drugs which are taken for months, years, or indefinitely, administration of a gastric residence system periodically, such as once weekly or once every two weeks can provide substantial advantages in patient compliance and convenience. Accordingly, the gastric residence systems of the invention can be administered once every three days, once every five days, once weekly, once every ten days, or once every two weeks. The administration frequency is timed to coincide with the designed gastric residence period of the gastric residence system which is administered, so that at about the same time that a gastric residence system passes out of the stomach after its residence period, a new gastric residence system is administered.

Once a gastric residence system has been administered to a patient, the system provides sustained release of drug over the period of gastric retention. After the period of gastric retention, the system degrades and passes out of the stomach. Thus, for a system with a gastric retention period of one week, the patient will swallow (or have administered to the stomach via other methods) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the drug in the system, comprises introducing a new gastric residence system every D-days into the stomach of the patient, by oral administration or other methods, over the total desired treatment period. The number of gastric residence systems administered to the patient will be (T-total) divided by (D-days). For example, if treatment of a patient for a year (T-total=365 days) is desired, and the gastric residence period of the system is 7 days (D-days=7 days), approximately 52 gastric residence systems will be administered to the patient over the 365 days, as a new system will be administered once every seven days.

Diseases Amenable to Treatment Using the Gastric Residence Systems of the Invention Adamantane-class drugs have been proposed for treatment of neurological disorders, most notably Alzheimer's disease. Memantine (sold under the brand name Namenda® by Forest Laboratories, New York, N.Y., USA) is approved for use in Alzheimer's disease in the United States, Japan, Europe, and other jurisdictions. Memantine is an N-methyl-D-aspartate (NMDA) receptor antagonist. Some other indications proposed for memantine include treatment of obsessive-compulsive disorder (OCD) (Pittenger, C.; Psychiatr. Ann. 45:308 (2015)); non-Alzheimer's degenerative dementia (López-Pousa, S. et al., Drugs Aging 29(9):733 (2012)); major depression (Szakacs, R. et al., Neuropsychopharmacol. Hung. 14(2):29 (2012)); and stroke, vascular dementia, HIV-associated dementia, neuropathic pain (including diabetic neuropathic pain), and glaucoma (Lipton, S. A.; NeuroRx 1(1):101 (2004)). Amantadine has been used as an anti-viral, for example, in influenza, such as influenza A.

Accordingly, the adamantane-class-drug-containing gastric residence systems of the invention can be used to treat neurological or psychiatric disorders. The adamantane-class-drug-containing gastric residence systems of the invention can be used to treat Alzheimer's Disease. The adamantane-class-drug-containing gastric residence systems of the invention can be used to treat dementia, such as Lewy Body dementia, HIV-associated dementia, or vascular dementia. The adamantane-class-drug-containing gastric residence systems of the invention can be used to treat organic brain syndrome.

The adamantane-class-drug-containing gastric residence systems of the invention can be used to treat spasticity, stroke or the resulting effects of stroke (that is, the sequelae of stroke), an autism spectrum disorder, Parkinson's Disease, neuropathic pain, attention deficit/hyperactivity disorder (ADHD), obsessive-compulsive disorder (OCD), or major depression.

The adamantane-class-drug-containing gastric residence systems of the invention can be used to treat glaucoma.

The adamantane-class-drug-containing gastric residence systems of the invention can be used to treat a viral infection, such as influenza, such as influenza A. A preferred compound for use in a gastric residence system used to treat a viral infection is amantadine.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days)) (rounded to an integral number), for administration every D-days. Alternatively, if the total treatment time in days is (T-total), and the gastric residence systems have an effective release period of (E-days), then the kit will contain a number of gastric residence systems equal to ((T-total) divided by (E-days)) (rounded to an integral number), for administration every E-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the agent or drug contained in the gastric residence systems. For example, if the total treatment period prescribed for the patient is one year, and the gastric residence system has a residence time of one week or an effective release period of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the drug contained in the gastric residence systems, are also included in the invention. The articles of manufacture may be supplied in appropriate packaging, such as dispensers, trays, or other packaging that assists the patient in administration of the gastric residence systems at the prescribed interval.

EXEMPLARY EMBODIMENTS

The invention is further described by the following embodiments. The features of each of the embodiments are combinable with any of the other embodiments where appropriate and practical.

Embodiment 1

A gastric residence system providing an extended release drug dosage form, comprising a therapeutically effective amount of an adamantane-class drug or a pharmaceutically acceptable salt thereof and a component adapted to provide extended release of the adamantane-class drug or a pharmaceutically acceptable salt thereof in an aqueous environment, wherein the system has a dissolution profile characterized by about 10% to 20% dissolution of the initial amount of adamantane-class drug or pharmaceutically acceptable salt thereof present in the system during an initial 24 hour period in the aqueous environment.

Embodiment 2

The gastric residence system of embodiment 1, wherein the system has a dissolution profile characterized by about 20% to 40% dissolution of the initial amount of adamantane-class drug or pharmaceutically acceptable salt thereof present in the system during an initial 48 hour period in the aqueous environment.

Embodiment 3

The gastric residence system of embodiment 1 or embodiment 2, wherein the system elutes about 20 mg to about 36 mg adamantane-class drug or pharmaceutically acceptable salt thereof per day in the aqueous environment.

Embodiment 4

The gastric residence system of any one of embodiments 1-3, wherein the adamantane-class drug or pharmaceutically acceptable salt thereof is memantine or pharmaceutically acceptable salt of memantine.

Embodiment 5

The gastric residence system of any one of embodiments 1-4, wherein the aqueous environment is the stomach of a human patient.

Embodiment 6

The gastric residence system of any one of embodiments 1-4, wherein the aqueous environment is simulated gastric fluid.

Embodiment 7

The gastric residence system of any one of embodiments 1-5, wherein the system has a gastric residence period of at least about four days when administered to a human patient.

Embodiment 8

The gastric residence system of embodiment 7, wherein the system has a gastric residence period of at about seven days.

Embodiment 9

The gastric residence system of any one of embodiments 1-3, wherein the adamantane-class drug or a pharmaceutically acceptable salt thereof is blended with the component adapted to provide extended release of the adamantane-class drug or pharmaceutically acceptable salt thereof.

Embodiment 10

The gastric residence system of embodiment 9, wherein the component adapted to provide extended release of the adamantane-class drug or pharmaceutically acceptable salt thereof comprises a carrier polymer and at least one excipient.

Embodiment 11

A gastric residence system comprising a therapeutically effective amount of an adamantane-class drug or a pharmaceutically acceptable salt thereof,
wherein the gastric residence system is characterized by one or more of the following characteristics:
a) the gastric residence system provides a human in vivo plasma profile which is characterized by a $t_{max}$ for the adamantane-class drug or pharmaceutically acceptable salt thereof of about 25 hours±15 hours after administration of a single gastric residence system to a human patient;
b) the gastric residence system provides a human in vivo plasma profile which is characterized by a $C_{max}/D$ for the adamantane-class drug or pharmaceutically acceptable salt thereof of about 1 ng/mL/mg±0.5 ng/mL/mg after administration of a single gastric residence system to a human patient, where D is the total mass in milligrams of the adamantane-class drug or pharmaceutically acceptable salt thereof in the gastric residence system;
c) the gastric residence system provides a human in vivo plasma profile which is characterized by a $C_{max}/D'$ for the adamantane-class drug or pharmaceutically acceptable salt thereof of about 1 ng/mL/mg±0.5 ng/mL/mg after administration of a single gastric residence system to a human patient, where D' is the total mass in milligrams of the drug released from the gastric residence system during its residence period in the stomach;
d) the gastric residence system provides a human in vivo plasma profile which is characterized by an AUC/D for the adamantane-class drug or pharmaceutically acceptable salt thereof for 0 to 72 hours of about 55 hours-ng/mL/mg±25 hours-ng/mL/mg after administration of a single gastric residence system to a human patient; or e) the gastric residence system provides a human in vivo plasma profile which is characterized by an AUC/D' for adamantane-class drug or pharmaceutically acceptable salt thereof for 0 to 72 hours of about 55 hours-ng/mL/mg±25 hours-ng/mL/mg after administration of a single gastric residence system to a human patient.

Embodiment 12

A gastric residence system comprising a therapeutically effective amount of an adamantane-class drug or a pharmaceutically acceptable salt thereof, wherein the gastric residence system provides a human in vivo plasma profile of adamantane-class drug or pharmaceutically acceptable salt thereof at steady state which is characterized by a fluctuation F of about 40%±35%.

Embodiment 13

The gastric residence system of any one of embodiments 11-12, wherein the adamantane-class drug or a pharmaceutically acceptable salt thereof comprises memantine or a pharmaceutically acceptable salt thereof.

Embodiment 14

The gastric residence system of any one of embodiments 11-13, wherein the adamantane-class drug or a pharmaceutically acceptable salt thereof comprises about 28 mg of memantine or a pharmaceutically acceptable salt thereof.

Embodiment 15

A gastric residence system comprising memantine or a pharmaceutically acceptable salt thereof, wherein the gastric residence system is characterized by one or more of the following characteristics:

a) the gastric residence system provides a human in vivo plasma profile which is characterized by a $t_{max}$ for the adamantane-class drug or pharmaceutically acceptable salt thereof of about 25 hours±15 hours after administration of a single gastric residence system to a human patient;

b) the gastric residence system provides a human in vivo plasma profile which is characterized by a $C_{max}/D$ for the adamantane-class drug or pharmaceutically acceptable salt thereof of about 1 ng/mL/mg±0.5 ng/mL/mg after administration of a single gastric residence system to a human patient, where D is the total mass in milligrams of the adamantane-class drug or pharmaceutically acceptable salt thereof in the gastric residence system;

c) the gastric residence system provides a human in vivo plasma profile which is characterized by a $C_{max}/D'$ for the adamantane-class drug or pharmaceutically acceptable salt thereof of about 1 ng/mL/mg±0.5 ng/mL/mg after administration of a single gastric residence system to a human patient, where D' is the total mass in milligrams of the adamantane-class drug or pharmaceutically acceptable salt thereof released from the gastric residence system during its residence period in the stomach;

d) the gastric residence system provides a human in vivo plasma profile which is characterized by an AUC/D for the adamantane-class drug or pharmaceutically acceptable salt thereof for 0 to 72 hours of about 55 hours-ng/mL/mg±25 hours-ng/mL/mg after administration of a single gastric residence system to a human patient;

e) the gastric residence system provides a human in vivo plasma profile which is characterized by an AUC/D' for the adamantane-class drug or pharmaceutically acceptable salt thereof for 0 to 72 hours of about 55 hours-ng/mL/mg±25 hours-ng/mL/mg after administration of a single gastric residence system to a human patient;

f) the gastric residence system provides a human in vivo plasma profile which is characterized by a $C_{max}$ for the adamantane-class drug or pharmaceutically acceptable salt thereof of about 30 ng/mL±15 ng/mL after administration of a single gastric residence system to a human patient; and g) the gastric residence system provides a human in vivo plasma profile which is characterized by an AUC for the adamantane-class drug or pharmaceutically acceptable salt thereof for 0 to 72 hours of about 1500 hours-ng/mL±750 hours-ng/mL after administration of a single gastric residence system to a human patient.

Embodiment 16

A gastric residence system comprising memantine or a pharmaceutically acceptable salt thereof, wherein the gastric residence system is characterized by one or more of the following characteristics:

a) the gastric residence system provides a human in vivo plasma profile at steady state having a $C_{max,ss}$ for the adamantane-class drug or pharmaceutically acceptable salt thereof of about 140 ng/mL±50 ng/mL;

b) the gastric residence system provides a human in vivo plasma profile at steady state having a $C_{min,ss}$ for the adamantane-class drug or pharmaceutically acceptable salt thereof of about 90 ng/mL±40 ng/mL, with the caveat that $C_{min,ss}$ is less than $C_{max,ss}$;

c) the gastric residence system provides a human in vivo plasma profile at steady state having a $C_{ave,ss}$ for the adamantane-class drug or pharmaceutically acceptable salt thereof of about 115 ng/mL±15 ng/mL, with the caveat that $C_{ave,ss}$ is greater than $C_{min,ss}$ and $C_{ave,ss}$ is less than $C_{max,ss}$; and d) the gastric residence system provides a human in vivo plasma profile at steady state having an $AUC_\tau$ for the adamantane-class drug or pharmaceutically acceptable salt thereof of about 2750 hour-ng/mL·±750 hour-ng/mL.

Embodiment 17

The gastric residence system of embodiment 15 or embodiment 16, wherein the gastric residence system comprises about 20 mg to about 60 mg of memantine or a pharmaceutically acceptable salt thereof, or wherein the gastric residence system comprises about 140 mg to about 420 mg of memantine or a pharmaceutically acceptable salt thereof.

Embodiment 18

The gastric residence system of embodiment 15 or embodiment 16, wherein the gastric residence system comprises about 20 mg to about 40 mg of memantine or a pharmaceutically acceptable salt thereof, or wherein the gastric residence system comprises about 140 mg to about 280 mg of memantine or a pharmaceutically acceptable salt thereof.

Embodiment 19

The gastric residence system of embodiment 15 or embodiment 16, wherein the gastric residence system comprises about 28 mg of memantine or a pharmaceutically acceptable salt thereof, or wherein the gastric residence system comprises about 196 mg of memantine or a pharmaceutically acceptable salt thereof.

Embodiment 20

A gastric residence system comprising a therapeutically effective amount of an adamantane-class drug or a pharmaceutically acceptable salt thereof, wherein: the gastric residence system has a compacted configuration and an uncompacted configuration, the gastric residence system comprises a plurality of elongate members affixed to a central elastomer, each elongate member comprises at least two segments joined by linkers, wherein the linkers are configured such that they no longer join the at least two segments of each elongate member after a specified gastric residence period; wherein the elongate members comprise: a) a carrier polymer, b) at least one excipient, and c) the adamantane-class drug or the pharmaceutically acceptable salt thereof; wherein the gastric residence system is configured to release the adamantane-class drug or the pharmaceutically acceptable salt thereof over the specified gastric residence period.

Embodiment 21

The gastric residence system of embodiment 20, wherein the adamantane-class drug or a pharmaceutically acceptable salt thereof is memantine or a pharmaceutically acceptable salt thereof.

Embodiment 22

The gastric residence system of embodiment 20 or embodiment 21, wherein at least one of the linkers comprises an enteric polymer.

Embodiment 23

The gastric residence system of any one of embodiments 20-22, wherein at least one of the linkers comprises a polymer that degrades in a time-dependent manner in an aqueous environment.

Embodiment 24

The gastric residence system of any one of embodiments 20-23, wherein the gastric residence period is at least about four days.

Embodiment 25

The gastric residence system of any one of embodiments 20-23, wherein the gastric residence period is about seven days.

Embodiment 26

The gastric residence system of any one of embodiments 20-25, wherein the carrier polymer is polycaprolactone.

Embodiment 27

The gastric residence system of any one of embodiments 20-26, wherein the at least one excipient is selected from the group consisting of soluble excipients, insoluble wicking excipients, degradable excipients, insoluble swellable excipients, and surfactants.

Embodiment 28

The gastric residence system of any one of embodiments 20-26, wherein the at least one excipient is selected from the group consisting of P407, Eudragit E, PEG, Polyvinylpyrrolidone (PVP), Polyvinyl acetate (PVAc), Polyvinyl alcohol (PVA), Eudragit RS, Eudragit RL, PLA, PLGA, PLA-PCL, polydioxanone, Crospovidone, Croscarmellose, HPMCAS, Lecithin, Taurocholate, SDS, Soluplus, Fatty acids, and Kolliphor RH40.

Embodiment 29

The gastric residence system of any one of embodiments 20-28, wherein at least one of the linkers is an enteric polymer, and the enteric polymer is selected from the group consisting of poly(methacrylic acid-co-ethyl acrylate), cellulose acetate phthalate, cellulose acetate succinate, hydroxypropyl methylcellulose phthalate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methacrylic acid methylmethacrylate copolymer, methyl acrylate-methacrylic acid copolymer, methacrylate-methacrylic acid-octyl acrylate copolymer; and copolymers, mixtures, blends and combinations thereof.

Embodiment 30

The gastric residence system of any one of embodiments 20-29, wherein the central elastomer comprises silicone rubber.

Embodiment 31

The gastric residence system of any one of embodiments 20-30, wherein the system further comprises a dispersant selected from the group comprising silicon dioxide, hydrophilic fumed silicon dioxide, a stearate salt, calcium stearate, magnesium stearate, microcrystalline cellulose, carboxymethylcellulose, hydrophobic colloidal silica, hypromellose, magnesium aluminum silicate, a phospholipid, a polyoxyethylene stearate, zinc acetate, alginic acid, lecithin, a fatty acid, sodium lauryl sulfate, a non-toxic metal oxide, aluminum oxide, a porous inorganic material, and a polar inorganic material.

Embodiment 32

The gastric residence system of any one of embodiments 20-31, wherein the adamantane-class drug or pharmaceutically acceptable salt thereof comprises particles of memantine or a pharmaceutically acceptable salt thereof in the form of particles disposed in the carrier polymer, wherein at least about 80% of the mass of particles have sizes between about 1 micron and about 50 microns in diameter.

Embodiment 33

The gastric residence system of any one of embodiments 20-32, wherein the adamantane-class drug or pharmaceutically acceptable salt thereof is memantine or a pharmaceutically acceptable salt thereof, and wherein the gastric residence system comprises about 150 mg to about 350 mg of memantine or a pharmaceutically acceptable salt thereof.

Embodiment 34

A formulation for extended release of an adamantane-class drug, comprising: an adamantane-class drug or a pharmaceutically acceptable salt thereof; silica; an acrylate polymer or co-polymer; a polyalkylene glycol; and a polylactone.

Embodiment 35

The formulation of embodiment 34, further comprising an anti-oxidant material.

Embodiment 36

A formulation for extended release of an adamantane-class drug, comprising:
a) about 10% to about 30% of an adamantane-class drug or a pharmaceutically acceptable salt thereof; b) about 0.1% to about 4% of silica; c) about 5% to about 30% of an acrylate polymer or co-polymer; and d) about 0.2% to about 10% of a polyalkylene glycol; wherein e) the remainder of the composition comprises a polylactone.

Embodiment 37

The formulation of embodiment 36, further comprising f) about 0.1% to about 2% of an anti-oxidant material.

Embodiment 38

The formulation of embodiment 37, wherein the anti-oxidant material comprises one or more compounds selected from the group consisting of a tocopherol, ascorbic acid, or a carotene.

Embodiment 39

The formulation of embodiment 37, wherein the anti-oxidant material comprises alpha-tocopherol.

Embodiment 40

The formulation of any one of embodiments 34-39, wherein the adamantane-class drug is memantine or a pharmaceutically acceptable salt thereof.

Embodiment 41

The formulation of any one of embodiments 34-40, wherein the silica comprises hydrophilic fumed silica particles.

Embodiment 42

The formulation of any one of embodiments 34-41, wherein the acrylate polymer or co-polymer comprises a co-polymer of ethyl acrylate, methyl methacrylate and trimethylammonioethyl methacrylate.

Embodiment 43

The formulation of embodiment 42, wherein the co-polymer of ethyl acrylate, methyl methacrylate and trimethylammonioethyl methacrylate comprises ethyl acrylate, methyl methacrylate and trimethylammonioethyl methacrylate in a molar ratio of about 1:2:0.1.

Embodiment 44

The formulation of any one of embodiments 34-43, wherein the polyalkylene glycol is selected from the group consisting of polyethylene glycol (PEG), polypropylene glycol (PPG), and a block copolymer of PEG and PPG.

Embodiment 45

The formulation of any one of embodiments 34-44, wherein the polyalkylene glycol comprises a block copolymer of PEG and PPG.

Embodiment 46

The formulation of embodiment 45, wherein the block copolymer of PEG and PPG comprises H—$(OCH_2CH_2)_x$—$(O$—$CH(CH_3)CH_2)_y$—$(OCH_2CH_2)_z$—OH, where x and z are about 101 and y is about 56.

Embodiment 47

The formulation of any one of embodiments 34-46, wherein the polylactone comprises polycaprolactone.

Embodiment 48

The formulation of embodiment 47, wherein the polycaprolactone has an average $M_n$ of about 60,000 to 100,000.

Embodiment 49

The formulation of embodiment 47, wherein the polycaprolactone has an average $M_n$ of about 75,000 to 85,000.

Embodiment 50

The formulation of embodiment 47, wherein the polycaprolactone has an average $M_n$ of about 80,000.

Embodiment 51

An elongate member formed from a material comprising a formulation according to any one of embodiments 34-50.

Embodiment 52

A gastric residence system comprising at least one elongate member according to embodiment 51.

Embodiment 53

The gastric residence system according to any one of embodiments 1-33, comprising at least one elongate member according to embodiment 51.

Embodiment 54

A method of making a gastric residence system, comprising: a) preparing at least three elongate members formed from a material comprising a formulation according to any one of embodiments 34-50; and b) attaching the elongate members to a central elastomer to form a gastric residence system having elongate members projecting radially from the central elastomer.

Embodiment 55

A method of treating a neurological or psychiatric disorder in a subject in need of treatment for the disorder, comprising administering the gastric residence system of any one of embodiments 1-33 or 52-53 to the subject.

Embodiment 56

The method of embodiment 55, wherein the neurological or psychiatric disorder is a central nervous system disorder.

Embodiment 57

The method of embodiment 55, wherein the neurological or psychiatric disorder is Alzheimer's Disease.

Embodiment 58

The method of embodiment 55, wherein the neurological or psychiatric disorder is dementia.

Embodiment 59

The method of embodiment 55, wherein the neurological or psychiatric disorder is Lewy Body dementia.

Embodiment 60

The method of embodiment 55, wherein the neurological or psychiatric disorder is HIV-associated dementia.

Embodiment 61

The method of embodiment 55, wherein the neurological or psychiatric disorder is vascular dementia.

Embodiment 62

The method of embodiment 55, wherein the neurological or psychiatric disorder is organic brain syndrome.

Embodiment 63

The method of embodiment 55, wherein the neurological or psychiatric disorder is spasticity.

Embodiment 64

The method of embodiment 55, wherein the neurological or psychiatric disorder is stroke or the resulting effects of stroke.

Embodiment 65

The method of embodiment 55, wherein the neurological or psychiatric disorder is an autism spectrum disorder.

Embodiment 66

The method of embodiment 55, wherein the neurological or psychiatric disorder is Parkinson's Disease.

Embodiment 67

The method of embodiment 55, wherein the neurological or psychiatric disorder is neuropathic pain.

Embodiment 68

The method of embodiment 55, wherein the neurological or psychiatric disorder is attention deficit/hyperactivity disorder (ADHD).

Embodiment 69

The method of embodiment 55, wherein the neurological or psychiatric disorder is obsessive-compulsive disorder (OCD).

Embodiment 70

The method of embodiment 55, wherein the neurological or psychiatric disorder is major depression.

Embodiment 71

The method of any one of embodiments 55-70, wherein the gastric residence system is administered to the patient on an approximately weekly basis over a period of at least about one month.

Embodiment 72

The gastric residence system of any one of embodiments 1-33 or 52-53, wherein the gastric residence system comprises at least one segment with a release rate-controlling polymer film.

Embodiment 73

A method of treating glaucoma in a subject in need of such treatment, comprising administering the gastric residence system of any one of embodiments 1-33, 52-53, or 72 to the subject.

Embodiment 74

A method of treating a viral infection in a subject in need of such treatment, comprising administering the gastric residence system of any one of embodiments 1-33, 52-53, or 72 to the subject.

Embodiment 75

The method of embodiment 74, wherein the viral infection is influenza.

Embodiment 76

The method of any one of embodiments 55-71 or 73-75, wherein the subject is a human.

Embodiment 77

A segment of a gastric residence system, the segment comprising: a carrier polymer; an adamantane-class drug or a salt thereof; and a release rate-modulating polymer film configured to control the release rate of the adamantane-class drug or salt thereof, wherein over a seven-day incubation of the segment in simulated gastric fluid, the amount of the adamantane-class drug or salt thereof released from the segment during day 5 is at least about 40% of the amount of adamantane-class drug or salt thereof released during day 2; and wherein at least about 7% of the total amount of adamantane-class drug or salt thereof in the segment is released on day 2 and at least about 7% of the total amount of adamantane-class drug or salt thereof is released on day 5.

Embodiment 78

A segment of a gastric residence system, the segment comprising: a carrier polymer; an adamantane-class drug or a salt thereof; and a release rate-modulating polymer film configured to control the release rate of the adamantane-class drug or salt thereof, wherein over a seven-day incubation of the segment in simulated gastric fluid, the amount of the adamantane-class drug or salt thereof released from the segment during day 7 is at least about 20% of the amount of adamantane-class drug or salt thereof released during day 1; and wherein at least about 4% of the total amount of adamantane-class drug or salt thereof in the segment is released on day 1 and at least about 4% of the total amount of adamantane-class drug or salt thereof is released on day 7.

Embodiment 79

A segment of a gastric residence system, the segment comprising: a carrier polymer, an adamantane-class drug or a salt thereof; and a release rate-modulating polymer film configured to control the release rate of the adamantane-class drug or salt thereof, wherein the release rate-modulating polymer film is configured such that the release of adamantane-class drug or salt thereof from the segment in 40% ethanol/60% simulated gastric fluid over one hour is no more than about 40% higher compared to release of adamantane-class drug or salt thereof from an equivalent segment in 100% simulated gastric fluid over one hour.

Embodiment 80

A segment of a gastric residence system, the segment comprising: a carrier polymer, an adamantane-class drug or a salt thereof; and a release rate-modulating polymer film configured to control the release rate of the adamantane-class drug or salt thereof, wherein the release rate-modulating polymer film is configured such that the release of adamantane-class drug or salt thereof from the segment in 40% ethanol/60% simulated gastric fluid over one hour is at least about 40% lower than the release of adamantane-class drug or salt thereof from a second segment in 40% ethanol/60% simulated gastric fluid over one hour, the second segment comprising the same combination of carrier polymer and adamantane-class drug or salt thereof but lacking the release rate-modulating polymer film.

Embodiment 81

A segment of a gastric residence system, the segment comprising: a carrier polymer, an adamantane-class drug or a salt thereof; and a release rate-modulating polymer film configured to control the release rate of the adamantane-class drug or salt thereof, wherein the release rate-modulating polymer film is configured such that the release of adamantane-class drug or salt thereof from the segment in simulated gastric fluid over an initial 6 hour period is at least about 40% lower than the release of adamantane-class drug or salt thereof from a second segment in simulated gastric fluid over an initial 6 hour period, the second segment comprising the same combination of carrier polymer and adamantane-class drug or salt thereof but lacking the release rate-modulating polymer film; and wherein the release of adamantane-class drug or salt thereof from the segment in simulated gastric fluid over a seven-day period is at least about 60% of the total amount of adamantane-class drug or salt thereof originally present in the segment.

Embodiment 82

The segment of embodiment 81, wherein the release of adamantane-class drug or salt thereof from the segment in simulated gastric fluid over a seven-day period is at least about 70% of the release of the total amount of adamantane-class drug or salt thereof originally present in the segment.

Embodiment 83

The segment of embodiment 81, wherein the release of adamantane-class drug or salt thereof from the segment in simulated gastric fluid over a seven-day period is at least about 80% of the release of the total amount of adamantane-class drug or salt thereof originally present in the segment.

Embodiment 84

A segment of a gastric residence system, the segment comprising: a carrier polymer; an adamantane-class drug or a salt thereof; and a release rate-modulating polymer film, wherein the polymer film is configured to control the release rate of the adamantane-class drug or salt thereof such that a best-fit linear regression model of the release rate of adamantane-class drug or salt thereof from the segment in simulated gastric fluid has a coefficient of determination $R^2$ of at least about 0.8 over an initial period of seven days; and wherein the segment releases about 40% to about 60% of the adamantane-class drug or salt thereof within a time of about 40% to about 60% of the seven-day period.

Embodiment 85

The segment of embodiment 84, wherein the polymer film is configured to control the release rate of the adamantane-class drug or salt thereof such that a best-fit linear regression model of the release rate of adamantane-class drug or salt thereof from the segment in simulated gastric fluid has a coefficient of determination $R^2$ of at least about 0.9 over an initial period of seven days; and wherein the segment releases about 40% to about 60% of the adamantane-class drug or salt thereof within a time of about 40% to about 60% of the seven-day period.

Embodiment 86

A segment of a gastric residence system, the segment comprising: a carrier polymer; an adamantane-class drug or a salt thereof; and a release rate-modulating polymer film, wherein the polymer film is configured to control the release rate of the adamantane-class drug or salt thereof from the segment over a seven-day period in simulated gastric fluid such that the release rate from the segment over any one of the seven days varies by no more than about 25% from the average daily total release from the segment over the seven days.

Embodiment 87

The segment of a gastric residence system according to any one of embodiments 77-86, wherein the release rate-modulating polymer film comprises one or more polyester materials.

Embodiment 88

The segment of embodiment 87, wherein the polymer film comprises polyester with a repeating unit of the form: —$R^1$—O—C(=O)— wherein $R^1$ is selected from the group consisting of $C_1$-$C_{12}$ alkylene groups, ethers containing between two and twelve carbon atoms, and polyethers containing between three and twelve carbon atoms.

Embodiment 89

The segment of embodiment 87, wherein the polymer film comprises polycaprolactone or polydioxanone.

Embodiment 90

The segment of embodiment 87, wherein the polymer film comprises polycaprolactone of about 10,000 to about 150,000 Mn.

Embodiment 91

The segment of embodiment 87, wherein the polymer film comprises polycaprolactone of about 80,000 Mn to about 110,000 Mn.

Embodiment 92

The segment of embodiment 87, wherein the polymer film comprises polycaprolactone of about 90,000 Mn.

Embodiment 93

The segment of embodiment 87, wherein the polymer film comprises polycaprolactone having intrinsic viscosity of about 1.5 dL/g to about 2.1 dL/g.

Embodiment 94

The segment of any one of embodiments 77-93, wherein polymer film further comprises a porogen.

Embodiment 95

The segment of any one of embodiments 77-93, wherein the porogen comprises a water-soluble polymer, a water-soluble small molecule, an inorganic salt, or an organic salt.

Embodiment 96

The segment of any one of embodiments 77-93, wherein the porogen comprises about 1% to about 30% by weight of the film.

Embodiment 97

The segment of any one of embodiments 77-93, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 98

The segment of any one of embodiments 77-93, wherein the porogen is selected from the group consisting of povidone, copovidone, and polyoxyl castor oil.

Embodiment 99

A segment of a gastric residence system, the segment comprising: a carrier polymer; an adamantane-class drug or a salt thereof; a release rate-modulating polymer film, wherein the polymer film comprises one or more polyester materials.

Embodiment 100

The segment of embodiment 99, wherein the polymer film comprises polyester with a repeating unit of the form: —$R^1$—O—C(=O)— wherein $R^1$ is selected from the group consisting of $C_1$-$C_{12}$ alkylene groups, ethers containing between two and twelve carbon atoms, and polyethers containing between three and twelve carbon atoms.

Embodiment 101

The segment of embodiment 99, wherein the polymer film comprises polycaprolactone or polydioxanone.

Embodiment 102

The segment of embodiment 99, wherein the polymer film comprises polycaprolactone of about 10,000 to about 150,000 Mn.

Embodiment 103

The segment of embodiment 99, wherein the polymer film comprises polycaprolactone of about 80,000 Mn to about 110,000 Mn.

Embodiment 104

The segment of embodiment 99, wherein the polymer film comprises polycaprolactone of about 90,000 Mn.

Embodiment 105

The segment of embodiment 99, wherein the polymer film comprises polycaprolactone having intrinsic viscosity of about 1.5 dL/g to about 2.1 dL/g.

Embodiment 106

A segment of a gastric residence system, the segment comprising: a carrier polymer; an adamantane-class drug or a salt thereof; a release rate-modulating polymer film, wherein the polymer film comprises a material selected from the group consisting of polycaprolactone, cellulose acetate, and ethyl cellulose.

Embodiment 107

A segment of a gastric residence system, the segment comprising: a carrier polymer; an adamantane-class drug or a salt thereof; and a release rate-modulating polymer film, wherein the polymer film comprises about 0.1% to about 10% of the total weight of the segment.

Embodiment 108

The segment of embodiment 107, wherein the polymer film comprises about 0.1% to about 5% of the total weight of the segment.

Embodiment 109

The segment of embodiment 107, wherein the polymer film comprises about 0.5% to about 5% of the total weight of the segment.

Embodiment 110

The segment of embodiment 107, wherein the polymer film comprises about 0.5% to about 2% of the total weight of the segment.

Embodiment 111

The segment of embodiment 107, wherein the polymer film comprises about 1% to about 2% of the total weight of the segment.

Embodiment 112

A segment of a gastric residence system, the segment comprising: a carrier polymer; an adamantane-class drug or a salt thereof; and a release rate-modulating polymer film, wherein the polymer film has a thickness between about 1 micron and about 20 microns.

Embodiment 113

The segment of embodiment 112, wherein the polymer film has a thickness between about 5 microns and about 15 microns.

Embodiment 114

The segment of any one of embodiments 107-113, wherein the polymer film comprises polyester with a repeating unit of the form: —$R^1$—O—C(=O)— wherein $R^1$ is selected from the group consisting of $C_1$-$C_{12}$ alkylene groups, ethers containing between two and twelve carbon atoms, and polyethers containing between three and twelve carbon atoms.

Embodiment 115

The segment of any one of embodiments 107-113, wherein the polymer film comprises polycaprolactone or polydioxanone.

Embodiment 116

The segment of any one of embodiments 107-113, wherein the polymer film comprises polycaprolactone of about 10,000 to about 150,000 Mn.

Embodiment 117

The segment of any one of embodiments 107-113, wherein the polymer film comprises polycaprolactone of about 80,000 Mn to about 110,000 Mn.

Embodiment 118

The segment of any one of embodiments 107-113, wherein the polymer film comprises polycaprolactone of about 90,000 Mn.

Embodiment 119

The segment of any one of embodiments 107-113, wherein the polymer film comprises polycaprolactone having intrinsic viscosity of about 1.5 dL/g to about 2.1 dL/g.

Embodiment 120

A segment of a gastric residence system, the segment comprising: a carrier polymer; an adamantane-class drug or a salt thereof; and a release rate-modulating polymer film, wherein the polymer film further comprises a porogen.

Embodiment 121

The segment of embodiment 120, wherein the porogen comprises a water-soluble polymer, a water-soluble small molecule, an inorganic salt, or an organic salt.

Embodiment 122

The segment of embodiment 120 or embodiment 121, wherein the porogen comprises about 1% to about 30% by weight of the film.

Embodiment 123

The segment of any one of embodiments 44-46, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 124

The segment of any one of embodiments 120-122, wherein the porogen is selected from the group consisting of povidone, copovidone, and polyoxyl castor oil.

Embodiment 125

The segment of any one of embodiments 120-124, wherein the polymer film further comprises a plasticizer.

Embodiment 126

The segment of embodiment 125, wherein the plasticizer comprises about 1% to 40% by weight of the film.

Embodiment 127

The segment of embodiment 125 or embodiment 126, wherein the plasticizer is selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, and poloxamer.

Embodiment 128

The segment of embodiment 125 or embodiment 126, wherein the plasticizer is selected from the group consisting of triethyl citrate and triacetin.

Embodiment 129

The segment of any one of embodiments 120-128, wherein the polymer film comprises polyester with a repeating unit of the form: —R$^1$—O—C(=O)— wherein R$^1$ is selected from the group consisting of $C_1$-$C_{12}$ alkylene groups, ethers containing between two and twelve carbon atoms, and polyethers containing between three and twelve carbon atoms.

Embodiment 130

The segment of any one of embodiments 120-128, wherein the polymer film comprises polycaprolactone or polydioxanone.

Embodiment 131

The segment of any one of embodiments 120-128, wherein the polymer film comprises polycaprolactone of about 10,000 to about 150,000 Mn.

Embodiment 132

The segment of any one of embodiments 120-128, wherein the polymer film comprises polycaprolactone of about 80,000 Mn to about 110,000 Mn.

Embodiment 133

The segment of any one of embodiments 120-128, wherein the polymer film comprises polycaprolactone of about 90,000 Mn.

Embodiment 134

The segment of any one of embodiments 120-128, wherein the polymer film comprises polycaprolactone having intrinsic viscosity of about 1.5 dL/g to about 2.1 dL/g.

Embodiment 135

A segment of a gastric residence system, the segment comprising: a carrier polymer; an adamantane-class drug or a salt thereof; and a release rate-modulating polymer film, wherein the polymer film further comprises a permeable component which is permeable to the adamantane-class drug or salt thereof and permeable to water.

Embodiment 136

The segment of embodiment 135, wherein the permeable component is a polymer or a swellable material.

Embodiment 137

The segment of embodiment 135 or embodiment 136, wherein the permeable component comprises about 1% to about 30% by weight of the film.

Embodiment 138

The segment of any one of embodiments 135-137, wherein the permeable component is selected from the group consisting of SSG, crospovidone, croscarmellose, and Carbopol (PAA).

Embodiment 139

The segment of any one of embodiments 135-138, wherein the polymer film further comprises a plasticizer.

Embodiment 140

The segment of embodiment 139, wherein the plasticizer comprises about 1% to 40% by weight of the film.

Embodiment 141

The segment of embodiment 139 or embodiment 140, wherein the plasticizer is selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, poloxamer, tributyl citrate, and dibutyl sebacate.

Embodiment 142

The segment of 139 or embodiment 140, wherein the plasticizer is selected from the group consisting of triethyl citrate and triacetin.

Embodiment 143

The segment of any one of embodiments 135-142, wherein the polymer film comprises polyester with a repeating unit of the form: —$R^1$—O—C(=O)— wherein $R^1$ is selected from the group consisting of $C_1$-$C_{12}$ alkylene groups, ethers containing between two and twelve carbon atoms, and polyethers containing between three and twelve carbon atoms.

Embodiment 144

The segment of any one of embodiments 135-142, wherein the polymer film comprises polycaprolactone or polydioxanone.

Embodiment 145

The segment of any one of embodiments 135-142, wherein the polymer film comprises polycaprolactone of about 10,000 to about 150,000 Mn.

Embodiment 146

The segment of any one of embodiments 135-142, wherein the polymer film comprises polycaprolactone of about 80,000 Mn to about 110,000 Mn.

Embodiment 147

The segment of any one of embodiments 135-142, wherein the polymer film comprises polycaprolactone of about 90,000 Mn.

Embodiment 148

The segment of any one of embodiments 135-142, wherein the polymer film comprises polycaprolactone having intrinsic viscosity of about 1.5 dL/g to about 2.1 dL/g.

Embodiment 149

A gastric residence system for administration to a patient, comprising: an elastomer component, and at least three elongate members attached to the elastomer component, wherein each elongate member comprises a proximal end, a distal end, and an outer surface therebetween, the proximal end of each elongate member is attached to the elastomer component and projects radially from the elastomer component, each elongate member has its distal end not attached to the elastomer component and located at a larger radial distance from the elastomer component than the proximal end; wherein at least one elongate member comprises a segment of any one of embodiments 77-148.

Embodiment 150

A gastric residence system for administration to a patient, comprising at least one segment of any one of embodiments 77-148.

Embodiment 151

A method of making a segment of a gastric residence system comprising: coating a segment comprising a carrier polymer and an adamantane-class drug or a salt thereof with a solution of a polymer film formulation to produce a film-coated segment; and drying the film-coated segment.

Embodiment 152

The method of embodiment 151, wherein the coating is performed by dip coating.

Embodiment 153

The method of embodiment 151, wherein the coating is performed by pan coating.

Embodiment 154

The method of embodiment 151, wherein the coating is performed by spray coating.

Embodiment 155

The method of embodiment 151, wherein the coating is performed by fluidized bed coating.

Embodiment 156

The method of any one of embodiments 151-155, wherein the solvent used in the solution of polymer film formulation comprises an organic solvent.

Embodiment 157

The method of embodiment 156, wherein the solvent used in the polymer film formulation comprises ethyl acetate, dichloromethane, acetone, or any combination thereof.

Embodiment 158

A method of making a segment of a gastric residence system comprising:
co-extruding a polymer film and a mixture of a carrier polymer and an adamantane-class drug or a salt thereof.

Embodiment 159

The method of any one of embodiments 151-158, wherein the polymer film formulation comprises polyester with a repeating unit of the form: —$R^1$—O—C(=O)— wherein $R^1$ is selected from the group consisting of $C_1$-$C_{12}$ alkylene groups, ethers containing between two and twelve carbon atoms, and polyethers containing between three and twelve carbon atoms.

Embodiment 160

The method of any one of embodiments 151-158, wherein the polymer film formulation comprises polycaprolactone or polydioxanone.

Embodiment 161

The method of any one of embodiments 151-158, wherein the polymer film formulation comprises polycaprolactone of about 10,000 to about 150,000 Mn.

Embodiment 162

The method of any one of embodiments 151-158, wherein the polymer film formulation comprises polycaprolactone of about 80,000 Mn to about 110,000 Mn.

Embodiment 163

The method of any one of embodiments 151-158, wherein the polymer film formulation comprises polycaprolactone of about 90,000 Mn.

Embodiment 164

The method of any one of embodiments 151-158, wherein the polymer film formulation comprises polycaprolactone having intrinsic viscosity of about 1.5 dL/g to about 2.1 dL/g.

Embodiment 165

The method of any one of embodiments 151-164, wherein polymer film further comprises a porogen.

Embodiment 166

The method of embodiment 164, wherein the porogen comprises a water-soluble polymer, a water-soluble small molecule, an inorganic salt, or an organic salt.

Embodiment 167

The method of any one of embodiments 165-166, wherein the porogen comprises about 1% to about 30% by weight of the film.

Embodiment 168

The method of any one of embodiments 165-167, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 169

The method of any one of embodiments 165-168, wherein the porogen is selected from the group consisting of povidone, copovidone, and polyoxyl castor oil.

Embodiment 170

The gastric residence system of embodiment 149, wherein the central elastomer is formed from liquid silicone rubber.

Embodiment 171

The gastric residence system of embodiment 149 or embodiment 170, wherein the elongate members are attached to the central elastomer via a disintegrating matrix.

Embodiment 172

The gastric residence system of embodiment 171, wherein the disintegrating matrix comprises HPMC-AS and polycaprolactone.

Embodiment 173

A method of administering a gastric residence system to a patient, comprising: administering a container containing a gastric residence system of any one of embodiments 149, 150, or 170-172 in a compacted state to a patient, wherein the container enters the stomach of the patient and dissolves after entry into the stomach, releasing the gastric residence system which then adopts its uncompacted state.

Embodiment 174

The method of embodiment 173, wherein the patient is a human.

Embodiment 175

The method of embodiment 173 or 174, wherein the container containing the gastric residence system is administered by swallowing, by feeding tube, or by gastrostomy tube.

Embodiment 176

The segment of any one of embodiments 77-148, wherein the adamantane-class drug or salt thereof is selected from the group consisting of memantine, amantadine, adapromine, nitromemantine, rimantadine, bromantane, tromantadine, neramexane, a pharmaceutically acceptable salt of memantine, a pharmaceutically acceptable salt of amantadine, a pharmaceutically acceptable salt of adapromine, a pharmaceutically acceptable salt of nitromemantine, a pharmaceutically acceptable salt of rimantadine, a pharmaceutically acceptable salt of bromantane, a pharmaceutically acceptable salt of tromantadine, and a pharmaceutically acceptable salt of neramexane.

Embodiment 177

The segment of any one of embodiments 77-148, wherein the adamantane-class drug or salt thereof is selected from the group consisting of memantine and a pharmaceutically acceptable salt of memantine.

Embodiment 178

The segment of any one of embodiments 77-148, wherein the adamantane-class drug or salt thereof is memantine.

Embodiment 179

The segment of any one of embodiments 77-148, wherein the adamantane-class drug or salt thereof is a pharmaceutically acceptable salt of memantine.

Embodiment 180

The segment of any one of embodiments 77-148, wherein the adamantane-class drug or salt thereof is memantine hydrochloride.

Embodiment 181

The gastric residence system of any one of embodiments 149-150 or 170-172, wherein the adamantane-class drug or salt thereof is selected from the group consisting of memantine, amantadine, adapromine, nitromemantine, rimantadine, bromantane, tromantadine, neramexane, a pharmaceutically acceptable salt of memantine, a pharmaceutically acceptable salt of amantadine, a pharmaceutically acceptable salt of adapromine, a pharmaceutically acceptable salt of nitromemantine, a pharmaceutically acceptable salt of rimantadine, a pharmaceutically acceptable salt of bromantane, a pharmaceutically acceptable salt of tromantadine, and a pharmaceutically acceptable salt of neramexane.

Embodiment 182

The gastric residence system of any one of embodiments 149-150 or 170-172, wherein the adamantane-class drug or salt thereof is selected from the group consisting of memantine and a pharmaceutically acceptable salt of memantine.

Embodiment 183

The gastric residence system of any one of embodiments 149-150 or 170-172, wherein the adamantane-class drug or salt thereof is memantine.

Embodiment 184

The gastric residence system of any one of embodiments 149-150 or 170-172, wherein the adamantane-class drug or salt thereof is a pharmaceutically acceptable salt of memantine.

Embodiment 185

The gastric residence system of any one of embodiments 149-150 or 170-172, wherein the adamantane-class drug or salt thereof is memantine hydrochloride.

Embodiment 186

The method of any one of embodiments 151-169 or 173-175, wherein the adamantane-class drug or salt thereof is selected from the group consisting of memantine, amantadine, adapromine, nitromemantine, rimantadine, bromantane, tromantadine, neramexane, a pharmaceutically acceptable salt of memantine, a pharmaceutically acceptable salt of amantadine, a pharmaceutically acceptable salt of adapromine, a pharmaceutically acceptable salt of nitromemantine, a pharmaceutically acceptable salt of rimantadine, a pharmaceutically acceptable salt of bromantane, a pharmaceutically acceptable salt of tromantadine, and a pharmaceutically acceptable salt of neramexane.

Embodiment 187

The method of any one of embodiments 151-169 or 173-175, wherein the adamantane-class drug or salt thereof is selected from the group consisting of memantine and a pharmaceutically acceptable salt of memantine.

Embodiment 188

The method of any one of embodiments 151-169 or 173-175, wherein the adamantane-class drug or salt thereof is memantine.

Embodiment 189

The method of any one of embodiments 151-169 or 173-175, wherein the adamantane-class drug or salt thereof is a pharmaceutically acceptable salt of memantine.

Embodiment 190

The method of any one of embodiments 151-169 or 173-175, wherein the adamantane-class drug or salt thereof is memantine hydrochloride.

Embodiment 191

A method of treating a neurological or psychiatric disorder in a subject in need of treatment for the disorder, comprising administering the gastric residence system of any one of embodiments 149-150 or 170-172 to the subject.

Embodiment 192

The method of embodiment 191, wherein the neurological or psychiatric disorder is a central nervous system disorder.

Embodiment 193

The method of embodiment 191, wherein the neurological or psychiatric disorder is Alzheimer's Disease.

Embodiment 194

The method of embodiment 191, wherein the neurological or psychiatric disorder is dementia.

Embodiment 195

The method of embodiment 191, wherein the neurological or psychiatric disorder is Lewy Body dementia.

Embodiment 196

The method of embodiment 191, wherein the neurological or psychiatric disorder is HIV-associated dementia.

Embodiment 197

The method of embodiment 191, wherein the neurological or psychiatric disorder is vascular dementia.

Embodiment 198

The method of embodiment 191, wherein the neurological or psychiatric disorder is organic brain syndrome.

Embodiment 199

The method of embodiment 191, wherein the neurological or psychiatric disorder is spasticity.

Embodiment 200

The method of embodiment 191, wherein the neurological or psychiatric disorder is stroke or the resulting effects of stroke.

Embodiment 201

The method of embodiment 191, wherein the neurological or psychiatric disorder is an autism spectrum disorder.

Embodiment 202

The method of embodiment 191, wherein the neurological or psychiatric disorder is Parkinson's Disease.

Embodiment 203

The method of embodiment 191, wherein the neurological or psychiatric disorder is neuropathic pain.

Embodiment 204

The method of embodiment 191, wherein the neurological or psychiatric disorder is attention deficit/hyperactivity disorder (ADHD).

Embodiment 205

The method of embodiment 191, wherein the neurological or psychiatric disorder is obsessive-compulsive disorder (OCD).

Embodiment 206

The method of embodiment 191, wherein the neurological or psychiatric disorder is major depression.

Embodiment 207

The method of any one of embodiments 191-206, wherein the gastric residence system is administered to the patient on an approximately weekly basis over a period of at least about one month.

Embodiment 208

A method of treating glaucoma in a subject in need of such treatment, comprising administering the gastric residence system of any one of embodiments 149-150 or 170-172 to the subject.

Embodiment 209

A method of treating a viral infection in a subject in need of such treatment, comprising administering the gastric residence system of any one of embodiments 149-150 or 170-172 to the subject.

Embodiment 210

The method of embodiment 209, wherein the viral infection is influenza.

Embodiment 211

The method of any one of embodiments 191-210, wherein the subject is a human.

Embodiment 212

The gastric residence system of any one of embodiments 11-12, wherein the adamantane-class drug or a pharmaceutically acceptable salt thereof comprises memantine, amantadine, adapromine, nitromemantine, rimantadine, bromantane, tromantadine, neramexane, a pharmaceutically acceptable salt of memantine, a pharmaceutically acceptable salt of amantadine, a pharmaceutically acceptable salt of adapromine, a pharmaceutically acceptable salt of nitromemantine, a pharmaceutically acceptable salt of rimantadine, a pharmaceutically acceptable salt of bromantane, a pharmaceutically acceptable salt of tromantadine, or a pharmaceutically acceptable salt of neramexane.

Embodiment 213

A gastric residence system comprising memantine or a pharmaceutically acceptable salt thereof, wherein the gastric residence system is characterized by one or more of the following characteristics:

a) the gastric residence system provides a human in vivo plasma profile which is characterized by a $t_{max}$ for memantine or pharmaceutically acceptable salt thereof of about 25 hours±15 hours after administration of a single gastric residence system to a human patient;

b) the gastric residence system provides a human in vivo plasma profile which is characterized by a $C_{max}/D$ for memantine or pharmaceutically acceptable salt thereof of about 1 ng/mL/mg±0.5 ng/mL/mg after administration of a single gastric residence system to a human patient, where D is the total mass in milligrams of the adamantane-class drug or pharmaceutically acceptable salt thereof in the gastric residence system;

c) the gastric residence system provides a human in vivo plasma profile which is characterized by a $C_{max}/D'$ for memantine or pharmaceutically acceptable salt thereof of about 1 ng/mL/mg±0.5 ng/mL/mg after administration of a single gastric residence system to a human patient, where D' is the total mass in milligrams of the adamantane-class drug or pharmaceutically acceptable salt thereof released from the gastric residence system during its residence period in the stomach;

d) the gastric residence system provides a human in vivo plasma profile which is characterized by an AUC/D for memantine or pharmaceutically acceptable salt thereof for 0 to 72 hours of about 55 hours-ng/mL/mg±25 hours-ng/mL/mg after administration of a single gastric residence system to a human patient;

e) the gastric residence system provides a human in vivo plasma profile which is characterized by an AUC/D' for memantine or pharmaceutically acceptable salt thereof for 0 to 72 hours of about 55 hours-ng/mL/mg±25 hours-ng/mL/mg after administration of a single gastric residence system to a human patient;

f) the gastric residence system provides a human in vivo plasma profile which is characterized by a $C_{max}$ for memantine or pharmaceutically acceptable salt thereof of about 30 ng/mL±15 ng/mL after administration of a single gastric residence system to a human patient; and g) the gastric residence system provides a human in vivo plasma profile which is characterized by an AUC for memantine or pharmaceutically acceptable salt thereof for 0 to 72 hours of about 1500 hours-ng/mL±750 hours-ng/mL after administration of a single gastric residence system to a human patient.

Embodiment 214

A gastric residence system comprising memantine or a pharmaceutically acceptable salt thereof, wherein the gastric residence system is characterized by one or more of the following characteristics:

a) the gastric residence system provides a human in vivo plasma profile at steady state having a $C_{max,ss}$ for memantine or pharmaceutically acceptable salt thereof of about 140 ng/mL±50 ng/mL;

b) the gastric residence system provides a human in vivo plasma profile at steady state having a $C_{min,ss}$ for memantine or pharmaceutically acceptable salt thereof of about 90 ng/mL±40 ng/mL, with the caveat that $C_{min,ss}$ is less than $C_{max,ss}$;

c) the gastric residence system provides a human in vivo plasma profile at steady state having a $C_{ave,ss}$ for memantine or pharmaceutically acceptable salt thereof of about 115 ng/mL±15 ng/mL, with the caveat that $C_{ave,ss}$ is greater than $C_{min,ss}$ and $C_{ave,ss}$ is less than $C_{max,ss}$; and d) the gastric residence system provides a human in vivo plasma profile at steady state having an $AUC_\tau$ for memantine or pharmaceutically acceptable salt thereof of about 2750 hour-ng/mL·±750 hour-ng/mL.

Embodiment 215

A gastric residence system providing an extended release drug dosage form, comprising a therapeutically effective amount of an adamantane-class drug or a pharmaceutically acceptable salt thereof and a component adapted to provide extended release of the drug or salt thereof in an aqueous environment, wherein upon administration of the gastric residence system to a dog, the dog absorbs at least 5% of the available adamantane-class drug or pharmaceutically acceptable salt thereof during each 24-hour day over a seven-day period after administration of the gastric residence system, wherein available adamantane-class drug or pharmaceutically acceptable salt thereof represents the total amount of adamantane-class drug or pharmaceutically acceptable salt thereof absorbed over the gastric residence period.

Embodiment 216

A gastric residence system providing an extended release drug dosage form, comprising a therapeutically effective amount of an adamantane-class drug or a pharmaceutically acceptable salt thereof and a component adapted to provide extended release of the drug or salt thereof in an aqueous environment, wherein upon administration of the gastric residence system to a dog, the average plasma concentration of adamantane-class drug or a pharmaceutically acceptable salt thereof over an interval of 24 hours after administration to seven days after administration is between about 8 ng/mL to about 60 ng/mL.

Embodiment 217

The gastric residence system of embodiments 215 or 216, wherein the dog is a beagle dog weighing about 8 kg to about 12 kg, preferably about 10 kg.

Embodiment 218

The gastric residence system of any one of embodiments 215-217, wherein the adamantane-class drug or pharmaceutically acceptable salt thereof is memantine or memantine hydrochloride.

Embodiment 219

The gastric residence system of any one of embodiments 215-217, wherein the adamantane-class drug or pharmaceutically acceptable salt thereof is memantine hydrochloride.

Embodiment 220

The gastric residence system of any one of embodiments 215-219, wherein the gastric residence system comprises about 100 mg to about 200 mg of memantine hydrochloride, preferably about 125 mg to about 175 mg of memantine hydrochloride, preferably about 150 mg of memantine hydrochloride.

Embodiment 221

The gastric residence system of any one of embodiments 215-220, wherein no more than about 25% of available adamantane-class drug or pharmaceutically acceptable salt thereof is absorbed during each 24-hour day over a seven-day period after administration of the gastric residence system.

Embodiment 222

The gastric residence system of any one of embodiments 215-220, wherein about 5% to about 25% of available adamantane-class drug or pharmaceutically acceptable salt thereof is absorbed during each 24-hour day over a seven-day period after administration of the gastric residence system.

Embodiment 223

The gastric residence system of any one of embodiments 215-222, wherein the gastric residence system comprises a plurality of elongate members affixed to a central elastomer, wherein at least one elongate member comprises the component adapted to provide extended release of the drug or salt thereof, wherein the component adapted to provide extended release of the drug or salt thereof comprises a carrier polymer.

Embodiment 224

The gastric residence system of any one of embodiments 215-223, wherein the gastric residence system further comprises a release rate-modulating polymer film.

Embodiment 225

The gastric residence system of embodiment 223, wherein at least one elongate member of the gastric residence system further comprises a release rate-modulating polymer film.

Embodiment 226

A gastric residence system comprising a carrier polymer; an adamantane-class drug or a salt thereof; and a release rate-modulating polymer film, wherein the polymer film is configured to control the release rate of the adamantane-class drug or salt thereof such that a best-fit linear regression model of the release rate of adamantane-class drug or salt thereof from the system in simulated gastric fluid has a coefficient of determination $R^2$ of at least about 0.9 over an initial period of seven days; and wherein the system releases about 40% to about 60% of the adamantane-class drug or salt thereof within a time of about 40% to about 60% of the seven-day period.

Embodiment A1

A gastric residence system comprising a therapeutically effective amount of an adamantane-class drug or a pharmaceutically acceptable salt thereof, wherein: the gastric residence system has a compacted configuration and an uncompacted configuration, the gastric residence system comprises a plurality of elongate members affixed to a central elastomer, wherein at least one elongate member comprises: a carrier polymer, the adamantane-class drug or the pharmaceutically acceptable salt thereof, and a release rate-modulating polymer film coated on the surface of the at least one elongate member; wherein the gastric residence system is configured to release the adamantane-class drug or the pharmaceutically acceptable salt thereof over a specified gastric residence period.

Embodiment A2

The gastric residence system of embodiment A1, wherein the elongate members are affixed to the central elastomer via linkers, wherein the linkers are configured to weaken or degrade to allow passage of the gastric residence system through the pylorus after the specified gastric residence period.

Embodiment A3

The gastric residence system of embodiment A1, wherein at least one elongate member comprises at least two segments joined by linkers, wherein the linkers are configured to weaken or degrade to allow passage of the gastric residence system through the pylorus after the specified gastric residence period.

Embodiment A4

The gastric residence system of any one of embodiments A1-A3, wherein the adamantane-class drug or the pharmaceutically acceptable salt thereof is selected from the group consisting of memantine; amantadine; adapromine; nitromemantine; rimantadine; bromantane; tromantadine; neramexane; and a pharmaceutically acceptable salt of any one of memantine, amantadine, adapromine, nitromemantine, rimantadine, bromantane, tromantadine, and neramexane.

Embodiment A5

The gastric residence system of any one of embodiments A1-A3, wherein the adamantane-class drug or the pharmaceutically acceptable salt thereof is selected from the group consisting of memantine; and a pharmaceutically acceptable salt of memantine.

Embodiment A6

The gastric residence system according to any one of embodiments A1-A3, wherein the release rate-modulating polymer film comprises one or more polyester materials.

Embodiment A7

The gastric residence system of embodiment A6, wherein the polymer film comprises polyester with a repeating unit of the form: —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms.

Embodiment A8

The gastric residence system of embodiment A7, wherein the polymer film comprises polycaprolactone.

Embodiment A9

The gastric residence system of embodiment A7, wherein the polymer film further comprises a porogen.

Embodiment A10

The gastric residence system of embodiment A9, wherein the porogen is selected from the group consisting of povidone, copovidone, and polyoxyl castor oil.

Embodiment A11

The gastric residence system according to any one of embodiments A1-A5, wherein the release rate-modulating polymer film comprises one or more polyester materials.

Embodiment A12

The gastric residence system of embodiment A11, wherein the polymer film comprises polyester with a repeating unit of the form: —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms.

Embodiment A13

The gastric residence system of embodiment A12, wherein the polymer film comprises polycaprolactone or polydioxanone.

Embodiment A14

The gastric residence system of embodiment A13, wherein the polymer film comprises polycaprolactone of about 10,000 to about 150,000 Mn.

Embodiment A15

The gastric residence system of embodiment A13, wherein the polymer film comprises polycaprolactone of about 80,000 Mn to about 110,000 Mn.

Embodiment A16

The gastric residence system of embodiment A13, wherein the polymer film comprises polycaprolactone of about 90,000 Mn.

Embodiment A17

The gastric residence system of embodiment A13, wherein the polymer film comprises polycaprolactone having intrinsic viscosity of about 1.5 dL/g to about 2.1 dL/g.

Embodiment A18

The gastric residence system of any one of embodiments A1-A17, wherein the polymer film further comprises a porogen.

Embodiment A19

The gastric residence system of embodiment A18, wherein the porogen comprises a water-soluble polymer, a water-soluble small molecule, an inorganic salt, or an organic salt.

Embodiment A20

The gastric residence system of embodiment A18 or embodiment A19, wherein the porogen comprises about 5% to about 30% by weight of the film.

Embodiment A21

The gastric residence system of any one of embodiments A18-A20, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment A22

The gastric residence system of any one of embodiments A18-A20, wherein the porogen is selected from the group consisting of povidone, copovidone, and polyoxyl castor oil.

Embodiment A23

The gastric residence system of any one of embodiments A1-A22, wherein the polymer film further comprises a plasticizer.

Embodiment A24

The gastric residence system of embodiment A23, wherein the plasticizer comprises triethyl citrate, triacetin, PEG, poloxamer, tributyl citrate, or dibutyl sebacate.

Embodiment A25

The gastric residence system of embodiment A23 or embodiment A24, wherein the plasticizer comprises about 5% to about 30% by weight of the film.

Embodiment A26

The gastric residence system of any one of embodiments A1-A25, wherein the polymer film further comprises an anti-tack agent.

Embodiment A27

The gastric residence system of embodiment A26, wherein the anti-tack agent is selected from the group consisting of magnesium stearate, talc, and glycerol monostearate.

Embodiment A28

The gastric residence system of any one of embodiments A1-A27, wherein the carrier polymer comprises a polylactone.

Embodiment A29

The gastric residence system of embodiment A28, wherein the polylactone comprises polycaprolactone.

Embodiment A30

The gastric residence system of embodiment A29, wherein the polycaprolactone has an average $M_n$ of about 60,000 to about 100,000.

Embodiment A31

The gastric residence system of embodiment A29, wherein the polycaprolactone has an average $M_n$ of about 75,000 to about 85,000.

Embodiment A32

The gastric residence system of embodiment A29, wherein the polycaprolactone has an average $M_n$ of about 80,000.

Embodiment A33

The gastric residence system of any one of embodiments A1-A32, wherein the elongate members further comprise at least one excipient.

Embodiment A34

The gastric residence system of embodiment A33, wherein the at least one excipient comprises a polyalkylene glycol.

Embodiment A35

The gastric residence system of embodiment A34, wherein the polyalkylene glycol is selected from the group consisting of polyethylene glycol (PEG), polypropylene glycol (PPG), and a block copolymer of PEG and PPG.

Embodiment A36

The gastric residence system of embodiment A34, wherein the polyalkylene glycol comprises a block copolymer of PEG and PPG.

Embodiment A37

The gastric residence system of embodiment A34, wherein the block copolymer of PEG and PPG comprises H—(OCH$_2$CH$_2$)$_x$—(O—CH(CH$_3$)CH$_2$)$_y$—(OCH$_2$CH$_2$)$_z$—OH, where x and z are about 101 and y is about 56.

Embodiment A38

The gastric residence system of any one of embodiments A1-A37, wherein the elongate members further comprise an anti-oxidant.

Embodiment A39

The gastric residence system of any one of embodiments A1-A38, wherein the elongate members further comprise silica.

Embodiment A40

The gastric residence system of any one of embodiments A1-A39, wherein the central elastomer comprises silicone rubber.

Embodiment A41

The gastric residence system of any one of embodiments A1-A40, wherein the plurality of elongate members comprises at least three elongate members.

Embodiment A42

The gastric residence system of any one of embodiments A1-A40, wherein the plurality of elongate members is six elongate members.

Embodiment A43

The gastric residence system of any one of embodiments A1-A42, wherein the system has a gastric residence period of about four days to about eight days when administered to a human patient.

Embodiment A44

The gastric residence system of any one of embodiments A1-A42, wherein the system has a gastric residence period of about seven days to about ten days when administered to a human patient.

Embodiment A45

The gastric residence system of any one of embodiments A1-A44, wherein the system is configured to have a dissolution profile characterized by about 10% to 20% dissolution of the initial amount of the adamantane-class drug or pharmaceutically acceptable salt thereof present in the system during an initial 24 hour period in an aqueous environment.

Embodiment A46

The gastric residence system of any one of embodiments A1-A44, wherein the system is configured to have a dissolution profile characterized by about 20% to 40% dissolution of the initial amount of the adamantane-class drug or pharmaceutically acceptable salt thereof present in the system during an initial 48 hour period in an aqueous environment.

Embodiment A47

The gastric residence system of any one of embodiments A1-A44, wherein the system is configured to elute about 20 mg to about 36 mg of the adamantane-class drug or pharmaceutically acceptable salt thereof per day during the first two days in an aqueous environment.

Embodiment A48

The gastric residence system of any one of embodiments A45-A47, wherein the adamantane-class drug or pharmaceutically acceptable salt thereof is memantine or a pharmaceutically acceptable salt of memantine.

Embodiment A49

The gastric residence system of any one of embodiments A45-A48, wherein the aqueous environment is the stomach of a mammal.

Embodiment A50

The gastric residence system of any one of embodiments A45-A48, wherein the aqueous environment is the stomach of a human patient.

Embodiment A51

The gastric residence system of any one of embodiments A45-A48, wherein the aqueous environment is simulated gastric fluid, fasted state simulated gastric fluid, or fed state simulated gastric fluid.

Embodiment A52

The gastric residence system of any one of embodiments A1-A51, wherein the gastric residence system is configured to provide a human in vivo plasma profile which is characterized by a $t_{max}$ for the adamantane-class drug or pharmaceutically acceptable salt thereof of about 25 hours±15 hours after administration of a single gastric residence system to a human patient; or wherein the gastric residence system is configured to provide a human in vivo plasma profile which is characterized by a $C_{max}/D$ for the adamantane-class drug or pharmaceutically acceptable salt thereof of about 1 ng/mL/mg±0.5 ng/mL/mg after administration of a single gastric residence system to a human patient, where D is the total mass in milligrams of the adamantane-class drug or pharmaceutically acceptable salt thereof in the gastric residence system; or wherein the gastric residence system is configured to provide a human in vivo plasma profile which is characterized by a $C_{max}/D'$ for the adamantane-class drug or pharmaceutically acceptable salt thereof of about 1 ng/mL/mg±0.5 ng/mL/mg after administration of a single gastric residence system to a human patient, where D' is the total mass in milligrams of the drug released from the gastric residence system during its residence period in the stomach; or wherein the gastric residence system is configured to provide a human in vivo plasma profile which is characterized by an AUC/D for the adamantane-class drug or pharmaceutically acceptable salt thereof for 0 to 72 hours of about 55 hours-ng/mL/mg±25 hours-ng/mL/mg after administration of a single gastric residence system to a human patient; or wherein the gastric residence system is configured to provide a human in vivo plasma profile which is characterized by an AUC/D' for adamantane-class drug or pharmaceutically acceptable salt thereof for 0 to 72 hours of about 55 hours-ng/mL/mg±25 hours-ng/mL/mg after administration of a single gastric residence system to a human patient; or wherein the gastric residence system is configured to provide a human in vivo plasma profile which is characterized by a $C_{max}$ for the adamantane-class drug or pharmaceutically acceptable salt thereof of about 30 ng/mL±15 ng/mL after administration of a single gastric residence system to a human patient; or wherein the gastric residence system is configured to provide a human in vivo plasma profile which is characterized by an AUC for the adamantane-class drug or pharmaceutically acceptable salt thereof for 0 to 72 hours of about 1500 hours-ng/mL±750 hours-ng/mL after administration of a single gastric residence system to a human patient; or wherein the gastric residence system is configured to provide a human in vivo plasma profile of adamantane-class drug or pharmaceutically acceptable salt thereof at steady state which is characterized by a fluctuation F of about 40%±35%; or wherein the gastric residence system is configured to provide a human in vivo plasma profile at steady state having a $C_{max,ss}$ for the adamantane-class drug or pharmaceutically acceptable salt thereof of about 140 ng/mL±50 ng/mL; or wherein the gastric residence system is configured to provide a human in vivo plasma profile at steady state having a $C_{min,ss}$ for the adamantane-class drug or pharmaceutically acceptable salt thereof of about 90 ng/mL±40 ng/mL, with the caveat that $C_{min,ss}$ is less than $C_{max,ss}$; or wherein the gastric residence system is configured to provide a human in vivo plasma profile at steady state having a $C_{ave,ss}$ for the adamantane-class drug or pharmaceutically acceptable salt thereof of about 115 ng/mL±15 ng/mL, with the caveat that $C_{ave,ss}$ is greater than $C_{min,ss}$ and $C_{ave,ss}$ is less than $C_{max,ss}$; or wherein the gastric residence system is configured to provide a human in vivo plasma profile at steady state having an $AUC_\tau$ for the adamantane-class drug or pharmaceutically acceptable salt thereof of about 2750 hour-ng/mL·±750 hour-ng/mL; or wherein the gastric residence system is configured to provide a human in vivo plasma profile at steady state having a $C_{max,ss}$ for the adamantane-class drug or pharmaceutically acceptable salt thereof of about 140 ng/mL±50 ng/mL; or wherein the gastric residence system is configured to provide a human in vivo plasma profile at steady state having a $C_{min,ss}$ for the adamantane-class drug or pharmaceutically acceptable salt thereof of about 90 ng/mL±40 ng/mL, with the caveat that $C_{min,ss}$ is less than $C_{max,ss}$; or wherein the gastric residence system is configured to provide a human in vivo plasma profile at steady state having a $C_{ave,ss}$ for the adamantane-class drug or pharmaceutically acceptable salt thereof of about 115 ng/mL±15 ng/mL, with the caveat that $C_{ave,ss}$ is greater than $C_{min,ss}$ and $C_{ave,ss}$ is less than $C_{max,ss}$; or wherein the gastric residence system is configured to provide a human in vivo plasma profile at steady state having an $AUC_\tau$ for the adamantane-class drug or pharmaceutically acceptable salt thereof of about 2750 hour-ng/mL·±750 hour-ng/mL.

Embodiment A53

The gastric residence system of any one of embodiments 1-52, wherein the adamantane-class drug or a pharmaceutically acceptable salt thereof comprises memantine or a pharmaceutically acceptable salt thereof.

Embodiment A54

The gastric residence system of any one of embodiments A1-A53, wherein the system comprises between about 80 mg to about 260 mg of adamantane-class drug or pharmaceutically acceptable salt thereof.

Embodiment A55

The gastric residence system of any one of embodiments A1-A53, wherein the gastric residence system comprises about 140 mg to about 420 mg of memantine or a pharmaceutically acceptable salt thereof.

Embodiment A56

The gastric residence system of any one of embodiments A1-A53, wherein the gastric residence system comprises about 140 mg to about 280 mg of memantine or a pharmaceutically acceptable salt thereof.

Embodiment A57

The gastric residence system of any one of embodiments A1-A53, wherein the gastric residence system comprises about 196 mg of memantine or a pharmaceutically acceptable salt thereof.

Embodiment A58

A gastric residence system comprising: a carrier polymer; an adamantane-class drug or a salt thereof; and wherein over a seven-day incubation of the system in simulated gastric fluid, the amount of the adamantane-class drug or salt thereof released from the system during day 5 is at least about 40% of the amount of adamantane-class drug or salt thereof released during day 2; and wherein at least about 7% of the total amount of adamantane-class drug or salt thereof in the system is released on day 2 and at least about 7% of the total amount of adamantane-class drug or salt thereof is released on day 5.

Embodiment A59

A gastric residence system comprising: a carrier polymer; an adamantane-class drug or a salt thereof; and wherein over a seven-day incubation of the system in simulated gastric fluid, the amount of the adamantane-class drug or salt thereof released from the system during day 7 is at least about 20% of the amount of adamantane-class drug or salt thereof released during day 1; and wherein at least about 4% of the total amount of adamantane-class drug or salt thereof in the system is released on day 1 and at least about 4% of the total amount of adamantane-class drug or salt thereof is released on day 7.

Embodiment A60

A gastric residence system comprising: a carrier polymer, an adamantane-class drug or a salt thereof; and wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour.

Embodiment A61

The gastric residence system of any one of embodiments A58-A60, further comprising a release rate-modulating polymer film configured to control the release rate of the adamantane-class drug or salt thereof.

Embodiment A62

A gastric residence system comprising: a carrier polymer, an adamantane-class drug or a salt thereof; and a release rate-modulating polymer film configured to control the release rate of the adamantane-class drug or salt thereof, wherein the release rate-modulating polymer film is configured such that the release of adamantane-class drug or salt thereof from the system in 40% ethanol/60% simulated gastric fluid over one hour is at least about 40% lower than the release of adamantane-class drug or salt thereof from a second system in 40% ethanol/60% simulated gastric fluid over one hour, the second system comprising the same combination of carrier polymer and adamantane-class drug or salt thereof but lacking the release rate-modulating polymer film.

Embodiment A63

A gastric residence system comprising: a carrier polymer, an adamantane-class drug or a salt thereof; and a release rate-modulating polymer film configured to control the release rate of the adamantane-class drug or salt thereof, wherein the release rate-modulating polymer film is configured such that the release of adamantane-class drug or salt thereof from the system in simulated gastric fluid over an initial 6 hour period is at least about 40% lower than the release of adamantane-class drug or salt thereof from a second system in simulated gastric fluid over an initial 6 hour period, the second system comprising the same combination of carrier polymer and adamantane-class drug or salt thereof but lacking the release rate-modulating polymer film; and wherein the release of adamantane-class drug or salt thereof from the system in simulated gastric fluid over a seven-day period is at least about 60% of the total amount of adamantane-class drug or salt thereof originally present in the system.

Embodiment A64

The gastric residence system of embodiment A63, wherein the release of adamantane-class drug or salt thereof from the system in simulated gastric fluid over a seven-day period is at least about 70% of the release of the total amount of adamantane-class drug or salt thereof originally present in the system.

Embodiment A65

The gastric residence system of embodiment A63, wherein the release of adamantane-class drug or salt thereof from the system in simulated gastric fluid over a seven-day period is at least about 80% of the release of the total amount of adamantane-class drug or salt thereof originally present in the system.

Embodiment A66

A gastric residence system comprising: a carrier polymer; an adamantane-class drug or a salt thereof; and a release rate-modulating polymer film, wherein the polymer film is configured to control the release rate of the adamantane-class drug or salt thereof such that a best-fit linear regression model of the release rate of adamantane-class drug or salt thereof from the system in simulated gastric fluid has a coefficient of determination $R^2$ of at least about 0.8 over an initial period of seven days; and wherein the system releases about 40% to about 60% of the adamantane-class drug or salt thereof within a time of about 40% to about 60% of the seven-day period.

Embodiment A67

A gastric residence system providing an extended release drug dosage form, comprising: a plurality of elongate members comprising a therapeutically effective amount of an adamantane-class drug or a pharmaceutically acceptable salt thereof and a carrier polymer, wherein the adamantane-class drug or a pharmaceutically acceptable salt thereof is blended with the carrier polymer such that the drug or salt thereof is distributed throughout the elongate member, and a release rate-modulating polymer film coating at least one elongate member; wherein the plurality of elongate members are attached to a central elastomer; and wherein said gastric residence system provides extended release of the adamantane-class drug or pharmaceutically acceptable salt thereof.

Embodiment A68

The gastric residence system of embodiment A67, wherein the elongate members further comprise one or more additional component selected from the group consisting of an excipient and an anti-oxidant, wherein the one or more additional component is blended together with the adamantane-class drug or a pharmaceutically acceptable salt thereof and the carrier polymer, such that the drug or salt thereof and one or more additional components are distributed throughout the elongate member.

Embodiment A69

The gastric residence system of embodiment A67 or embodiment A68, wherein the carrier polymer is blended with the adamantane-class drug or a pharmaceutically acceptable salt thereof and the one or more additional component if present, by melting and mixing together the carrier polymer, the adamantane-class drug or a pharmaceutically acceptable salt thereof, and the one or more additional component if present.

Embodiment A70

The gastric residence system of any one of embodiments A67-A69, wherein the elongate members are attached to the central elastomer via linkers, wherein the linkers are configured to weaken or degrade to allow passage of the gastric residence system through the pylorus after the specified gastric residence period.

Embodiment A71

The gastric residence system of any one of embodiments A67-A69, wherein at least one elongate member comprises at least two segments joined by linkers, wherein the linkers are configured to weaken or degrade to allow passage of the gastric residence system through the pylorus after the specified gastric residence period.

Embodiment A72

The gastric residence system of embodiment A70, wherein the release rate-modulating polymer film is coated onto the elongate member by coating the elongate member with a solution of a polymer film formulation to produce a film-coated elongate member; and drying the film-coated elongate member.

Embodiment A73

The gastric residence system of embodiment A71, wherein the release rate-modulating polymer film is coated onto the segments by coating the segments with a solution of a polymer film formulation to produce a film-coated segment; and drying the film-coated segment.

Embodiment A74

The gastric residence system of embodiment A72 or embodiment A73, wherein the coating is performed by dip coating.

Embodiment A75

The gastric residence system of embodiment A72 or embodiment A73, wherein the coating is performed by pan coating.

Embodiment A76

The gastric residence system of embodiment A72 or embodiment A73, wherein the coating is performed by spray coating.

Embodiment A77

The gastric residence system of embodiment A72 or embodiment A73, wherein the coating is performed by fluidized bed coating.

Embodiment A78

The gastric residence system of any one of embodiments A72-A77, wherein the solvent used in the solution of polymer film formulation comprises an organic solvent.

Embodiment A79

The gastric residence system of embodiment A78, wherein the solvent used in the polymer film formulation comprises ethyl acetate, dichloromethane, acetone, isopropyl alcohol, or any combination thereof.

Embodiment A80

A segment of a gastric residence system coated with a release rate-modulating polymer film or an elongate member of a gastric residence system coated with a release rate-modulating polymer film, prepared by co-extruding a polymer film and a mixture of a carrier polymer and an adamantane-class drug or a pharmaceutically acceptable salt thereof to form the segment or elongate member.

Embodiment A81

A method of making a segment of a gastric residence system coated with a release rate-modulating polymer film or an elongate member of a gastric residence system coated with a release rate-modulating polymer film, comprising: co-extruding a polymer film and a mixture of a carrier polymer and an adamantane-class drug or a pharmaceutically acceptable salt thereof to form the segment or elongate member.

Embodiment A82

A method of making a gastric residence system, comprising: blending an agent comprising an adamantane-class drug or a pharmaceutically acceptable salt thereof with a carrier polymer to form a carrier polymer-drug blend or a carrier polymer-drug salt blend, such that the agent or salt thereof is distributed throughout the carrier polymer-drug blend or the carrier polymer-drug salt blend; forming a plurality of elongate members from the carrier polymer-drug blend or the carrier polymer-drug salt blend, wherein the agent or salt thereof is distributed throughout the elongate member; coating the plurality of elongate members with a release rate-modulating polymer film; and attaching the plurality of elongate members to a central elastomer.

Embodiment A83

The method of embodiment A82, wherein at least one elongate member comprises at least two segments joined by linkers, wherein the linkers are configured such that they no longer join the at least two segments of each elongate member after the specified gastric residence period.

Embodiment A84

A method of making a gastric residence system, comprising: blending an agent comprising an adamantane-class drug or a pharmaceutically acceptable salt thereof with a carrier polymer to form a carrier polymer-drug blend or a carrier polymer-drug salt blend, such that the agent or salt thereof is distributed throughout the carrier polymer-drug blend or the carrier polymer-drug salt blend; forming a plurality of segments from the carrier polymer-drug blend or the carrier polymer-drug salt blend, wherein the agent or salt thereof is distributed throughout the segments; coating the segments with a release rate-modulating polymer film; forming a plurality of elongate members by joining at least two segments together via a linker to make the elongate members; and attaching the plurality of elongate members to a central elastomer.

Embodiment A85

The method of any one of embodiments A82-A84, further comprising blending one or more additional component selected from the group consisting of an excipient and an anti-oxidant with the adamantane-class drug or a pharmaceutically acceptable salt thereof and the carrier polymer, such that the drug or salt thereof and one or more additional components are distributed throughout the carrier polymer-drug blend or the carrier polymer-drug salt blend.

Embodiment A86

The method of any one of embodiments A82-A85, wherein the blending of the adamantane-class drug or a pharmaceutically acceptable salt thereof and the one or more additional components if present, comprises melting and mixing together the carrier polymer, the drug or pharmaceutically acceptable salt thereof, and the one or more additional component if present.

Embodiment A87

The method of any one of embodiments A82-A86, wherein the elongate members are attached to the central elastomer via linkers, wherein the linkers are configured such that they no longer join the elongate members to the central elastomer after a specified gastric residence period.

Embodiment A88

The method of any one of embodiments A82-A87, wherein the coating of the release rate-modulating polymer film onto the elongate members or the segments comprises: coating the elongate members or segments with a solution of a polymer film formulation to produce a film-coated elongate member or a film-coated segment; and drying the film-coated elongate member or film-coated segment.

Embodiment A89

The method of any one of embodiments A82-A88, wherein the coating comprises dip coating.

Embodiment A90

The method of any one of embodiments A82-A88, wherein the coating comprises pan coating.

Embodiment A91

The method of any one of embodiments A82-A88, wherein the coating comprises spray coating.

Embodiment A92

The method of any one of embodiments A82-A88, wherein the coating comprises fluidized bed coating.

Embodiment A93

The method of any one of embodiments A88-A92, wherein the solvent used in the solution of polymer film formulation comprises an organic solvent.

Embodiment A94

The method of embodiment A93, wherein the solvent used in the polymer film formulation comprises ethyl acetate, dichloromethane, acetone, isopropyl alcohol, or any combination thereof.

Embodiment A95

A gastric residence system, made by any of the methods of embodiments A82-A94.

Embodiment A96

A method of making a segment of a gastric residence system coated with a release rate-modulating polymer film or an elongate member of a gastric residence system coated with a release rate-modulating polymer film, comprising: co-extruding a polymer film and a mixture of a carrier polymer and an adamantane-class drug or a pharmaceutically acceptable salt thereof to form the segment or elongate member.

Embodiment A97

A gastric residence system providing an extended release drug dosage form, comprising a therapeutically effective amount of an adamantane-class drug or a pharmaceutically acceptable salt thereof and a component adapted to provide extended release of the drug or salt thereof in an aqueous environment, wherein the system has a dissolution profile characterized by about 10% to 20% dissolution of the initial amount of drug present in the system during an initial 24 hour period in the aqueous environment.

Embodiment A98

The gastric residence system of embodiment A97, wherein the system has a dissolution profile characterized by about 20% to 40% dissolution of the initial amount of drug present in the system during an initial 48 hour period in the aqueous environment.

Embodiment A99

The gastric residence system of embodiment A97 or embodiment A98, wherein the system elutes about 20 mg to about 36 mg drug per day in the aqueous environment.

Embodiment A100

The gastric residence system of any one of embodiments A97-A99, wherein the adamantane-class drug or pharmaceutically acceptable salt thereof is memantine or a pharmaceutically acceptable salt of memantine.

Embodiment A101

The gastric residence system of any one of embodiments A97-A100, wherein the aqueous environment is the stomach of a human patient.

Embodiment A102

The gastric residence system of any one of embodiments A97-A100, wherein the aqueous environment is simulated gastric fluid.

Embodiment A103

The gastric residence system of any one of embodiments A97-A101, wherein the system has a gastric residence period of at least about four days when administered to a human patient.

Embodiment A104

The gastric residence system of embodiment A103, wherein the system has a gastric residence period of at about seven days.

Embodiment A105

The gastric residence system of any one of embodiments A97-A100, wherein the adamantane-class drug or a pharmaceutically acceptable salt thereof is blended with the component adapted to provide extended release of the drug or salt thereof.

Embodiment A106

The gastric residence system of embodiment A105, wherein the component adapted to provide extended release of the drug or salt thereof comprises a carrier polymer and at least one excipient.

Embodiment A107

A gastric residence system providing an extended release drug dosage form, comprising a therapeutically effective amount of an adamantane-class drug or a pharmaceutically acceptable salt thereof and a component adapted to provide extended release of the adamantane-class drug or a pharmaceutically acceptable salt thereof in an aqueous environment, wherein the system has a dissolution profile characterized by about 10% to 20% dissolution of the initial amount of adamantane-class drug or pharmaceutically acceptable salt thereof present in the system during an initial 24 hour period in the aqueous environment.

Embodiment A108

A segment of a gastric residence system, the segment comprising: a carrier polymer; an adamantane-class drug or a salt thereof; and a release rate-modulating polymer film configured to control the release rate of the adamantane-class drug or salt thereof, wherein over a seven-day incubation of the segment in simulated gastric fluid, the amount of the adamantane-class drug or salt thereof released from the segment during day 5 is at least about 40% of the amount of adamantane-class drug or salt thereof released during day 2; and wherein at least about 7% of the total amount of adamantane-class drug or salt thereof in the segment is released on day 2 and at least about 7% of the total amount of adamantane-class drug or salt thereof is released on day 5.

Embodiment A109

A gastric residence system providing an extended release drug dosage form, comprising a plurality of elongate members, wherein at least one elongate member comprises a therapeutically effective amount of an adamantane-class drug or a pharmaceutically acceptable salt thereof and a carrier polymer, and wherein the adamantane-class drug or a pharmaceutically acceptable salt thereof is blended with the carrier polymer such that the drug or salt thereof is distributed throughout the at least one elongate member; wherein the adamantane-class drug or a pharmaceutically acceptable salt thereof comprises about 40% to about 60% by weight of the at least one elongate member; wherein the plurality of elongate members are attached to a central elastomer; and wherein said gastric residence system provides extended release of the adamantane-class drug or pharmaceutically acceptable salt thereof.

Embodiment A110

A gastric residence system providing an extended release drug dosage form, comprising: a plurality of elongate members, wherein at least one elongate member comprises a therapeutically effective amount of an adamantane-class drug or a pharmaceutically acceptable salt thereof and a carrier polymer, wherein the adamantane-class drug or a pharmaceutically acceptable salt thereof is blended with the carrier polymer such that the drug or salt thereof is distributed throughout the at least one elongate member, and a release rate-modulating polymer film coating the at least one elongate member; wherein the adamantane-class drug or a pharmaceutically acceptable salt thereof comprises about 40% to about 60% by weight of the at least one elongate member; wherein the plurality of elongate members are attached to a central elastomer; and wherein said gastric residence system provides extended release of the adamantane-class drug or pharmaceutically acceptable salt thereof.

Embodiment A111

The gastric residence system of any one of embodiments A1-A57, A67-A79, A95, A97-A107, A109, or A110, or the segment of embodiment A80 or embodiment A108, wherein the adamantane-class drug or a pharmaceutically acceptable salt thereof comprises about 40% to about 60% by weight of the at least one elongate member of embodiments A1-A57, A67-A79, A95, A97-A107, A109, or A110 or about 40% to about 60% by weight of the segment of embodiment A80 or embodiment A108, excluding the weight of any elastomer or linker attached to the at least one elongate member or the segment.

Embodiment A112

The gastric residence system of any one of embodiments A1-A57, A67-A79, A95, A97-A107, A109, or A110, or the segment of embodiment A80 or embodiment A108, wherein the adamantane-class drug or a pharmaceutically acceptable salt thereof comprises about 51% to about 60% by weight of the at least one elongate member of embodiments A1-A57, A67-A79, A95, A97-A107, A109, or A110 or about 51% to about 60% by weight of the segment of embodiment A80 or embodiment A108.

Embodiment A113

The gastric residence system of any one of embodiments A58-A66, wherein the adamantane-class drug or a pharmaceutically acceptable salt thereof is present in an amount by weight of between about 67% and about 150% of the weight of the carrier polymer.

Embodiment A114

A method of treating a neurological or psychiatric disorder in a subject in need of treatment for the disorder, comprising administering the gastric residence system of any one of embodiments A1-A79, A95, A97-A107, A109, A110, or A113 to the subject.

Embodiment A115

The method of embodiment A114, wherein the neurological or psychiatric disorder is a central nervous system disorder.

Embodiment A116

The method of embodiment A114, wherein the neurological or psychiatric disorder is Alzheimer's Disease.

Embodiment A117

The method of embodiment A114, wherein the neurological or psychiatric disorder is dementia.

Embodiment A118

The method of embodiment A114, wherein the neurological or psychiatric disorder is Lewy Body dementia, HIV-associated dementia, vascular dementia, organic brain syndrome, spasticity, stroke or the resulting effects of stroke, an autism spectrum disorder, Parkinson's Disease, neuropathic pain, attention deficit/hyperactivity disorder (ADHD), obsessive-compulsive disorder (OCD), or major depression.

Embodiment A119

The method of any one of embodiments A114-A118, wherein the gastric residence system is administered to the patient on an approximately weekly basis over a period of at least about one month.

Embodiment A120

A method of treating glaucoma in a subject in need of such treatment, comprising administering the gastric residence system of any one of embodiments A1-A79, A95, A109, A110, or A113 to the subject.

Embodiment A121

A method of treating a viral infection in a subject in need of such treatment, comprising administering the gastric residence system of any one of embodiments A1-A79, A95, A109, A110, or A113 to the subject.

Embodiment A122

The method of embodiment A121, wherein the viral infection is influenza.

Embodiment A123

The method of any one of embodiments A114-A122, wherein the subject is a human.

Embodiment A124

The gastric residence systems, methods of making or using gastric residence systems, or segments of any of the foregoing embodiments 1-226 or embodiments A1-A123, wherein the carrier polymer and adamantane-class drug or salt thereof is combined with one of the combinations of excipients and additional additives from the following table:

EPO, P407, Silica, α-tocopherol
EPO, Silica, α-tocopherol
Eudragit RL, Eudragit RS, Kolliphor P407, Silica, α-tocopherol
Eudragit RL, Kolliphor P407, Silica, α-tocopherol
Eudragit RL, Eudragit RS, Kolliphor P407, Silica, α-tocopherol
Eudragit RL, Kolliphor P407, Silica, α-tocopherol
Eudragit RL, Kolliphor P407, Silica, α-tocopherol
Eudragit RS, P407, Silica, α-tocopherol
Eudragit RS, Silica, α-tocopherol
Kollidon VA64, Silica, α-tocopherol
Kolliphor P407, Silica, α-tocopherol
Kolliphor RH40, Silica, α-tocopherol
PDO, Silica, α-tocopherol
PEG-PCL, Silica, α-tocopherol
Poly Vinyl Acetate, Silica, α-tocopherol
PVP, Silica, α-tocopherol
SIF, Silica, α-tocopherol
Silica, P188, P407, α-tocopherol
Silica, α-tocopherol Embodiment A125

The gastric residence systems, methods of making or using gastric residence systems, or segments of any of the foregoing embodiments 1-226 or embodiments A1-A124, where the release rate-controlling polymer film if present is selected from a composition in the following table:

Eudragit RS
PCL 55k
Ethyl Cellulose
75:25 PLGA
50:50 PLGA
25:75 PLGA
50:50 PLGA

Ethyl Cellulose
Cellulose Acetate
PCL 55k
PCL 15k
PLGA 50:50 Ester Terminated 35-45k
PLGA 50:50 Acid Terminated 35-45k
PCL 80k
Ethyl Cellulose Cp 10
Ethyl Cellulose Cp 10
Polycaprolactone, copovidone, triethyl citrate, Mg stearate
Ethyl Cellulose:PVP 1.3M
PCL 80k:TEC
Ethyl Cellulose Cp10:TEC
80k PCL:PVP
80k PCL:Kolliphor RH40
80k PCL:Kollidon VA64
PCL 80k:TEC
Ethyl Cellulose Cp10:TEC
PCL 55k:P407
PCL 55k:P188
PCL 55k:PEG 10k
PCL 55k:PEG 100k
PCL 55k:P407
PCL 55k:P188
PCL 55k:PVP 1M
Ethyl Cellulose:PEG 1M
Ethyl Cellulose:PEG 100k
PCL 80k:TEC
Ethyl Cellulose Cp10:TEC
PVP
80k PCL:Kolliphor RH40
80k PCL:Kollidon VA64

Embodiment A126

In any of the foregoing embodiments 1-226 or embodiments A1-A125, the term "about" indicates a variation of plus-or-minus 10% of the number indicated.

EXAMPLES

The invention is further illustrated by the following non-limiting examples.

Example 1

HPLC Detection of Memantine

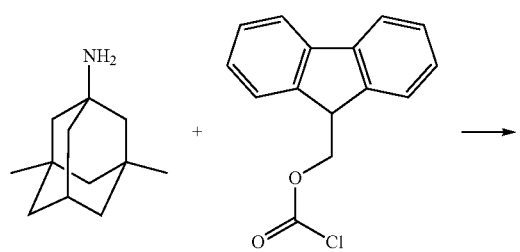

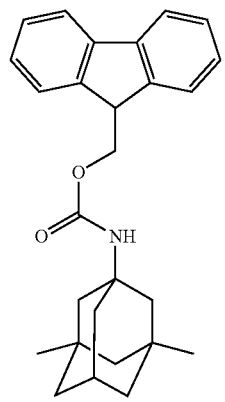

Figure 23A:
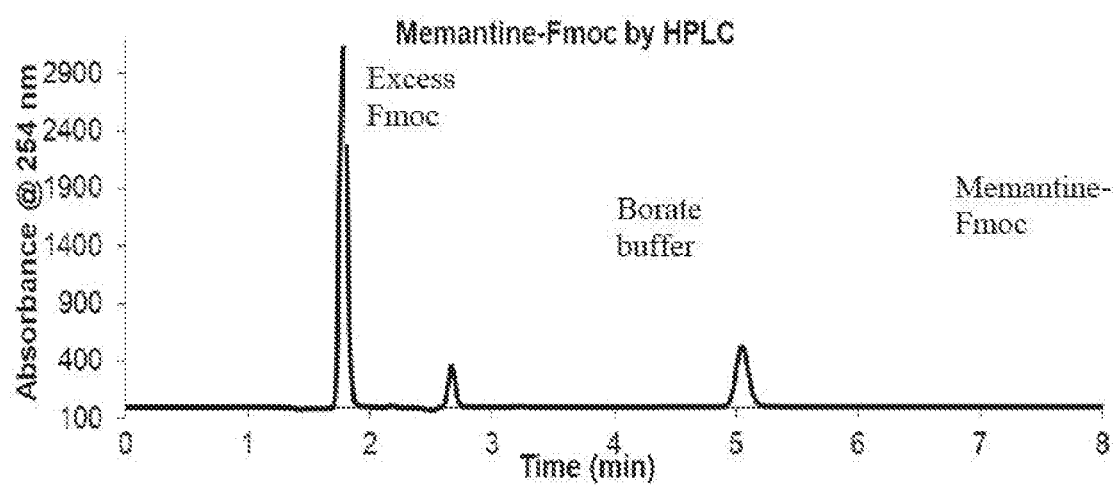
FIG. 23A shows an HPLC chromatogram of Fmoc-memantine. The peak just before 2 minutes is excess Fmoc. The peak between two and three minutes is borate buffer. The peak at about five minutes is Fmoc-memantine.
Figure 23B:
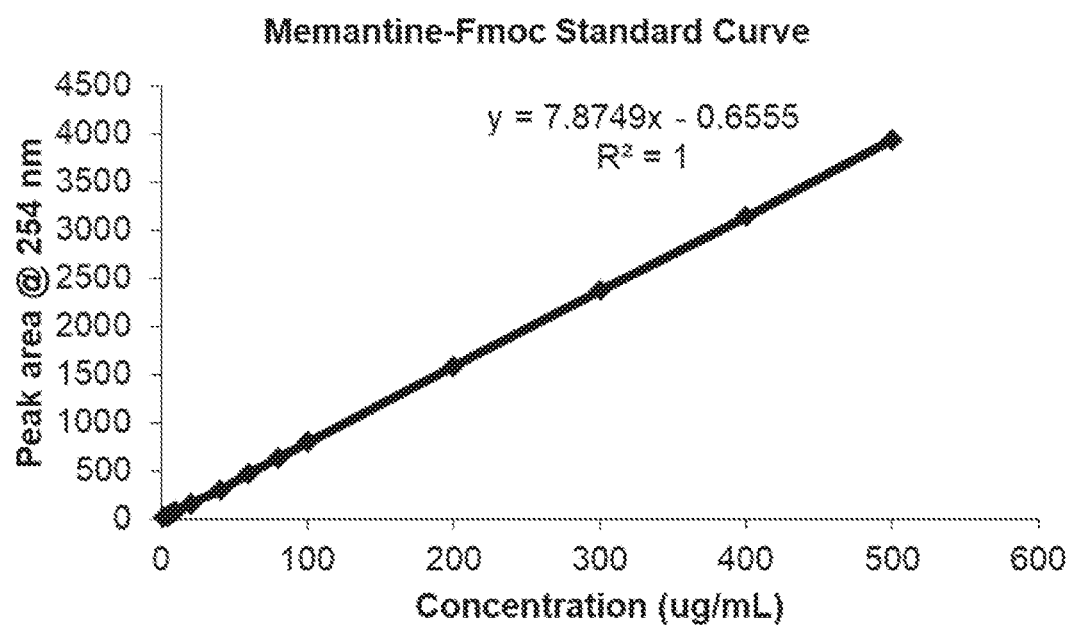
FIG. 23B shows an Fmoc-memantine standard curve. The curve parameters are y=7.8749x−0.6555; the $R^2$ of the fit is 0.99997.

Memantine is conveniently derivatized with a fluorenyl-methyloxycarbonyl group for HPLC detection. Derivatization is carried out by combining 1 mL memantine solution in 0.1 N HCl with 3 mL 0.25M borate buffer, pH 8.5 (pH after addition to memantine >=8.0); 5.8 mL acetonitrile to solubilize Fmoc-Cl, and 200 μL 100 mM Fmoc-Cl. The reaction is run at 30° C. for at least 30 min. An HPLC chromatogram is shown in FIG. 23A, while a memantine-Fmoc standard curve is shown in FIG. 23B. The HPLC conditions used were: Eclipse XDB C18 column (150 mm×4.6 mm×5 μm); column at 25° C.; isocratic elution with 5% 0.1M TEAA buffer, 95% acetonitrile at 1 mL/min; absorbance was measured at 254 nm. The elution time of Fmoc-memantine was 5.05 min.

Example 2

Milling of Memantine

Milling of memantine prior to formulation provides a more uniform blend with carrier polymer and excipient(s). FIG. 34 shows bright field microscopy images of memantine powder before milling (left panel) and after milling (right panel) (scale bar=400 microns). The milled particles show a reduction in size and increase in uniformity.

Example 3

Release Rate of Memantine from Formulations

In vitro release rates of memantine from various carrier polymer-excipient-drug formulations were evaluated in simulated gastric fluid.

Fasted state simulated gastric fluid (FaSSGF) was prepared according to the vendor's instructions (Biorelevant.com, London, United Kingdom). A NaCl/HCl solution was prepared by dissolving 2.0 g of NaCl in about 0.9 L of purified water. The pH was adjusted to 1.6 with HCl. The volume was made up to 1.0 L with purified water at room temperature. 0.060 g of FaSSIF, FeSSIF & FaSSGF Powder was added to about 0.5 L HCl/NaCl solution, and the volume was made up to 1.0 L with HCl/NaCl solution at room temperature to make FaSSGF (also referred to herein as SGF).

Fed state simulated gastric fluid (FeSSGF) was prepared using the recipe disclosed in Jantratid et al., Pharm. Res. 25(7):1663-76 (2008). Acetate buffer is prepared using NaCl, 237.02 mmol/L; acetic acid, 17.12 mmol/L; sodium acetate, 29.75 mmol/L; demineralized water is added to bring the total volume to 1000 mL. A 1:1 mixture of Vanilla Ensure® to acetate buffer was prepared, and adjusted to pH 5.0 with concentrated HCl. (ENSURE is a registered trademark of Abbott Laboratories for a nutritional beverage.)

Various formulations of carrier polymers and excipients blended with memantine were tested, and were designated as M1, M2, etc. Memantine was ball milled with 1% silica and sifted through a 75-micron sieve. The formulations contained the following ingredients: 20% memantine, 0.5% silicon dioxide (Cab-O-Sil), 0.5% alpha tocopherol, and the additional excipients listed in Table 4; the balance of the formulation was made up with polycaprolactone (MW 80,000). In vitro release assays were performed and analyzed by HPLC for drug quantification at each time point.

TABLE 4

| Formulation | Additional Excipients |
| --- | --- |
| M1 | 9% Eudragit E |
| M2 | 9% P407 |
| M3 | 4.5% Eudragit E, 4.5% P407 |
| M4 | 9% Poly Vinyl Acetate |
| M5 | 9% PVP |
| M6 | 9% Kollidon VA64 |
| M7 | 5% Kolliphor RH40 |
| M17 | 7% Eudragit E, 2% P407 |
| M18 | 25% Eudragit RS 5% P407 |
| M19 | 5% Taurocholate/Lecithin |
| M20 | 9% Taurocholate/Lecithin |
| M21 | 25% Eudragit RL, 5% P407 |
| M22 | 30% polydioxanone |
| M23 | 9% Eudragit E |
| M24 | 20% Eudragit RS, 2% P407 |
| M25 | 19.85% Eudragit RS, 0% P407 |
| M26 | 17.5% Eudragit RS, 5% P407 |
| M27 | 10% Eudragit RS and 5% P407 |
| M28 | 14.78% Eudragit RS, 0.226% P407 |
| M29 | 25% Eudragit RS, 0% P407 |
| M30 | 21.25% Eudragit RS, 2.5% P407 |
| M31 | 25% Eudragit RS, 5% P407 |

FIG. 3 to FIG. 22 show the release rate of memantine in FaSSGF and FeSSGF from various formulations of carrier polymer and excipients.

Figure 3:
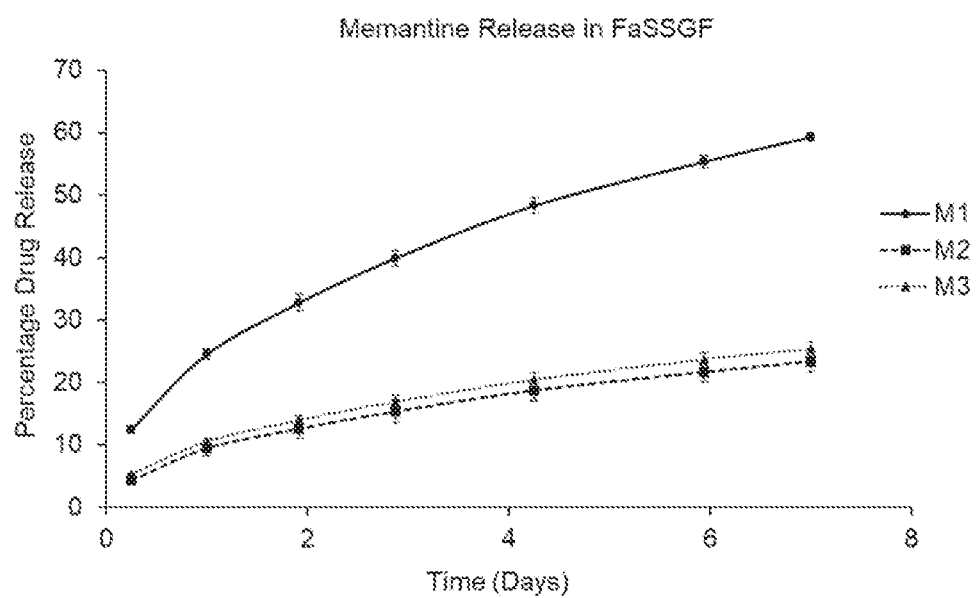
FIG. 3 shows memantine release in FaSSGF (fasted state simulated gastric fluid) from formulations M1, M2, and M3 (excipients: P407 and Eudragit E).

FIG. 3 shows in vitro release data for memantine formulations M1, M2 and M3, which contain varying amounts of Eudragit E and P407. Formulation M3 contains the base formulation with the addition of 9% P407 and results in a total release of about 24%, a linear release of about 16%, and a burst release of about 5%. Formulation M1 contains the base formulation with the addition of 9% Eudragit E and results in a much higher total release of about 60%, a linear release of about 40%, and maintains a low burst release of about 12%. When the formulation contains 4.5% Eudragit E and 4.5% P407, there is a lower total release of about 26%, linear release of about 18%, and burst release of about 5%.

Figure 4:
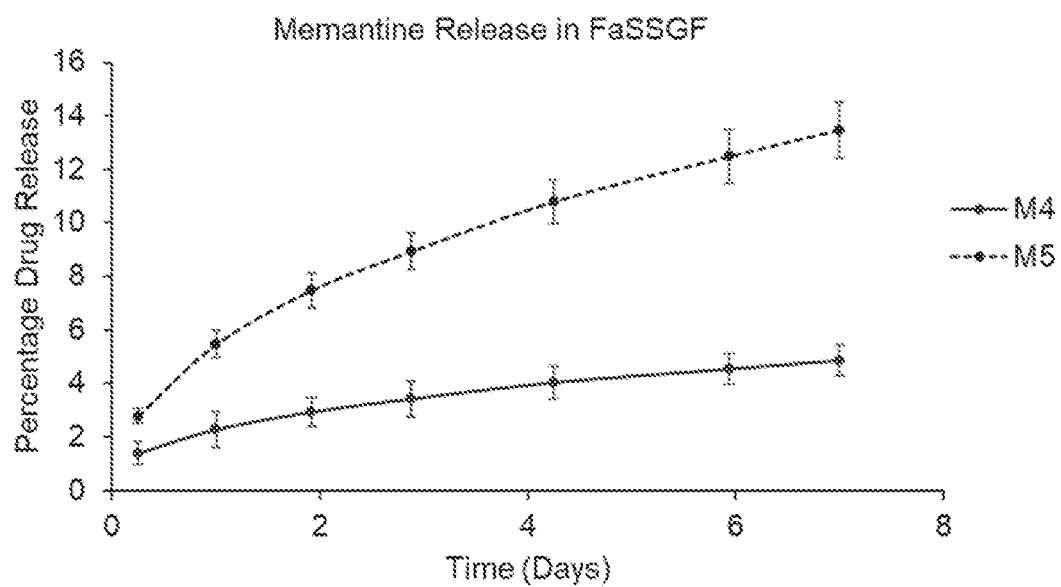
FIG. 4 shows memantine release in FaSSGF from formulations M4 and M5 (excipients: polyvinyl acetate and polyvinyl pyrrolidone).

FIG. 4 shows in vitro release data for formulations M4 and M5, which contain the base formulation with the addition of 9% polyvinyl acetate (PVA) or 9% polyvinylpyrrolidone (PVP), respectively. The addition of PVA resulted in only about 5% total release and the addition of PVP resulted in a slightly higher total release of about 13%.

Figure 5:
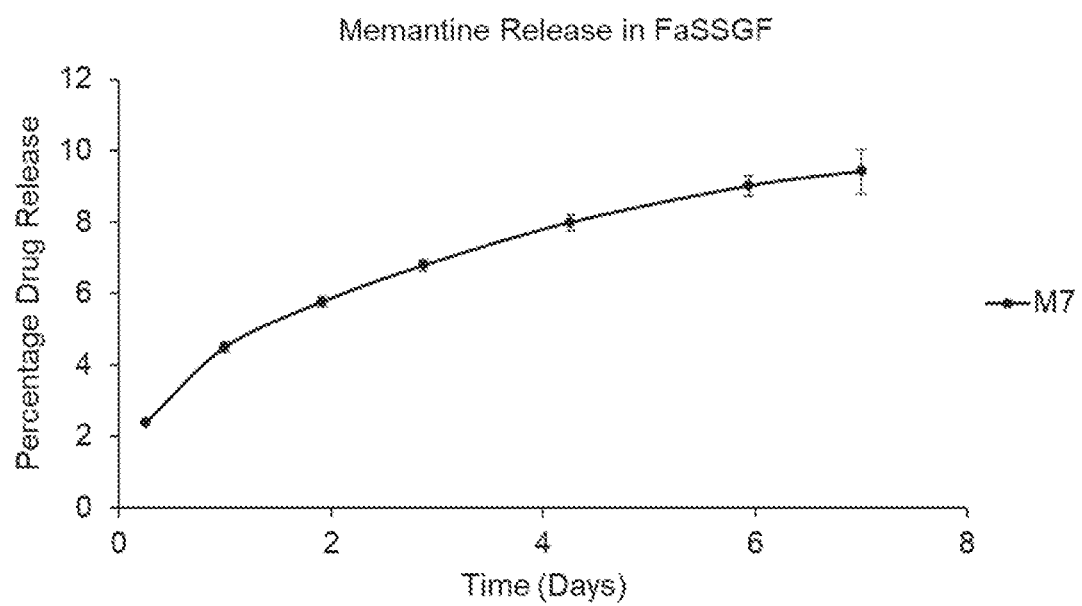
FIG. 5 shows memantine release in FaSSGF from formulation M7 (excipient: Kolliphor RH40).
Figure 6:
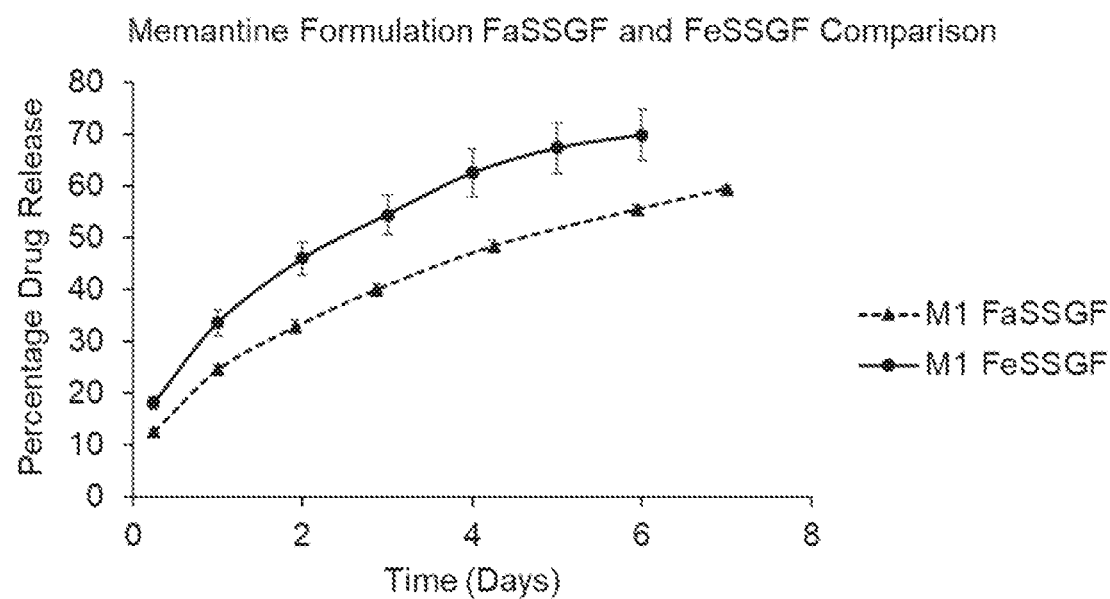
FIG. 6 shows memantine release in FaSSGF and FeSSGF (fed state simulated gastric fluid) from formulation M1.

FIG. 5 shows in vitro release data for formulation M7, which contains the base formulation with the addition of 5% Kolliphor RH40. This formulation has a low total drug release of about 9%, linear release of about 7%, and a burst release of about 2%.

Figure 7:
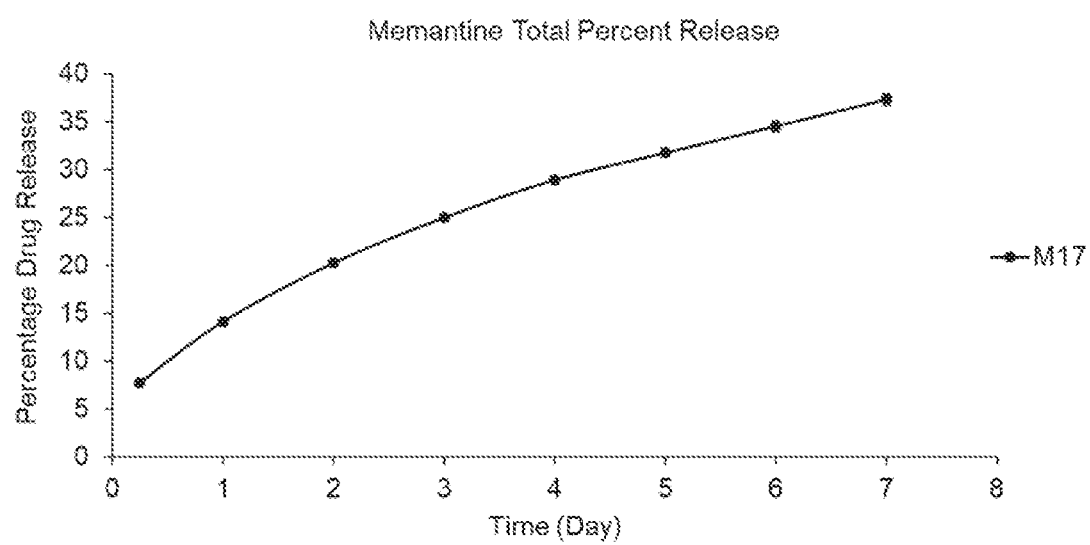
FIG. 7 shows memantine release in FaSSGF from formulation M17 (excipient: P407 and Eudragit E).

FIG. 7 shows in vitro release data for formulation M17, which contains the base formulation with the addition of 2% P407 and 7% Eudragit E. This results in a total release of about 37%, linear release of about 25%, and burst release of about 7%.

Figure 8:
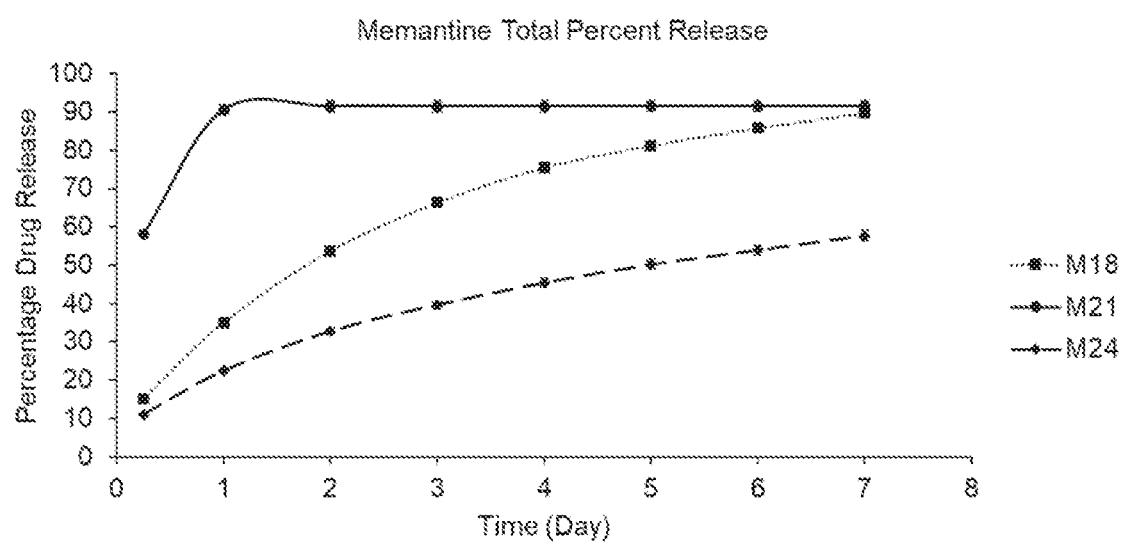
FIG. 8 shows memantine release in FaSSGF from formulations M18, M21, and M24 (excipients: P407 and Eudragit RL/RS).

FIG. 8 shows in vitro release data for formulations M18, M21, and M24, which contain the base formulation and varying amounts of P407 and Eudragit RS. M21 contains 5% P407 and no additional Eudragit RS and results in a very high total release of about 92%. However, this formulation also showed a high linear release of about 92% and a burst of about 58%. Formulation M24, containing both 2% P407 and 20% Eudragit RS, resulted in a more favorable total release of about 58%, linear release of about 40%, and a burst release of about 12%. Formulation M18, containing 5% P407 and 25% Eudragit RS, resulted in a high total release of about 90%, a linear release of about 68%, and a low burst release of about 15%.

Figure 9:
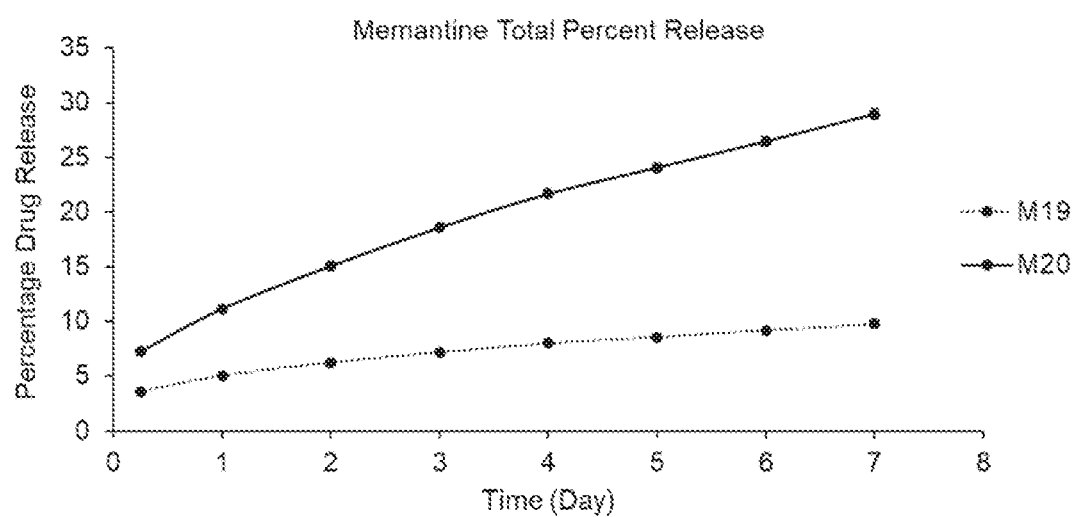
FIG. 9 shows memantine release in FaSSGF from formulations M19 and M20 (excipients: taurocholate and lecithin).

FIG. 9 shows in vitro release data for formulations M19 and M20, which contain the base formulation with the addition of 5% or 9% Taurocholate/Lecithin, respectively. This yielded a total drug release of about 10% for M19. M20 resulted in a total release of about 29%, with a linear release of about 18% and a burst release of about 7%.

Figure 10:
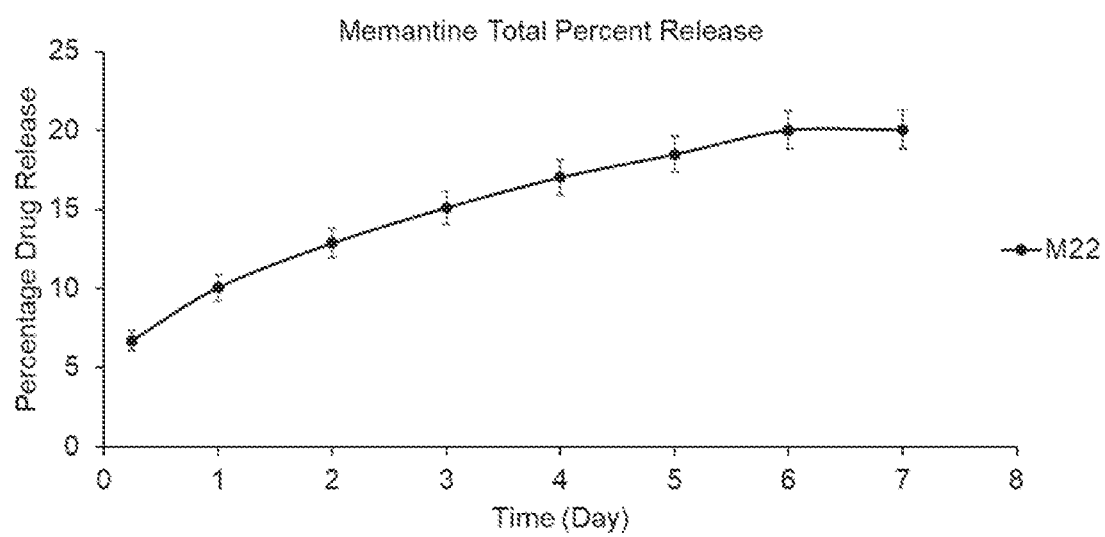
FIG. 10 shows memantine release in FaSSGF from formulation M22 (excipient: polydioxanone).

FIG. 10 shows in vitro release data for formulation M22, which contains the base formulation with the addition of 30% polydioxanone. This formulation had a total drug release of about 20%, linear release of about 15%, and a burst release of about 7%.

Figure 11:
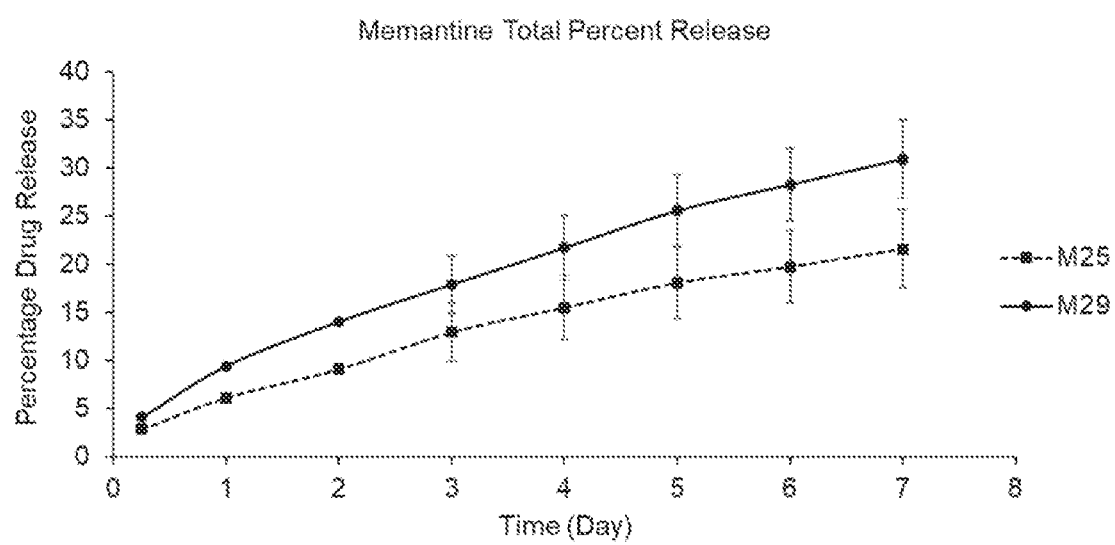
FIG. 11 shows memantine release in FaSSGF from formulations M25 and M29 (excipient: Eudragit RS).

FIG. 11 shows in vitro release data for formulations M25 and M29, which contain the base formulation with the addition of 19.85% and 25% Eudragit RS, respectively. M25 resulted in a total release of about 22%, linear release of about 12%, and a burst release of about 3%. M29 resulted in a higher total drug release of about 31%, linear release of about 18%, and a burst release of about 4%.

Figure 12:
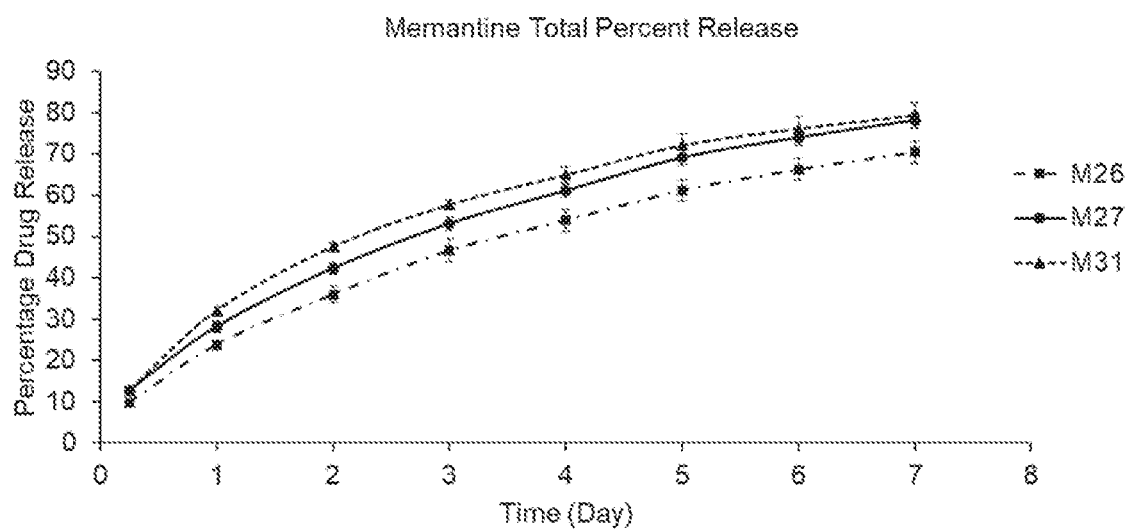
FIG. 12 shows memantine release in FaSSGF from formulations M26, M27, and M31 (excipients: Eudragit RS, 5% P407).

FIG. 12 shows in vitro release data for formulations M26, M27, and M31, which contain the base formulation, 5% P407, and varying amounts of Eudragit RS. The M31 formulation is identical to M18 but the drug-loaded formulation was prepared in a separate milling batch, resulting in slight differences in particle size and particle size distribution. M26 contains 17.5% Eudragit RS and resulted in a 70% total release, 47% linear release, and 10% burst release. M27 contains 10% Eudragit RS and resulted in 79% total release, 54% linear release, and 12% burst release. M31 contains 25% Eudragit RS and resulted in 79% total release, 58% linear release, and 12% burst release.

Figure 13:
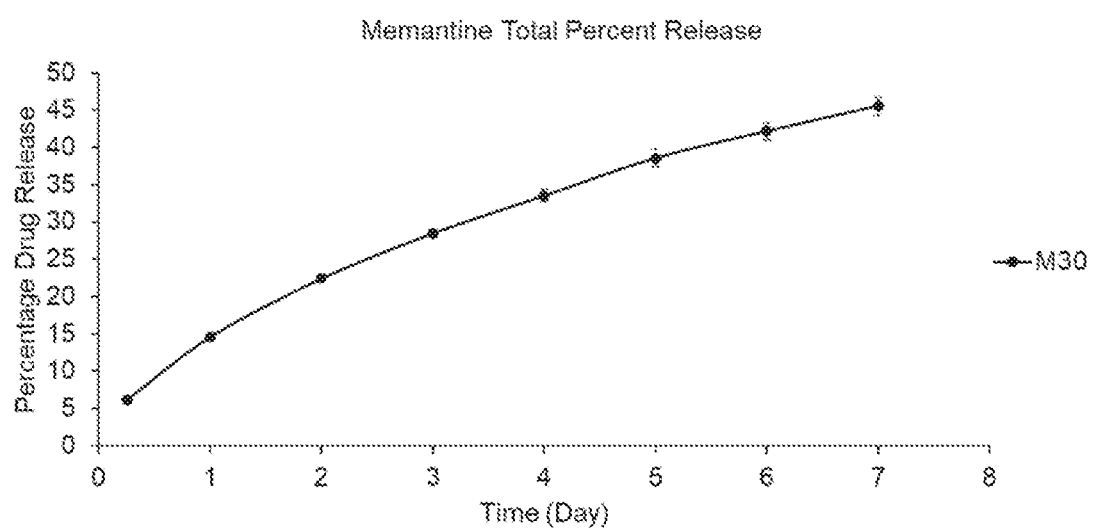
FIG. 13 shows memantine release in FaSSGF from formulation M30 (excipients: Eudragit RS, 2.5% P407).
Figure 14:
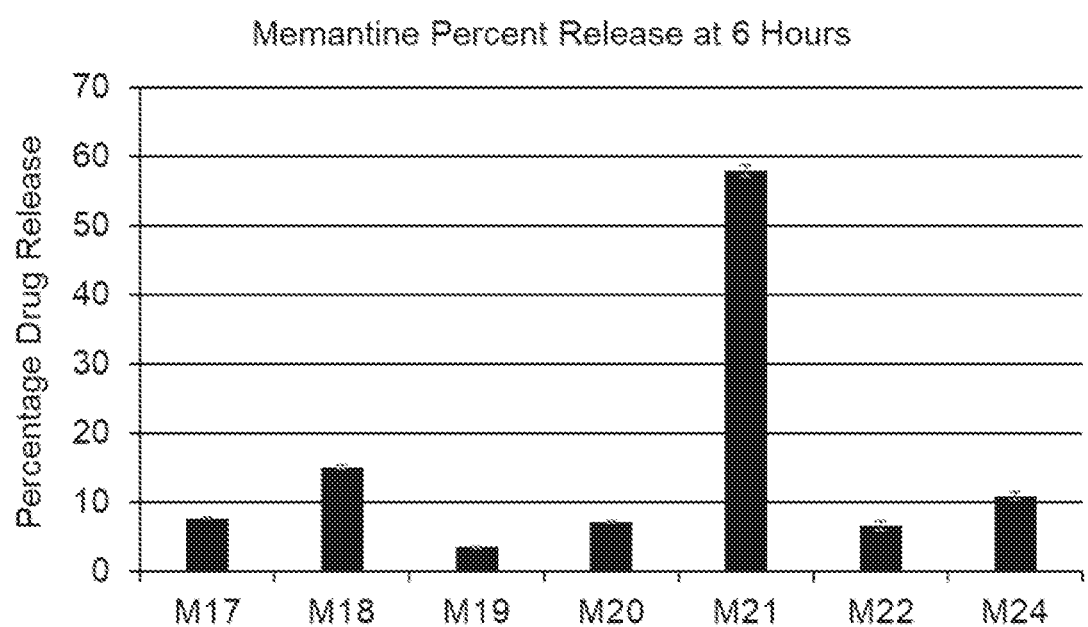
FIG. 14 shows percent memantine release after 6 hours (that is, burst release) in FaSSGF from formulations M17, M18, M19, M20, M21, M22, and M24.

FIG. 13 shows in vitro release data for formulation M30, which contains the base formulation with the addition of 2.5% P407 and 21.25% Eudragit RS. This formulation results in total drug release of about 45%, linear release of about 29%, and burst release of about 6%.

Example 4

Simulated Human Plasma Values

Using the release rates determined in Example 3, simulated values for human plasma concentrations for each formulation were calculated using the following pharmacokinetic parameters: mean volume of distribution=9-11 L/kg; rate of absorption ($K_a$)=0.21/hr, and clearance (CL)=5.2 L/hr.

The cumulative in vitro release profiles for nine formulations, M16-M24, were used for the simulations. Analyses were conducted after transforming the release values to the quantity of drug remaining in the system (i.e., 100% minus the released fraction). For each formulation, release during the first collection interval (0-6 hours) was markedly more rapid than in subsequent intervals, suggesting a "burst" during that interval. Thus, the release rate (modeled as a rate constant, i.e., the instantaneous fraction of drug transferred from the system to the absorption compartment) for the first interval was modeled independently of the release rate for subsequent intervals; it was modeled by assuming first-order release between time zero and the end of the first interval (by fitting a linear regression to log-transformed data). Two approaches were used to incorporate the subsequent data from these release profiles into a pharmacokinetic (PK) simulation. In one, the release rate from the entire remaining profile was modeled as a single first-order process by fitting a linear regression to log-transformed data. In the other, this same procedure was applied to each sampling interval. The first of these approaches assumes that changes in slope of the log-transformed data between intervals is a result of "residual error" such that a common release rate is more appropriate than release rates determined over shorter time periods. Typically, differences between the two approaches were small and therefore not of consequence to the analysis.

These release profiles were then coupled with the pharmacokinetic parameters as indicated above to estimate the resulting memantine plasma concentration profile. Assumptions of the analysis were:

1. Release from each system terminated abruptly at 168 hours, even if drug remained in the system.
2. The PK characteristics of memantine were linear with respect to time and dose. Therefore, the PK profile from a single system would be simulated (dose=196 mg), following which the PK profile for weekly administration would be simulated using the principle of superposition (i.e., that Cp profiles from repeated doses are additive).

In addition to simulating the PK profile of the Lyndra systems, the PK profile of immediate-release memantine was simulated using the same absorption and systemic PK parameters.

Figure 24A:
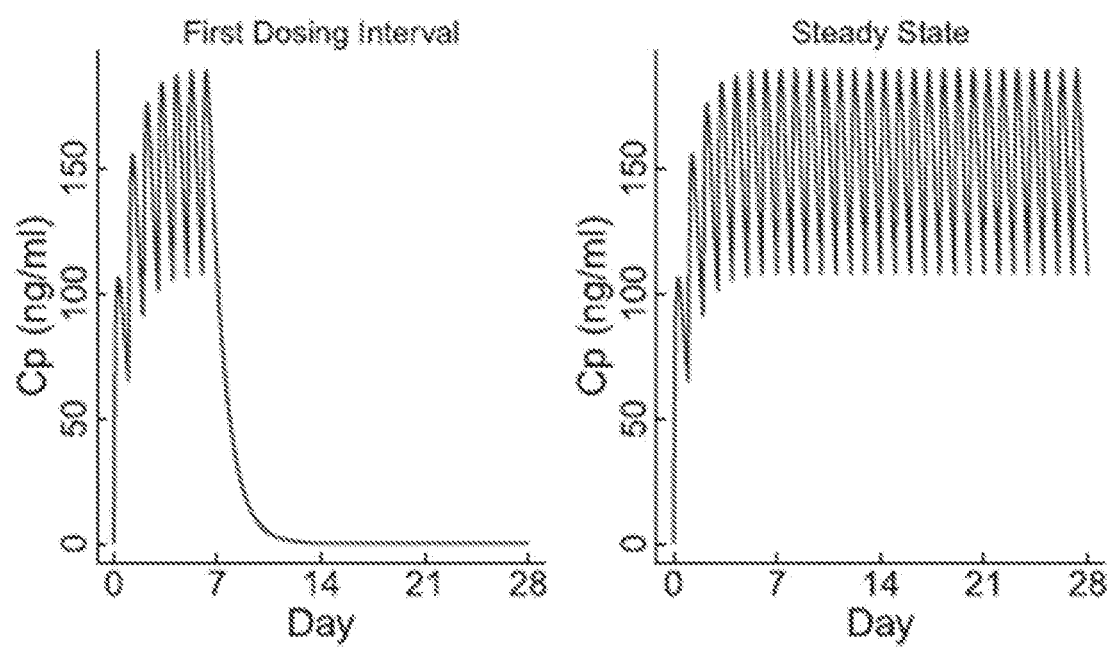
FIG. 24A shows simulation of human pharmacokinetic parameters for memantine from an immediate release formulation (28 mg per dose).
Figure 24B:
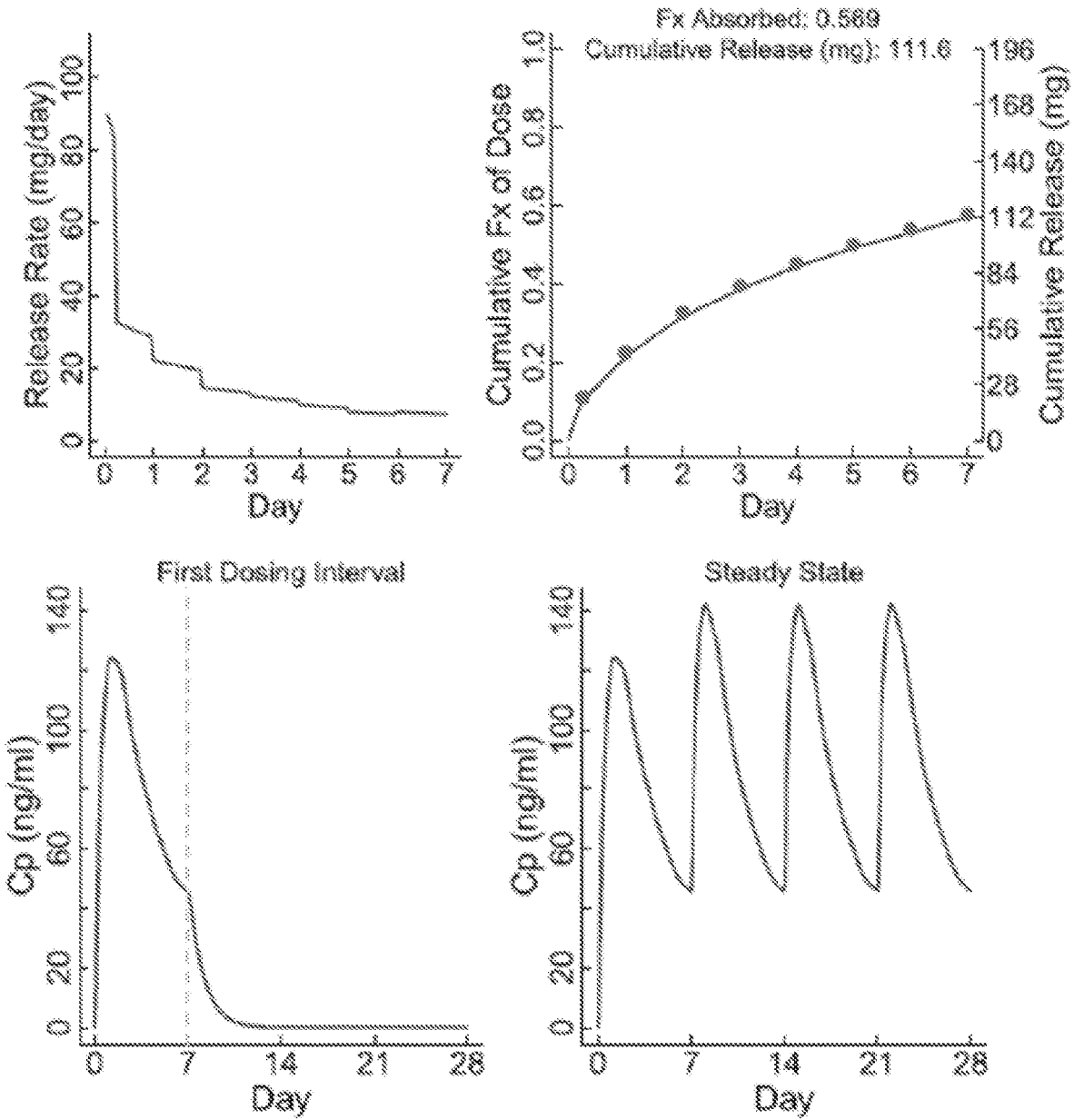
FIG. 24B shows simulation of human pharmacokinetic parameters for memantine from formulation M24.
Figure 25A:
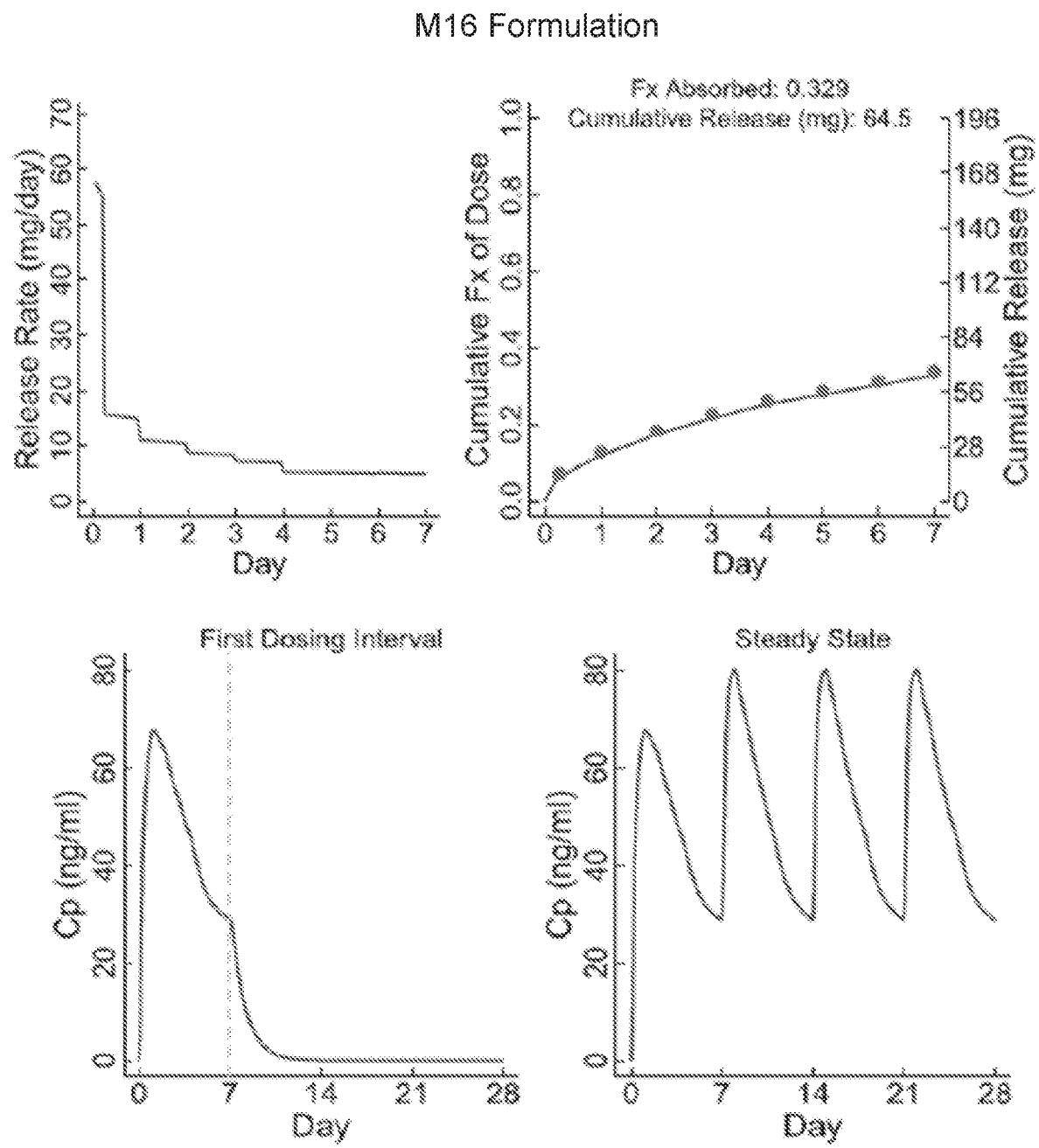
FIG. 25A shows simulation of human pharmacokinetic parameters for memantine from formulation M16.
Figure 25B:
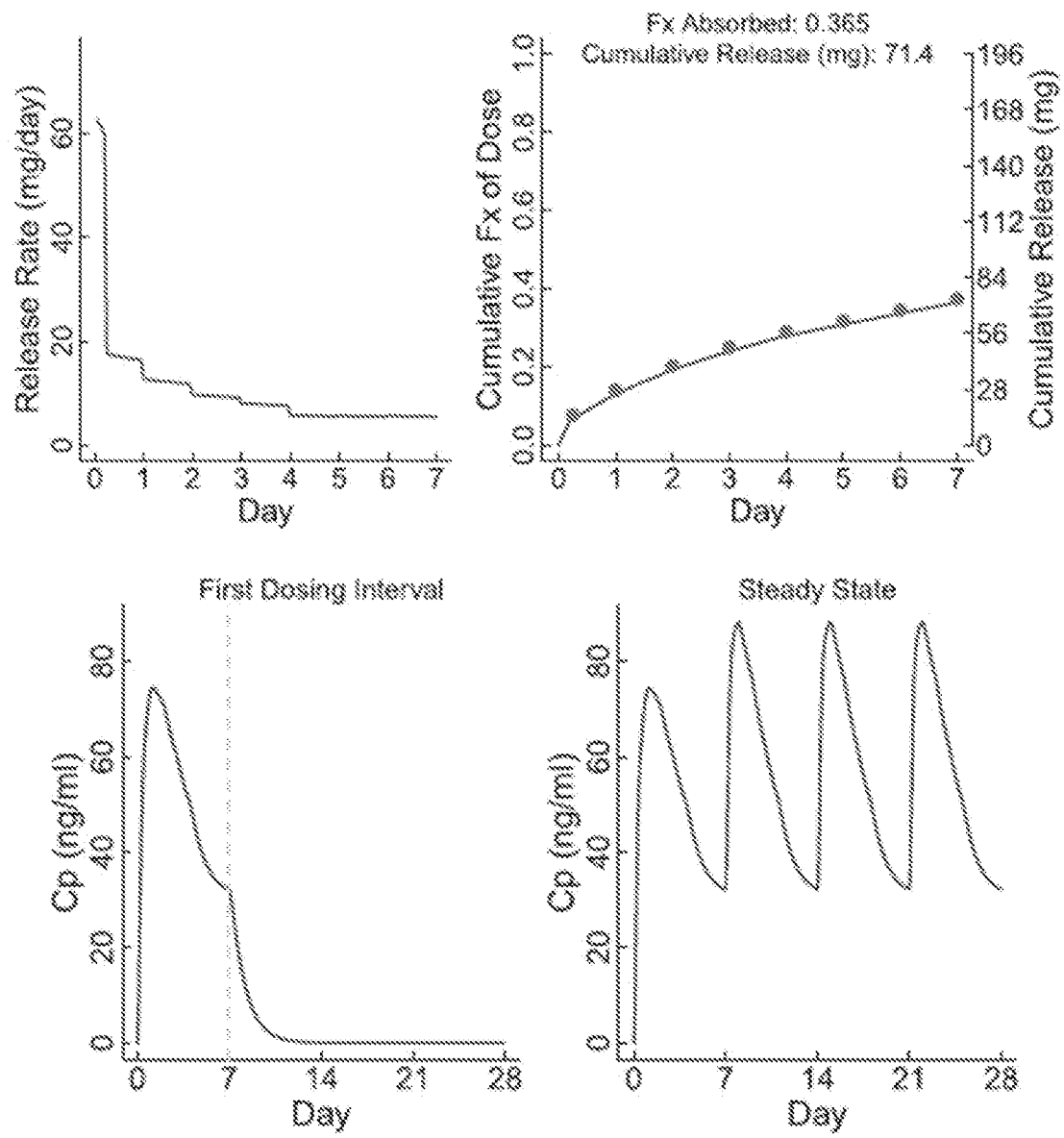
FIG. 25B shows simulation of human pharmacokinetic parameters for memantine from formulation M17.
Figure 26A:
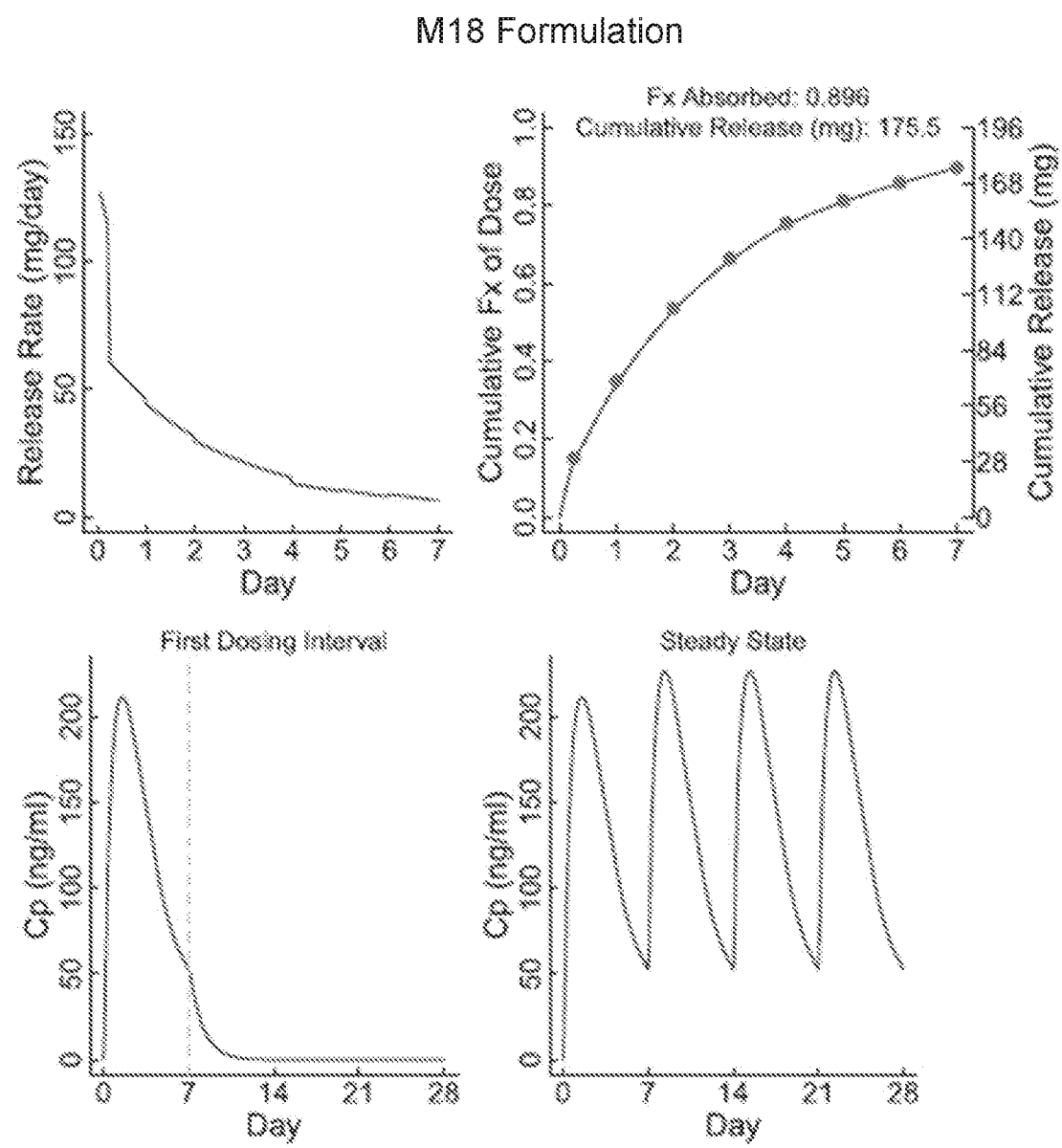
FIG. 26A shows simulation of human pharmacokinetic parameters for memantine from formulation M18.
Figure 26B:
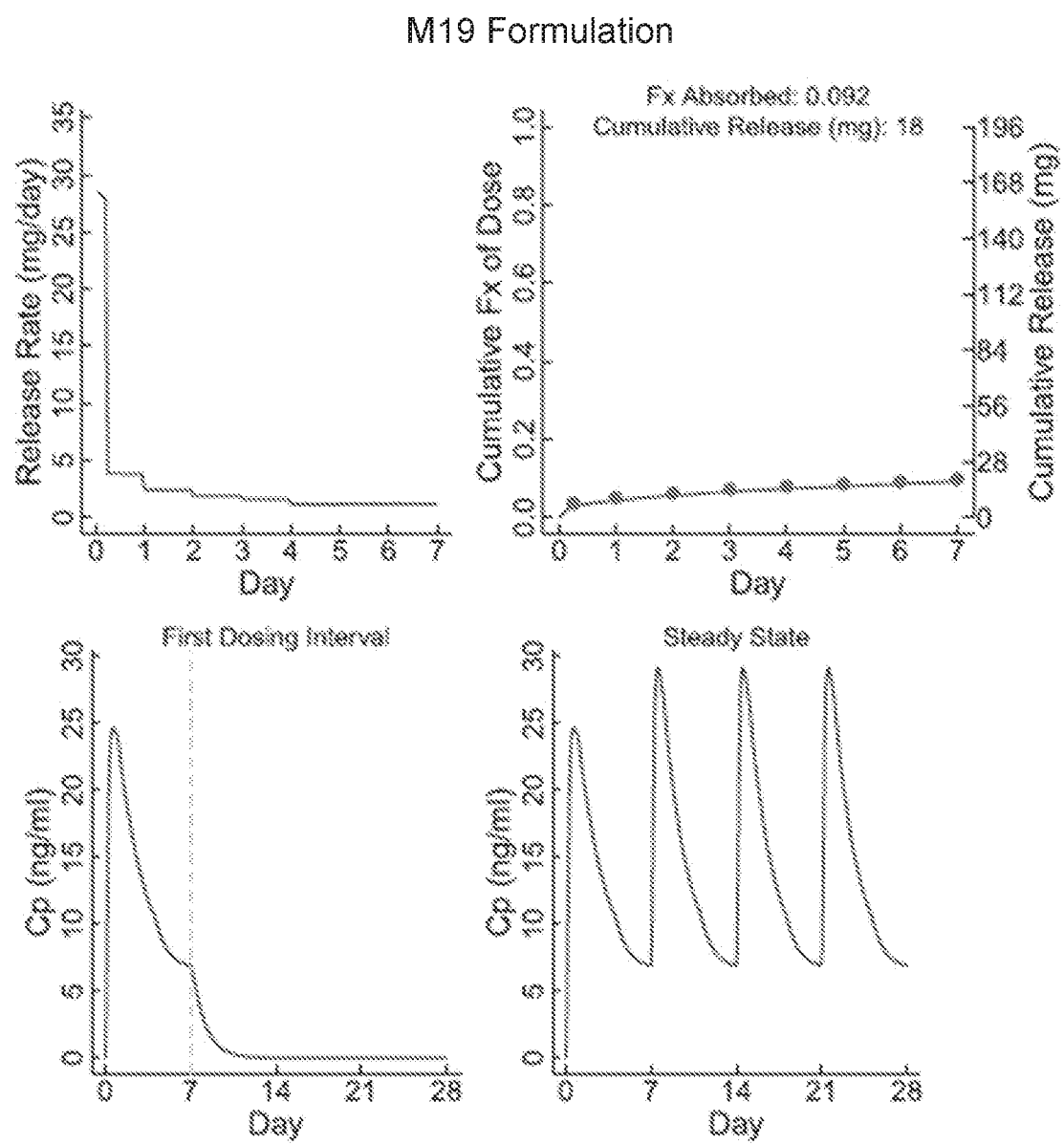
FIG. 26B shows simulation of human pharmacokinetic parameters for memantine from formulation M19.
Figure 26C:
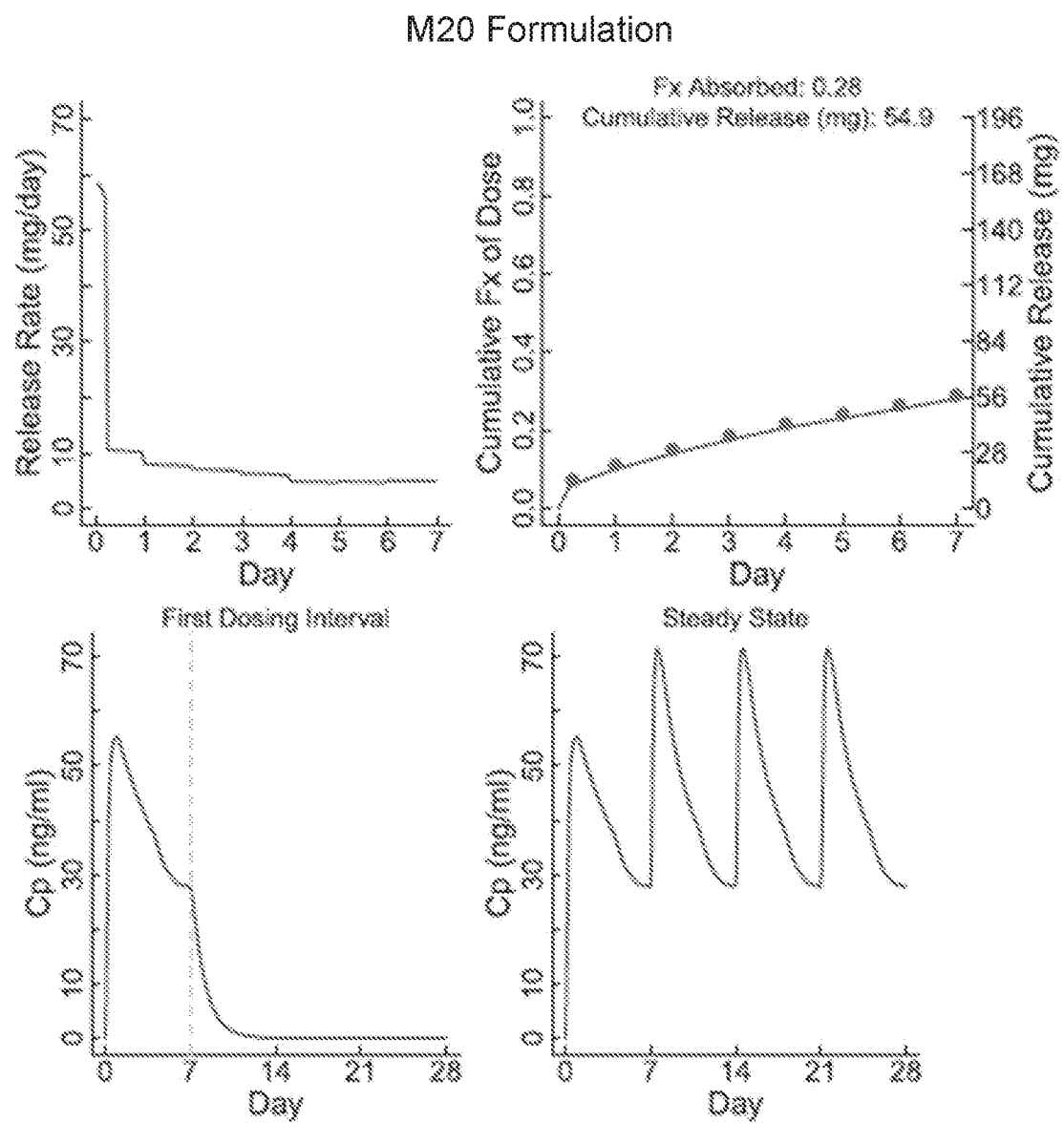
FIG. 26C shows simulation of human pharmacokinetic parameters for memantine from formulation M20.
Figure 27A:
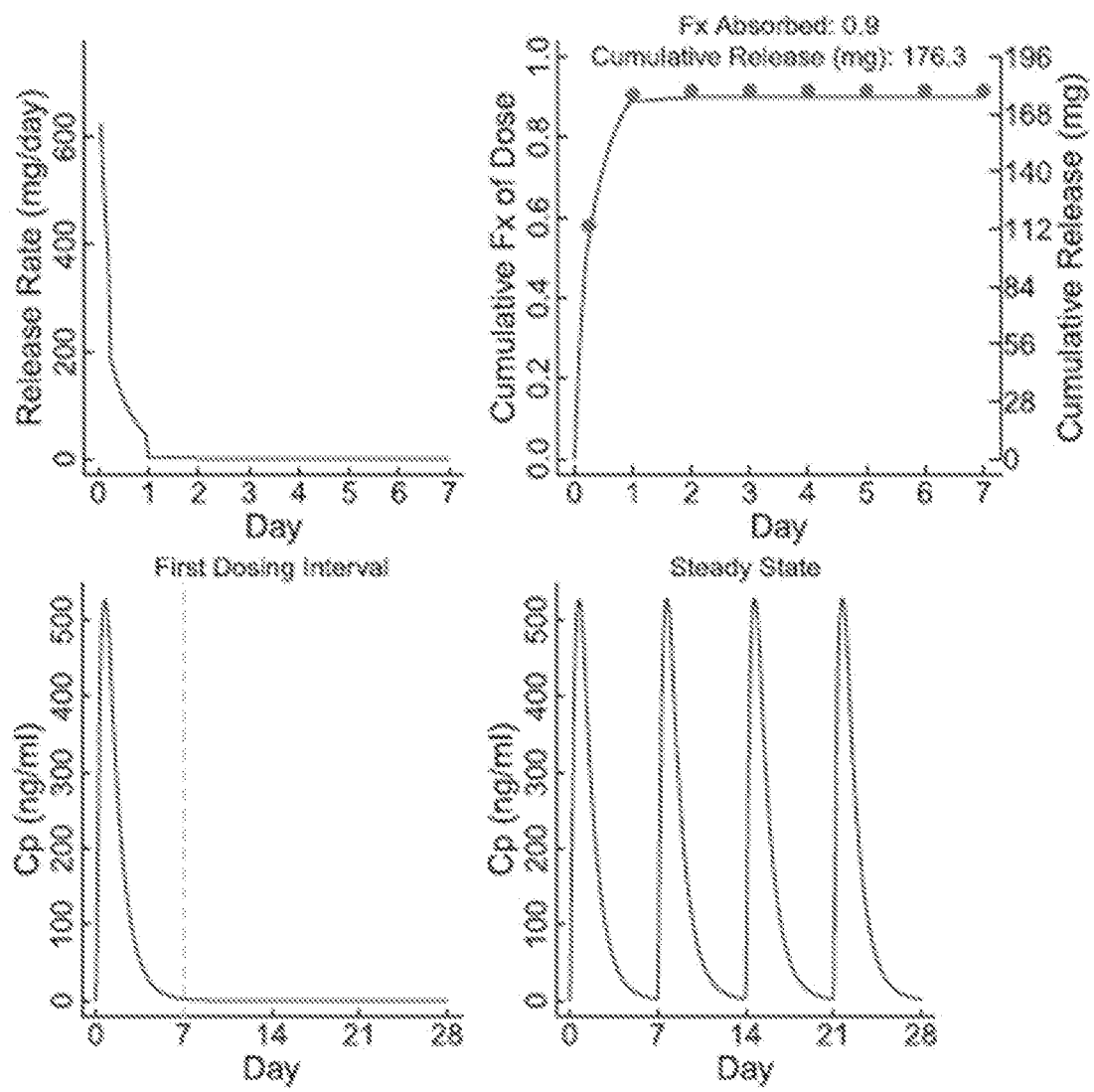
FIG. 27A shows simulation of human pharmacokinetic parameters for memantine from formulation M21.
Figure 27B:
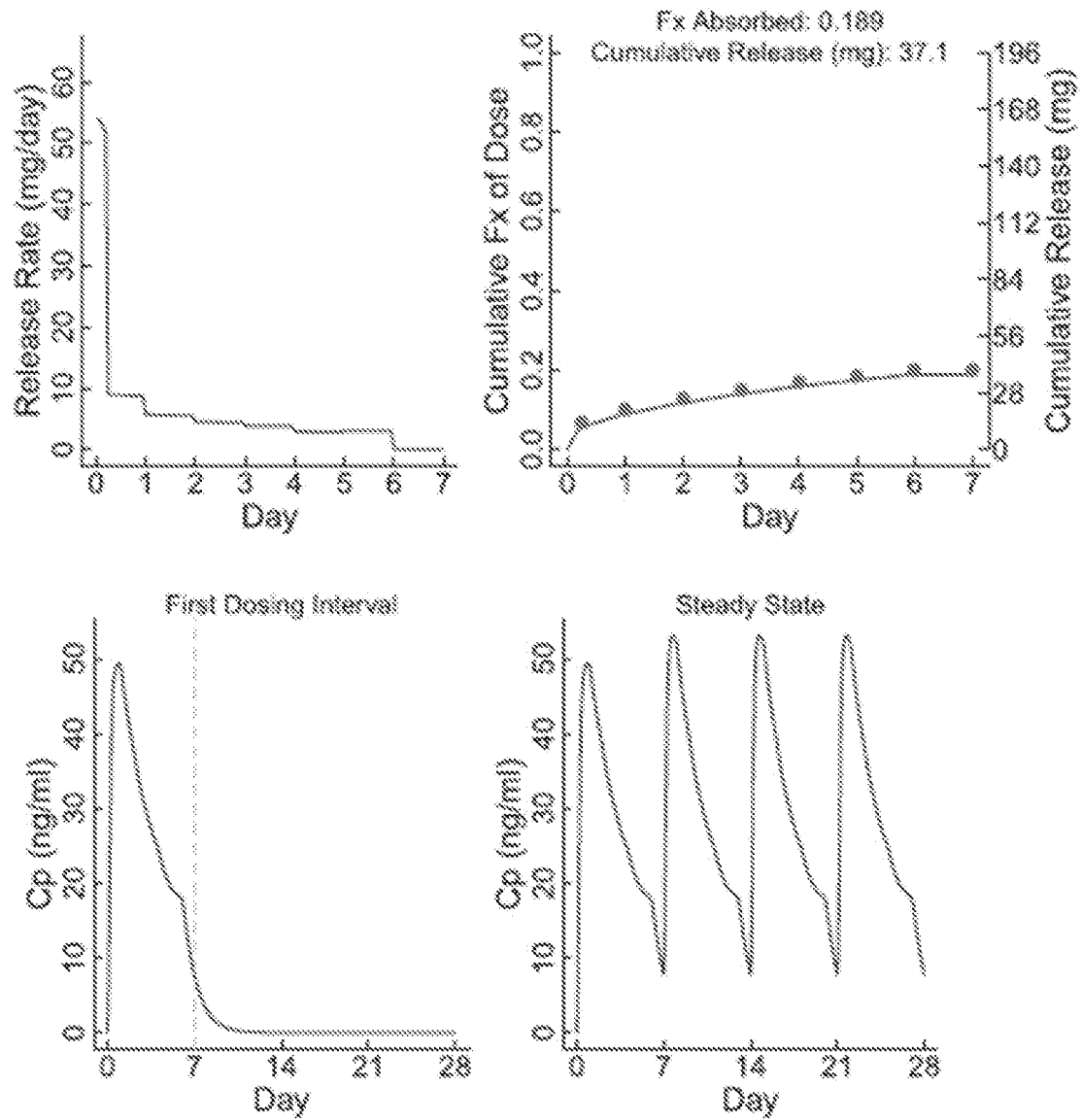
FIG. 27B shows simulation of human pharmacokinetic parameters for memantine from formulation M22.
Figure 27C:
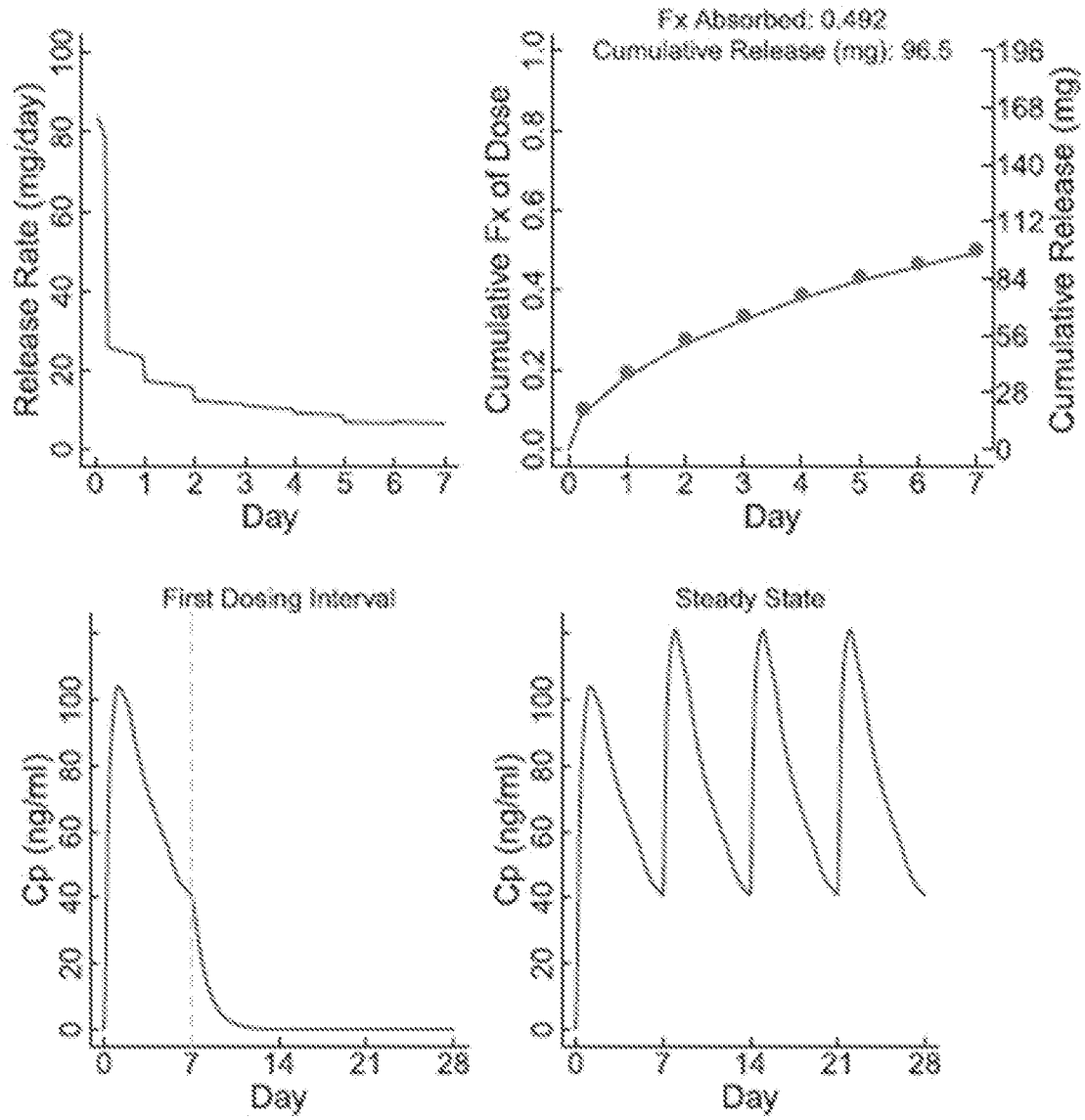
FIG. 27C shows simulation of human pharmacokinetic parameters for memantine from formulation M23.
Figure 28:
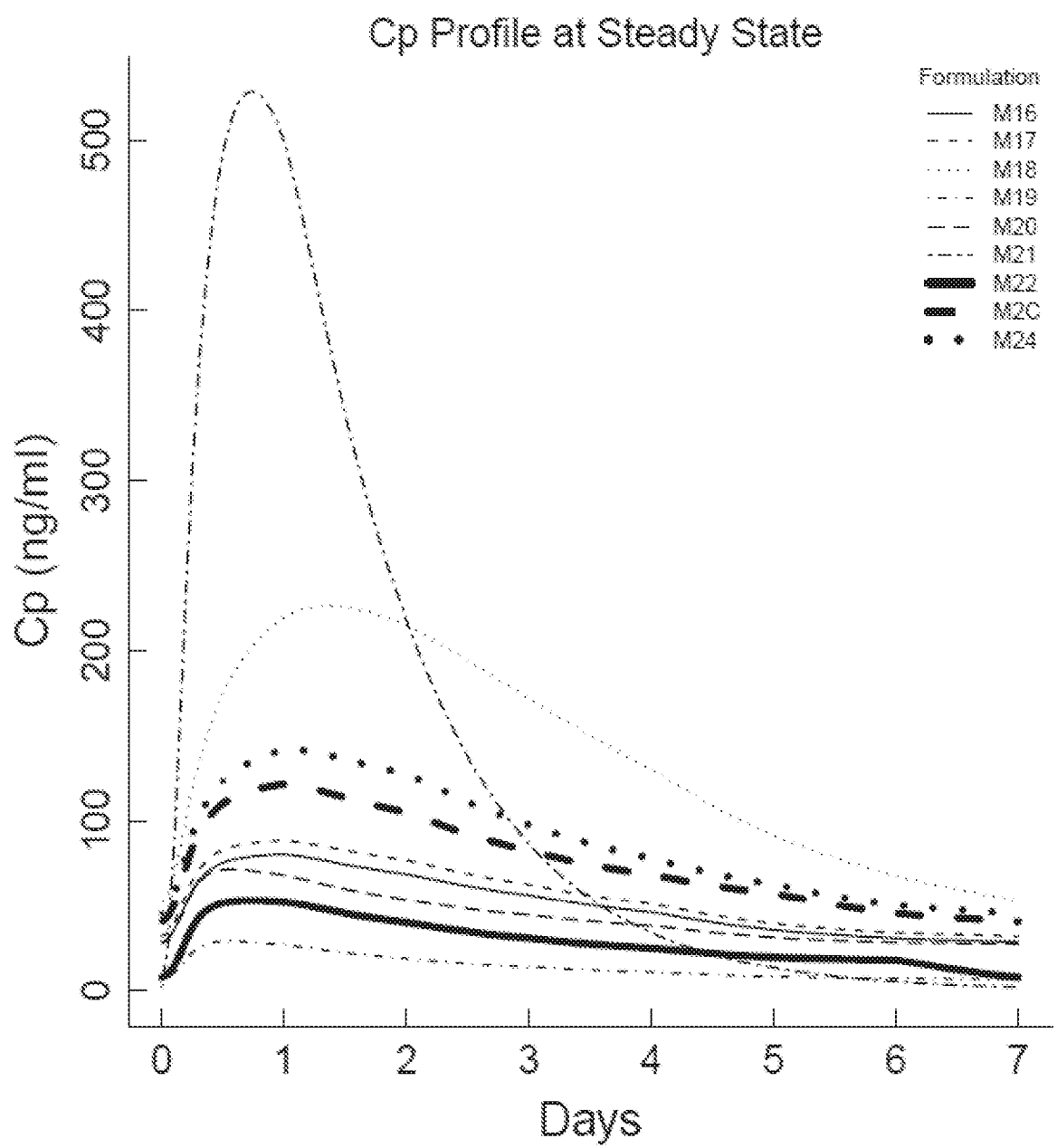
FIG. 28 shows the simulated plasma concentration at steady state for formulations M16, M17, M18, M19, M20, M21, M22, M23, and M24.
Figure 29:
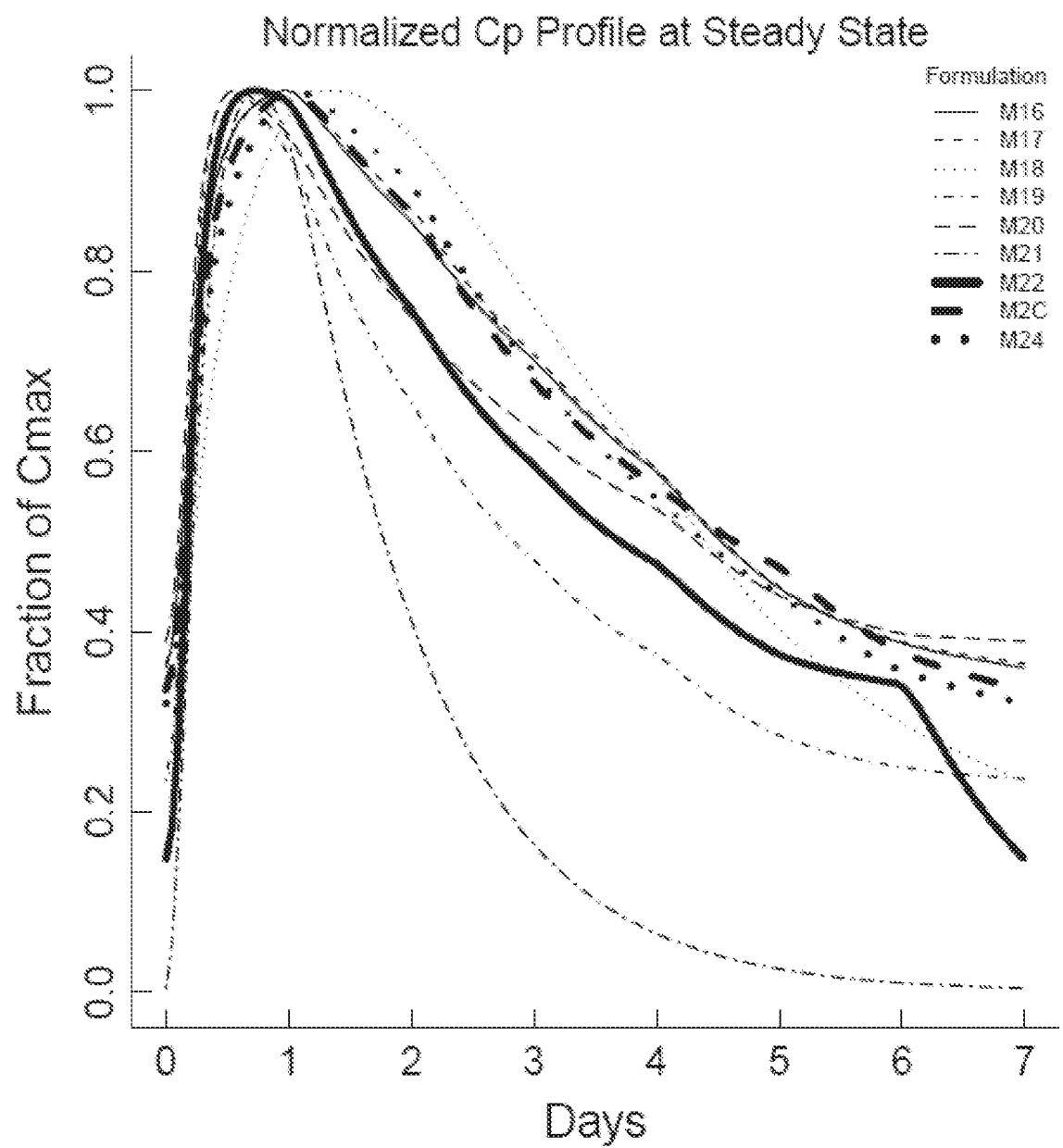
FIG. 29 shows the simulated plasma concentration at steady state for formulations M16, M17, M18, M19, M20, M21, M22, M23, and M24, normalized to the $C_{max}$ for each formulation.

Graphics were prepared showing the modeled release profile, the modeled cumulative release profile (and a comparison to the observed values), the Cp profile from a single administered system, and the Cp profile from 4 systems administered at weekly intervals (for the immediate-release system, only the latter two panels were prepared). The immediate release (28 mg per dose) memantine profile is shown in FIG. 24A. Formulation M24 is also shown in FIG. 24B. Formulations M16 and M17 are shown in FIG. 25A & FIG. 25B respectively. Formulations M18, M19, and M20 are shown in FIG. 26A, FIG. 26B & FIG. 26B respectively, and formulations M21, M22, and M23 are shown in FIG. 27A, FIG. 27B & FIG. 27C respectively. Summary graphics were then prepared to superimpose the steady-state Cp profiles for all the Lyndra systems (based on the final administered system) on a single panel. Two versions of these graphics were prepared, one showing raw concentration data (FIG. 28), the other normalizing the data as a fraction of the maximum Cp for that system (FIG. 29).

Example 5

Administration of Memantine to Dogs

Figure 30:
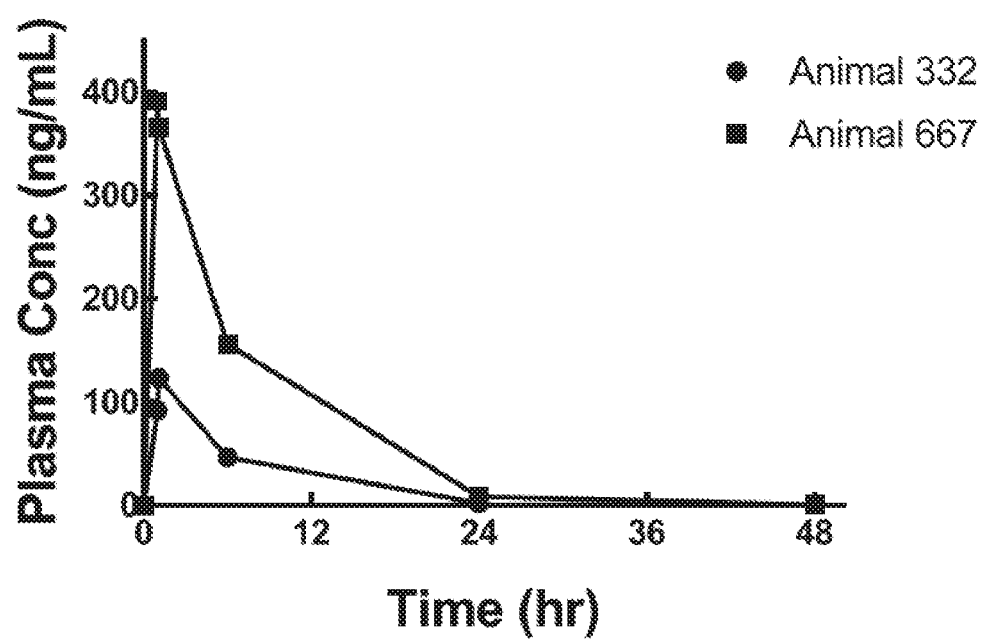
FIG. 30 shows the memantine serum concentration in two hound dogs after oral administration of a solution of memantine.
Figure 39A:
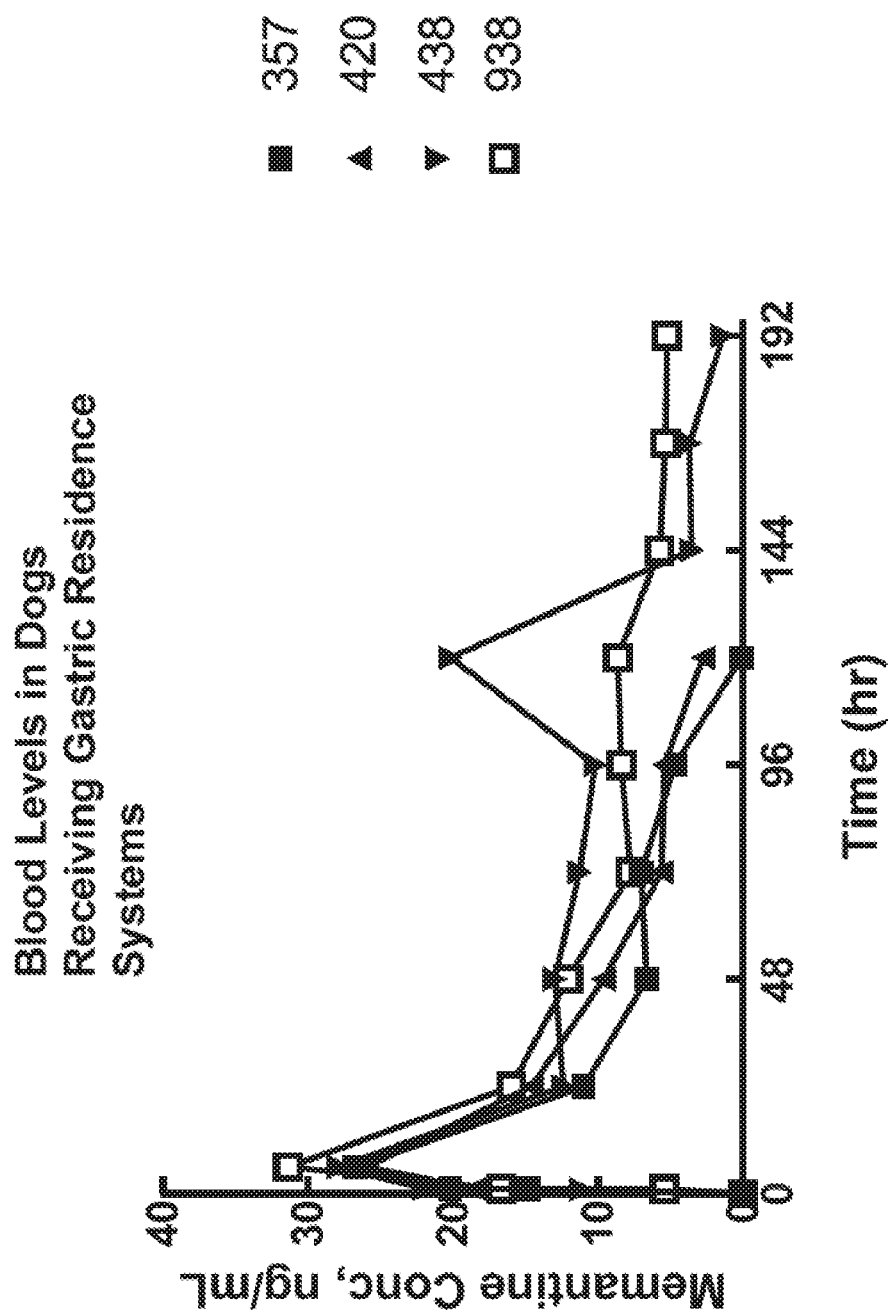
FIG. 39A shows the pharmacokinetics of memantine serum concentration in four hound dogs after administration of two stellate gastric residence systems per dog.
Figure 39B:
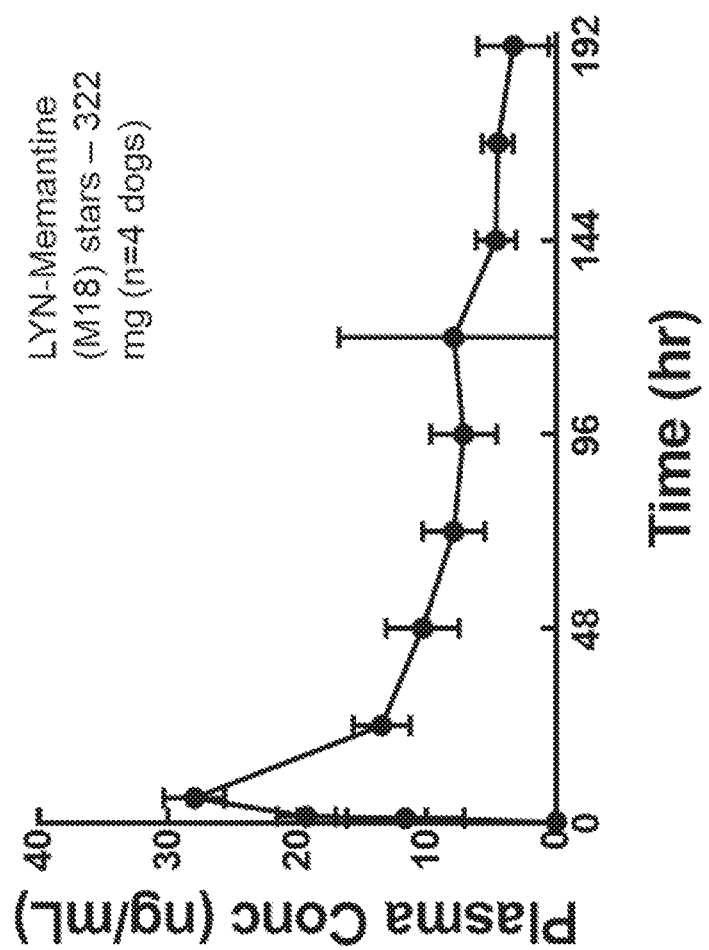
FIG. 39B shows the average of the four curves in FIG. 39A.

A study was done in hound dogs to compare plasma levels obtained after administration of memantine in a gastric residence system, versus plasma levels obtained after administration of an immediate release formulation (an oral solution of memantine). Formulation M18 was used for delivery of memantine in the gastric residence systems to four dogs. An oral solution containing 100 mg memantine was administered to two dogs for comparison. Animal 322 vomited extensively after oral administration, and thus it is likely that drug absorption and plasma levels were decreased substantially in that animal. Serum levels of memantine are shown in Table 5, in units of nanograms per milliliter (ng/mL). Graphs of the serum levels in the four animals that received stellate systems are shown in FIG. 39A, the serum levels averaged over those four animals are shown in FIG. 39B, and the serum levels in the two animals that received oral solutions are shown in FIG. 30.

The results show that the gastric residence systems of the invention can provide significant plasma levels of memantine over an extended period of time.

TABLE 5

| | Animals administered 322 mg memantine (two stellate gastric residence systems with 161 mg per system) | | | | Animals administered 100 mg memantine oral solution | |
|---|---|---|---|---|---|---|
| Time (days) | Animal 420 | Animal 357 | Animal 938 | Animal 438 | Animal 667 | Animal 322* |
| 0 | 0 | 0 | 0 | 0 | 0 | 0 |
| 0.041666667 | 15.3 | 14.8 | 5.45 | 11.2 | 391 | 92.0 |
| 0.0625 | 18.5 | 20.2 | 16.7 | 22.0 | 366 | 123 |
| 0.25 | 26.0 | 26.8 | 31.4 | 27.9 | 156 | 46.8 |
| 1 | 14.6 | 11.0 | 16.0 | 12.4 | 8.32 | 2.05 |
| 2 | 9.66 | 6.69 | 12.1 | 13.0 | 0.807 | 0 |
| 3 | 5.66 | 7.04 | 7.79 | 11.3 | 0 | 0 |
| 4 | 5.45 | 4.70 | 8.41 | 10.2 | 0 | 0 |
| 5 | 2.79 | 0.166 | 8.68 | 20.2 | 0 | 0 |
| 6 | 0 | 0 | 5.77 | 3.58 | 0 | 0 |
| 7 | | | 5.39 | 3.71 | 0 | 0 |
| 8 | | | 5.27 | 1.42 | 0 | 0 |

*Animal 322 vomited extensively post-administration

Example 6

Raman and FTIR Spectra of Memantine Formulations

Figure 31:
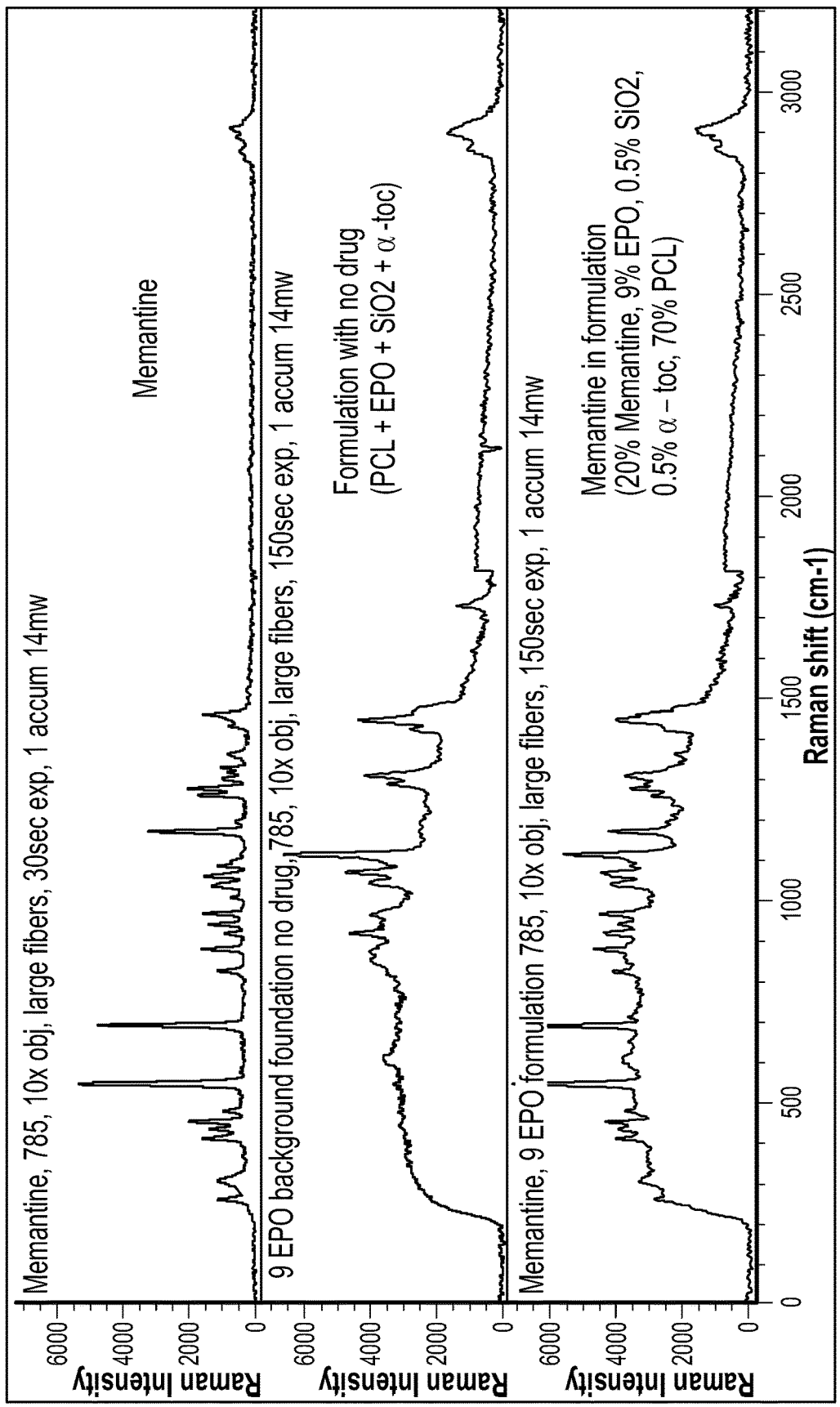
FIG. 31 shows Raman spectra of memantine (top spectrum), a formulation containing no drug (middle spectrum), and that formulation containing memantine (bottom spectrum).
Figure 32:
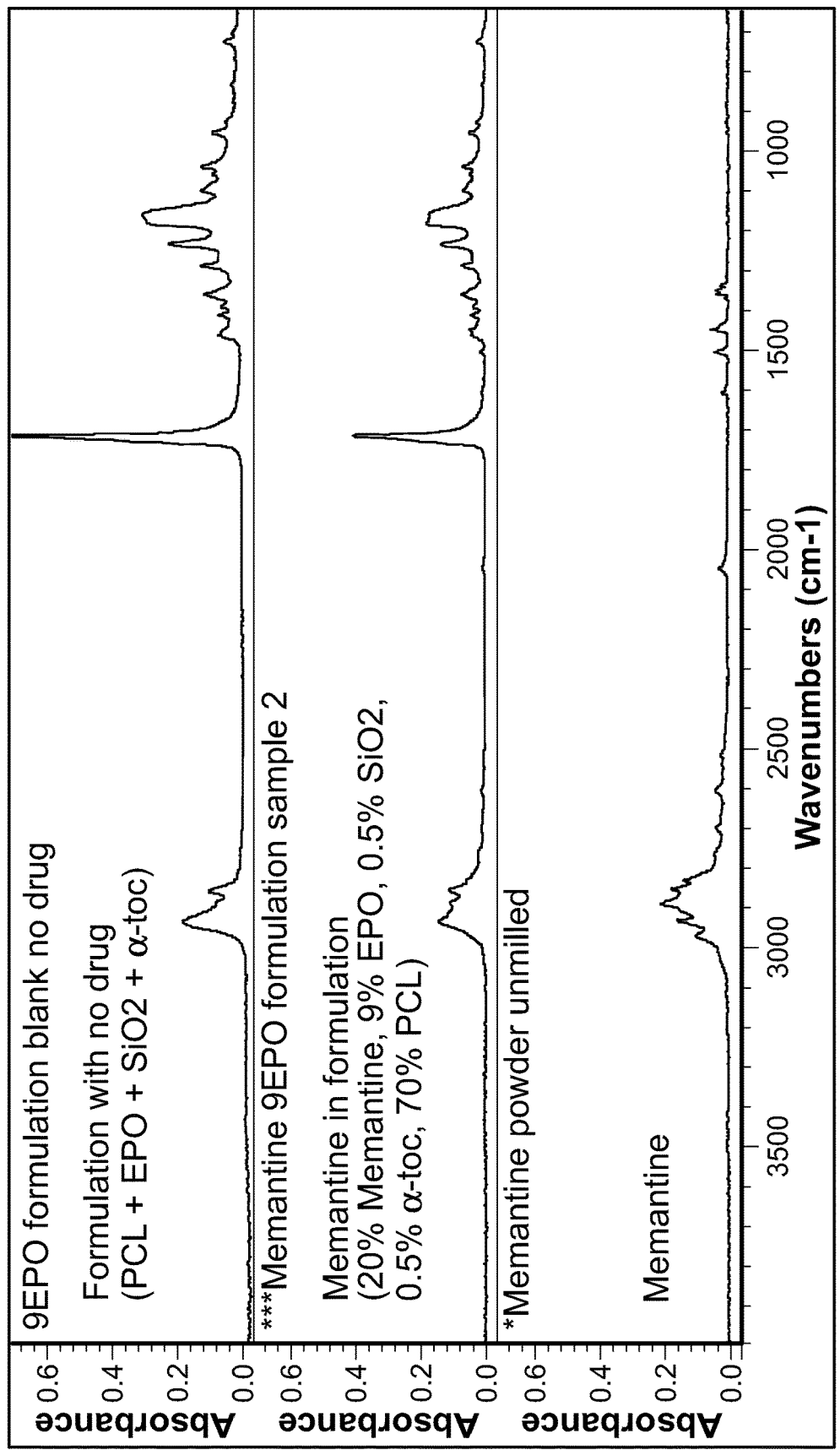
FIG. 32 shows Fourier-transform infrared spectra of the same formulation as FIG. 31 (top spectrum), memantine in the formulation (middle spectrum), and memantine powder (unmilled; bottom spectrum).

FIG. 31 shows Raman spectra of memantine (top spectrum), a formulation containing no drug (middle spectrum, comprising Eudragit EPO, silicon dioxide, alpha tocopherol, and 80,000 MW polycaprolactone), and that formulation containing memantine (bottom spectrum, 20% memantine, 9% EPO, 0.5% silica, 0.5% alpha tocopherol, 70% 80,000 MW polycaprolactone). Characteristic peaks for memantine occur between 500 and 700 $cm^{-1}$, showing that Raman spectroscopy is capable of distinguishing memantine from other formulation components. Raman spectroscopy can thus be used for monitoring of formulations during manufacture and storage. FIG. 32 shows Fourier-transform infrared spectra of the same formulation (top spectrum), memantine in the formulation (middle spectrum), and memantine powder (unmilled; bottom spectrum). FTIR can also be used to monitor formulations during manufacture and storage, although its use is more limited than Raman spectroscopy due to lack of a strong IR signal for memantine that does not overlap with signals for the formulation without drug.

Example 7

X-Ray Diffraction Patterns of Memantine Formulations

Figure 33:
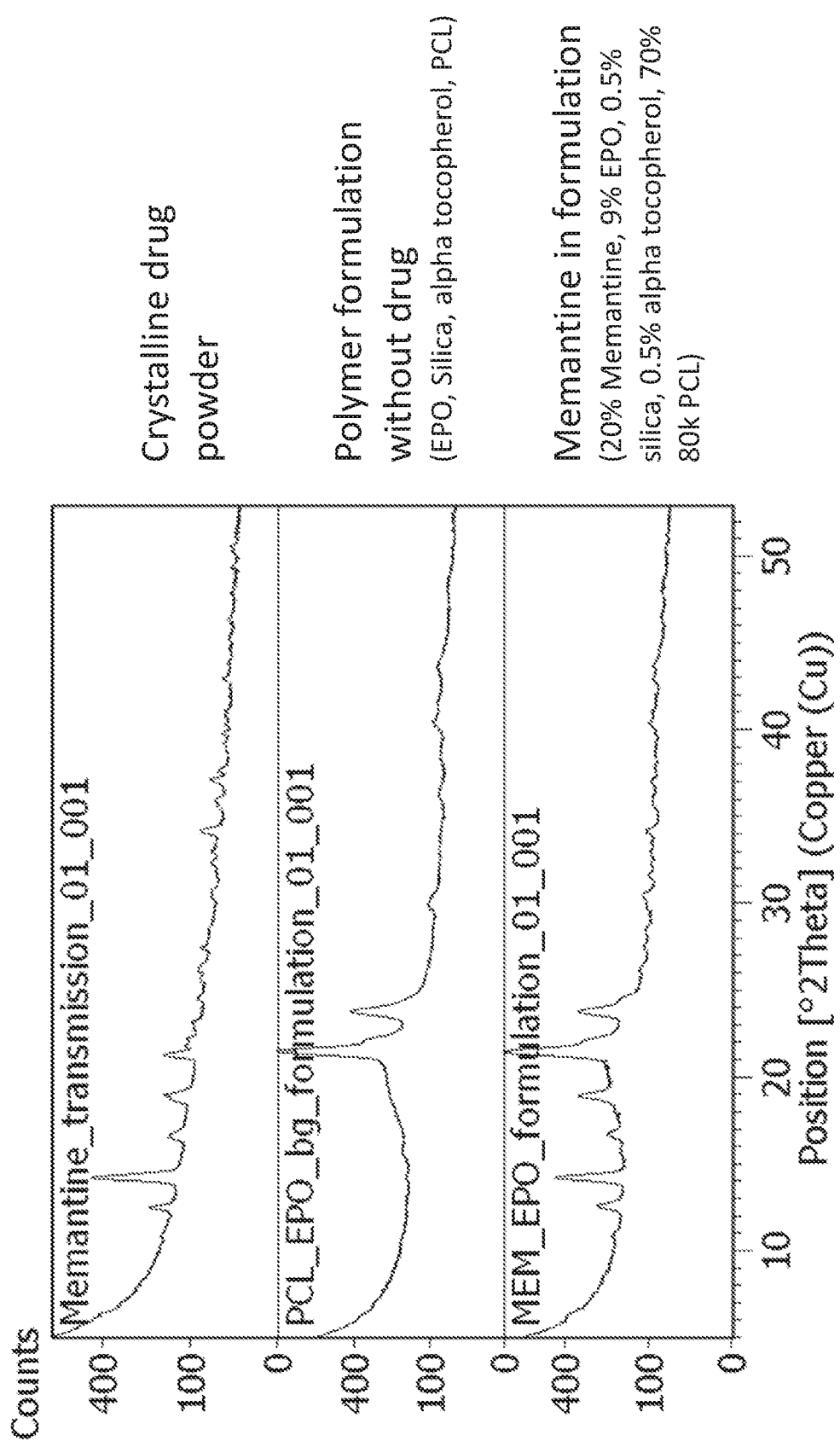
FIG. 33 shows X-ray diffraction patterns of memantine (top), the same formulation as FIG. 31 and FIG. 32 containing no drug (middle), and that formulation containing memantine (bottom).

FIG. 33 shows X-ray diffraction patterns of memantine (top), a formulation containing no drug (middle, comprising Eudragit EPO, silicon dioxide, alpha tocopherol, and 80,000 MW polycaprolactone), and that formulation containing memantine (bottom s, 20% memantine, 9% EPO, 0.5% silica, 0.5% alpha tocopherol, 70% 80,000 MW polycaprolactone). Unique peaks can be observed for memantine, indicating that X-ray diffraction can also be used for quality control and monitoring during manufacture and storage. Curve-fitting software can enable integration of memantine peaks for approximate quantitation of drug crystallinity. As can be seen in FIG. 33, the crystalline form of memantine was preserved during the hot melt extrusion process used to prepare the drug in its carrier polymer formulation.

Example 8

Thermal Stability of Memantine During Formulation

Figure 35:
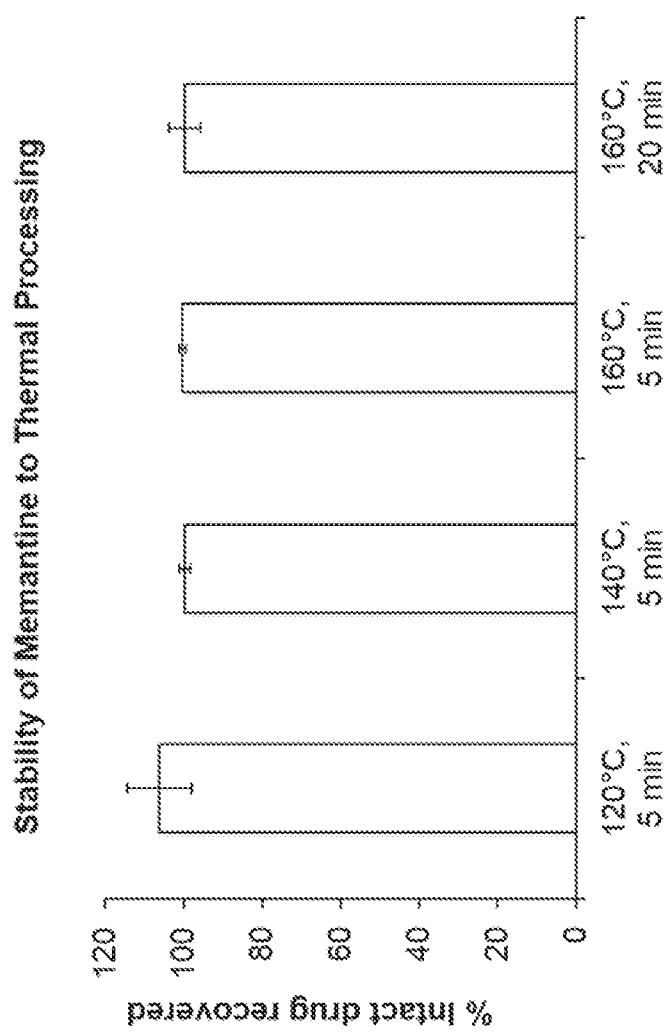
FIG. 35 shows results of tests of stability of memantine during high-temperature formulation in carrier polymer.

The stability of memantine under conditions of hot melt processing was tested. The formulation used for hot melt processing was 20% drug, 0.5% SiO2, 0.5% alpha tocopherol, 2% P407, 20% Eudragit RS, with the balance of material made up of PCL. As can be seen from the results in FIG. 35, memantine blended with polymer can be processed at up to 160° C. for up to 20 minutes without significant degradation.

Example 9

Die Designs for Producing Star Arms

Star arms for the stellate gastric residence systems can be produced by hot melt extrusion through a die. Examples of dies used to prepare stellate arms with approximately triangular cross-sections are shown in FIG. 36.

Example 10

Mechanical Stability of Formulations Containing Memantine

The mechanical strength of two formulations of memantine-loaded star arms was compared to that of pure polycaprolactone (PCL). A standard 4-point bending assay was used. Formulation M23 contained 20% drug, 0.5% SiO2, 0.5% alpha tocopherol, 9% Eudragit E, with the balance of material made up of PCL. Formulation M24 contained 20% drug, 0.5% SiO2, 0.5% alpha tocopherol, 2% P407, 20% Eudragit RS, with the balance of material made up of PCL.

Figure 37:
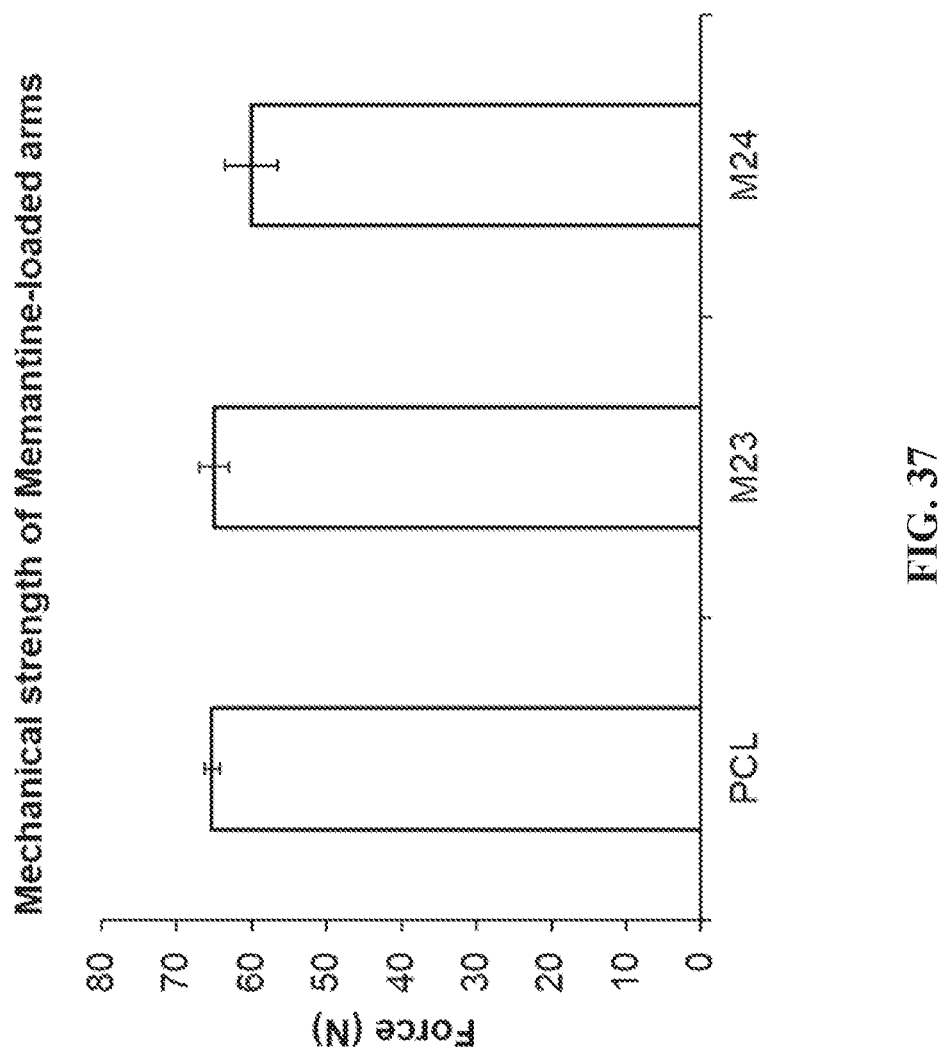
FIG. 37 shows results of mechanical strength tests of star arms for gastric residence systems.

The results are shown in FIG. 37, and show that the mechanical strength of memantine-loaded arms is comparable to that of pure polycaprolactone.

Example 11

In Vivo Comparison of Serum Levels of Memantine Provided by Gastric Residence Systems Versus Memantine Extended Release Formulation in Capsules A preclinical non-GLP study was done in the dog (hound) model to compare the pharmacokinetics of daily Namenda XR with the gastric residence systems of the invention. Namenda XR is an extended release form of memantine, supplied in capsules. The studies were performed at Tufts University Cummings School of Veterinary Medicine (North Grafton, Mass., USA).

The stellate gastric residence systems were designed with a single time-dependent linker and contained memantine. Each stellate system had six arms projecting from a central polycaprolactone-polyurethane elastomer; the elastomer was 5 mm in diameter. The arms were heat-welded to the elastomer center with a time dependent linker consisting of an extruded blend of a mixture of a linear block copolymer of dioxanone (80%) and ethylene glycol (20%) with polycaprolactone at a 30/70 ratio of linear block copolymer to PCL. Memantine particles were milled and sieved to <75 um, and memantine was incorporated into the drug-polymer arms at 20% drug load, using Formulation M18. Total drug load per system was about 156 mg for an estimated potential release of about 22 mg/day per system over 7 days. The systems were placed in 00EL HPMC capsules (Capsugel) for administration. Two encapsulated systems were administered to the back of the throat in four hound dogs, followed by food chasing. This provides potential release of about 44 mg/day over 7 days. X-ray visualization was acquired within 1 hr of dose administration to ensure full deployment of the stellate dose form, and then on days 0, 1-7, 9, and 11 (or until the systems exited the body) via left lateral abdominal radiograph. Dogs were fasted x 12 hr prior to administration, then fed a standard daily dog diet.

For the dogs receiving stellate gastric residence systems, blood samples were collected at 0, 0.5, 1, 1.5, and 6 hr on Day 1, and then daily for the duration of the experiment. Blood was collected in red top collection tubes (3 mL collected per time point after wasting 1 mL), centrifuged, and the serum pipetted into Eppendorf tubes and frozen at −20° C. Blood was then shipped to Agilux Laboratories for bioanalysis.

For comparison, another group of dogs received commercial extended release capsules. Namenda XR (28 mg capsules) were administered to the back of the throat in six hound dogs daily for 5 days. Blood samples were collected at 0, 2, 4 and 6 hr on Day 1, and at 0 (prior to dose administration) and 4 hr on Days 2 through 5. Blood was processed to serum and shipped to Agilux Laboratories (Worcester, Mass.) for bioanalysis.

All of the stellate gastric residence systems deployed correctly. The residence periods of the systems in each dog is shown FIG. 38A and FIG. 38B. Two six-arm stellate systems were administered to each dog, for a total of 12 arms in each dog. In the comparison group, Namenda XR was dosed without incident and well tolerated.

Figure 40:
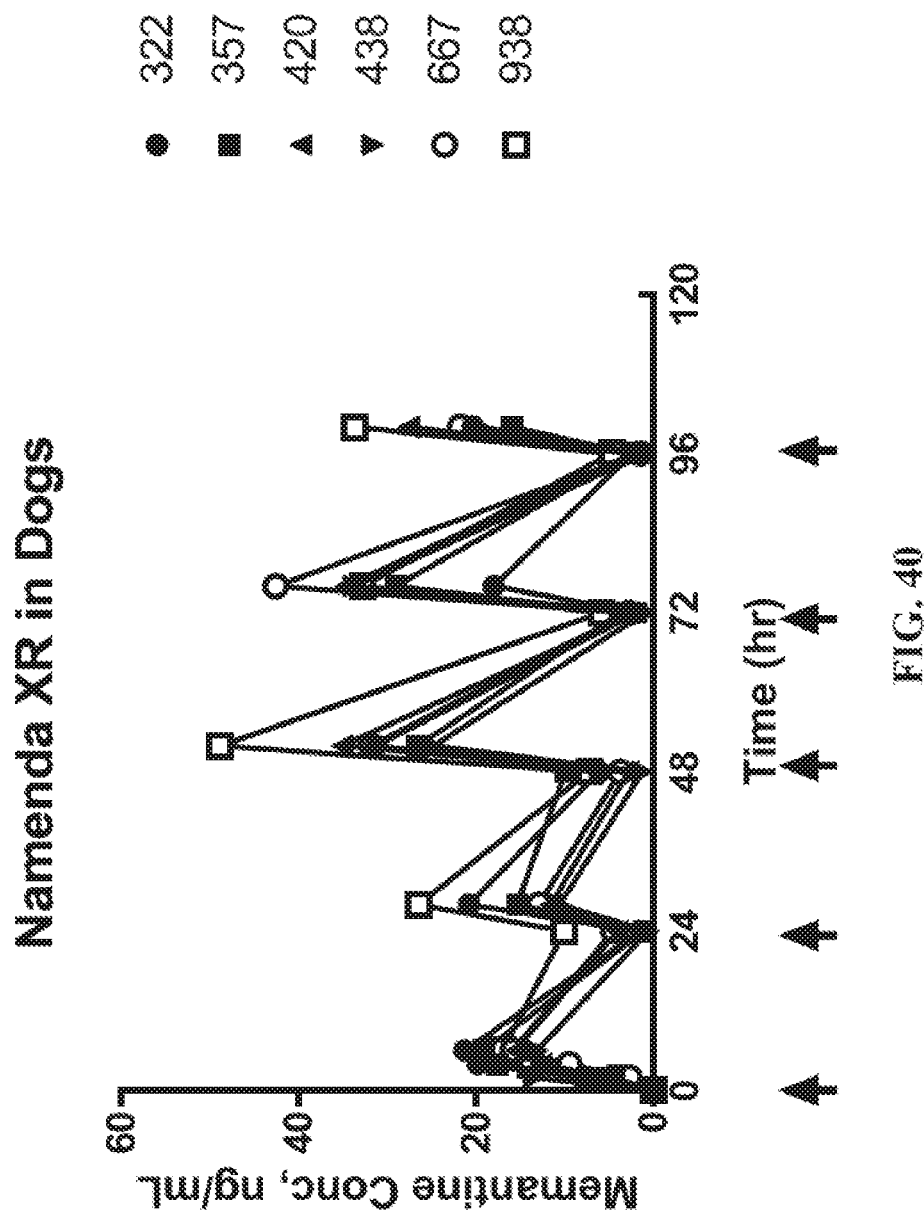
FIG. 40 shows the pharmacokinetics of memantine after administration of Namenda XR.
Figure 41:
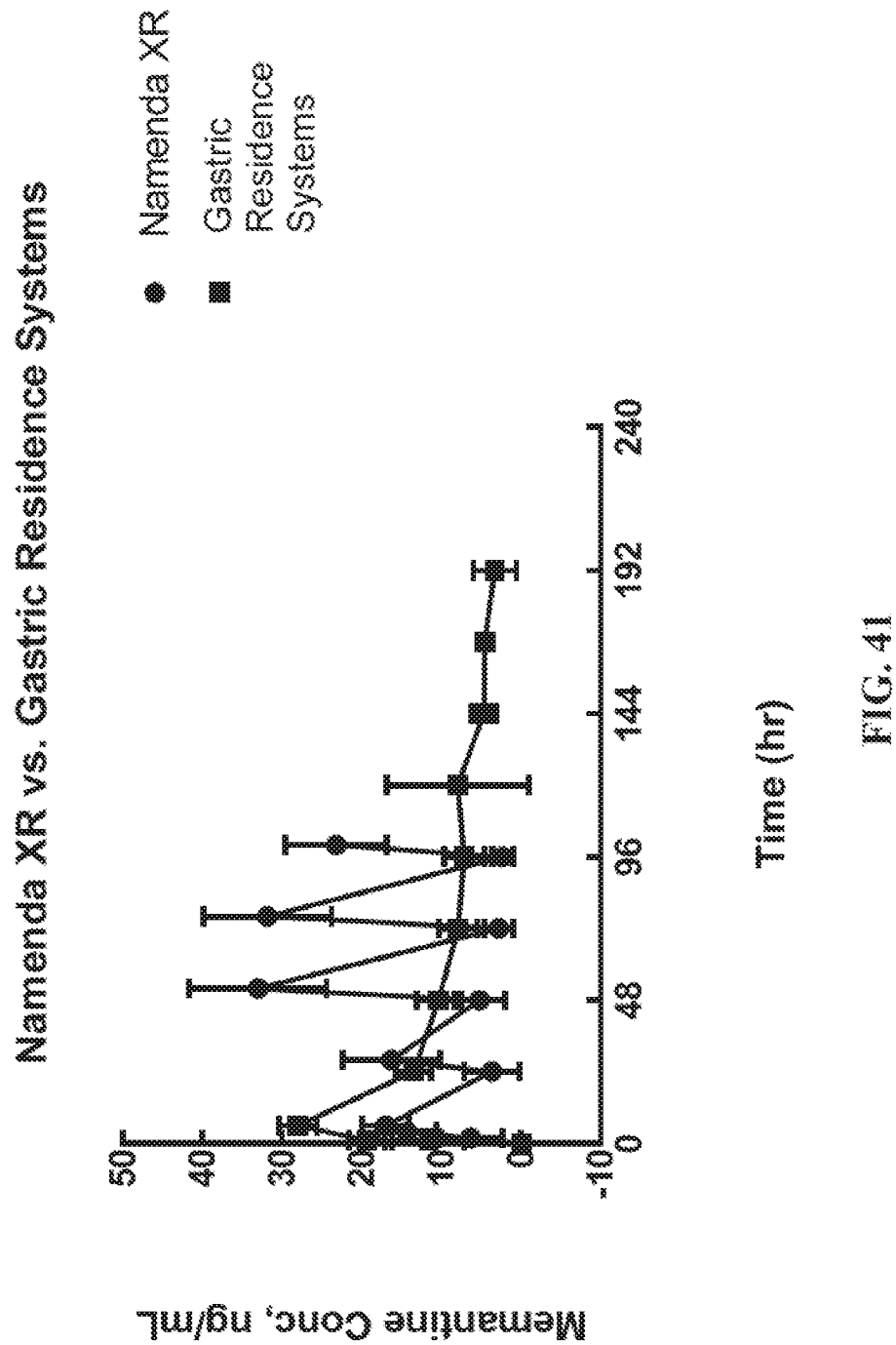
FIG. 41 shows an overlay of the pharmacokinetic data of the two different dosage forms shown in FIG. 39B and FIG. 40.
Figure 42:
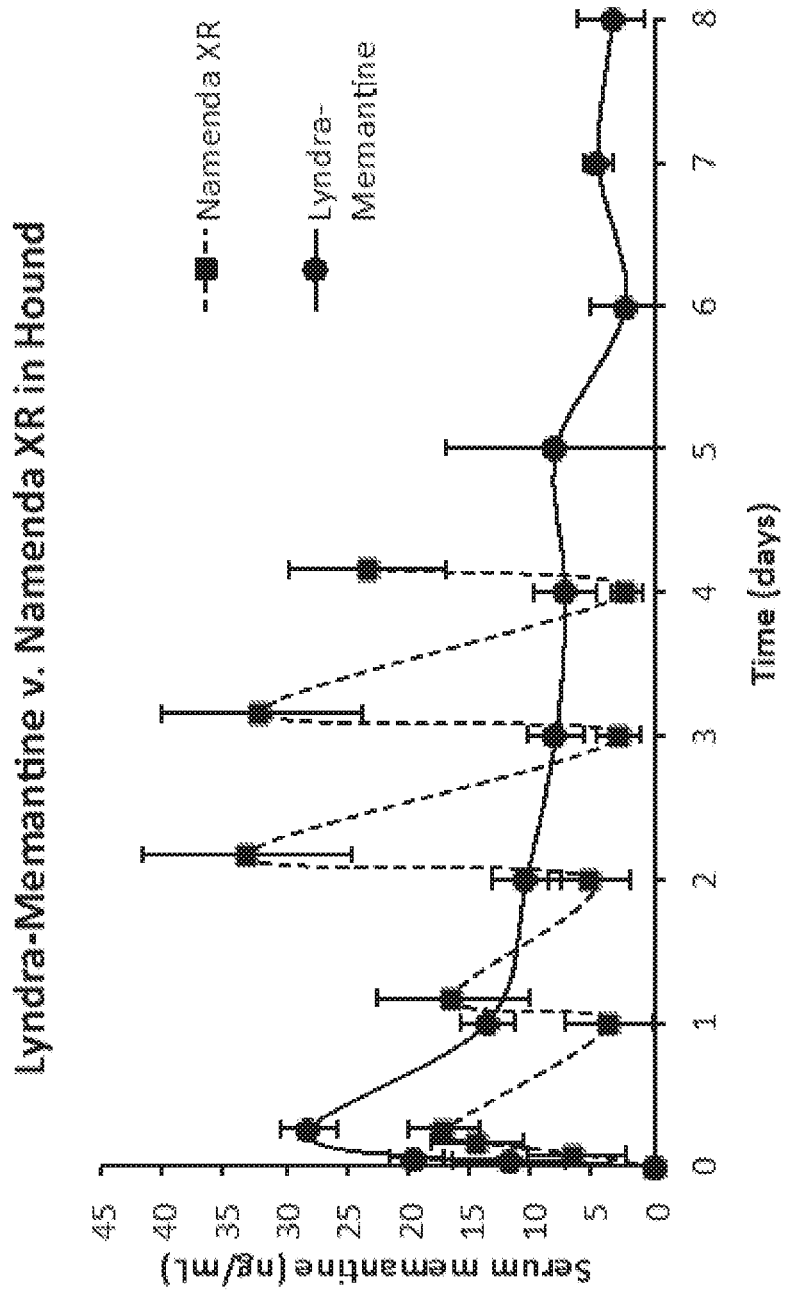
FIG. 42 shows a similar graph as FIG. 41, comparing in vivo pharmacokinetics of Lyndra-Memantine formulation M18 and Namenda XR memantine capsules in dogs.

The pharmacokinetics of the in vivo memantine concentration after administration of the stellate gastric residence system are depicted in FIG. 39A for individual dogs tested (animals 357, 420, 438, and 938); FIG. 39B shows the memantine concentration averaged over the four dogs. The pharmacokinetics of memantine after administration of Namenda XR are depicted in FIG. 40. FIG. 41 shows an overlay of the pharmacokinetic data of the two different dosage forms. FIG. 42 shows a graph similar to FIG. 41, comparing in vivo pharmacokinetics of the stellate gastric residence system (Lyndra-Memantine) formulation M18 and Namenda XR memantine capsules in dogs. The two stellate systems combined contained 322 mg of memantine.

The results show that oral administration of the gastric residence systems in dogs, via swallowing, is readily achievable and the systems deploy correctly. The gastric residence systems are retained in the stomach for up to 11 days (range: 3-11 days).

The $C_{max}$ of memantine from initial administration of the gastric residence systems (with potential average elution of about 44 mg per day) is similar to the $C_{max}$ after 3 doses of 28 mg of Namenda XR. Notably, the serum levels of memantine from the gastric residence systems are more consistent than those from Namenda XR daily dosing. There were no adverse events in this safety study in a hound model in either the Namenda XR or gastric residence test animals.

Example 12

PCL/SGF Partition Coefficient

Partitioning of active pharmaceutical ingredient (API), such as an adamantane-class drug such as memantine, between the structural polymer, polycaprolactone (PCL), and fasted state simulated gastric fluid (FaSSGF) is of interest for predicting API release rate from PCL-based formulations. To measure the PCL-SGF partition coefficient of an API, a concentrated stock solution of API was added to a mixture of 1 mL FaSSGF and 1 mL of 5:1 PCL diol (MW 530):ethyl acetate. The sample was vortexed and centrifuged at 10000 rpm for 5 minutes. The SGF phase was analyzed by HPLC to measure drug concentration. The PCL phase was diluted in methanol prior to quantification on HPLC. The PCL/SGF partition coefficient of memantine is shown in Table 6.

TABLE 6

Comparison of PCL/SGF partition coefficient of memantine with octanol/water partition coefficient

| Active Pharmaceutical Ingredient | PCL/SGF Partition Coefficient | LogP (PCL/SGF) | LogP (Octanol/water) |
| --- | --- | --- | --- |
| Memantine | 0.28 | −0.56 | 3.28 |

Example 13

Heat Welding of Memantine-Containing Arms

Drug-loaded formulations (20% Memantine, 25% Eudragit RS, 5% P407, 0.5% Silica, 0.5% alpha tocopherol) were prepared by extrusion and compression molding. The drug-loaded formulations were prepared by combining memantine, polycaprolactone (PCL) structural polymer, and excipients. Memantine and excipient powders were blended and then combined with polymer pellets by hot melt extrusion (HME). Hot melt extrusion was performed on Thermo Fisher HAAKE MiniCTW extruder with counter rotating twin screws. The blend was batch mixed at 100° C. and a screw speed of 75 rpm for 10 minutes before extrusion at a rate of 20-30 rpm. Sections of extruded melt were placed into an aluminum compression mold and shaped into 20 mm long and 2 mm wide triangular rods. Upon cooling to ambient temperature, arms were trimmed to remove excess formulation and were stored in the freezer (~−20° C.).

The drug-loaded arms were thermally welded to triangular rods of 80k PCL. Welding was performed using a custom fixture that enables control of weld temperature and alignment. Weld temperature was varied from 93-170° C. and welded parts were stored at room temperature or at 8° C. for 24 hours (n=6 samples per condition). Weld strength was characterized using a 4-point bending assay with a displacement of 600 microns. Maximum flexural force was recorded for each sample, as well as the number of welds that failed during the bending assay. Results are shown in Table 7.

TABLE 7

Heat welding of Memantine formulations.

| Heat Weld Temp | Time/Temp After Weld Before Bending | % Welds broken | Average Bending Force (N) |
| --- | --- | --- | --- |
| 93° C. | 24 hr/RT | 0% | 66.65-95.48 |
| 140° C. | 24 hr/RT | 67% | 96.68 ± 6.25 |
| 160° C. |  | 50% | 98.00 ± 2.17 |
| 140° C. | 24 hr/8° C. | 17% | 102.72 ± 3.97 |
| 160° C. |  | 0% | 100.39 ± 2.41 |
| 170° C. |  | 17% | 98.95 ± 3.29 |

Example 14

Memantine Release in Fed Vs. Fasted State

Figure 43:
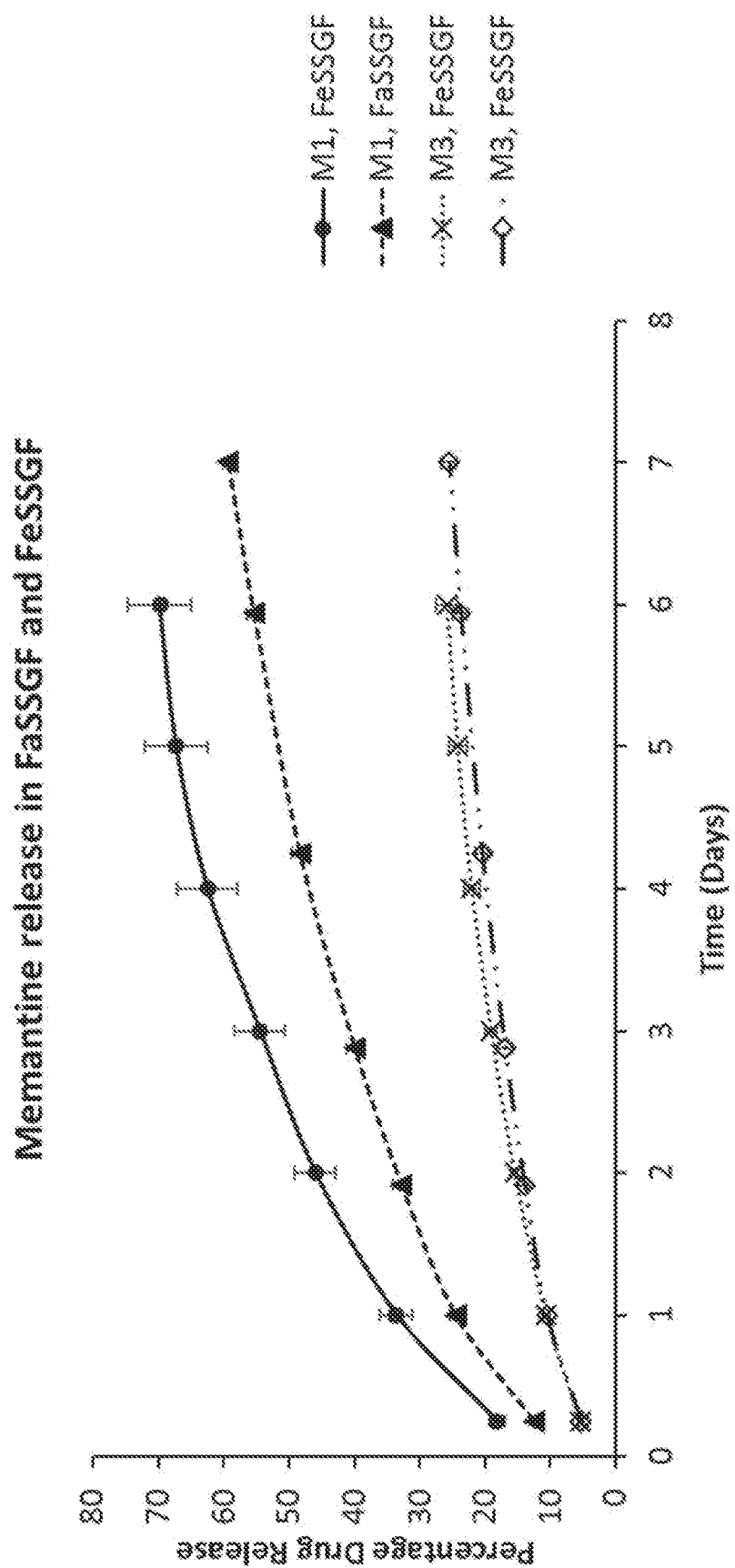
FIG. 43 shows an in vitro release assay for memantine formulations M1 and M3 in FaSSGF and FeSSGF.

Memantine formulations were evaluated for the effect of media pH and composition on in vitro release profiles. FIG. 43 shows a comparison of the drug release from formulation M1 and M3 in fasted state simulated gastric fluid (FaSSGF) and fed state simulated gastric fluid (FeSSGF). Samples of formulations were incubated in fasted state simulated gastric fluid (FaSSGF, pH 1.6) and fed state simulated gastric fluid (FeSSGF, pH 5.0) media. Formulations were subjected to a seven-day release study at 37° C., 200 rpm. In FaSSGF, total drug release from M1 was about 60%, linear release was about 40%, and burst release was about 12%. The same formulation showed a higher drug release in FeSSGF, with a total release of about 70% (sample was tested on Day 6 rather than Day 7), linear release of about 55%, and a burst release of about 19%. Formulation M3 showed similar release in FaSSGF and FESSGF, with a total release of about 20%.

Figure 44:
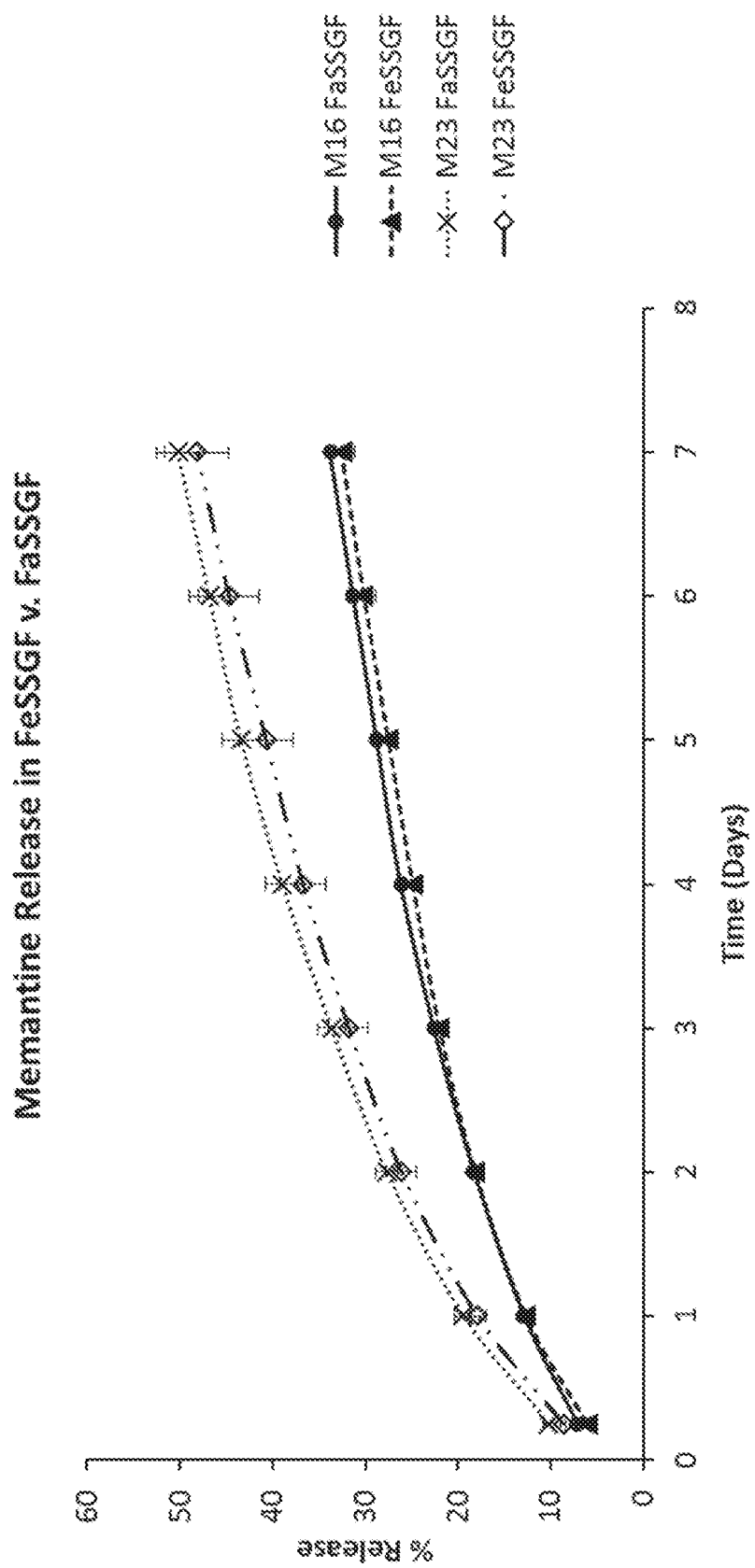
FIG. 44 shows an in vitro release assay for memantine formulations M16 and M23 in FaSSGF and FeSSGF.

FIG. 44 shows comparison of in vitro drug release from formulation M16 and M23 in fasted state simulated gastric fluid (FaSSGF) and fed state simulated gastric fluid (FeSSGF). Both M16 and M23 are different milling batches with the same composition as formulation M1 (20% memantine, 9% Eudragit E, 0.5% silica, 0.5% alpha tocopherol, balance 80k PCL. Formulation M16 resulted in a total release of about 30% in both fasted and fed states. Formulation M23 shows similar results in both fasted and fed states, with a total release of about 50%, linear release of about 33%, and a burst release of about 10%.

Example 15

Drug Release from Monolithic Matrix Formulations Slows Over Time

Figure 45A:
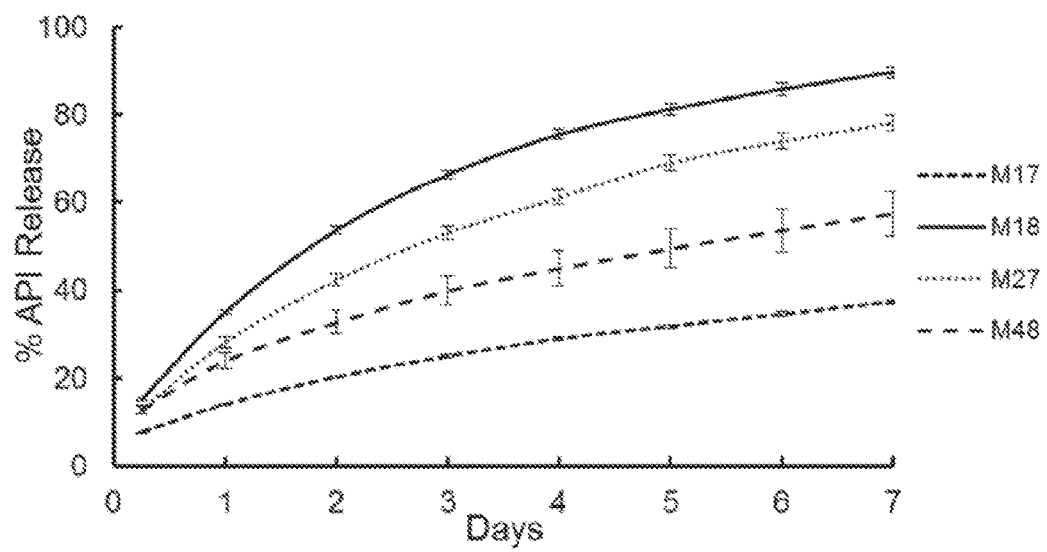
FIG. 45A depicts tapering release profiles for representative formulations of memantine hydrochloride over time.
Figure 45B:
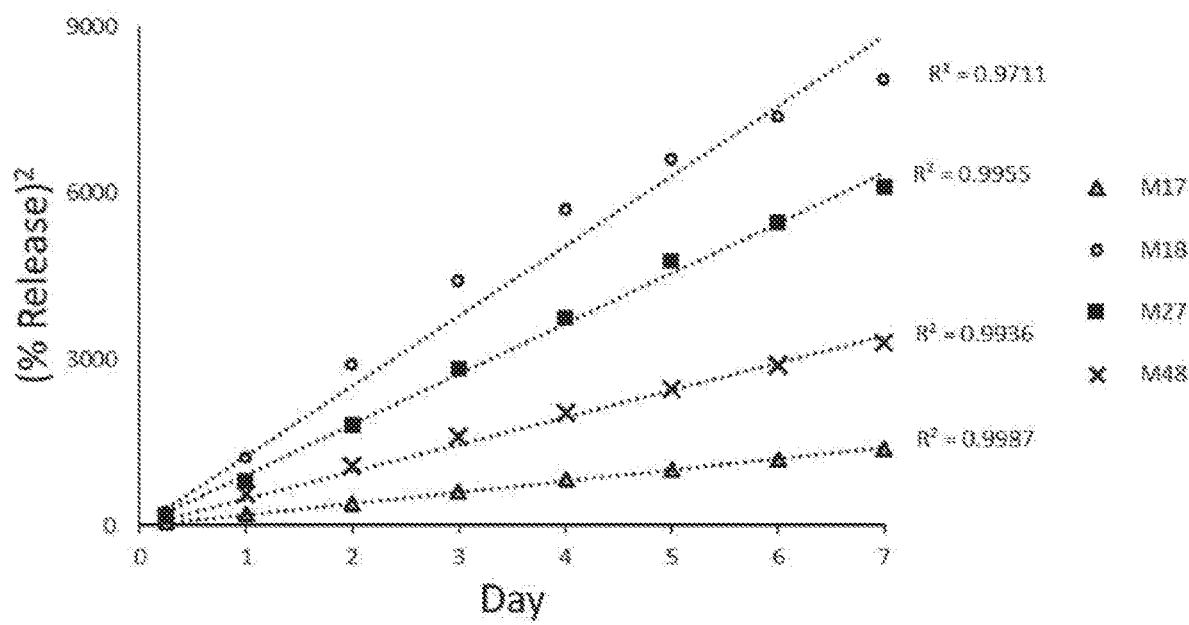
FIG. 45B depicts the linear relationship between the square of cumulative release and time for representative monolithic matrix based formulations, which is consistent with the Higuchi model for matrix-based drug release.
Figures 45C, 46A:
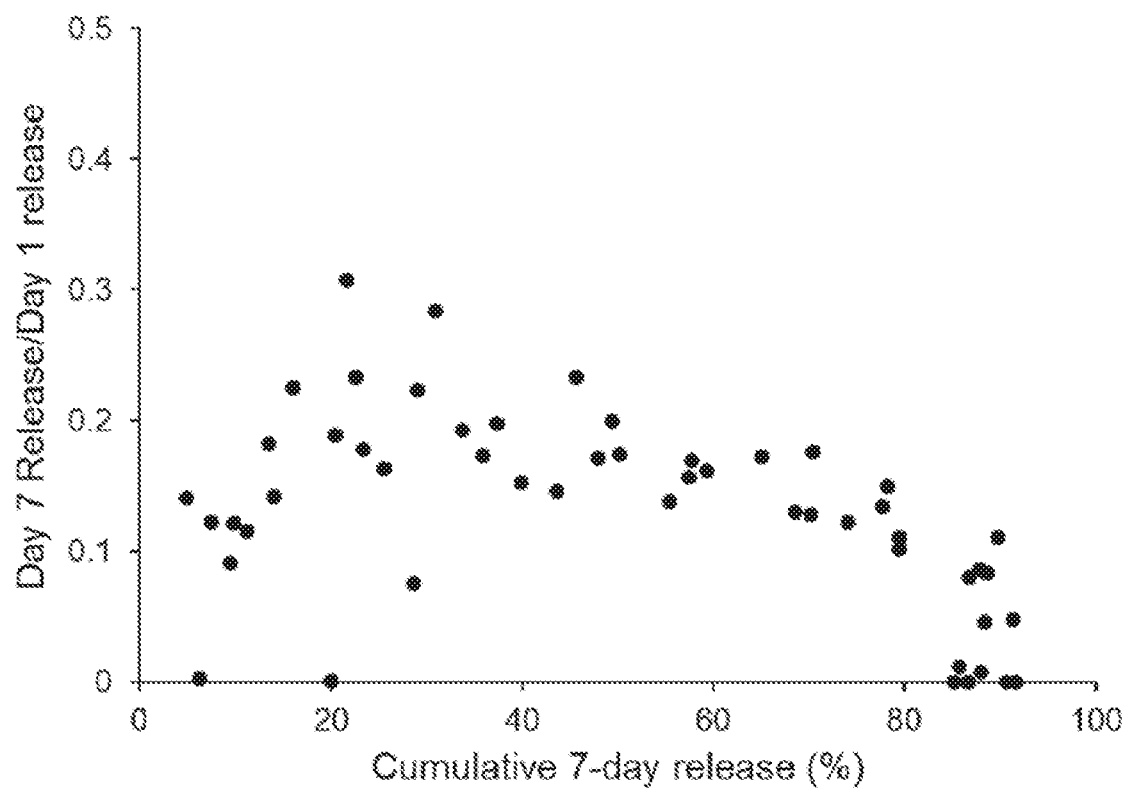
FIG. 45C depicts linearity versus extent of release for about 50 formulations of memantine hydrochloride studied.
FIG. 46A depicts compositions of coating solutions used in ethanol release studies.

Monolithic polymer matrix formulations were tested for their drug release rate over time. As can be seen from FIG. 45A, representative monolithic polymer matrix formulations of memantine hydrochloride showed tapering release rates over time (see Table 8 below). All formulations contained 0.5% w/w silica, 0.5% w/w alpha tocopherol, drug content and excipients listed below, and the balance 80k polycaprolactone (PCL). M17: 20% w/w memantine, 7% Eudragit E, 2% P407; M18: 20% w/w memantine, 25% Eudragit RS, 5% P407; M27: 20% w/w memantine, 10% Eudragit RS, 5% P407; M48: 35% w/w memantine, 2% Poloxamer P188. This slowing over time drug release manner for monolithic polymer matrix formulations is consistent with the Higuchi model for matrix-based drug release. In the Higuchi model, cumulative release is proportional to the square root of time and the proportionality constant depends on the properties of the matrix (porosity, tortuosity) and drug solubility (Dash et al., Acta Poloniae Pharmaceutica—Drug Research, Vol. 67 No. 3 pp. 217n223, 2010). A linear relationship between time and the square of cumulative release was observed for a wide range of drug-polymer blends studied, with representatives shown in FIG. 45B. While drug release from the matrix could be accelerated or decelerated by varying the properties of the polymer matrix, in each case the release rate slowed significantly over time. In the monolithic matrix systems studied, the dose of drug delivered on day 1 was typically four- to six-fold greater than the dose delivered on day 7. While this tapering dose profile may be acceptable for certain applications, a more linear release profile is desired for many indications. The linearity versus extent of release for about 50 formulations of memantine hydrochloride studied is shown in FIG. 45C. Total release over 7 days (X-value in Table 8) is plotted versus the ratio of (Day 7 Release/Day 1 Release) (Y-value in Table 8) in FIG. 45C. Formulations closer to the upper right corner of the plot (where good total release and good linearity of release occur) are preferable. As can be seen from FIG. 45C, drug release on day 7 was typically 10-30% of release on day 1. Linearity of release, as measured by the ratio of release on day 7 to release on day 1, correlated negatively with total release at 7 days. Thus, in developing matrix-based systems, achieving complete release in a 7-day treatment time requires sacrificing linearity of release, which is consistent with the Higuchi model.

Example 16A

Dip Coated Polycaprolactone Provides Superior Ethanol Resistance

Cellulose acetate (CA), ethyl cellulose (EC), copolymers of acrylate and methacrylate esters (e.g., Eudragit RS) and polycaprolactone (PCL) were tested as release rate-modulating polymer films.

Formulation Preparation

Memantine hydrochloride was blended with PCL and other excipients on a Haake MiniCTW micro-compounder. The components were batch mixed at 100-120° C. for 10 min and then extruded into 2-mm cylinders. The molten extrudate was pressed into a compression mold in the shape of a 20-mm rod of triangular cross section and allowed to cool at room temperature.

Representative formulations are listed in Table 8.

TABLE 8

Representative formulations of memantine.

| Formulation Code | Memantine (% ww) | 80K PCL (% ww) | Excipient (% ww) | Y-value | X-value |
|---|---|---|---|---|---|
| M1 | 20 | 70 | 9% EPO, 0.5% Silica, 0.5% α-tocopherol | 0.16 | 59.35 |
| M2 | 20 | 70 | 9% P407, 0.5% Silica, 0.5% α-tocopherol | 0.18 | 23.36 |
| M3 | 20 | 70 | 4.5% EPO, 4.5% P407, 0.5% Silica, 0.5% α-tocopherol | 0.16 | 25.48 |
| M4 | 20 | 70 | 9% Poly Vinyl Acetate, 0.5% Silica, 0.5% α-tocopherol | 0.14 | 4.87 |
| M5 | 20 | 70 | 9% PVP, 0.5% Silica, 0.5% α-tocopherol | 0.18 | 13.47 |
| M6 | 20 | 70 | 9% Kollidon VA64, 0.5% Silica, 0.5% α-tocopherol | 0.08 | 28.63 |
| M7 | 20 | 74 | 5% Kolliphor RH40, 0.5% Silica, 0.5% α-tocopherol | 0.09 | 9.41 |
| M16 | 20 | 70 | 9% EPO, 0.5% Silica, 0.5% α-tocopherol | 0.19 | 33.77 |
| M17 | 20 | 70 | 7% EPO, 2% P407, 0.5% Silica, 0.5% α-tocopherol | 0.20 | 37.33 |
| M18 | 20 | 49 | 25% Eudragit RS, 5% P407, 0.5% Silica, 0.5% α-tocopherol | 0.11 | 89.73 |
| M19 | 20 | 74 | 5% SIF, 0.5% Silica, 0.5% α-tocopherol | 0.12 | 9.81 |
| M20 | 20 | 70 | 9% SIF, 0.5% Silica, 0.5% α-tocopherol | 0.22 | 28.97 |
| M21 | 20 | 49 | 25% Eudragit RL, 5% P407, 0.5% Silica, 0.5% α-tocopherol | 0.00 | 91.57 |
| M22 | 20 | 49 | 30% PDO, 0.5% Silica, 0.5% α-tocopherol | 0.00 | 20.04 |
| M23 | 20 | 70 | 9% EPO, 0.5% Silica, 0.5% α-tocopherol | 0.17 | 50.17 |
| M24 | 20 | 57 | 20% Eudragit RS, 2% P407, 0.5% Silica, 0.5% α-tocopherol | 0.17 | 57.73 |
| M25 | 20 | 59.2 | 19.8% Eudragit RS, 0.5% Silica, 0.5% α-tocopherol | 0.31 | 21.61 |
| M26 | 20 | 56.5 | 17.5% Eudragit RS, 5% P407, 0.5% Silica, 0.5% α-tocopherol | 0.18 | 70.45 |
| M27 | 20 | 64 | 10% Eudragit RS, 5% P407, 0.5% Silica, 0.5% α-tocopherol | 0.15 | 78.20 |
| M28 | 20 | 64 | 14.78% Eudragit RS, 0.226% P407, 0.5% Silica, 0.5% α-tocopherol | 0.22 | 16.08 |
| M29 | 20 | 54 | 25% Eudragit RS, 0.5% Silica, 0.5% α-tocopherol | 0.28 | 30.93 |
| M30 | 20 | 55.25 | 21.25% Eudragit RS, 2.5% P407, 0.5% Silica, 0.5% α-tocopherol | 0.23 | 45.59 |
| M31 | 20 | 49 | 25% Eudragit RS, 5% P407, 0.5% Silica, 0.5% α-tocopherol | 0.10 | 79.42 |
| M32 | 14.37 | 56.63 | 39.5% PEG-PCL, 0.36% Silica, 0.36% α-tocopherol | 0.00 | 6.27 |
| M33 | 20 | 62.5 | 10% Eudragit RS, 5% P407, 2% Silica, 0.5% α-tocopherol | 0.13 | 68.62 |
| M34 | 20 | 65 | 10% Eudragit RS, 2.5% P407, 2% Silica, 0.5% α-tocopherol | 0.23 | 22.65 |
| M35 | 20 | 69 | 3.5% Eudragit RS, 5% P407, 2% Silica, 0.5% α-tocopherol | 0.17 | 35.89 |
| M36 | 20 | 71.5 | 3.5% Eudragit RS, 2.5% P407, 2% Silica, 0.5% α-tocopherol | 0.12 | 11.14 |
| M37 | 22.5 | 64.5 | 6.75% Eudragit RS, 3.75% P407, 2% Silica, 0.5% α-tocopherol | 0.20 | 49.37 |
| M38 | 25 | 57.5 | 10% Eudragit RS, 5% P407, 2% Silica, 0.5% α-tocopherol | 0.12 | 74.11 |
| M39 | 25 | 64 | 3.5% Eudragit RS, 5% P407, 2% Silica, 0.5% α-tocopherol | 0.13 | 77.66 |
| M40 | 25 | 66.5 | 3.5% Eudragit RS, 2.5% P407, 2% Silica, 0.5% α-tocopherol | 0.19 | 20.43 |
| M41 | 20 | 64 | 10% Eudragit RS, 5% P407, 0.5% Silica, 0.5% α-tocopherol | 0.17 | 65.14 |
| M42 | 35 | 64 | 0.5% Silica, 0.5% α-tocopherol | 0.12 | 7.40 |
| M43 | 35 | 62 | 2% P407, 0.5% Silica, 0.5% α-tocopherol | 0.17 | 47.96 |
| M44 | 35 | 62 | 0.5% Silica, 2% P407, 0.5% α-tocopherol | 0.13 | 70.22 |
| M45 | 35 | 62 | 0.5% Silica, 2% P407, 0.5% α-tocopherol | 0.15 | 39.91 |
| M46 | 35 | 62 | 0.5% Silica, 2% P407, 0.5% α-tocopherol | 0.14 | 55.38 |
| M47 | 35 | 62 | 0.5% Silica, 2% P407, 0.5% α-tocopherol | 0.15 | 43.59 |
| M48 | 35 | 62 | 0.5% Silica, 2% P407, 0.5% α-tocopherol | 0.16 | 57.47 |
| M49 | 35 | 59 | 0.5% Silica, 3% Eudragit RS, 2% P407, 0.5% α-tocopherol | 0.08 | 86.84 |
| M50 | 35 | 60 | 0.5% Silica, 2% P188, 2% P407, 0.5% α-tocopherol | 0.09 | 87.84 |
| M51 | 40 | 57 | 0.5% Silica, 2% P407, 0.5% α-tocopherol | 0.05 | 91.39 |

TABLE 8-continued

Representative formulations of memantine.

| Formulation Code | Memantine (% ww) | 80K PCL (% ww) | Excipient (% ww) | Y-value | X-value |
|---|---|---|---|---|---|
| M52 | 40 | 59 | 0.5% Silica, 0.5% α-tocopherol | 0.14 | 14.08 |
| M53 | 45 | 52 | 0.5% Silica, 2% P407, 0.5% α-tocopherol | 0.00 | 86.72 |
| M54 | 45 | 54 | 0.5% Silica, 0.5% α-tocopherol | 0.11 | 79.42 |
| M55 | 50 | 47 | 0.5% Silica, 2% P407, 0.5% α-tocopherol | 0.00 | 85.24 |
| M56 | 50 | 49 | 0.5% Silica, 0.5% α-tocopherol | 0.00 | 90.63 |
| M57 | 20 | 62 | 12% Eudragit RL, 5% Kolliphor P407, 0.5% Silica, 0.5% α-tocopherol | 0.01 | 85.77 |
| M58 | 20 | 62 | 6% Eudragit RL, 6% Eudragit RS, 5% Kolliphor P407, 0.5% Silica, 0.5% α-tocopherol | 0.05 | 88.40 |
| M59 | 20 | 62 | 9% Eudragit RL, 3% Eudragit RS, 5% Kolliphor P407, 0.5% Silica, 0.5% α-tocopherol | 0.01 | 87.95 |
| M60 | 20 | 62 | 3% Eudragit RL, 9% Eudragit RS, 5% Kolliphor P407, 0.5% Silica, 0.5% α-tocopherol | 0.08 | 88.63 |
| M62 | 20 | 68 | 6% Eudragit RL, 5% Kolliphor P407, 0.5% Silica, 0.5% α-tocopherol | 0.00 | 86.67 |
| M77 | 27.5 | 66.5 | 5% Kolliphor P407, 0.5% Silica, 0.5% α-tocopherol | 1.42 | 91.30 |
| M104 | 40 | 58 | 1% Kolliphor P407, 0.5% Silica, 0.5% α-tocopherol | 0.01 | 103.8 |
| M107 | 45 | 52 | 2% Kolliphor P407, 0.5% Silica, 0.5% α-tocopherol | 0.00 | 94.8 |

Dip Coating

Coating solutions were prepared by dissolving coating components into appropriate organic solvents. Compositions of coating solutions used in ethanol release studies are shown in FIG. 46A. Drug arms were gripped with forceps, completely submerged in the coating solution, and immediately removed. Coated arms were dried in a fume hood overnight.

In Vitro Release

Fasted state simulated gastric fluid (FaSSGF) was prepared per the manufacturer's instructions (<http://www.biorelevant.com>). Individual coated drug arms were incubated in 10 mL release media in a shaking incubator at 37° C. for 7 days. Drug content in the release media was typically analyzed after 6 hours, 24 hours, and then daily for up to 7 days by HPLC. At each time point, the entire volume of release media was replaced with fresh media. For ethanol release studies, drug arms were incubated in 40% ethanol in FaSSGF for the first hour of the study. After one hour, the release media was sampled for analysis and the ethanolic release media was replaced with FaSSGF for the remainder of the 7-day study.

Coating Stability to Ethanol

Figure 46B:
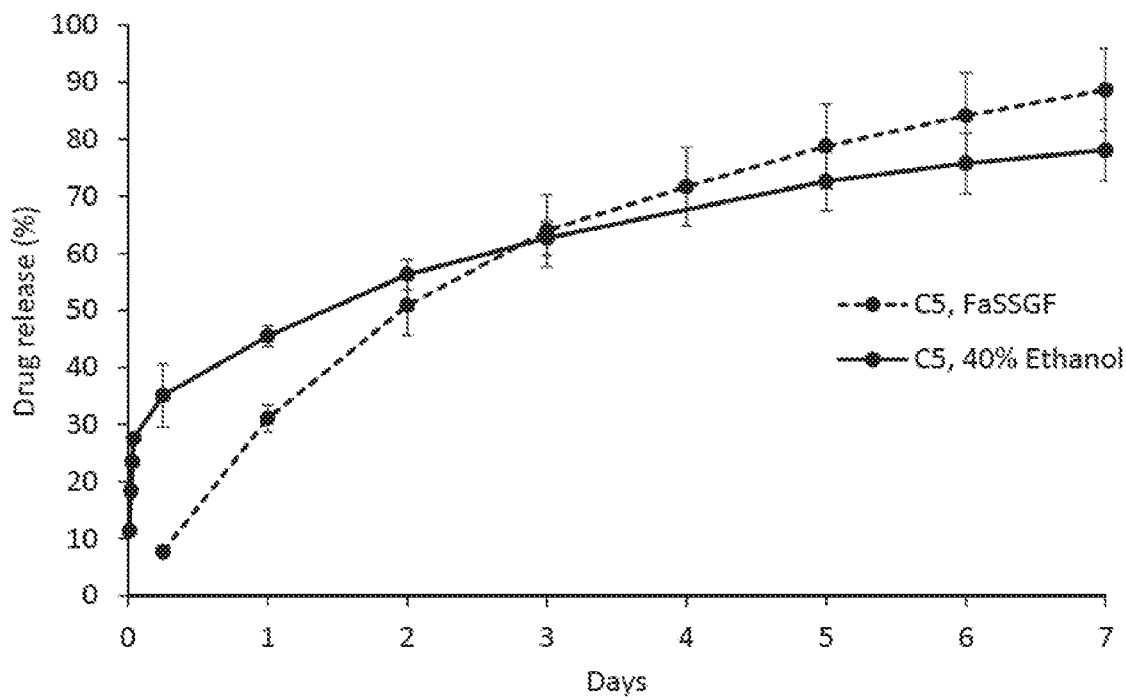
FIGS. 46B, 46C, 46D, and 46E depict drug release profiles for coating C5 (1 g Eudragit RS in 3 mL dichloromethane) on M18 release (FIG. 46B), coating C8 (1 g 55K PCL in 6 mL dichloromethane) on M18 release (FIG. 46C), coating C25 (1 g ethyl cellulose in 15 mL acetone) on M18 release (FIG. 46D), and coating C31 (1.5 g cellulose acetate in 15 mL acetone) on M18 release (FIG. 46E) in FaSSGF for 7 days and in 40% ethanol, 60% FaSSGF for one hour followed by the remainder of the 7 days in FaSSGF.

Drug arms were prepared as above and contained 20% w/w memantine hydrochloride, 0.5% silica, 0.5% alpha tocopherol, 25% Eudragit RS, 5% P407, and balance 80k PCL. Arms were coated by dip coating using the coating solutions described in FIG. 46A. Memantine release from coated drug arms was evaluated over 7 days in FaSSGF as well as 1 hour in 40% ethanol in FaSSGF followed by the remainder of the 7 days in FaSSGF. During the 1 hour in 40% ethanol, drug content was analyzed at 15-minute intervals. Results are shown in FIGS. 46B-3E.

Figure 46C:
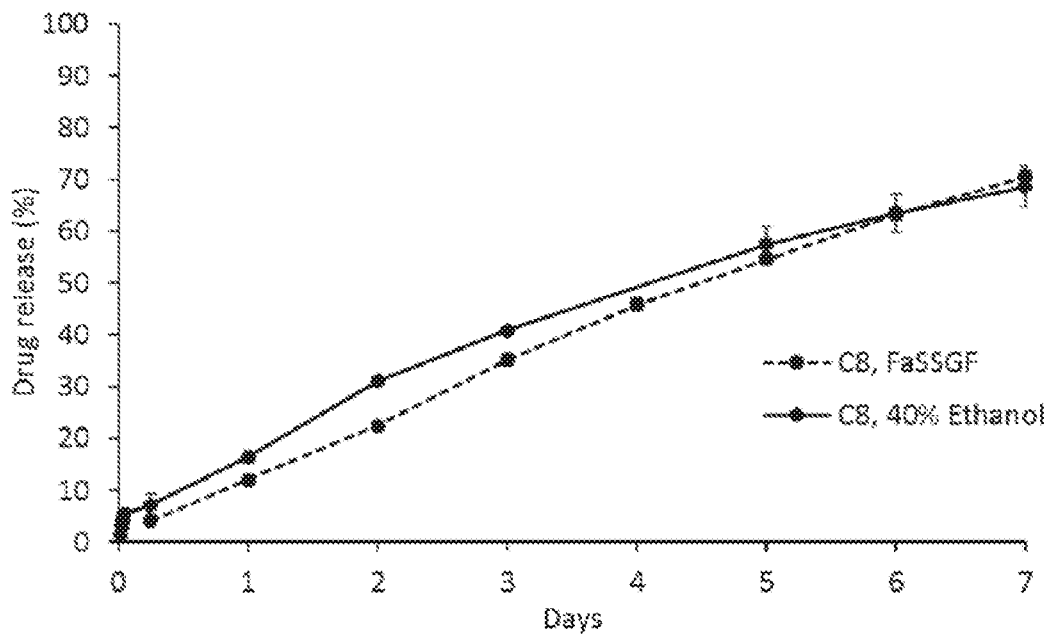
Figure 46D:
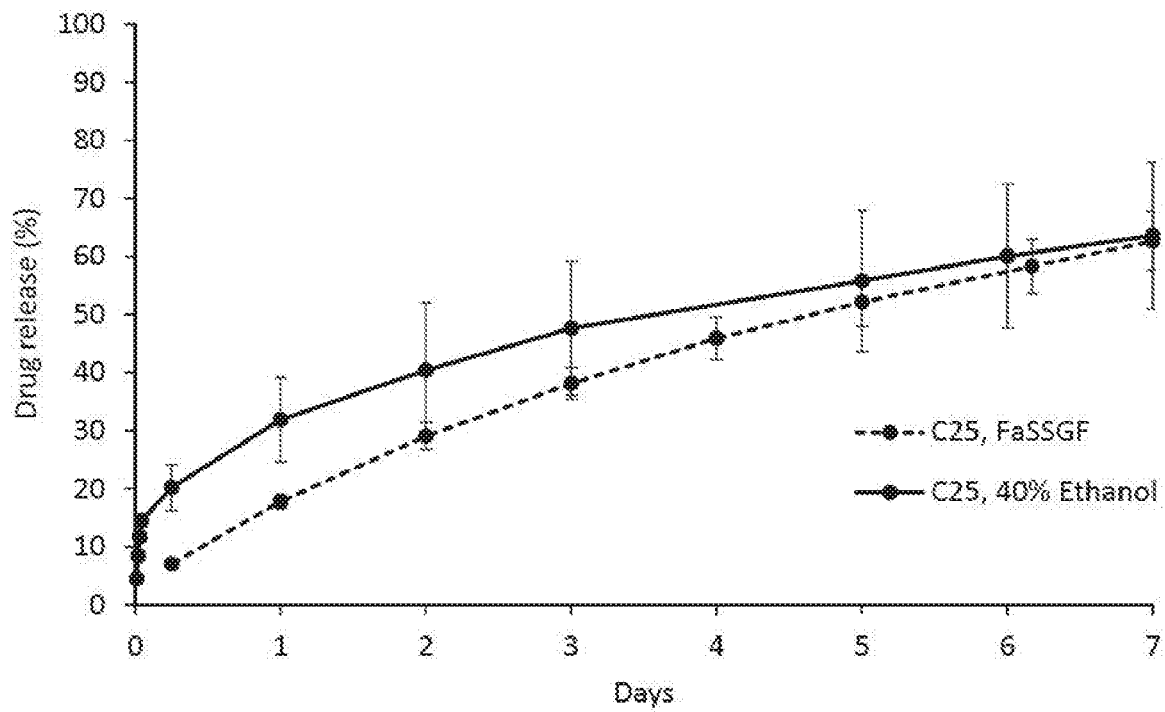
Figure 46E:
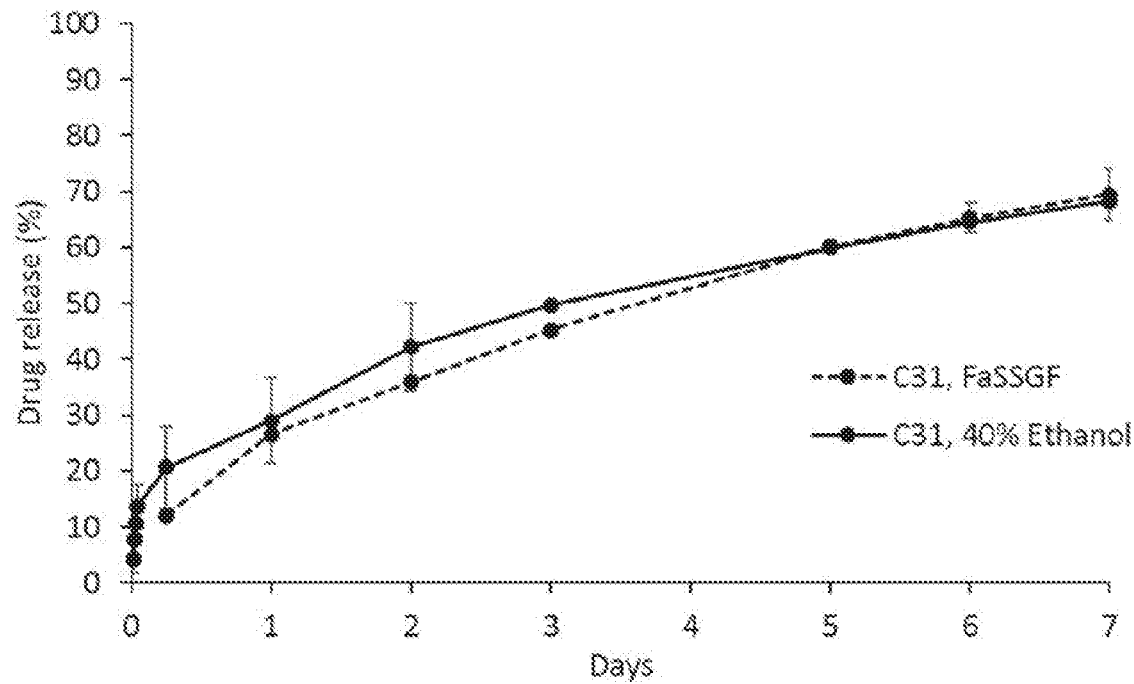

In each case, release was accelerated upon exposure to ethanol during the first hour. Clear differences were observed among coatings with regard to their ability to resist dose dumping in ethanol Ethanol soluble coatings, such as Eudragit RS, were most susceptible to dose dumping, with a greater than five-fold increase in drug release in 6 hours (FIG. 46B). Coatings that are insoluble in ethanol, such as PCL, demonstrated minimal change in drug release upon exposure to ethanol (FIG. 46C). Ethyl cellulose (FIG. 46D) and cellulose acetate (FIG. 46E) coatings displayed intermediate ethanol stability. After switching from ethanol to FaSSGF, the remainder of the release profile was generally similar to the release profile observed in FaSSGF without ethanol exposure.

Example 16B

Pan Coating

This experiment was performed to explore Ethyl Cellulose (EC) coatings on M57 (20% w/w memantine, 62% w/w 80k PCL, 12% w/w Eudragit RL, 5% w/w Kolliphor P407, 0.5% w/w silica, 0.5% w/w α-tocopherol) drug loaded arms using a pharmaceutical pan coating process in an effort to create a dosage form with linear release over seven days.

Solutions of EC were prepared in both 100% acetone and 80:20 acetone:isopropyl alcohol with the plasticizer triethyl citrate (TEC) in an EC:TEC ratio of 9:1 and solid concentrations of 2.3-10% w/v. The solution was then applied to drug loaded arms using a Vector LDCS pharmaceutical pan coater. The coating solution was applied to a pre-weighed bed of placebo arms with a small quantity of drug loaded arms spiked in. The pan speed was set at 20 RPM and the product temperature was approximately 35-40° C. After coating, the arms were dried for approximately 5 minutes to drive off any residual acetone. The entire batch of coated placebo and drug loaded arms were weighed to determine the percent mass gain of coating applied. Coatings were applied to a percent mass gain of approximately 2-7% w/w.

The resulting drug loaded arms all had coatings that were not well adhered. The coated placebo and active arms had visual imperfections where the coating was clearly not in contact with the drug arm matrix. Coatings could be easily removed by scratching the surface of the drug arm. Lack of coating adhesion was likely due to the drug arm having a smooth surface that does not allow adequate integration of the coating layer and surface.

Example 17

Solvent Selection for Dip Coating with PCL

This example demonstrates investigation of solvents useful for dip coating PCL films.

Dip coating requires dissolution of coating polymers in a volatile solvent at a concentration sufficient to leave a continuous polymer film on a dipped material. Coating thickness, and in turn drug release rate, can be modulated by varying the solution concentration and/or viscosity. For 80k PCL coatings, a minimum solution concentration of about 3% wt/vol was necessary to deposit a polymer layer that provided some control over drug release. Concentrations of 5-10% wt/vol are preferred for robust coating performance. This requires high solubility of PCL in the coating solvent and limits the possible solvent systems that can be used to apply coatings. FIG. 47 summarizes solvents used for dip coating PCL films. Dichloromethane and ethyl acetate were both able to dissolve PCL at high concentrations and to form uniform coatings with good performance. Ethyl acetate was chosen as the preferred solvent over dichloromethane for operator safety during processing. For coatings incorporating porogens, the appropriate solvent selection criteria include dissolution of an adequate concentration of porogen. If necessary, co-solvent systems such as ethyl acetate/isopropanol allow addition of porogens to a PCL coating solution.

Example 18

Coatings Comprising Water Soluble Polymers (WSP) Achieve Linear and Complete Release The burst release from the uncoated drug formulation could be controlled by coating the drug arm matrix with a 5% w/v PCL coating solution, however, it also reduced the total drug released in 7 days from ~90% (uncoated) to ~60% cumulative release. In this experiment, the effect of adding porogens to the 5% w/v PCL coating to speed up the linear release profile and increase the cumulative drug released in 7 days was studied. Dissolution tests were performed for 7 days in fasted state SGF media.

The coating process was performed by dipping the drug-loaded formulation (arms) into a coating solution. Coating solutions of 80k PCL were prepared in ethyl acetate at 5% w/v with 90:10 PCL to porogens (Kollidon VA64, Kolliphor RH40 and PVP). In case of PVP, a co-solvent system of 8:2 ethyl acetate to isopropyl alcohol (IPA) was used. In vitro release (dissolution) assay described in Example 16A was performed to study the effect of addition of porogen to coating solution using various porogens.

The addition of porogen to the outer coating layer increases the cumulative 7 day release to >80%, similar to the cumulative 7-day release of the uncoated formulation, while controlling the burst release. Dissolution results from this study showed that a controlled release coating with porogens allows control of the burst release and improved linearity of release, while achieving a high 7-day cumulative drug release (FIG. 48).

Example 19

Porogen Incorporation Improves Reproducibility of Release Kinetics for PCL-Based Coatings The coating process was performed by dipping the drug-loaded formulation (arms) into coating solutions as described in Example 2 on two separate experimental runs (Run 1 and Run 2). Two coating solutions were prepared for each run: 5% w/v 80k PCL only in ethyl acetate and 80k PCL with porogen (Kollidon VA64) solution was prepared in ethyl acetate at 5% w/v with 90:10 PCL to porogen. For both Run 1 and 2, dissolution assays were performed by incubating dosage forms for 7 days in FaSSGF as described in the in vitro release method in Example 2.

Figure 49:
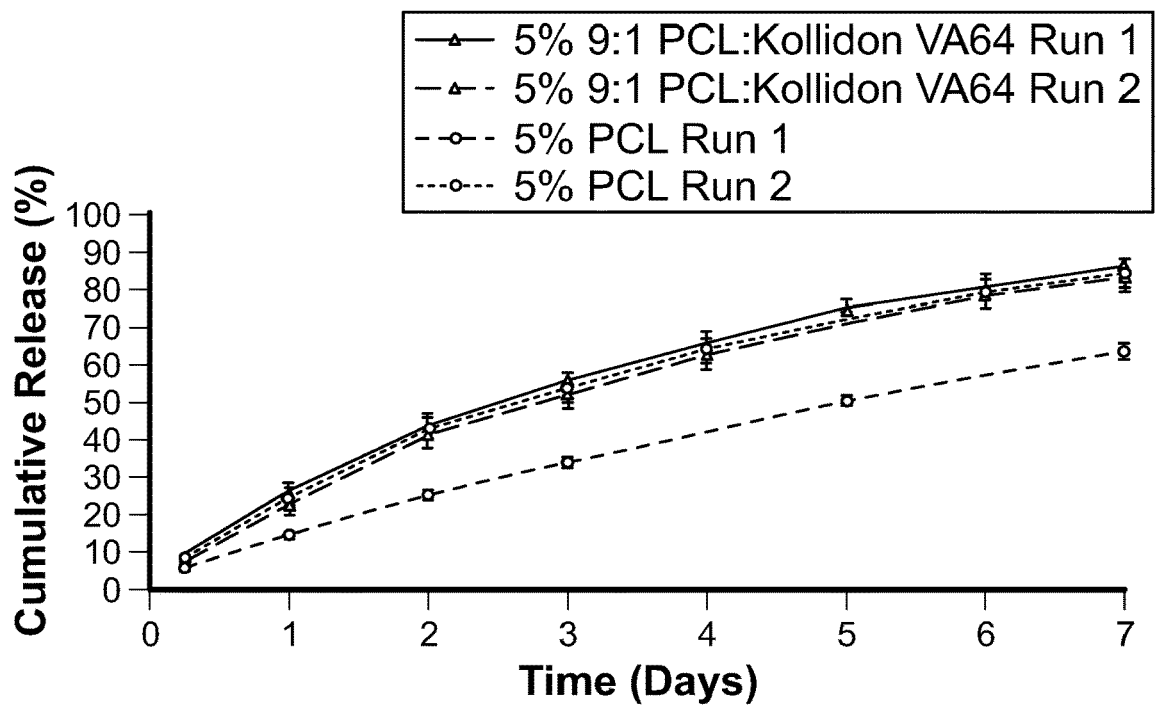
FIG. 49 depicts batch variability of release rate profiles of M77 formulations with dip coatings of PCL only and PCL with the addition of porogens (Kollidon VA64 and Kolliphor RH40).

Dissolution results from this study (FIG. 49) showed that addition of porogen to the 80k PCL coating solution helps improve batch-to-batch reproducibility of drug release profile of Run 1 and Run 2. The PCL only coating solution leads to variability in the release profile of Run 1 and Run 2 (FIG. 49).

Example 20

Release Rate can be Tuned by Varying the Ratio of Porogens

This experiment was performed to study the effect of changing the composition of the 80k PCL and porogen coating on tuning the release rate of the dosage form after dip coating. Coating solutions of 80k PCL and porogens were prepared at 5% w/v with the appropriate solvent as described in Examples 3 and 4 at two different ratios of PCL to porogens, 90:10 and 70:30. Drug arms were dip coated and dissolution tests were performed for 7 days as described in Example 2.

Figure 50:
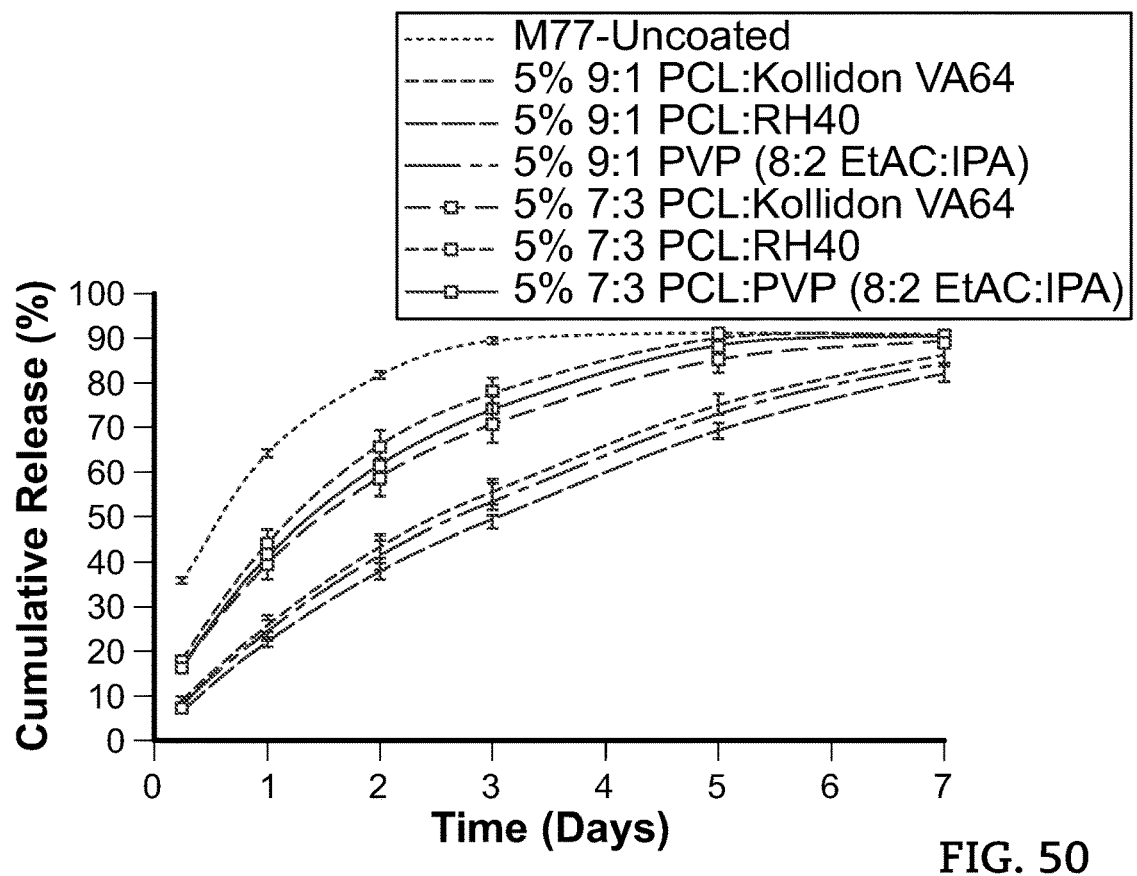
FIG. 50 depicts the tuning effect of release rate profiles for M77 formulations with dip coatings of PCL with the addition of varying levels of porogens.

Dissolution results from this study (FIG. 50) showed that drug arms coated with 70:30 PCL:porogen ratios have a faster release profile than arms coated with 90:10 PCL: porogen ratios, for various porogens tested (Kollidon VA64, Kolliphor RH40 and PVP). Increasing the amount of porogen in the coating solution increases the rate of drug release from the coated formulations in case of various porogens added to the PCL coating solution (FIG. 50). Varying the level of porogen allows tuning the release rate of the coated dosage forms (FIG. 50).

Example 21

Linearity of Release Depends on the Type of Porogen Used in the Coating

This experiment was performed to explore how the level of the porogen poly(ethylene glycol) (PEG 6000) in a PCL coating affects the release rate of the dosage unit. Coating solutions were prepped using fixed amounts of plasticizer with varying ratios of PCL to PEG 6000.

Solutions of PCL, PEG 6000 and TEC were prepared in ethyl acetate at 3.3% w/v with 70:30, 80:20 and 90:10 ratios of PCL to PEG 6000 and 30% triethyl citrate by coating material, with 2% magnesium stearate as a processing aid. The solution was then applied to M57 (20% w/w memantine, 62% w/w 80k PCL, 12% w/w Eudragit RL, 5% w/w Kolliphor P407, 0.5% w/w Silica, 0.5% w/w α-tocopherol) drug loaded arms using a Vector LDCS pharmaceutical pan coater. The coating solution was applied to a pre-weighed bed of placebo arms (approximately 500 g) with a small quantity (approximately 80 arms) of drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 2.5% w/w mass gain.

Dissolution results from this study showed that incorporating PEG 6000 into the coating does not result in a linear release profile and does not create consistent results batch to batch as displayed in runs 1 and 2, both coated with 80:20

Figure 51:
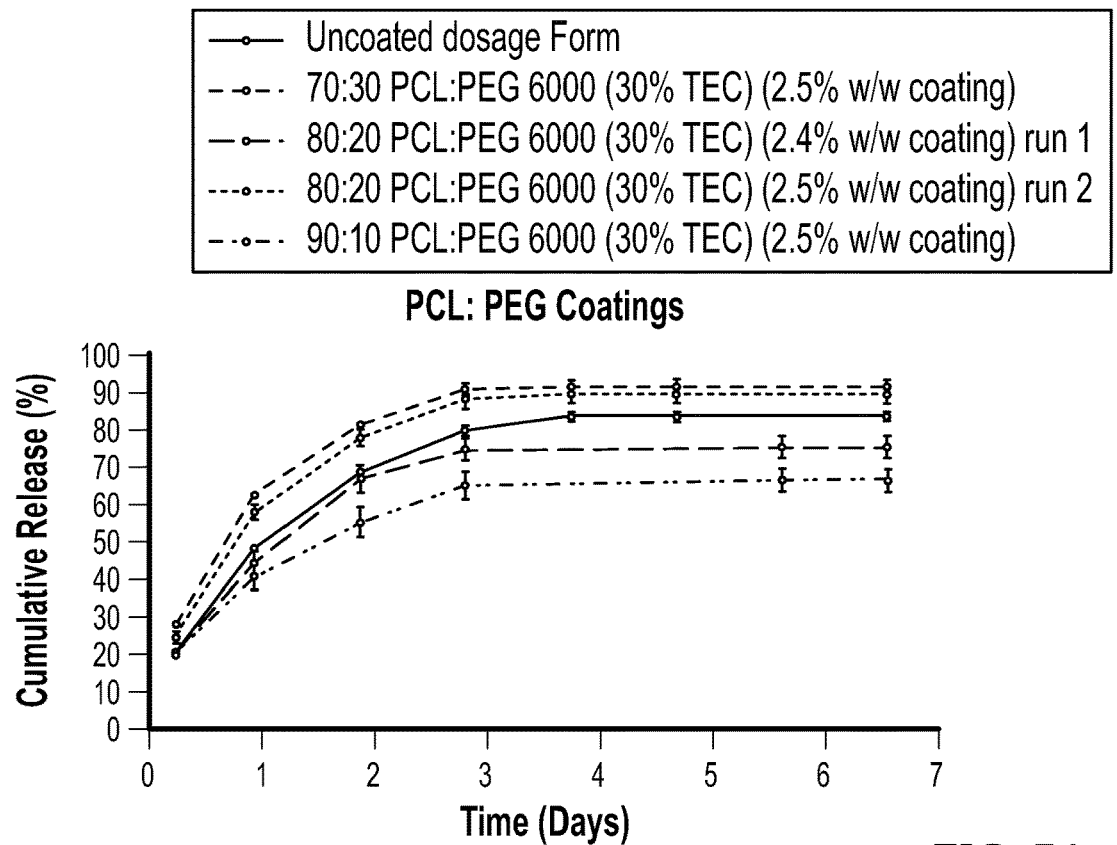
FIG. 51 depicts release rate profiles for formulations with different levels of PEG 6000 in PCL coating.

PCL: PEG 6000 with 30% TEC at approximately 2.5% mass gain (FIG. 51). Phase separation of PCL and PEG 6000 was observed during the coating which is the likely cause of the lack of controlled release.

Example 22

Plasticizer Concentration in Coatings can be Used to Tune the Release Rate (Pan Coating)

This experiment was performed to explore how the level of the plasticizer TEC in a PCL coating affects the release rate of the dosage unit after coating in a pharmaceutical pan coater. Coating solutions were prepped using fixed ratios of PCL to the porogen copovidone with varying levels of the plasticizer TEC.

Solutions of PCL and copovidone were prepared in ethyl acetate at 3.3% w/v with a 80:20 ratio of PCL to copovidone. Triethyl citrate was added to the solution at a level of 10 or 30% w TEC/w polymer. Magnesium stearate (2% w/w polymer) was added as a processing aid. The solution was then applied to M77 (27.5% w/w memantine, 66.5% w/w 80k PCL, 5% w/w Kolliphor P407, 0.5% w/w Silica, 0.5% w/w α-tocopherol) drug loaded arms using a Vector LDCS pharmaceutical pan coater. The coating solution was applied to a pre-weighed bed of placebo arms (approximately 450 g) with a small quantity (approximately 80 arms) of drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 1.5% and 2.5% w/w mass gain.

Figure 52A:
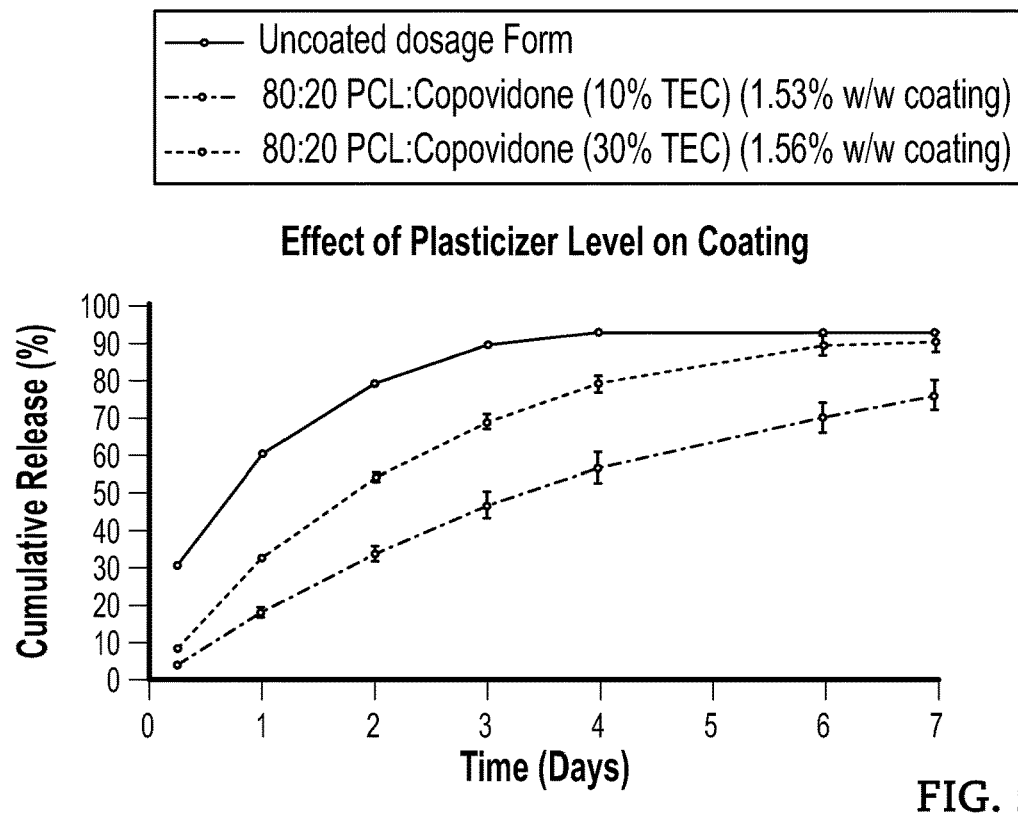
FIG. 52A depicts release rate profiles for formulations with increasing levels of TEC in PCL coating.
Figure 52B:
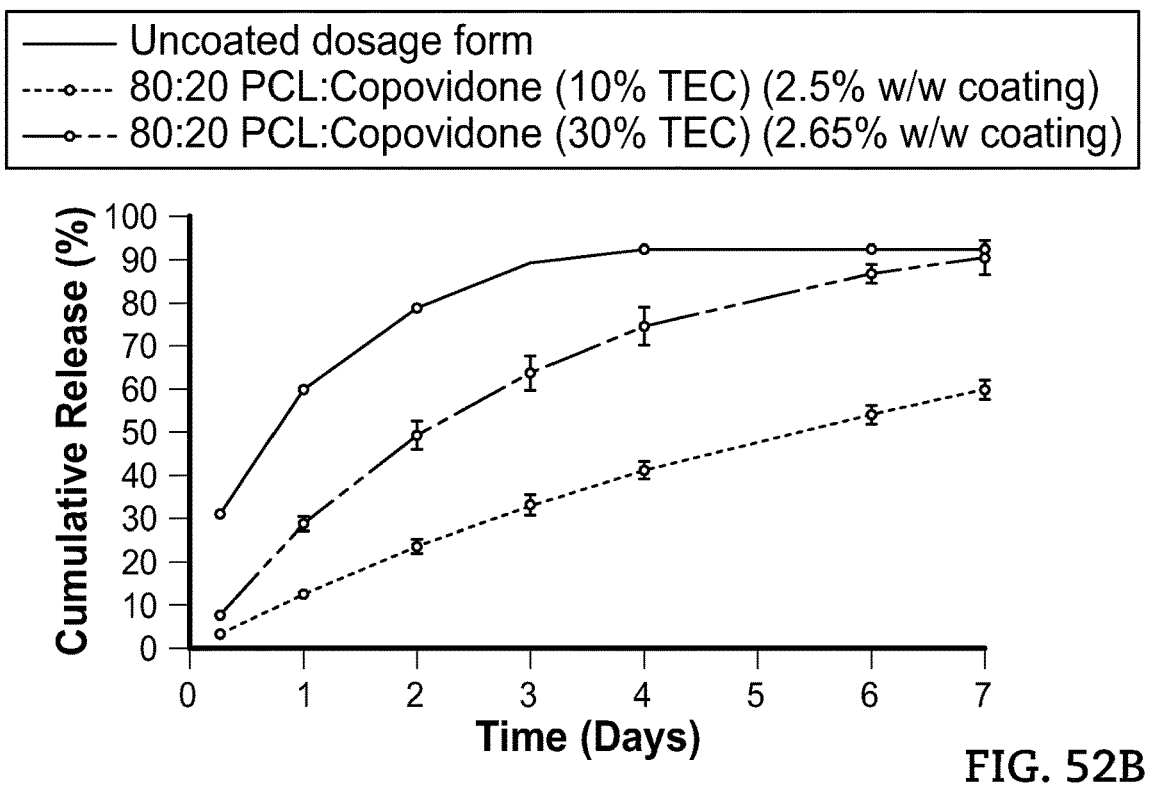
FIG. 52B depicts additional release rate profiles for formulations with increasing levels of TEC in PCL coating.

The dissolution results for these arms show that release rate can be tuned by adjusting the amount of TEC in the coating solution (FIGS. 52A and 52B). Increased ratios of TEC to PCL results in faster dissolution when the ratio of PCL to copovidone and coating % mass gain are held constant.

Example 23

Release Rate can be Tuned by Varying the Ratio of Porogens (Pan Coating)

This experiment was performed to explore how the level of the porogen copovidone in a PCL coating affects the release rate of the dosage unit after pharmaceutical pan coating. Coating solutions were prepped using fixed amounts of plasticizer with varying ratios of PCL to copovidone.

Solutions of PCL and copovidone were prepared in ethyl acetate at 3.3% w/v with a 80:20 ratio of PCL to copovidone. Triethyl citrate was added to the solution at a level of 10 or 30% w TEC/w polymer. Magnesium stearate (2% w/w polymer) was added as a processing aid. The solution was then applied to drug loaded arms using a Vector LDCS pharmaceutical pan coater. The coating solution was applied to a pre-weighed bed of placebo arms (approximately 500 g) with a small quantity (approximately 80 arms) of M77 (27.5% w/w memantine, 66.5% w/w 80k PCL, 5% w/w Kolliphor P407, 0.5% w/w Silica, 0.5% w/w α-tocopherol) drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 2.5% w/w mass gain.

Figure 53A:
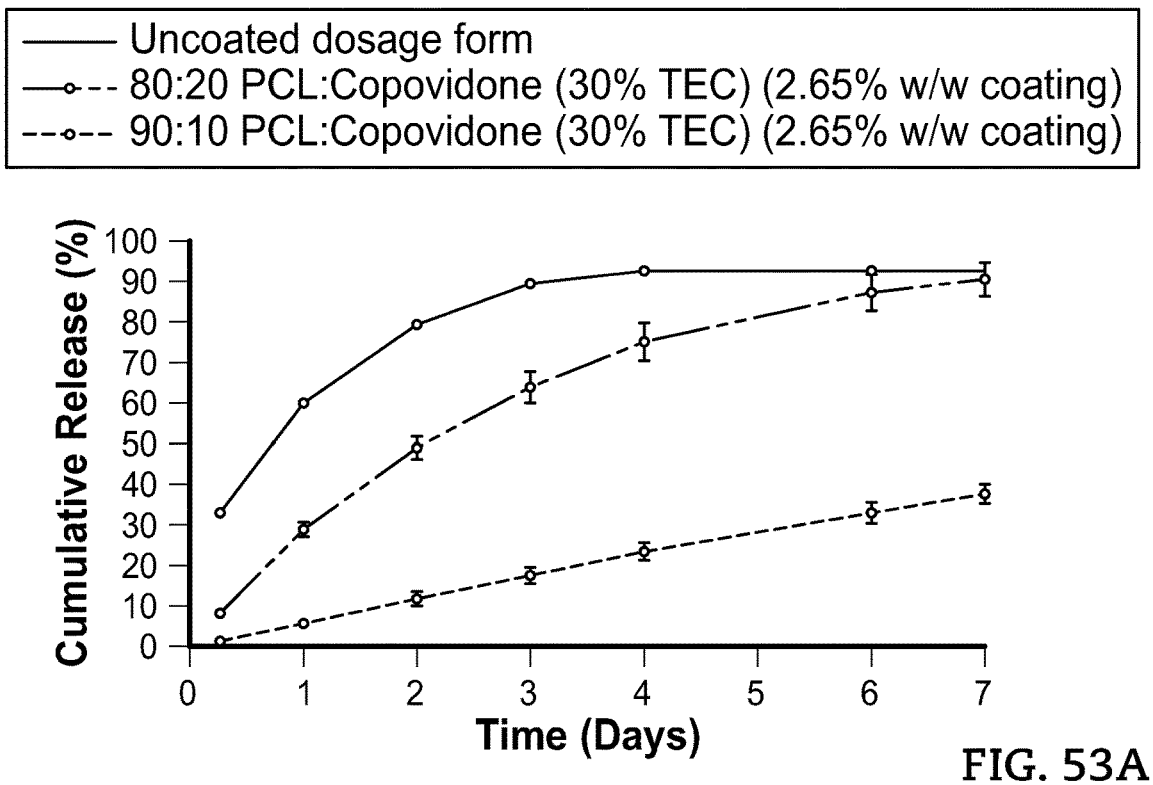
FIG. 53A depicts release rate profiles for formulations with varying ratios of PCL:copovidone and 10% or 30% triethyl citrate in the coating.
Figure 53B:
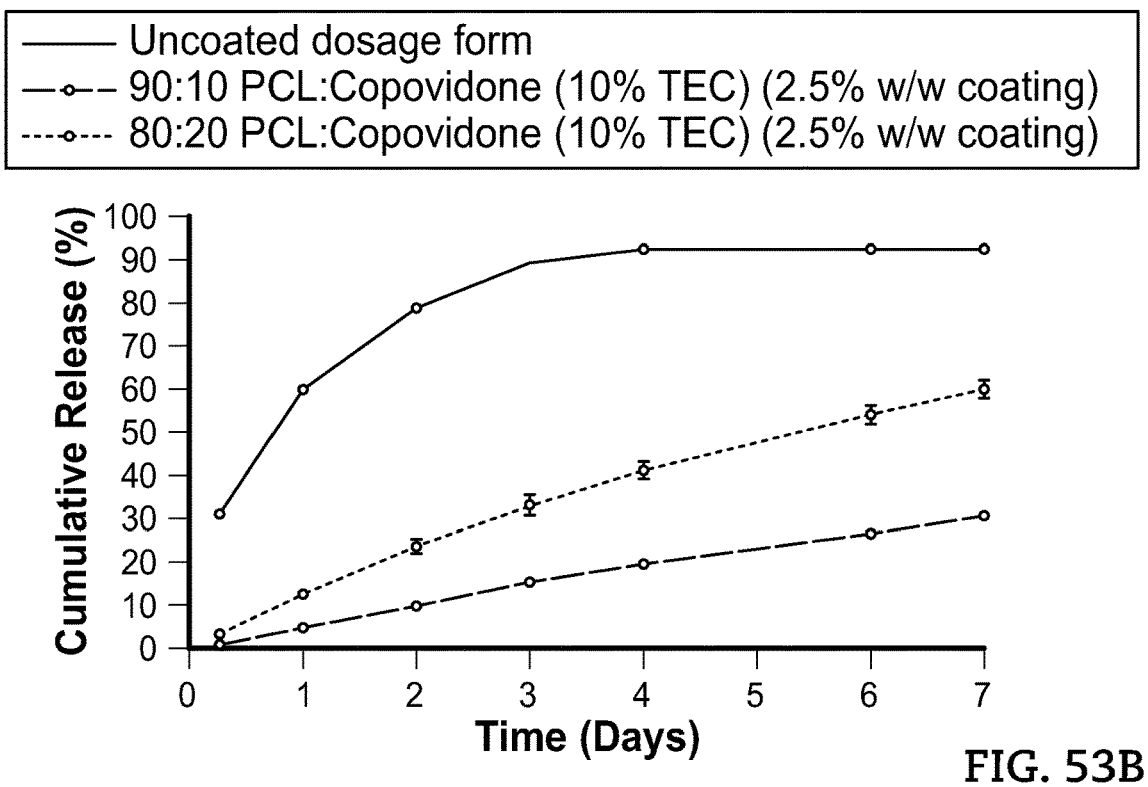
FIG. 53B depicts additional release rate profiles for formulations with varying ratios of PCL:copovidone and 10% or 30% triethyl citrate in the coating.

The dissolution results for these arms show that release rate can be tuned by adjusting the ratio of PCL:copovidone in the coating solution (FIGS. 53A and 53B). Increased ratios of PCL:copovidone results in slower dissolution when the amount of TEC and coating % mass gain is held constant.

Example 24

Coatings Applied by Pan Coating can Control Rate of Release with Minimal Coating Mass This experiment was performed to explore whether low coating weights (<2.5% w/w mass gain which gives about 6 to 12 um coating thickness range) of PCL pan coated drug loaded arms were able to control release rate and provide linear release for 7 days.

Figure 54:
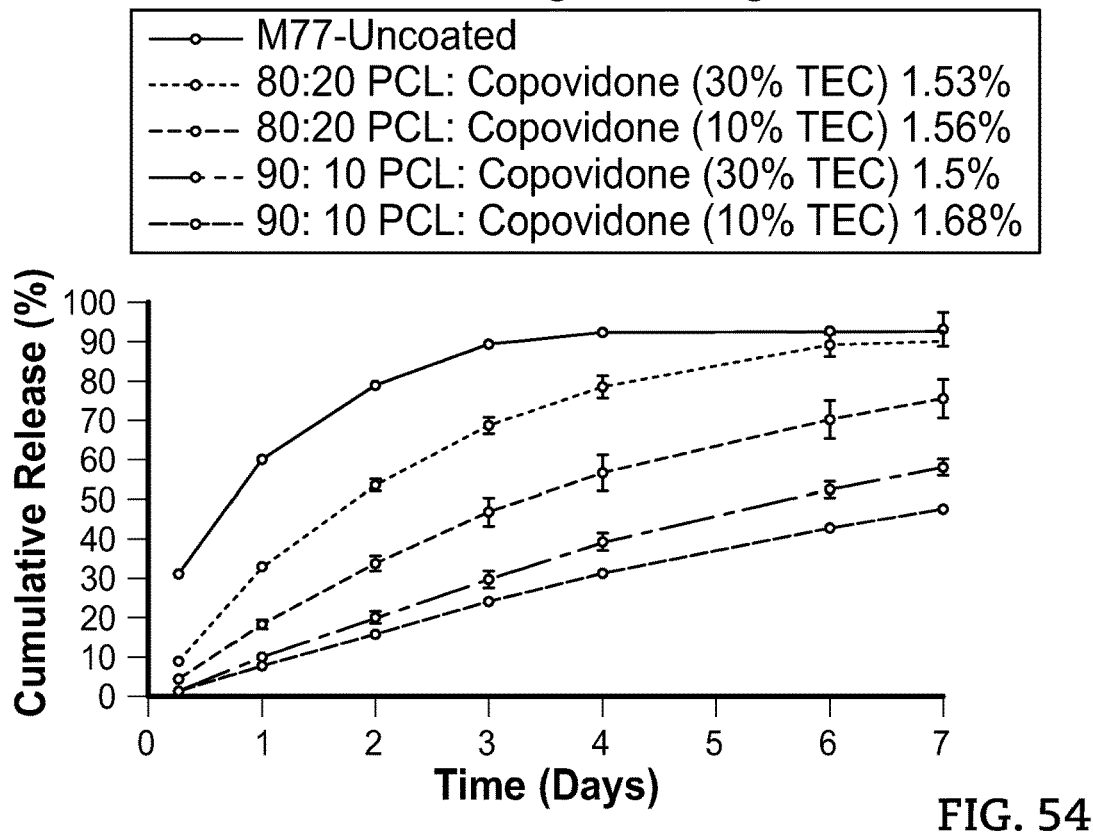
FIG. 54 depicts the effects of low weight coating on drug release rate, with varying ratios of PCL:copovidone and 10% or 30% triethyl citrate in the coating.

Solutions of PCL and copovidone were prepared in ethyl acetate at 3.3% w/v with a 80:20 ratio of PCL to copovidone. Triethyl citrate was added to the solution at a level of 10 or 30% w TEC/w polymer. Magnesium stearate (2% w/w polymer) was added as a processing aid. The solution was then applied to drug loaded arms using a Vector LDCS pharmaceutical pan coater. The coating solution was applied to a pre-weighed bed of placebo arms (approximately 500 g) with a small quantity (approximately 80 arms; approximately 10 g) of M77 (27.5% w/w memantine, 66.5% w/w 80k PCL, 5% w/w Kolliphor P407, 0.5% w/w silica, 0.5% w/w α-tocopherol) drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 1.5% w/w mass gain. The dissolution data for these arms show that release rate can controlled at coating percent mass gains of less than 2.5% and as low as 1.5% (FIG. 54).

Example 25

Coating of Drug Polymer Arms in Wurster Coater

Drug polymer arms can also be coated in a fluid bed using a Wurster coating process. In this process, the drug polymer arms are fluidized with heated air and coated with a coating solution, e.g., 5% w/w PCL in ethyl acetate, while circulating through the Wurster column. The dissolved coating solution is applied to the drug polymer arms as they enter the Wurster column and pass through the spray zone situated under the column. Solvent evaporation occurs as the arms travel through the column and circulate back down to the bed of polymer drug arms. This process is continued until the appropriate amount of coating has been applied to the drug polymer arms. Arms are then dried by turning off the coating spray and allowing the heat and air flow to drive off remaining solvent.

Example 26

Coated Drug Arms Lead to More Consistent Drug Serum Levels of Memantine HCl than Uncoated Dose Forms in the Absence of Alcohol Challenge Eight male beagles (n=4/group) weighing between 9.3 and 11.1 kg were used in this study. Dogs were fasted for 12 hr prior to dose administration. Dosage forms consisted of 90 A durometer polyurethane elastomers heat welded to M57 (20% w/w memantine, 62% w/w 80k PCL, 12% w/w Eudragit RL, 5% w/w Kolliphor P407, 0.5% w/w Silica, 0.5% w/w α-tocopherol) drug arms that were dip coated with a solution of 6.67% ethyl cellulose w/v in acetone or uncoated. Memantine was incorporated into the drug-polymer arms at a total load of ~155 mg/dosage form for an estimated ~22 mg/day of potential release over 7 days. (Formulations for animal studies in Examples 12-14 are listed in Table 9)

TABLE 9

Memantine formulations.

| Formulation Code | Memantine (% ww) | 80K PCL (% ww) | Excipient (% ww) | Coating Solution Composition |
|---|---|---|---|---|
| M57 | 20 | 62 | 12% Eudragit RL, 5% Kolliphor P407, 0.5% Silica, 0.5% α-tocopherol | 6.67% ethyl cellulose w/v in acetone |
| M69 | 27.5 | 56.5 | 12% Eudragit RL, 3% Kolliphor P407, 0.5% Silica, 0.5% α-tocopherol | 5% PCL w/v in ethyl acetate |
| M77 | 27.5 | 66.5 | 5% Kolliphor P407, 0.5% Silica, 0.5% α-tocopherol | 4.5% PCL/0.5% Kollidon VA64 w/v in ethyl acetate |

Figure 55:
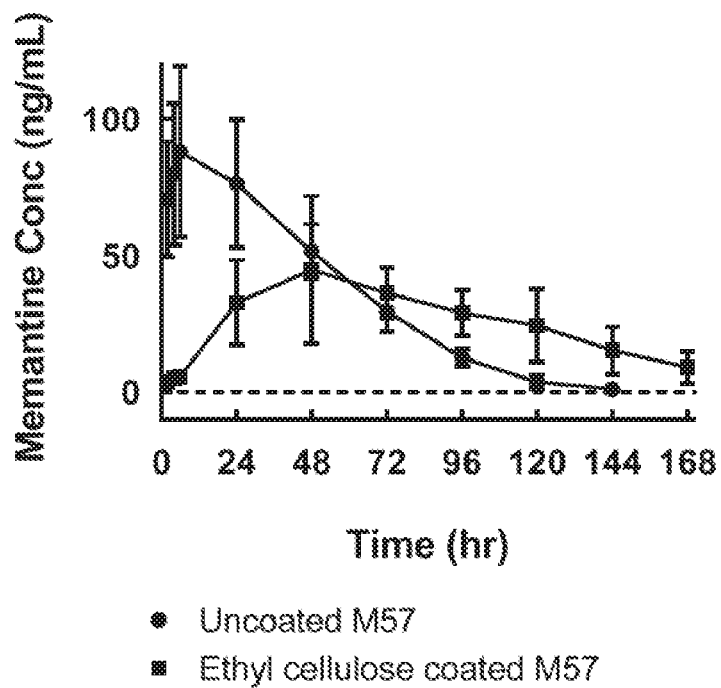
FIG. 55 depicts the effect of ethyl cellulose coating on consistent drug serum levels of Memantine HCl, compared to an uncoated dosage form.

Coated and uncoated dosage forms were placed into capsules immediately before dosing. Capsules were placed at the back of the dog's throat and after swallowing, dogs were offered a food chase of canned food. Blood samples (2 mL) were collected from left or right jugular veins pre-dose and at 2, 4, 6, 24, 48, 72, 96, 120, 144 and 168 hr after dosing. Blood samples were collected into $K_3$EDTA tubes and plasma collected by centrifugation at 5,000 rpm for 5 min Plasma samples were analyzed for memantine content using a protein precipitation method followed by quantitation on LC-MS/MS (FIG. 55).

Example 27

PCL Coating Results in Near Constant Plasma Drug Concentrations Despite Variations in the Underlying Formulation: Six Dog Study Six male beagles weighing between 9.1 and 10.8 kg were used in this study. Dogs were fasted for 12 hr prior to dose administration. Dosage forms consisted of 90 A durometer polyurethane elastomers heat welded to M69 (27.5% w/w memantine, 56.5% w/w 80k PCL, 12% w/w Eudragit RL, 3% w/w Kolliphor P407, 0.5% w/w Silica, 0.5% w/w α-tocopherol) drug arms that were dip coated with a solution of 5% PCL w/v in ethyl acetate. Memantine was incorporated into the drug-polymer arms at a total load of ~183 mg/dosage form for an estimated ~26 mg/day of potential release over 7 days. (See Table 9 above for memantine formulations.) Coated and uncoated dosage forms were placed into capsules immediately before dosing.

Figure 56:
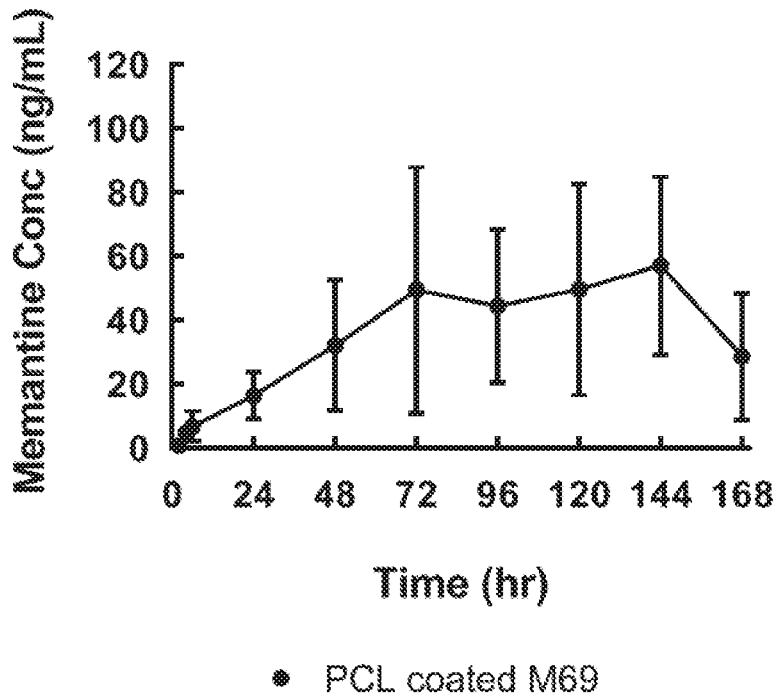
FIG. 56 depicts a near constant plasma drug concentrations for dosage formulations with a PCL coating. The dosage forms consisted of 90 A durometer polyurethane elastomers heat-welded to M69 drug arms that were dip coated with a solution of 5% PCL w/v in ethyl acetate.

Capsules were placed at the back of the dog's throat and after swallowing, dogs were offered a food chase of canned food. Blood samples (2 mL) were collected from left or right jugular veins pre-dose and at 2, 4, 6, 24, 48, 72, 96, 120, 144 and 168 hr after dosing. Blood samples were collected into $K_3$EDTA tubes and plasma collected by centrifugation at 5,000 rpm for 5 min Plasma samples were analyzed for memantine content using a protein precipitation method followed by quantitation on LC-MS/MS. The results of the study are shown in FIG. 56.

Example 28

PCL Coating Results in Near Constant Plasma Drug Concentrations Despite Variations in the Underlying Formulation: Sixteen Dog Study Sixteen male beagles weighing between 8.2 and 10.1 kg were used in this study. Dogs were fasted for 12 hr prior to dose administration, and then subjected to one of three different feeding regimens: (food 1 hour prior to dose administration. food 1 hour after dose administration, and food 4 hours after dose administration). Dosage forms consisted of 60 A durometer LSR elastomers IR welded to 50/50 PCL/HPMAS disintegrating matrices and M77 (27.5% w/w memantine, 66.5% w/w 80k PCL, 5% w/w Kolliphor P407, 0.5% w/w Silica, 0.5% w/w α-tocopherol) drug arms that were coated with a solution of 4.5% PCL/0.5% kollidon VA64 w/v in ethyl acetate. Memantine was incorporated into the drug-polymer arms at a total load of ~145 mg/dosage form for an estimated ~21 mg/day of potential release over 7 days. (See Table 9 above for memantine formulations.) Coated and uncoated dosage forms were placed into capsules immediately before dosing.

Figure 57:
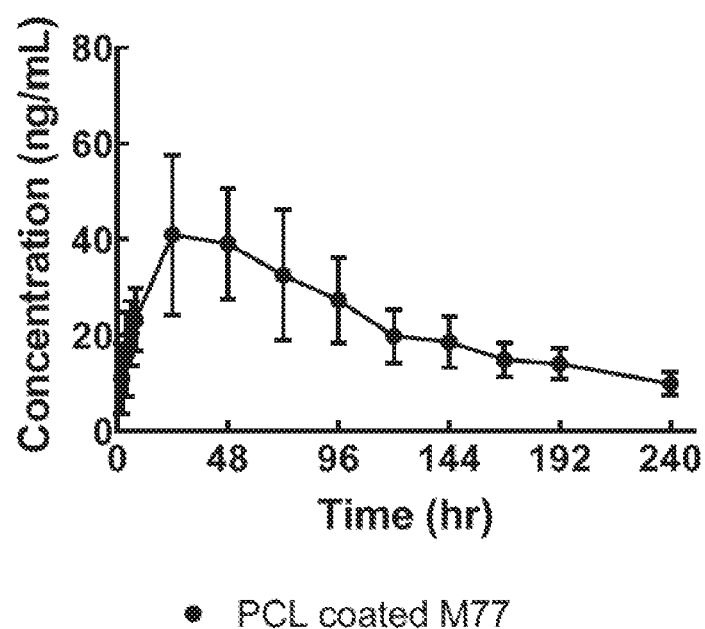
FIG. 57 depicts a near constant plasma drug concentrations for dosage formulations with a PCL coating. The dosage form consisted of 60 A durometer LSR elastomers IR welded to 50/50 PCL/HPMAS disintegrating matrices and M77 drug arms that were coated with a solution of 4.5% PCL/0.5% kollidon VA64 w/v in ethyl acetate.

Capsules were placed at the back of the dog's throat and after swallowing, dogs were offered a food chase of canned food. Blood samples (2 mL) were collected from left or right jugular veins pre-dose and at 2, 4, 6, 8, 24, 48, 72, 96, 120, 144, 168, 192 and 240 hr after dosing. Blood samples were collected into $K_3$EDTA tubes and plasma collected by centrifugation at 5,000 rpm for 5 min Plasma samples were analyzed for memantine content using a protein precipitation method followed by quantitation on LC-MS/MS. The results are shown in FIG. 57.

For comparison, the same animals were administered Namenda XR containing 28 mg of memantine and plasma samples were collected and analyzed in a similar manner. Pharmacokinetic parameters for individual animals are shown in FIG. 59. The mean $C_{max}$ values for the dosage form and Namenda XR were 46.1±15.2 and 64.9±20.7 ng/mL, respectively, and mean AUC values for the dosage form and Namenda XR were 7438±1590 and 1,113±382 hr*ng/mL, respectively. Despite the range of fed/fasted conditions, the variability of $C_{max}$ and AUC observed with coated dosage forms was equal or less than for Namenda XR. The relative standard deviations (RSD) of the dosage form $C_{max}$ and AUC were 33% and 21%, respectively, while the corresponding RSDs for Namenda XR were 32% and 34%. In addition, the $C_{max}$ observed following dosage form administration was lower than the value observed following the lower dose of Namenda XR. The AUC observed following dosage form administration was approximately 7 times higher than the Namenda XR AUC, indicating that the bioavailability of memantine was similar for both formulations.

Example 29

Coating of Drug-Polymer Matrix Increases Linearity of Drug Release

Figure 15:
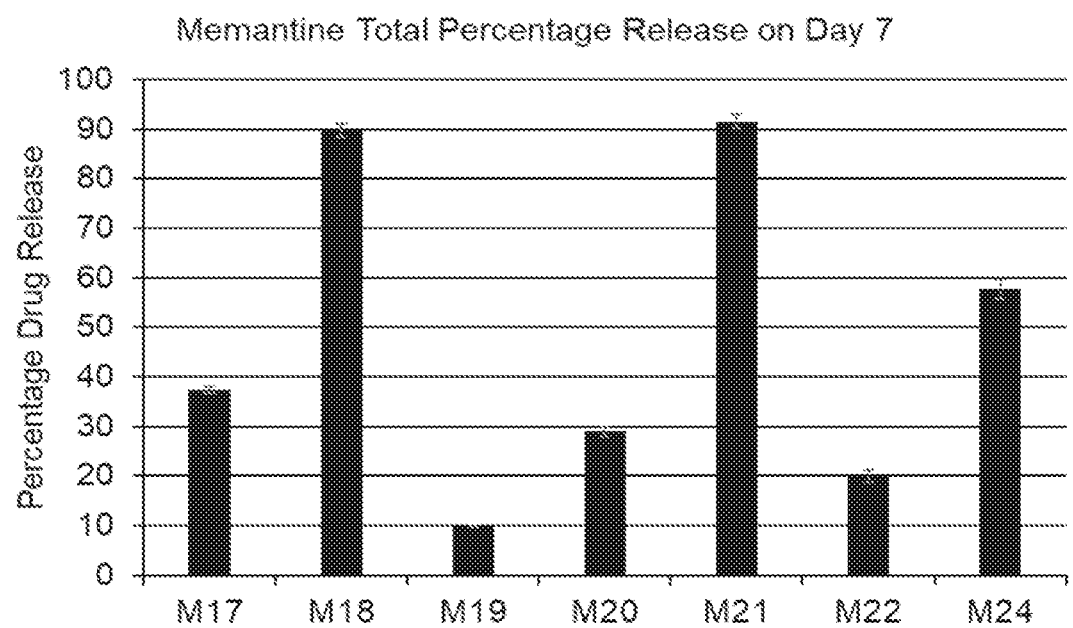
FIG. 15 shows percent memantine release after 7 days in FaSSGF from formulations M17, M18, M19, M20, M21, M22, and M24.
Figure 16:
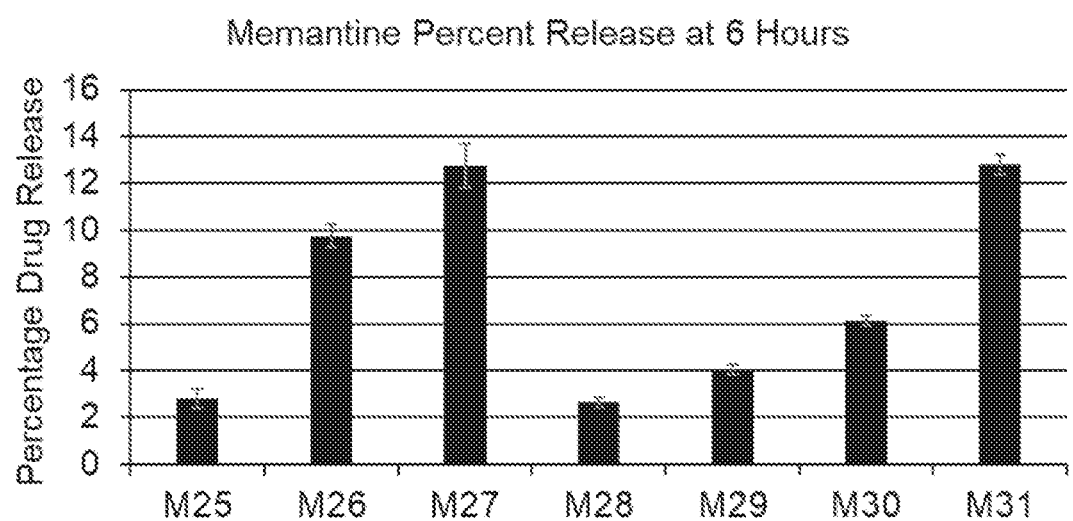
FIG. 16 shows percent memantine release after 6 hours (that is, burst release) in FaSSGF from formulations M25, M26, M27, M28, M29, M30, and M31.
Figure 17:
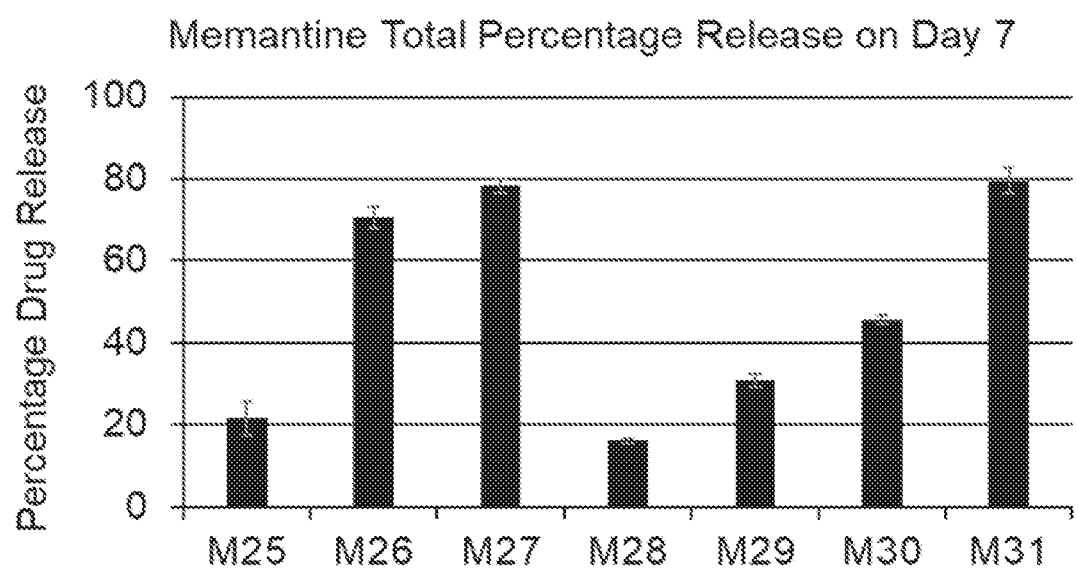
FIG. 17 shows percent memantine release after 7 days in FaSSGF from formulations M25, M26, M27, M28, M29, M30, and M31.
Figure 18:
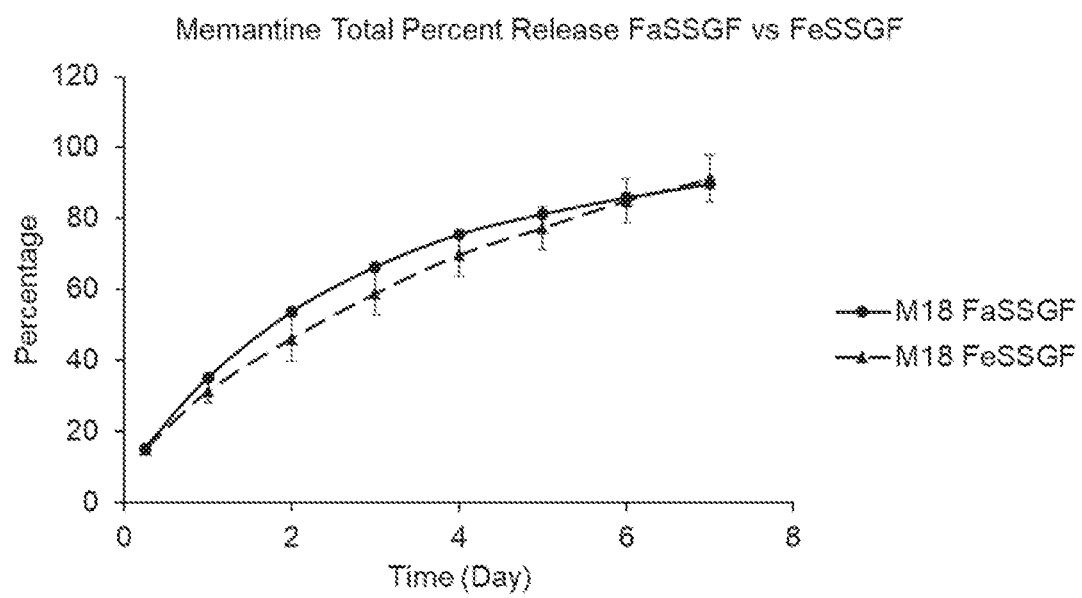
FIG. 18 shows memantine release in FaSSGF versus FeSSGF from formulation M18.
Figure 19:
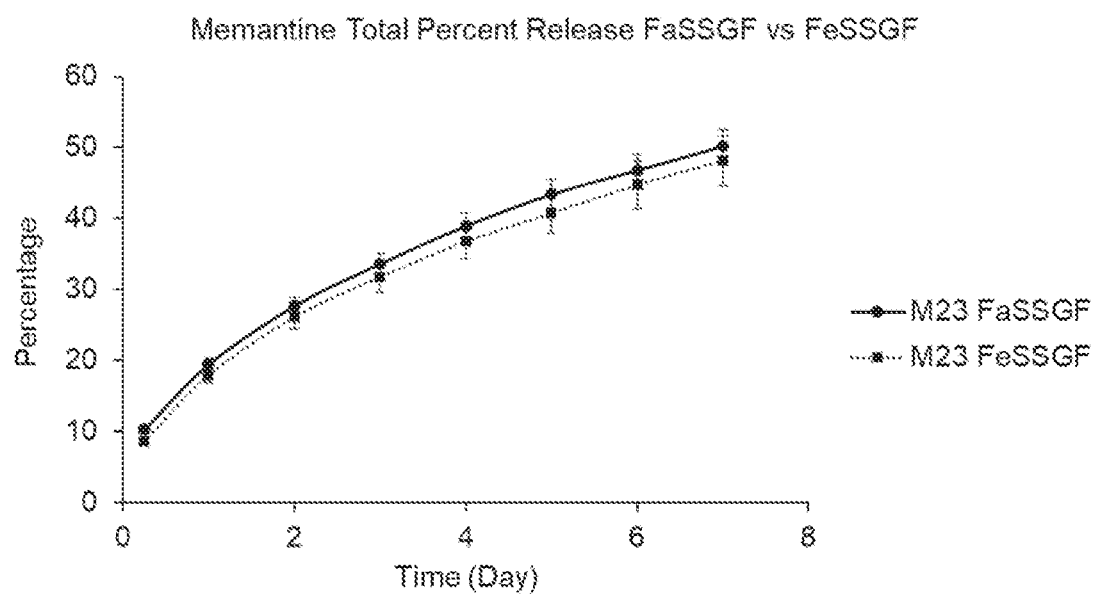
FIG. 19 shows memantine release in FaSSGF versus FeSSGF from formulation M23.
Figure 20:
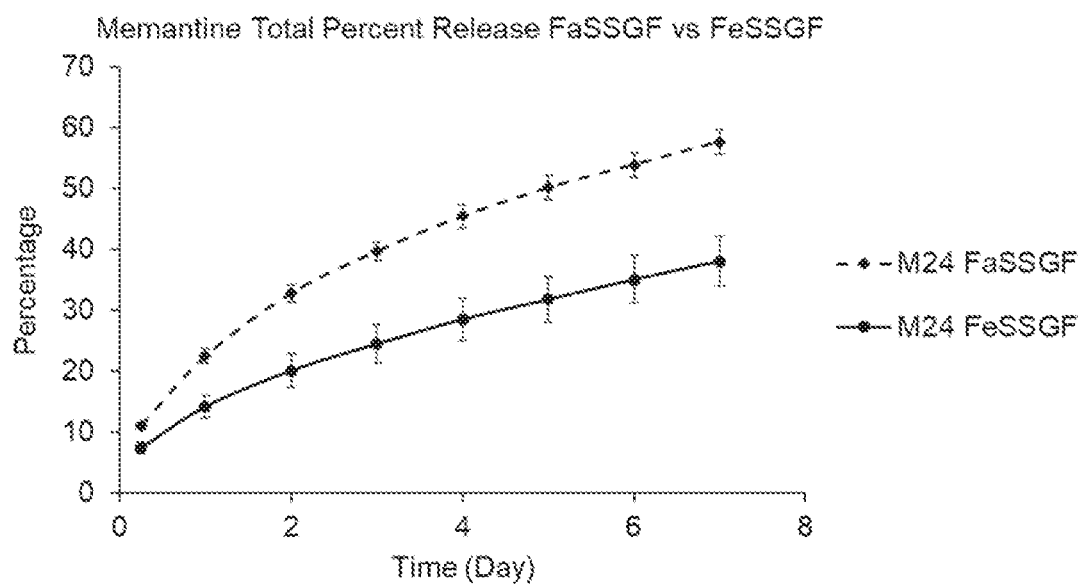
FIG. 20 shows memantine release in FaSSGF versus FeSSGF from formulation M24.
Figure 21:
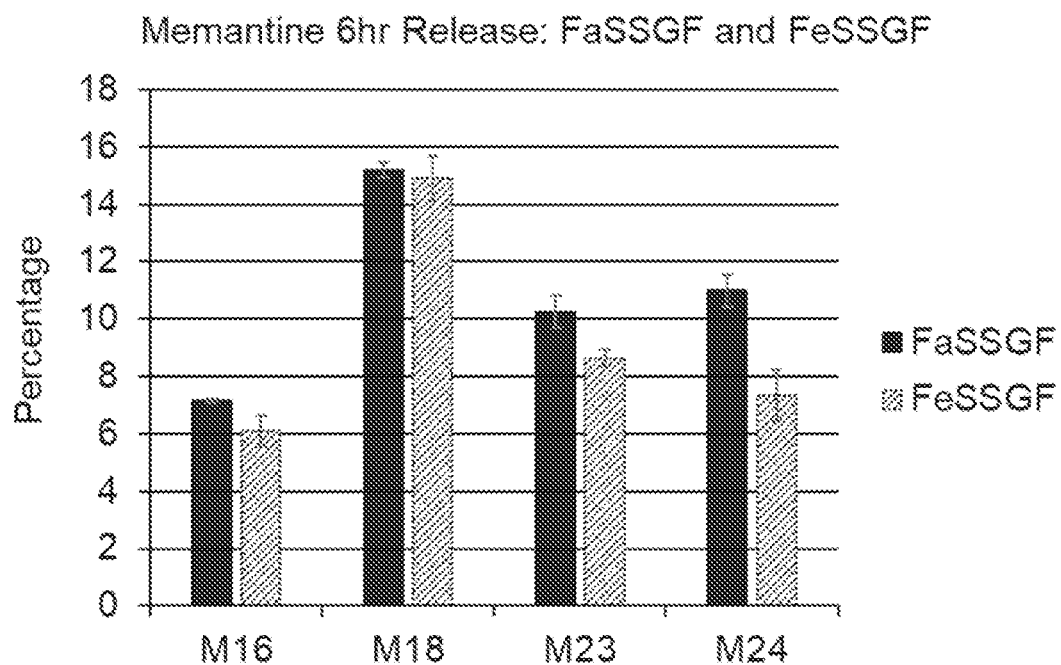
FIG. 21 shows percent memantine release after 6 hours (that is, burst release) in FaSSGF versus FeSSGF from formulations M16, M18, M23, and M24.
Figure 22:
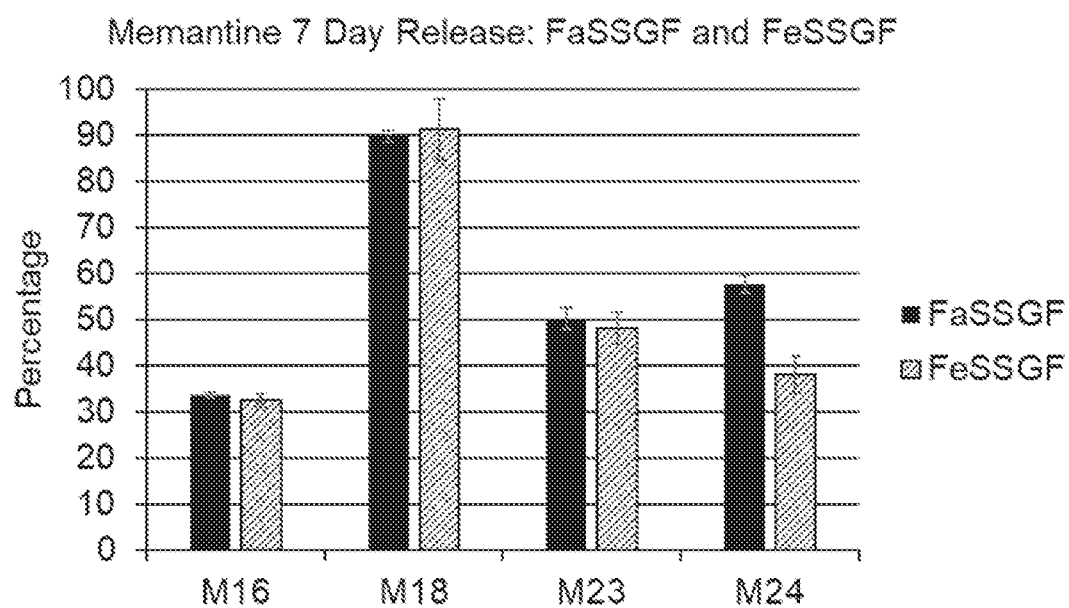
FIG. 22 shows percent memantine release after 7 days in FaSSGF versus FeSSGF from formulations M16, M18, M23, and M24.
Figure 58:
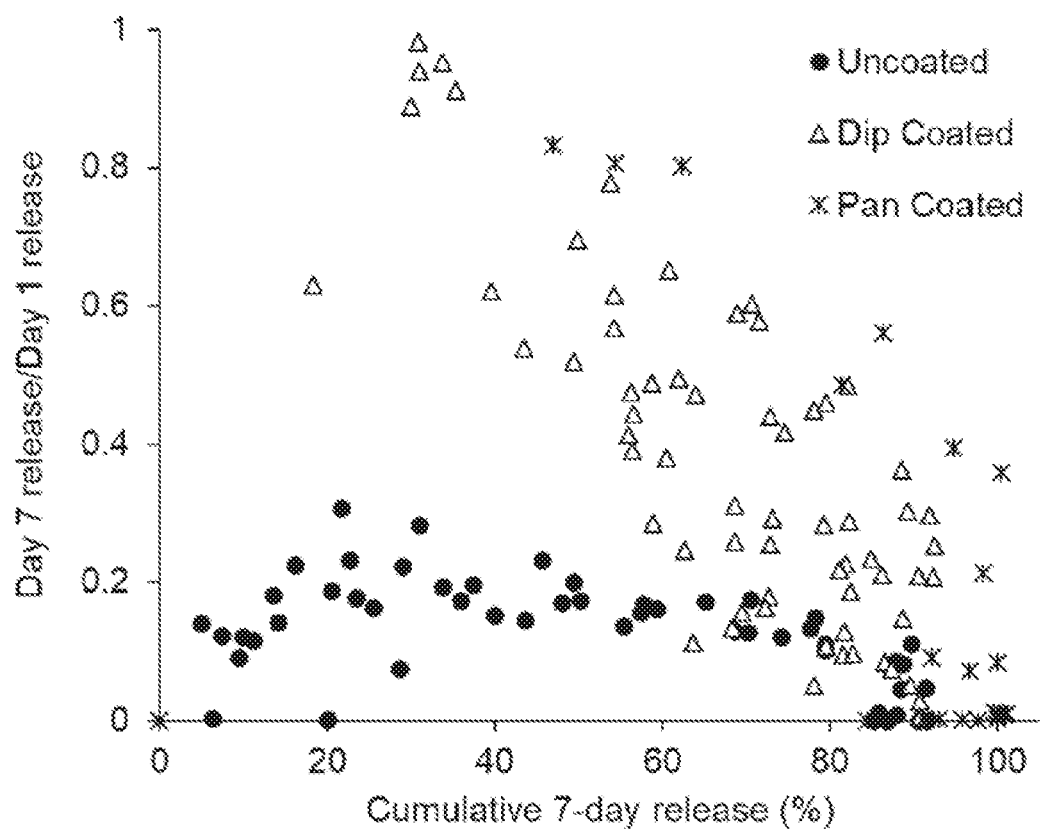
FIG. 58 depicts the linearity versus extent of release comparison between coated drug formulations and those without coating.

Linearity versus extent of release for about 50 formulations of memantine hydrochloride was evaluated, in which drug-polymer matrices were coated in accordance with the present invention in comparison with uncoated formulations (Example 1). As can be seen in FIG. 15, drug release on day 7 was up to 100% of release on day 1. Linearity of release, as measured by the ratio of release on day 7 to release on day 1, was greater than 30% for many formulations, including many formulations that displayed near complete cumulative release at Day 7. In systems of the present invention, achieving complete release in a 7-day treatment time is possible while maintaining near linear release (Day 7 release/Day 1 release >0.3). Coating formulations were as listed in Table 10. Total release over 7 days (X-value in Table 10) is plotted versus the ratio of (Day 7 Release/Day 1 Release) (Y-value in Table 10) in FIG. 58. Formulations that fall near or in the upper right quadrant of FIG. 58 are preferred, as they show good linearity and high release.

TABLE 10

Coating formulations.

| Formulation Code | Coating Formulation | Coating Solvent | Coating Solution Concentration (% w/v) | Y-value | X-value |
|---|---|---|---|---|---|
| M18 | 9:1, PCL 55k:P407 | DCM | 33.3 | 0.94 | 30.92 |
| M18 | 9:1, PCL 55k:P188 | DCM | 33.3 | 0.69 | 49.84 |
| M18 | Eudragit RS | DCM | 33.3 | 0.15 | 88.68 |
| M18 | 9:1, PCL 55k:PEG 10k | DCM | 33.3 | 0.95 | 33.73 |
| M18 | 9:1, PCL 55k:PEG 100k | DCM | 33.3 | 0.91 | 35.34 |
| M18 | PCL 55k | DCM | 16.7 | 0.60 | 70.61 |
| M18 | 9:1, PCL 55k:P407 | DCM | 16.7 | 0.62 | 54.22 |
| M18 | 9:1, PCL 55k:P188 | DCM | 16.7 | 0.57 | 54.21 |
| M18 | 9:1, PCL 55k:PVP 1M | DCM | 16.7 | 0.42 | 74.51 |
| M18 | Ethyl Cellulose | Acetone | 6.7 | 0.19 | 82.44 |
| M18 | 9:1 Ethyl Cellulose:PVP 1.3M | Acetone | 6.7 | 0.23 | 81.86 |
| M18 | 9:1 Ethyl Cellulose:PEG 1M | Acetone | 6.7 | 0.44 | 72.87 |
| M18 | 9:1 Ethyl Cellulose:PEG 100k | Acetone | 6.7 | 0.28 | 79.19 |
| M18 | 75:25 PLGA | Acetone | 16.7 | 0.54 | 43.48 |
| M18 | 50:50 PLGA | Acetone | 16.7 | 0.49 | 61.98 |
| M18 | 25:75 PLGA | Acetone | 13.9 | 0.28 | 58.86 |
| M18 | 50:50 PLGA | Acetone | 13.9 | 0.13 | 81.72 |
| M18 | 50:50 PLGA | Acetone | 13.9 | 0.18 | 72.64 |
| M18 | Ethyl Cellulose | Acetone | 6.7 | 0.25 | 62.67 |
| M18 | Cellulose Acetate | Acetone | 6.7 | 0.11 | 79.50 |
| M18 | 9:1 Ethyl Cellulose:PEG 1M | Acetone | 6.7 | 0.16 | 72.18 |
| M18 | 9:1 Cellulose Acetate:PEG 1M | Acetone | 6.7 | 0.10 | 81.60 |
| M18 | Cellulose Acetate | Acetone | 10.0 | 0.16 | 69.48 |
| M18 | PCL 55k | Acetone | 20.0 | 0.08 | 86.53 |
| M18 | PCL 55k | Acetone | 20.0 | 0.07 | 87.36 |
| M18 | PLGA 50:50 Ester Terminated 35-45k | Acetone | 16.7 | 0.39 | 56.45 |
| M18 | PLGA 50:50 Acid Terminated 35-45k | Acetone | 16.7 | 0.26 | 72.86 |
| M18 | PCL 80k | Acetone | 10.0 | 0.10 | 82.69 |
| M18 | PCL 80k | Ethyl Acetate | 10.0 | 0.26 | 68.57 |
| M57 | Ethyl Cellulose | Acetone | 6.7 | 0.29 | 73.18 |
| M57 | PCL 80k | Ethyl Acetate | 10.0 | 0.49 | 58.76 |
| M58 | Ethyl Cellulose | Acetone | 6.7 | 0.41 | 56.02 |
| M58 | PCL 80k | Ethyl Acetate | 10.0 | 0.62 | 39.53 |
| M59 | Ethyl Cellulose | Acetone | 6.7 | 0.38 | 60.50 |
| M59 | PCL 80k | Ethyl Acetate | 10.0 | 0.44 | 56.53 |
| M60 | Ethyl Cellulose | Acetone | 6.7 | 0.47 | 56.19 |
| M60 | PCL 80k | Ethyl Acetate | 10.0 | 0.52 | 49.40 |
| M57 | PCL 80k | Ethyl Acetate | 10.0 | 0.48 | 82.11 |
| M57 | PCL 80k | Ethyl Acetate | 15.0 | 0.78 | 53.78 |
| M57 | 9:1 PCL 80k:TEC | Ethyl Acetate | 15.0 | 0.65 | 60.77 |
| M57 | 8:2 PCL 80k:TEC | Ethyl Acetate | 15.0 | 0.59 | 68.87 |
| M57 | 7:3 PCL 80k:TEC | Ethyl Acetate | 15.0 | 0.36 | 88.57 |
| M57 | Ethyl Cellulose | Acetone | 6.7 | 0.45 | 78.07 |
| M57 | Ethyl Cellulose Cp 10 | Acetone | 6.7 | 0.21 | 92.28 |
| M57 | Ethyl Cellulose Cp 10 | Acetone | 13.3 | 0.21 | 90.63 |
| M57 | 9:1 Ethyl Cellulose Cp10:TEC | Acetone | 13.3 | 0.30 | 89.24 |
| M57 | 8:2 Ethyl Cellulose Cp10:TEC | Acetone | 13.3 | 0.30 | 91.88 |
| M57 | 7:3 Ethyl Cellulose Cp10:TEC | Acetone | 13.3 | 0.25 | 92.46 |
| M62 | PCL 80k | Ethyl Acetate | 10.0 | 0.46 | 79.46 |
| M77 | PCL 80k | Ethyl Acetate | 3.0 | 0.22 | 81.19 |
| M77 | PCL 80k | Ethyl Acetate | 5.0 | 0.47 | 63.90 |
| M77 | PCL 80k | Ethyl Acetate | 10.0 | 0.58 | 71.51 |
| M77 | 7:3 80k PCL:PVP | 8:2 Ethyl Acetate:IPA | 5.0 | 0.03 | 90.69 |
| M77 | 91:PVP | 8:2 Ethyl Acetate:IPA | 5.0 | 0.23 | 84.89 |

TABLE 10-continued

Coating formulations.

| Formulation Code | Coating Formulation | Coating Solvent | Coating Solution Concentration (% w/v) | Y-value | X-value |
|---|---|---|---|---|---|
| M77 | 7:3 80k PCL:Kolliphor RH40 | Ethyl Acetate | 5.0 | 0.01 | 90.74 |
| M77 | 9:1 80k PCL:Kolliphor RH40 | Ethyl Acetate | 5.0 | 0.29 | 82.26 |
| M77 | 7:3 80k PCL:Kollidon VA64 | Ethyl Acetate | 5.0 | 0.05 | 89.56 |
| M77 | 9:1 80k PCL:Kollidon VA64 | Ethyl Acetate | 5.0 | 0.21 | 86.21 |
| M104 | 1.25% weight gain of C3 (Table 12) | Ethyl Acetate | 3.3 | 0.01 | 100.03 |
| M104 | 2.5% weight gain of C3 (Table 12) | Ethyl Acetate | 3.3 | 0.01 | 101.12 |
| M107 | 1.25% weight gain of C3 (Table 12) | Ethyl Acetate | 3.3 | 0.00 | 95.85 |
| M107 | 2.5% weight gain of C3 (Table 12) | Ethyl Acetate | 3.3 | 0.00 | 92.99 |
| M104 | 1.25% weight gain of C4 (Table 12) | Ethyl Acetate | 3.3 | 0.08 | 100.02 |
| M104 | 2.5% weight gain of C4 (Table 12) | Ethyl Acetate | 3.3 | 0.09 | 92.20 |
| M107 | 1.25% weight gain of C4 (Table 12) | Ethyl Acetate | 3.3 | 0.00 | 100.00 |
| M107 | 2.5% weight gain of C4 (Table 12) | Ethyl Acetate | 3.3 | 0.01 | 99.96 |
| M104 | 1.25% weight gain of C5 (Table 12) | Ethyl Acetate | 3.3 | 0.01 | 100.85 |
| M104 | 2.5% weight gain of C5 (Table 12) | Ethyl Acetate | 3.3 | 0.01 | 99.56 |
| M107 | 1.25% weight gain of C5 (Table 12) | Ethyl Acetate | 3.3 | 0.00 | 84.45 |
| M107 | 2.5% weight gain of C5 (Table 12) | Ethyl Acetate | 3.3 | 0.00 | 97.68 |
| M104 | 1.25% weight gain of C6 (Table 12) | Ethyl Acetate | 3.3 | 0.49 | 81.38 |
| M104 | 2.5% weight gain of C6 (Table 12) | Ethyl Acetate | 3.3 | 0.81 | 54.35 |
| M107 | 1.25% weight gain of C6 (Table 12) | Ethyl Acetate | 3.3 | 0.39 | 94.73 |
| M107 | 2.5% weight gain of C6 (Table 12) | Ethyl Acetate | 3.3 | 0.80 | 62.42 |
| M104 | 1.25% weight gain of C7 (Table 12) | Ethyl Acetate | 3.3 | 0.07 | 96.68 |
| M104 | 2.5% weight gain of C7 (Table 12) | Ethyl Acetate | 3.3 | 0.36 | 100.41 |
| M107 | 1.25% weight gain of C7 (Table 12) | Ethyl Acetate | 3.3 | 0.00 | 91.11 |
| M107 | 2.5% weight gain of C7 (Table 12) | Ethyl Acetate | 3.3 | 0.21 | 98.27 |
| M107 | 1.25% weight gain of C8 (Table 12) | Ethyl Acetate | 3.3 | 0.56 | 86.36 |
| M107 | 2.5% weight gain of C8 (Table 12) | Ethyl Acetate | 3.3 | 0.83 | 46.97 |

Example 30

Memantine High Drug Loading

This experiment was performed to explore the extrusion of high drug load memantine formulations. Memantine formulations were extruded at 35, 40, 45 and 55% w/w API (named M103, M104, M105 and M106 respectively). All extrusions were performed at a 500 g scale. The formulations in Table 11 were compounded and profile extruded using a Leistritz 18" hot melt extruder. Each formulation was bag blended to create a homogenous mixture. The blended powder was fed into the extruder hopper and compounded using a feed rate of 0.5 kg/hr. The extrudate was cooled and pelletized using an in-line cutter to make pellets of appropriate size (~0.6-2.0 mm) for profile extrusion.

Figure 60:
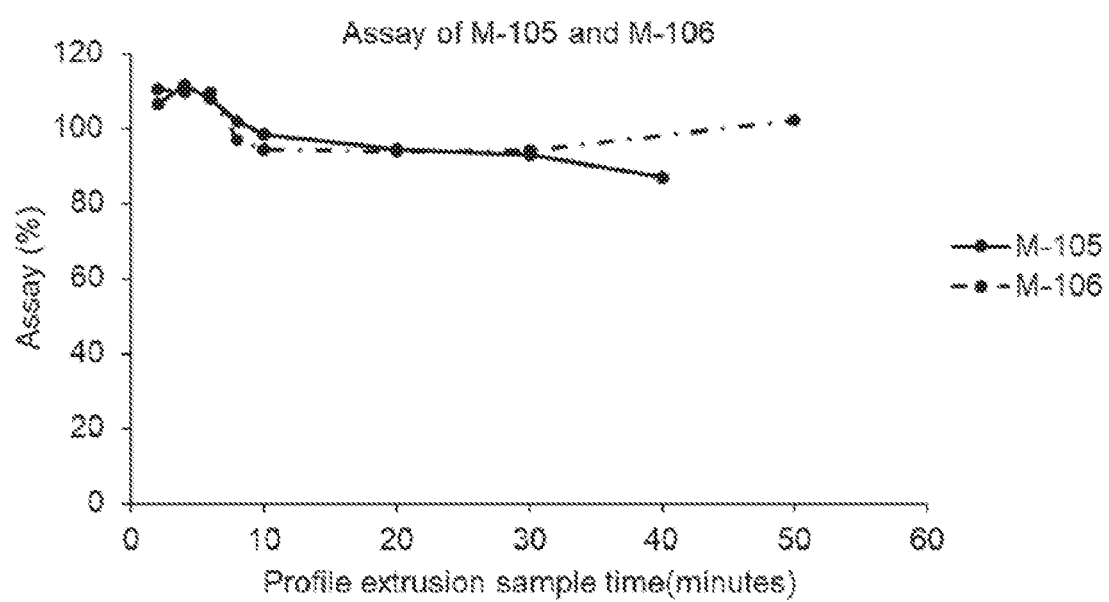
FIG. 60 depicts assays of formulations M105 and M106.
Figure 61:
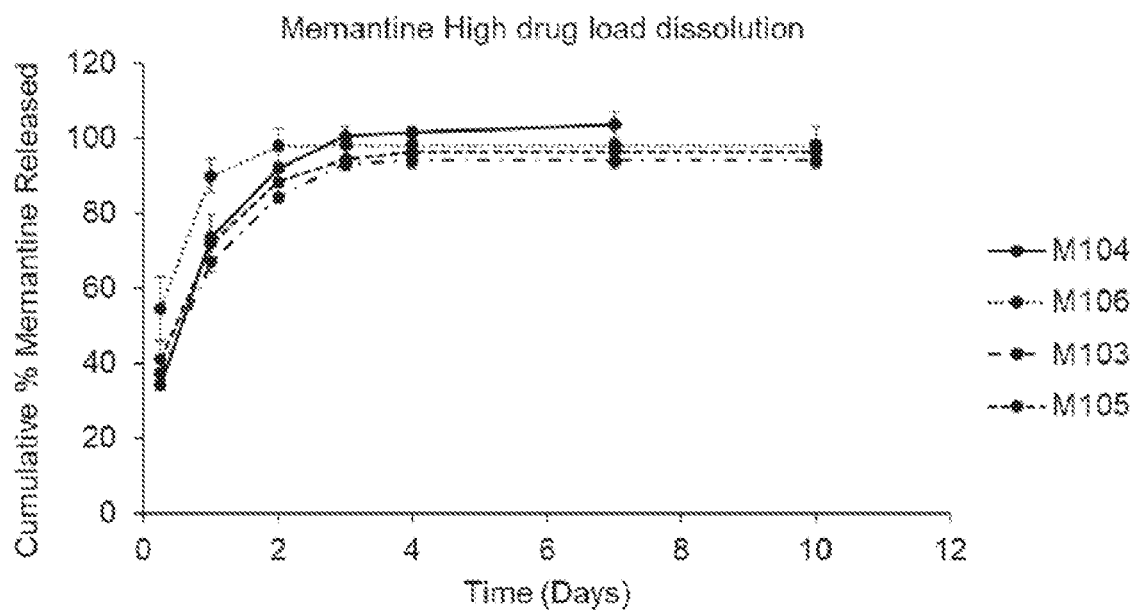
FIG. 61 shows the dissolution of uncoated M103, M104, M105 and M106 formulations in fasted-state simulated gastric fluid (FaSSGF).

The pellets were then fed into the twin screw extruder and profile extruded using a custom triangular die and a feed rate of 0.4-0.5 kg/hr. Samples of the profile extruded drug arms were taken every 2 minutes for the first 10 minutes and one additional sample was taken at the beginning, middle, and end of the process. Samples for M105 and M106 were run for Memantine content analysis. The results show reasonable uniformity with all samples having assay of 85-115% (see FIG. 60). Samples were run for dissolution in fasted simulated gastric fluid (FaSSGF). All samples showed complete release over 3-4 days (see FIG. 61).

TABLE 11

% Composition of Memantine High Drug Load Formulations

|  | M103 | M104 | M105 | M106 | M107 |
|---|---|---|---|---|---|
| Memantine HCl | 35.0 | 40.0 | 45.0 | 55.0 | 45.0 |
| Polycaprolactone | 62.0 | 58.0 | 54.0 | 44.0 | 52.0 |
| Poloxamer P407 | 2.0 | 1.0 | 0.0 | 0.0 | 2.0 |
| Colloidal Silicon Dioxide | 0.5 | 0.5 | 0.5 | 0.5 | 0.5 |
| Vitamin E Succinate | 0.5 | 0.5 | 0.5 | 0.5 | 0.5 |
| Total | 100.0 | 100.0 | 100.0 | 100.0 | 100.0 |

Example 31

Coating of High Drug Load Memantine to Control Release Rate

This experiment was performed to explore how coatings containing polycaprolactone, the porogen copovidone and plasticizer triethyl citrate (TEC) can control the release rate of M103, M104, and M105 when applied in a LCDS pan coater.

Two solutions of PCL, copovidone and triethyl citrate were prepared in ethyl acetate at 3.3% w/v. The first coating solution (C1) contained a 95:5 ratio of PCL to copovidone and 10% TEC by coating material, with 2% magnesium stearate as a processing aid. The second solution (C2) contained 80:20 ratio of PCL to copovidone and 15% TEC by coating material, with 2% magnesium stearate as a processing aid. The solution was then applied to drug loaded arms using a Vector LDCS pharmaceutical pan coater. The coating solution was applied to approximately 480 g placebo arms with approximately 5 g of M105 drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 2.5% and 5.0% w/w mass gain.

The process was repeated for M103 and M104. Coating solutions C1 and C2 were prepared again and applied to a coating pan containing approximately 465 g placebo arms with approximately 10 g of M103 and 10 g of M104 drug loaded arms spiked in. Processing conditions were the same as in the previous paragraph.

Figure 62:
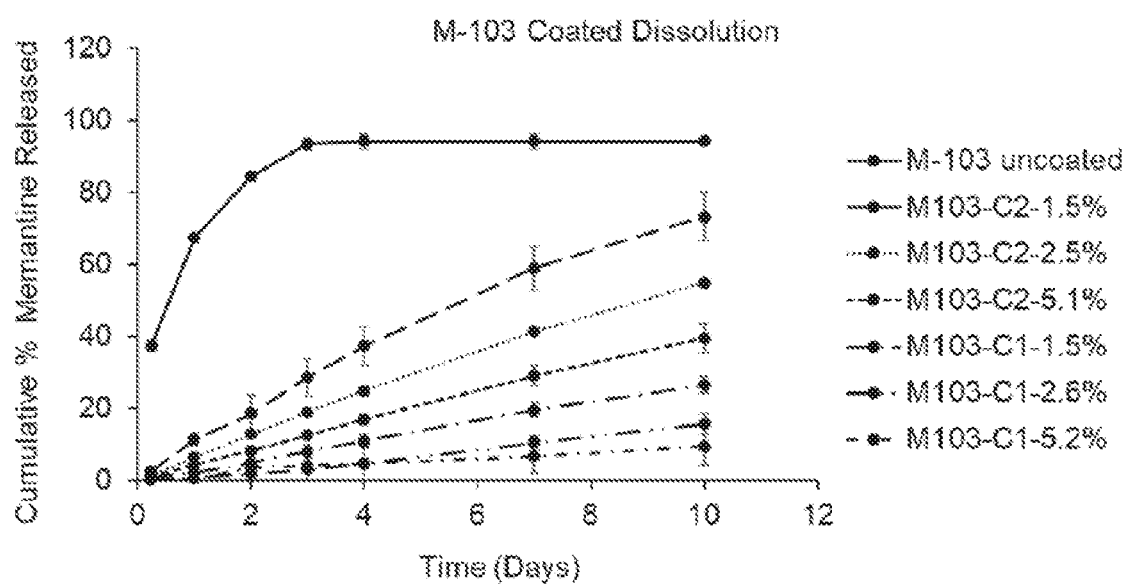
FIG. 62 shows the dissolution of M103 formulations with various coatings (coatings C1, C2 versus uncoated).
Figure 63:
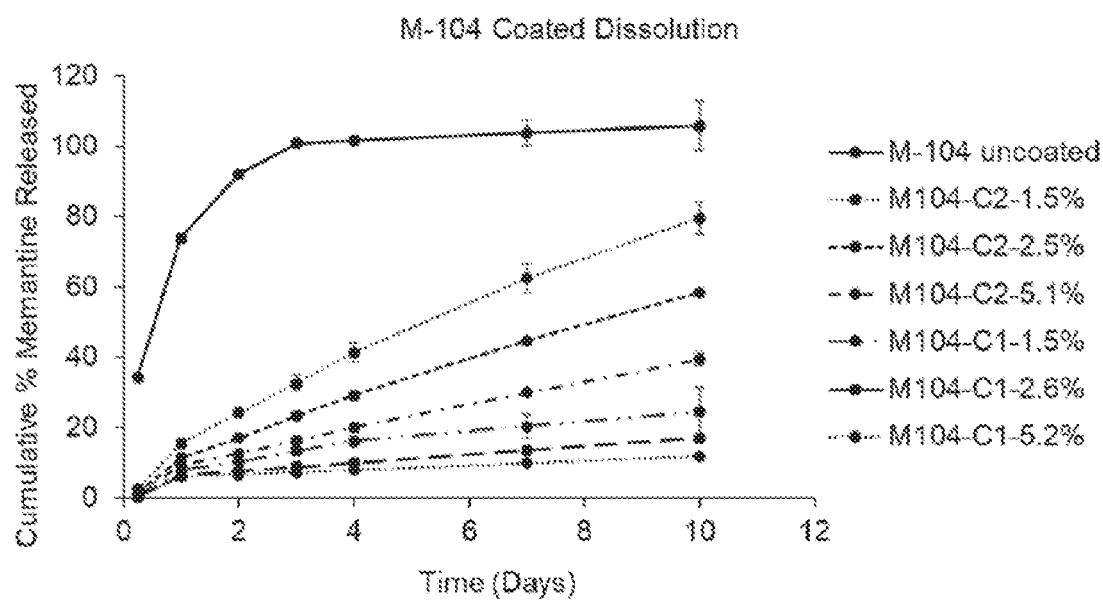
FIG. 63 shows the dissolution of M104 formulations with various coatings (coatings C1, C2 versus uncoated).
Figure 64:
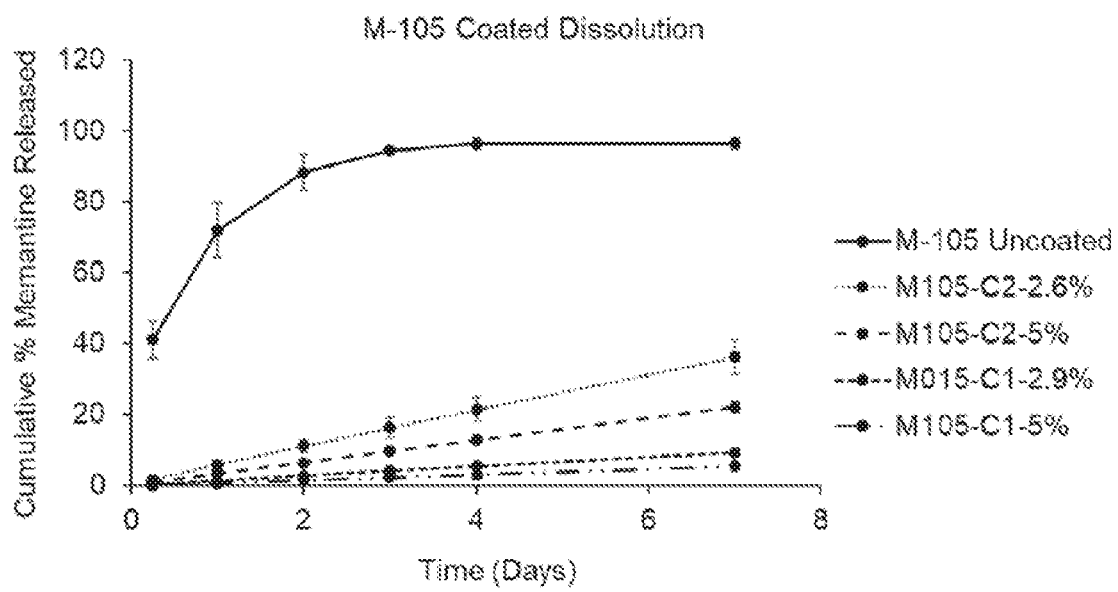
FIG. 64 shows the dissolution of M105 formulations with various coatings (coatings C1, C2 versus uncoated).

All coated material was run for dissolution in FaSSGF. Results showed that the lower amounts of porogen and plasticizer in the C1 coating solution result in relatively slower dissolution at similar coating weights when compared to drug arms coated with the C2 formulation. FIG. 62 shows a graph of dissolution of formulation M103 with C1 coating, C2 coating, and uncoated; FIG. 63 shows a graph of dissolution of formulation M104 with C1 coating, C2 coating, and uncoated; and FIG. 64 shows a graph of dissolution of formulation M105 with C1 coating, C2 coating, and uncoated. For both coating formulations, increased coating weight causes slower dissolution. These dissolution experiments show that the rate of release from all high drug load Memantine formulations tested can be controlled with as little as 1.5% coating weight. Coated formulations show higher linearity than the corresponding uncoated formulation. For example, formulation M104 with C1 coating display correlation co-efficient ($R^2$) values of 0.89, 0.84, 0.73 respectively for coating weights of 1.5%, 2.5%, 5.1% and M104 with C2 coating display correlation co-efficient ($R^2$) values of 0.98, 0.98, 0.96 respectively for coating weights of 1.5%, 2.5%, 5.2% while the uncoated M104 formulation displays a correlation co-efficient ($R^2$) value of 0.58.

Example 32

Coating of High Drug Load Formulations to Increase Extent of Release

This experiment was performed to increase the extent of API release from Example 31 using polycaprolactone coatings, with increased amounts of porogen and the plasticizer triethyl citrate (TEC) to control the release rate of M104 and M107 when applied in a LCDS pan coater.

Six additional solutions of PCL, copovidone and triethyl citrate were prepared in ethyl acetate at 3.3% w/v. The first coating solution (C3) contained a 70:30 ratio of PCL to copovidone and 30% TEC by coating material, with 2% magnesium stearate as a processing aid. The second solution (C4) contained 80:20 ratio of PCL to copovidone and 30% TEC by coating material, with 2% magnesium stearate as a processing aid. The third solution (C5) contained 70:30 ratio of PCL to copovidone and 20% TEC by coating material, with 2% magnesium stearate as a processing aid. The forth solution (C6) contained 80:20 ratio of PCL to copovidone and 20% TEC by coating material, with 2% magnesium stearate as a processing aid. The fifth solution (C7) contained 75:25 ratio of PCL to copovidone and 15% TEC by coating material, with 2% magnesium stearate as a processing aid. The sixth solution (C8) contained 80:20 ratio of PCL to copovidone and 10% TEC by coating material, with 2% magnesium stearate as a processing aid. Coating formulations are summarized in Table 12. The solution was then applied to drug loaded arms using a Vector LDCS pharmaceutical pan coater. The coating solution was applied to approximately 480 g placebo arms with approximately 5 g of M105 drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 1.25% and 2.5% w/w mass gain. For every run M104 and M107 were coated in the same batch.

Figure 65:
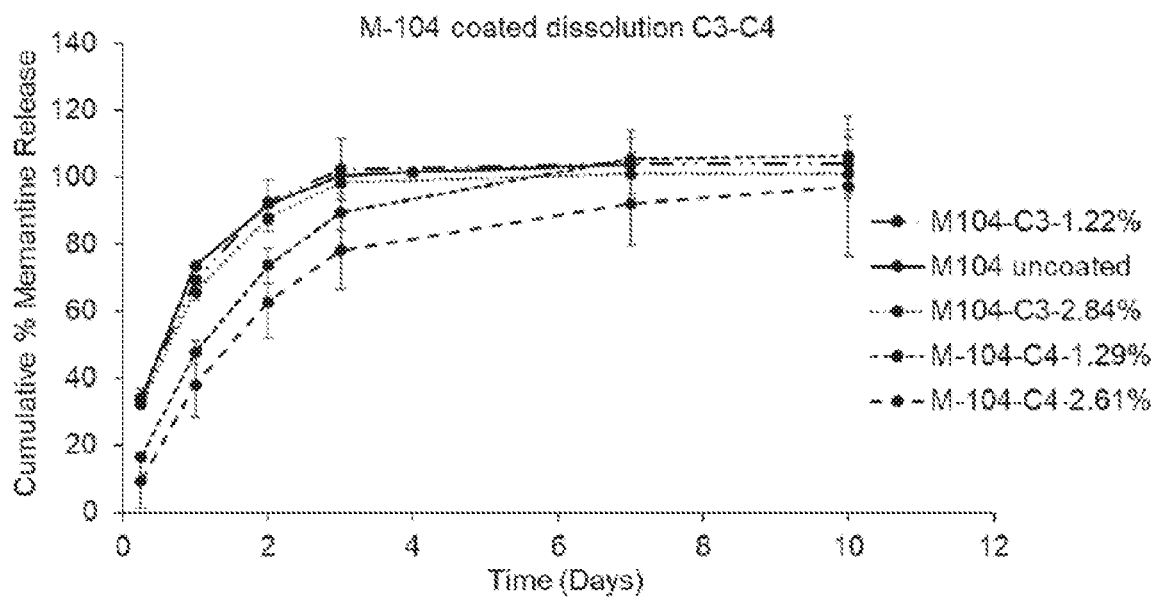
FIG. 65 shows the dissolution of M104 formulations with various coatings (coatings C3, C4 versus uncoated).
Figure 66:
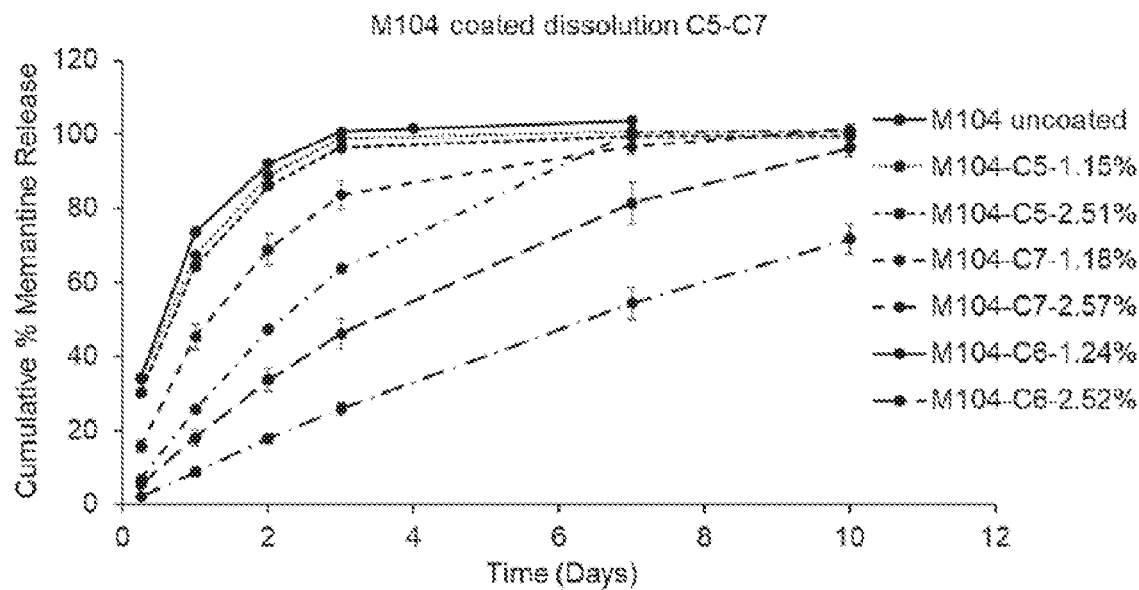
FIG. 66 shows the dissolution of M104 formulations with various coatings (coatings C5, C6, C7 versus uncoated).
Figure 67:
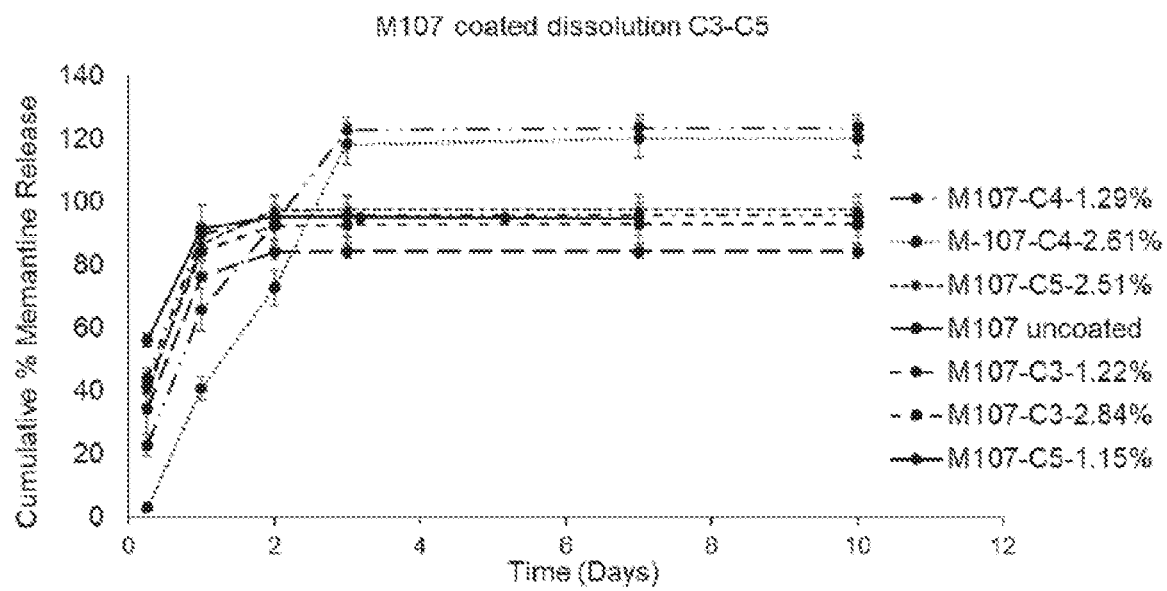
FIG. 67 shows the dissolution of M107 formulations with various coatings (coatings C3, C4, C5 versus uncoated).
Figure 68:
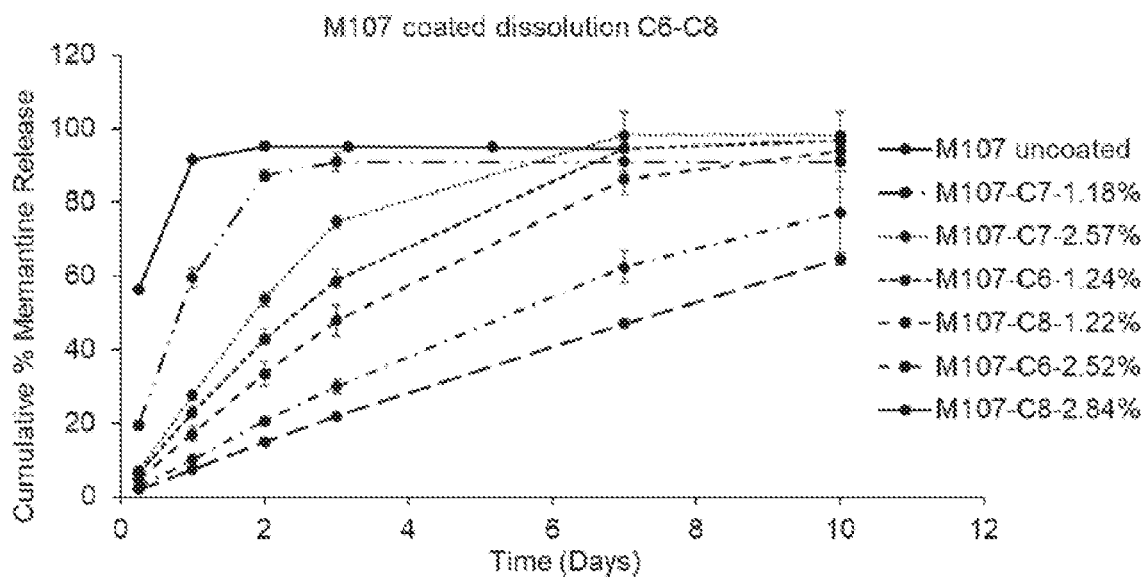
FIG. 68 shows the dissolution of M107 formulations with various coatings (coatings C6, C7, C8 versus uncoated).

All coated material was run for dissolution in FaSSGF. Results showed that the increased amounts of porogen and plasticizer in the C3, C4, C5 and C7 coating solution offer essentially no control of drug release compared to the uncoated arms at the coating weights tested. However, coatings C6 and C8 show sustained release over seven days for both drug arm formulations at all coating weights. Only coatings with <20% copovidone and <20% triethyl citrate show controlled release compared to the uncoated drug arms. FIG. 65 shows a graph of dissolution of formulation M104 with C3 coating, C4 coating, and uncoated. FIG. 66 shows a graph of dissolution of formulation M104 with C5 coating, C6 coating, C7 coating, and uncoated. FIG. 67 shows a graph of dissolution of formulation M107 with C3 coating, C4 coating, C5 coating, and uncoated. FIG. 68 shows a graph of dissolution of formulation M107 with C6 coating, C7 coating, C8 coating, and uncoated.

TABLE 12

| | % w/w Composition of Coating Formulations | | | | | | | |
|---|---|---|---|---|---|---|---|---|
| | C1 | C2 | C3 | C4 | C5 | C6 | C7 | C8 |
| polycaprolactone | 83.8 | 66.7 | 48.0 | 54.9 | 54.9 | 62.7 | 62.5 | 70.6 |
| copovidone | 4.4 | 16.6 | 20.6 | 13.7 | 23.5 | 15.7 | 20.8 | 17.6 |
| Triethyl citrate | 9.8 | 14.7 | 29.4 | 29.4 | 19.6 | 19.6 | 14.7 | 9.8 |
| Magnesium stearate | 2.0 | 2.0 | 2.0 | 2.0 | 2.0 | 2.0 | 2.0 | 2.0 |
| Total | 100.0 | 100.0 | 100.0 | 100.0 | 100.0 | 100.0 | 100.0 | 100.0 |

Example 33

In Vivo Release Rates Based on Analysis of Dog PK Data; Plasma Concentrations

Pharmacokinetic plasma profiles in dogs described in Example 26, Example 27, and Example 28 were analyzed to extract the kinetics of in vivo release. The Wagner-Nelson method was used to calculate the fraction of available drug absorbed vs. time for each formulation based on mean plasma concentrations (plotted in FIG. 55, FIG. 56, and FIG. 57), assuming a one compartment model for memantine in dog and an elimination rate constant ($k_e$) of 0.076 hr$^{-1}$. The fraction of available drug absorbed during 24 hour time intervals for each formulation is tabulated below in Table 13. "Available drug" is defined as the total amount of drug absorbed over the gastric residence period.

TABLE 13

| Time interval (h) | Fraction of available drug absorbed (%) | | |
|---|---|---|---|
| | PCL-coated M77 | EC coated-M57 | PCL-coated M69 |
| 0-24 | 20.7 | 17.5 | 6.6 |
| 24-48 | 16.5 | 23.8 | 11.7 |
| 48-72 | 13.7 | 18.8 | 17.9 |
| 72-96 | 11.5 | 15.0 | 15.8 |
| 96-120 | 8.3 | 12.6 | 17.8 |
| 120-144 | 7.9 | 7.8 | 20.5 |
| 144-168 | 6.3 | 4.6 | 9.7 |

The average plasma concentrations (ng/mL) measured for the same formulations are given in Table 14.

TABLE 14

| Time (hr) | M57 average | M77 Average | M69 average | Range (ng/mL) |
|---|---|---|---|---|
| 2 | 3.70 | 11.05 | 0.856 | |
| 4 | 5.24 | 16.11 | 4.71 | 4.7-16.1 |
| 6 | 5.68 | 20.42 | 6.85 | 5.6-20.4 |
| 24 | 32.73 | 41.04 | 16.4 | 16.4-32.7 |
| 48 | 44.80 | 39.16 | 32.1 | 32.1-44.8 |
| 72 | 36.28 | 32.62 | 49.5 | 39.1-49.5 |
| 96 | 28.96 | 27.38 | 44.5 | 29.0-44.5 |
| 120 | 24.36 | 19.88 | 49.7 | 24.4-49.7 |
| 144 | 15.34 | 18.66 | 57.2 | 25.3-57.2 |
| 168 | 9.089 | 14.98 | 28.7 | 9.1-28.7 |

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A gastric residence system comprising a therapeutically effective amount of an adamantane-class drug or a pharmaceutically acceptable salt thereof, wherein:
   the gastric residence system has a compacted configuration and an uncompacted configuration,
   the gastric residence system comprises a plurality of elongate members affixed to a central elastomer,
   wherein at least one elongate member comprises:
      a carrier polymer,
      the adamantane-class drug or the pharmaceutically acceptable salt thereof, and
      a release rate-modulating polymer film coated on the surface of the at least one elongate member, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
   wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
   wherein the gastric residence system is configured to release the adamantane-class drug or the pharmaceutically acceptable salt thereof over a specified gastric residence period.

2. The gastric residence system of claim 1, wherein the elongate members are affixed to the central elastomer via linkers, wherein the linkers are configured to weaken or degrade to allow passage of the gastric residence system through a pylorus after the specified gastric residence period.

3. The gastric residence system of claim 1, wherein the adamantane-class drug or the pharmaceutically acceptable salt thereof is selected from the group consisting of memantine; amantadine; adapromine; nitromemantine; rimantadine; bromantane; tromantadine; neramexane; and a pharmaceutically acceptable salt of any one of memantine, amantadine, adapromine, nitromemantine, rimantadine, bromantane, tromantadine, and neramexane.

4. A gastric residence system comprising a therapeutically effective amount of an adamantane-class drug or a pharmaceutically acceptable salt thereof, wherein:
   the gastric residence system has a compacted configuration and an uncompacted configuration,
   the gastric residence system comprises a plurality of elongate members affixed to a central elastomer,
   wherein at least one elongate member comprises:
      a carrier polymer;
      an adamantane-class drug or a salt thereof; and
      a release rate-modulating polymer film, wherein the release rate-modulating polymer film comprises one or more polyester materials with a repeating unit of the form —$R^1$—O—C(=O)—, wherein $R^1$ is selected from the group consisting of C1-C12 alkylene groups, ethers containing between two and twelve carbon atoms, and polyethers containing between three and twelve carbon atoms, and
   wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
   wherein over a seven-day incubation of the system in simulated gastric fluid, the amount of the adamantane-class drug or salt thereof released from the system during day 5 is at least about 40% of the amount of adamantane-class drug or salt thereof released during day 2; and
   wherein at least about 7% of the total amount of adamantane-class drug or salt thereof in the system is released on day 2 and at least about 7% of the total amount of adamantane-class drug or salt thereof is released on day 5.

5. A gastric residence system comprising a therapeutically effective amount of an adamantane-class drug or a pharmaceutically acceptable salt thereof, wherein:

the gastric residence system has a compacted configuration and an uncompacted configuration,
the gastric residence system comprises a plurality of elongate members affixed to a central elastomer,
wherein at least one elongate member comprises:
a carrier polymer;
an adamantane-class drug or a salt thereof; and
a release rate-modulating polymer film, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
wherein over a seven-day incubation of the system in simulated gastric fluid, the amount of the adamantane-class drug or salt thereof released from the system during day 7 is at least about 20% of the amount of adamantane-class drug or salt thereof released during day 1; and wherein at least about 4% of the total amount of adamantane-class drug or salt thereof in the system is released on day 1 and at least about 4% of the total amount of adamantane-class drug or salt thereof is released on day 7.

6. A gastric residence system comprising a therapeutically effective amount of an adamantane-class drug or a pharmaceutically acceptable salt thereof, wherein:
the gastric residence system has a compacted configuration and an uncompacted configuration,
the gastric residence system comprises a plurality of elongate members affixed to a central elastomer,
wherein at least one elongate member comprises:
a carrier polymer,
an adamantane-class drug or a salt thereof, and
a release rate-modulating polymer film, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms;
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour.

7. A gastric residence system comprising a therapeutically effective amount of an adamantane-class drug or a pharmaceutically acceptable salt thereof, wherein:
the gastric residence system has a compacted configuration and an uncompacted configuration,
the gastric residence system comprises a plurality of elongate members affixed to a central elastomer,
wherein at least one elongate member comprises:
a carrier polymer,
an adamantane-class drug or a salt thereof; and
a release rate-modulating polymer film configured to control the release rate of the adamantane-class drug or salt thereof, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms,
wherein the release rate-modulating polymer film is configured such that the release of adamantane-class drug or salt thereof from the system in 40% ethanol/60% simulated gastric fluid over one hour is at least about 40% lower than the release of adamantane-class drug or salt thereof from a second system in 40% ethanol/60% simulated gastric fluid over one hour, the second system comprising the same combination of carrier polymer and adamantane-class drug or salt thereof but lacking the release rate-modulating polymer film.

8. A gastric residence system comprising a therapeutically effective amount of an adamantane-class drug or a pharmaceutically acceptable salt thereof, wherein:
the gastric residence system has a compacted configuration and an uncompacted configuration,
the gastric residence system comprises a plurality of elongate members affixed to a central elastomer,
wherein at least one elongate member comprises:
a carrier polymer,
an adamantane-class drug or a salt thereof; and
a release rate-modulating polymer film configured to control the release rate of the adamantane-class drug or salt thereof, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour,
wherein the release rate-modulating polymer film is configured such that the release of adamantane-class drug or salt thereof from the system in simulated gastric fluid over an initial 6 hour period is at least about 40% lower than the release of adamantane-class drug or salt thereof from a second system in simulated gastric fluid over an initial 6 hour period, the second system comprising the same combination of carrier polymer and adamantane-class drug or salt thereof but lacking the release rate-modulating polymer film; and
wherein the release of adamantane-class drug or salt thereof from the system in simulated gastric fluid over a seven-day period is at least about 60% of the total amount of adamantane-class drug or salt thereof originally present in the system.

9. A gastric residence system comprising a therapeutically effective amount of an adamantane-class drug or a pharmaceutically acceptable salt thereof, wherein:
the gastric residence system has a compacted configuration and an uncompacted configuration,
the gastric residence system comprises a plurality of elongate members affixed to a central elastomer, wherein at least one elongate member comprises:
a carrier polymer;
an adamantane-class drug or a salt thereof; and
a release rate-modulating polymer film, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour,
wherein the polymer film is configured to control the release rate of the adamantane-class drug or salt thereof such that a best-fit linear regression model of the release rate of adamantane-class drug or salt thereof from the system in simulated gastric fluid has a coefficient of determination $R^2$ of at least about 0.8 over an initial period of seven days; and wherein the system releases about 40% to about 60% of the adamantane-class drug or salt thereof within a time of about 40% to about 60% of the seven-day period.

10. A gastric residence system providing an extended release drug dosage form, comprising:
a plurality of elongate members comprising a therapeutically effective amount of an adamantane-class drug or a pharmaceutically acceptable salt thereof and a carrier polymer, wherein the gastric residence system has a compacted configuration and an uncompacted configuration,
wherein the adamantane-class drug or a pharmaceutically acceptable salt thereof is blended with the carrier polymer such that the drug or salt thereof is distributed throughout the elongate member, and
a release rate-modulating polymer film coating at least one elongate member, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
wherein the plurality of elongate members are attached to a central elastomer; and
wherein said gastric residence system provides extended release of the adamantane-class drug or pharmaceutically acceptable salt thereof.

11. A gastric residence system providing an extended release drug dosage form, comprising a therapeutically effective amount of an adamantane-class drug or a pharmaceutically acceptable salt thereof and a component adapted to provide extended release of the adamantane-class drug or a pharmaceutically acceptable salt thereof in an aqueous environment,
wherein the gastric residence system has a compacted configuration and an uncompacted configuration,
the gastric residence system comprises a plurality of elongate members affixed to a central elastomer,
wherein at least one elongate member comprises a carrier polymer and the adamantane-class drug or the pharmaceutically acceptable salt thereof;
wherein the gastric residence system comprises a release rate-modulating polymer film, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
wherein the system has a dissolution profile characterized by about 10% to 20% dissolution of the initial amount of adamantane-class drug or pharmaceutically acceptable salt thereof present in the system during an initial 24 hour period in the aqueous environment.

12. A gastric residence system providing an extended release drug dosage form, comprising:
a plurality of elongate members, wherein at least one elongate member comprises a therapeutically effective amount of an adamantane-class drug or a pharmaceutically acceptable salt thereof and a carrier polymer,
wherein the gastric residence system has a compacted configuration and an uncompacted configuration,
wherein the adamantane-class drug or a pharmaceutically acceptable salt thereof is blended with the carrier polymer such that the drug or salt thereof is distributed throughout the at least one elongate member, and
a release rate-modulating polymer film coating the at least one elongate member, wherein the release rate-modulating polymer film comprises one or more polyester materials with a repeating unit of the form —$R^1$—O—C(=O)—, wherein $R^1$ is selected from the group consisting of $C_1$-C 12 alkylene groups, ethers containing between two and twelve carbon atoms, and polyethers containing between three and twelve carbon atoms, and
wherein the release rate-modulating polymer film is configured such that the release of adamantane-class drug or salt thereof from the system in 40% ethanol/60% simulated gastric fluid over one hour is no more than about 40% higher compared to release of adamantane-class drug or salt thereof from an equivalent system in 100% simulated gastric fluid over one hour;
wherein the adamantane-class drug or a pharmaceutically acceptable salt thereof comprises about 40% to about 60% by weight of the at least one elongate member;
wherein the plurality of elongate members are attached to a central elastomer; and
wherein said gastric residence system provides extended release of the adamantane-class drug or pharmaceutically acceptable salt thereof.

13. The gastric residence system of claim 1, wherein the adamantane-class drug or the pharmaceutically acceptable salt thereof is memantine or a pharmaceutically acceptable salt of memantine.

14. The gastric residence system of claim 1, wherein the release rate-modulating polymer film comprises polycaprolactone.

15. The gastric residence system of claim 1, wherein the release rate-modulating polymer film further comprises a porogen.

16. The gastric residence system of claim 1, wherein the release rate-modulating polymer film further comprises a plasticizer.

17. The gastric residence system of claim 1, wherein the polymer film further comprises an anti-tack agent.

18. The gastric residence system of claim 1, wherein the elongate members further comprise at least one excipient.

19. The gastric residence system of claim 1, wherein the elongate members further comprise an anti-oxidant.

20. The gastric residence system of claim 1, wherein the elongate members further comprise silica.

21. The gastric residence system of claim 1, wherein the central elastomer comprises silicone rubber.

22. The gastric residence system of claim 1, wherein the gastric residence system comprises about 140 mg to about 420 mg of memantine or a pharmaceutically acceptable salt thereof.

\* \* \* \* \*